(12) United States Patent
Bird et al.

(10) Patent No.: US 7,094,780 B1
(45) Date of Patent: Aug. 22, 2006

(54) 3-AMINOQUINAZOLIN-2,4-DIONE ANTIBACTERIAL AGENTS

(75) Inventors: Paul Bird, Edmonton (CA); Edmund Lee Ellsworth, Brighton, MI (US); Dai Quoc Nguyen, Edmonton (CA); Joseph Peter Sanchez, South Lyon, MI (US); Howard Daniel Hollis Showalter, Ann Arbor, MI (US); Rajeshwar Singh, Edmonton (CA); Michael Andrew Stier, Ypsilanti, MI (US); Tuan Phong Tran, Canton, MI (US); Brian Morgan Watson, Carmel, IN (US); Judy Yip, Edmonton (CA)

(73) Assignee: Warner Lambert Company LLC, Morris Plains, NJ (US)

( * ) Notice: Subject to any disclaimer, the term of this patent is extended or adjusted under 35 U.S.C. 154(b) by 256 days.

(21) Appl. No.: 10/182,221

(22) PCT Filed: Dec. 12, 2000

(86) PCT No.: PCT/US00/33656

§ 371 (c)(1),
(2), (4) Date: Dec. 9, 2002

(87) PCT Pub. No.: WO01/53273

PCT Pub. Date: Jul. 26, 2001

Related U.S. Application Data

(60) Provisional application No. 60/241,267, filed on Oct. 18, 2000, provisional application No. 60/178,252, filed on Jan. 24, 2000.

(51) Int. Cl.
*C07D 239/96* (2006.01)
*C07D 403/04* (2006.01)
*A61K 31/505* (2006.01)

(52) U.S. Cl. .............. 514/234.5; 514/252.17; 514/266.2; 514/266.22; 514/266.3; 514/266.31; 544/119; 544/284; 544/285

(58) Field of Classification Search ............ 544/119, 544/284, 285; 514/234.5, 252.17, 266.2, 514/266.22, 266.3, 266.31
See application file for complete search history.

(56) References Cited

FOREIGN PATENT DOCUMENTS

| | | | |
|---|---|---|---|
| EP | 35619 | A | 9/1981 |
| GB | 2097784 | A | 11/1982 |
| WO | WO 9414809 | A | 7/1994 |
| WO | WO 9818781 | A | 5/1998 |
| WO | WO 9921840 | A | 5/1999 |
| WO | WO 9961444 | A | 12/1999 |

OTHER PUBLICATIONS

Snyder et al., PubMed Abstract (J Med Liban. 48(4):208-14) Jul.-Aug. 2000.*

Chemical Abstracts, Abstract No. 237941k, vol. 133:17 (Oct. 23, 2000).

Garcia-Quintana, H.G., et al., Study of benzotriaxepines and quinazolines obtained by synthesis on bacterial populations, J. Vet. Med., Series B, vol. 34(5): 341-346 (1987).

Kornet, M.J., et al., Synthesis of 3-amino-2-4 (1H, 3H)-quinazolinediones for testing as anticonvulsants, J. Hetero. Chem., vol. 21(5): 1533-1535 (1984).

Langis, C., The synthesis of 1,3,4-benzotriazepine-1H-2,5-diones, Chim. Ther., vol. 2: 349-351 (1967).

Peet, N.P., et al., Synthesis of 3,4-dihydro-1H-1,3,4-benzotriazepine,2,5-diones, J. Org. Chem., vol. 40(13):1909-1914 (1975).

Baronnet, R., et al., Synthesis and pharmacodynamics of 3-dialkylamino-1H, 3H-quinazoline-2,4-diones and derivatives, Eur. J. Med. Chem.—Chim. Ther., vol. 18(3):241-247 (1983).

Davidson, J.S., The preparation of 5-(2-aminophenyl)-1,3,4-oxadiazol-2(3H)-one and its rearrangement to 3-amino-2,4(1H, 3H)-quinazolinedione, Monatshefte fur Chem., vol. 115(5):565-572 (1984).

Zhuo, J-C., et al., Boron-containing heterocycles: Synthesis, Structures, and Benzoborauracil Nucleoside, J. Org. Chem., vol. 64(26):9566-9574 (1999).

Database Caplus, Chemical Abstract Service, AN—1998:699954; Bull. Korean Chem. Soc., vol. 19(10):1117-1119 (1998).

Database Caplus, Chemical Abstract Service, AN—1996:275827; J. Hetero. Chem., vol. 33(4):1131-1135 (1996).

Database Caplus, Chemical Abstract Service, AN—1997:468311; J. Org. Chem., vol. 45(15):2551-2556 (1977).

Database Caplus, Chemical Abstract Service, AN—1968:2872; Helv. Chim. Acta., vol. 50(7):2019-2022 (1968).

(Continued)

*Primary Examiner*—Deepak Rao
(74) *Attorney, Agent, or Firm*—Robert N. Young; Charles W. Ashbrook

(57) ABSTRACT

Antibacterial 3-aminoquinazolin-2,4-diones have formula (I) wherein: $R_1$ and $R_3$ include alkyl, alkenyl, cycloalkyl, aryl, hetero-cyclic, and heteroaryl; $R_5$, $R_6$, and $R_8$ include H, alkyl, alkoxy, halo, $NO_2$, CN, $NH_2$, alkyl and dialkylamino; $R_7$ includes hydrogen, alkyl, cycloalkyl, hetero-cyclic, fused heterocyclic, aryl and fused aryl; J and K are C or N; and pharmaceutically acceptable salts thereof.

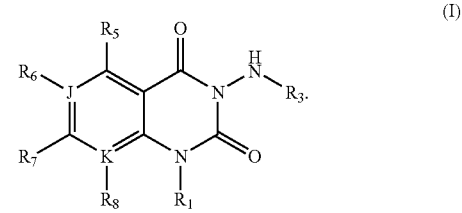

(I)

14 Claims, No Drawings

OTHER PUBLICATIONS

Database Caplus, Chemical Abstract Service, AN—1997:522336; Arch. Pharm., vol. 330(5): 129-134 (1997).

Database Crossfile, Beilstein Reg. No. 214132 (1910); Chem. Berich., vol. 43: 1236 (1910).

Database Crossfile, Beilstein Reg. No. 657750 (1965); Chem. Berich., vol. 98: 1505-1510 (1965).

Database Crossfile, Beilstein Reg. No. 169392 (1967); Chem. Ther., vol. 2: 1236 (1967).

* cited by examiner

3-AMINOQUINAZOLIN-2,4-DIONE ANTIBACTERIAL AGENTS

This application is a 371 of PCT/US00/33656 filed Dec. 12, 2000 which claims the benefit of U.S. Provisional Application No. 60/241,267 filed Oct. 18, 2000 and 60/178,252 filed Jan. 24, 2000.

FIELD OF THE INVENTION

This invention relates to 3-aminoquinazolin-2,4-diones that have potent in vitro and in vivo antibacterial activity. In addition, this invention relates to a method of inhibiting both wild-type and quinolone resistant mutants of DNA gyrase. This invention further relates to a method of treating patients having antibiotic resistance and in need of treatment for bacterial infections.

BACKGROUND OF THE INVENTION

Antibiotic resistance is a worldwide problem with catastrophic potential. The American Society of Microbiology Task Force recently issued a report defining the resistance problem and calling for new antibacterial agents with novel structures or mechanisms to offer alternatives to existing therapeutic choices (*Southern Med. J,* 1995; 88:797).

The quinolones are a class of antibacterials that are widely used throughout the world. The quinolones are potent inhibitors of gram positive and gram negative bacteria, and may be administered orally or intravenously. The quinolones are routinely used even though they have side effects (*J. Antimicrob. Chemother.,* 1994; 33:685), and significant resistance has been frequently noted (Gootz, *Medicinal Research,* 1996; Rev. 16:433). One of the most widely used quinolones is ciprofloxacin, which has the following chemical structure:

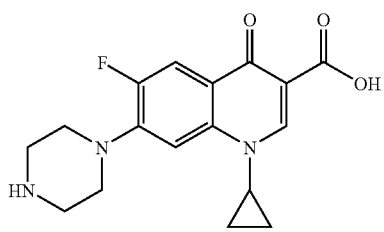

The quinolones have a distinct structure activity relationship (SAR) which is defined by several thousands of analogs prepared over the last 30 years (S. Mitsuhashi, ed. *Progress in Drug Research,* 1992; 38:11–147). In the quinolone SAR (referring to the formula below representing substituted quinolones), it is well-established that the $N_1$ group, in combination with the $C_3$-carboxyl and the $C_4$-carbonyl, are essential for activity, and that any substituents at $C_2$ detract from activity (*J. Antimicrob. Chemother,* 1994; 33:685 and Gootz, supra., 1996). It is also well-established that $R_6$ is ideally fluorine, and that $R_7$ is a nitrogen containing heterocycle. $R_1$ is ideally a small alkyl, a cycloalkyl, or a phenyl group.

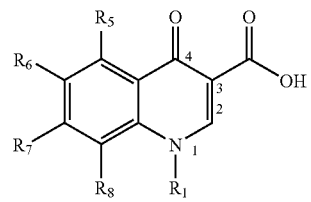

The quinolones inhibit bacterial growth by inhibition of DNA gyrase and topoisomerase IV (Gootz, supra., 1996). The gyrase interaction appears to rely on the $N_1/C_4$-carbonyl/$C_3$-carboxyl relationship.

Attempts to design novel quinolone mimics have focused on the $N_1/C_4$-carbonyl/$C_3$-carboxyl relationship. Certain tricyclic isothiazole analogs were designed to keep an all-planar relationship, and to have the NH of the isothiazole ring be as acidic as the quinolone $C_3$-carboxyl group (Chu, *Drugs Exptl. Clin. Res.,* 1990; 16:215).

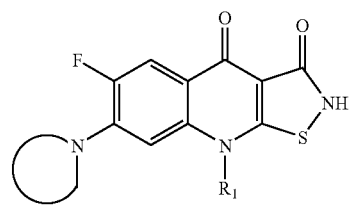

While maintaining excellent antibacterial activity, these compounds also show antitumor and mammalian topoisomerase activity (*Drugs of the Future,* 1992; 17:1101). These activities are undesired in an antibacterial agent.

Several publications (U.S. Pat. No. 5,283,248; *J. Med. Chem.,* 1992; 35:1358; *Antimicrob. Agents Chemother.,* 1995; 39:163) disclose tricyclic compounds (such as the structure below) having antibacterial activity and DNA gyrase inhibiting activity.

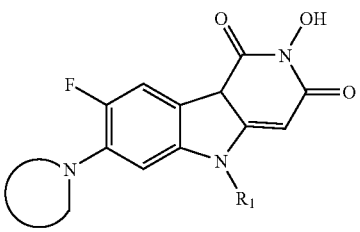

For such compounds, the relationship of the $N_1$ to the $C_4$-carbonyl is skewed. Compounds of this type are ineffective against bacteria that are quinolone resistant.

Other tricyclic analogs of the following structure are disclosed as quinolone mimics (JP 4,091,090 3/92; Interscience Conference on Antimicrobial Agents and Chemotherapy 1991, Abstract 1494).

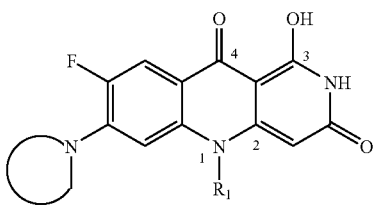

While the ideal quinolone $N_1$–$C_4$-carbonyl relationship is maintained, the $C_2$ region, where substitution is undesirable, is part of a fused-ringed system. These compounds are not active against quinolone resistant bacteria.

WO 96/04288 describes a series of benzoheterocycles of the formulas

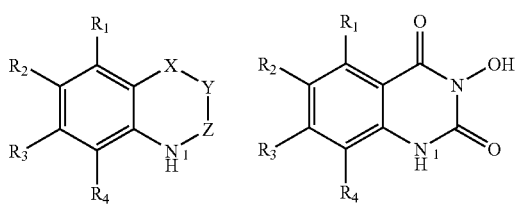

where X, Y, and Z are hydrogen bond acceptor and donator groups. Among the compounds depicted are N-hydroxy-quinazoline-2,4-diones, where $R_1$–$R_4$ can represent hydroxy, amino, nitro, a variety of alkyls, esters, and amides. In all cases, the substituent on $N_1$ is hydrogen. None of the substituents $R_1$–$R_4$ are nitrogen containing heterocycles. No antibacterial activity is disclosed for these compounds.

U.S. Pat. No. 5,155,110 describes $N_1$-aryl-N-hydroxy-quinazoline-2,4-diones of the formula

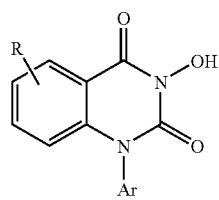

where R may be halo, cyano, hydroxy, alkoxy, and substituted amino. Amino heterocycles are not included in R, and no antibacterial activity is reported for such compounds.

Compounds taught in International Publication No. WO 95/19346 as AMPA, NMDA, and kinase receptor antagonists have the formula

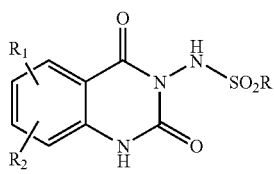

where R substituents are defined as alkyl or phenyl, and $R_1$ and $R_2$ are defined as H, alkyl, alkoxy, alkenyl, halogen, $NO_2$, (un)substituted $NH_2$, CN, etc. Again, no antibacterial activity is disclosed for these compounds.

Kornet and coworkers (Kornet M. J. et al., *J. Heterocyl. Chem.*, 1984; 21:1533–1535) disclosed anticonvulsant compounds having the formula

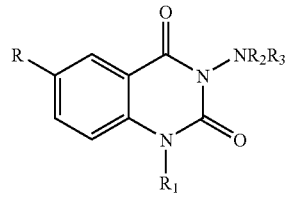

where R is defined as H, Me, or Cl; $R_1$ and $R_2$ as H or Me; and $R_3$ as Me or t-butyl. Alternatively, $R_2$ and $R_3$, together with the nitrogen atom to which they are attached, can form a heterocyclic ring such as piperidinyl, morpholinyl, etc. These compounds are not reported to have antibacterial activity.

A number of publications teach compounds having diuretic and sedative activities and with the generic structure as follows (ES 80/489675, JP 80/33323, BE 80/199792, FR 78/33438, JP 70/97932; Baronnet R., Callendret R., Blanchard L., Foussard-Blanpin O., Bretaudeau J., *Eur. J. Med.-Chim. Ther.*, 1983; 18:241–247).

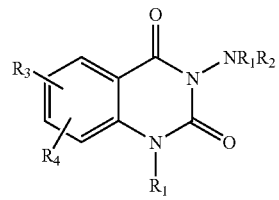

These are compounds in which $NR_1R_2$ can form a heterocycle, or $R_1$ and $R_2$ independently can represent H or a small alkyl. $R_3$ and $R_4$ can represent H, halogen, sulphonamide, alkyl, or alkoxy. No antibacterial activity is reported for these compounds.

International Publication No. WO 99/21840 describes 3-hydroxy-quinazoline-2,4-diones as antibacterial agents.

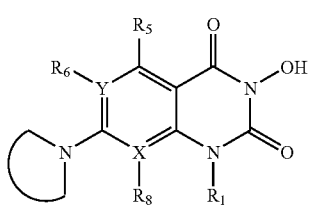

Compounds of this type are quinolone mimics where the 3-position exocyclic carboxylic acid of the quinolones is replaced by an oxo at the 2-position and a hydroxy at the N-3-position. Compounds of this type are designed to keep an all-planar relationship and to have the N—OH remain acidic, as in the quinolone $CO_2H$ (Chu, *Drugs Exptl. Clin. Res.*, 1990; 16:215). These compounds inhibit DNA gyrase and topoisomerase IV, and demonstrate antibacterial activity in vitro. However, such compounds are not effective against quinolone resistant bacteria.

The need continues to find new antibacterial agents that have the potency of the quinolones, but which are active against quinolone resistant bacterial strains. The present invention provides such compounds, which are characterized as 3-aminoquinazolin-2,4-diones. An object of this invention is to provide these new compounds, and a method for treating bacterial infections in mammals by administering these compounds.

SUMMARY OF THE INVENTION

The present invention provides 3-aminoquinazolin-2,4-diones having antibacterial activity. The compounds inhibit DNA gyrase, but are not cross-resistant with quinolone mutants that are no longer sensitive to agents such as ciprofloxacin.

The invention provides compounds of Formula I

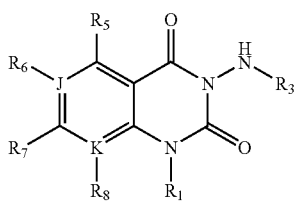

I or a pharmaceutically acceptable salt thereof wherein:
$R_1$ and $R_3$ independently are H,
  $C_1$–$C_{12}$ alkyl and substituted alkyl,
  $C_2$–$C_{12}$ alkenyl and substituted alkenyl,
  $C_2$–$C_{12}$ alkynyl and substituted alkynyl,
  $C_3$–$C_{12}$ cycloalkyl and substituted cycloalkyl,
  aryl and substituted aryl,
  heterocyclic and substituted heterocyclic,
  or heteroaryl and substituted heteroaryl;
$R_5$, $R_6$, and $R_8$ independently are H,
  $(O)_n C_1$–$C_{12}$ alkyl and substituted alkyl;
  $(O)_n C_2$–$C_{12}$ alkenyl and substituted alkenyl;
  $(O)_n C_2$–$C_{12}$ alkynyl and substituted alkynyl;
  halo,
  $NO_2$,
  CN,
  NR'R" wherein n is 0 or 1;
R' and R" independently are H,
  $C_1$–$C_{12}$ alkyl and substituted alkyl,
  $C_2$–$C_{12}$ alkenyl and substituted alkenyl,
  $C_2$–$C_{12}$ alkynyl and substituted alkynyl,
  CO—$C_1$–$C_{12}$ alkyl and substituted alkyl,
  or R' and R" taken together with the nitrogen to which they are attached form a 3- to 7-membered ring containing from 1 to 3 heteroatoms selected from N, O, and S, said ring being unsubstituted or substituted with up to 4 substituent groups;
$R_1$ and $R_8$ can be taken together with the atoms to which they are attached to form a cyclic ring having from 1 to 3 heteroatoms selected from N, O, and S, and optionally substituted by R' and R";
$R_7$ is hydrogen,
  $C_1$–$C_{12}$ alkyl and substituted alkyl,
  $C_2$–$C_{12}$ alkenyl and substituted alkenyl,
  $C_2$–$C_{12}$ alkynyl and substituted alkynyl,
  halo,
  $NO_2$,
  CN,
  NR'R",
  COOR',
  aryl,
  fused aryl,
  heterocyclic,
  fused heterocyclic,
  bicyclic heterocyclic, or
  spiro heterocyclic wherein all ring groups can be substituted;
J and K independently are C or N, provided that when J or K is N, $R_6$ or $R_8$ is absent at that position.

$R_7$ is referred to herein as the "side chain" of the 3-aminoquinazolin-2,4-dione nucleus. The $R_7$ side chain can be any group known in the quinolone art as a suitable substituent at the 7-position of the quinolone ring.

Preferred compounds of this invention have Formula II

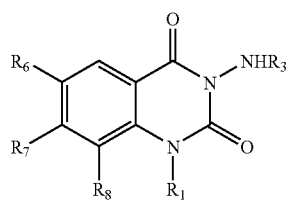

II wherein $R_1$, $R_3$, $R_6$, $R_7$, and $R_8$ are as defined above.

Further preferred compounds have Formula III

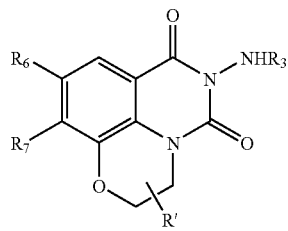

III wherein $R_3$, $R_6$, $R_7$, and R' are as defined above.

Another preferred group of compounds have Formula IV

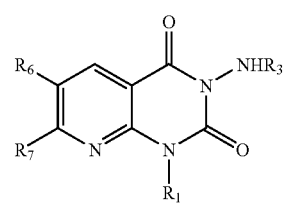

IV wherein $R_1$, $R_3$, $R_6$, and $R_7$ are as defined above.

The most preferred compounds of this invention have Formula V

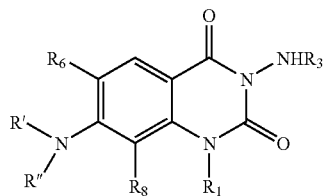

wherein $R_1$, $R_3$, $R_6$, $R_8$, R', and R" are as defined above. An especially preferred embodiment are compounds of Formula V wherein R' and R" are taken together with the nitrogen to which they are attached to complete a ring which is optionally substituted with groups such as alkyl and substituted alkyl, and amino, alkylamino, dialkylamino, and aryl amino.

A further preferred group of compounds have Formula VI

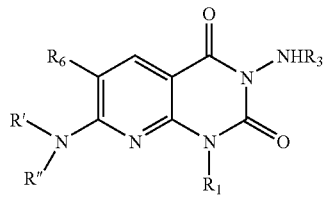

wherein $R_1$, $R_3$, $R_6$, R', and R" are as defined above.

Still another preferred group of invention compounds are those of Formula VII

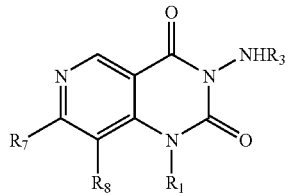

wherein $R_1$, $R_3$, $R_7$, and $R_8$ are as defined above.

Especially preferred compounds provided by the invention are:

3-Amino-7-(3-aminomethylpyrrolidin-1-yl)-8-chloro-1-cyclopropyl-6-fluoro-1H-quinazoline-2,4-dione;
3-Amino-8-chloro-1-cyclopropyl-6-fluoro-7-piperazin-1-yl-1H-quinazoline-2,4-dione;
3-Amino-7-[3-(aminomethyl)-3-methylpyrrolidin-1-yl]-8-chloro-1-cyclopropyl-6-fluoro-1H-quinazoline-2,4-dione;
3-Amino-7-(6-amino-3-aza-bicyclo[3.1.0]hex-3-yl)-8-chloro-1-cyclopropyl-6-fluoro-1H-quinazolin-2,4-dione;
3-Amino-7-((S)-3-N-methylaminopyrrolidin-1-yl)-8-chloro-1-cyclopropyl-6-fluoro-1H-quinazoline-2,4-dione;
3-Amino-7-((S)-3-aminopyrrolidin-1-yl)-8-chloro-1-(2,4-difluoroanilino)-6-fluoro-1H-quinazoline-2,4-dione;
3-Amino-7-[(S)-3-aminopyrrolidin-1-yl]-1-cyclopropylamino-6,8-difluoro-1H-quinazoline-2,4-dione;
3-Amino-7-[(S)-3-aminopyrrolidin-1-yl]-1-cyclopropylamino-5,8-difluoro-1H-quinazoline-2,4-dione;
3-Amino-7-((S)-3-aminopyrrolidin-1-yl)-1-cyclopropyl-5,6,8-trifluoro-1H-quinazoline-2,4-dione;
3-Amino-7-(3-aminopyrrolidin-1-yl)-8-chloro-1-cyclopropyl-6-fluoro-1H-quinazoline-2,4-dione;
7-((S)-3-Aminopyrrolidin-1-yl)-1-cyclopropyl-3,5-diamino-6,8-difluoro-1H-quinazoline-2,4-dione;
3-Amino-7-(3-hydroxymethylpyrrolidin-1-yl)-8-chloro-1-cyclopropyl-6-fluoro-1H-quinazoline-2,4-dione;
3-Amino-7-(3-aminoethylpyrrolidin-1-yl)-8-chloro-1-cyclopropyl-6-fluoro-1H-quinazoline-2,4-dione;
3-Amino-7-((S)-7-amino-5-azaspiro[2.4]hept-5-yl)-8-chloro-1-cyclopropyl-6-fluoro-1H-quinazoline-2,4-dione;
3-Amino-7-[(R)-3-(1-amino-1-methylethyl)pyrrolidin-1-yl]-8-chloro-1-cyclopropyl-6-fluoro-1H-quinazoline-2,4-dione;
3-Amino-7-(3-aminomethylpyrrolidin-1-yl)-1-cyclopropyl-6-fluoro-1H-quinazoline-2,4-dione;
3-Amino-7-(pyrrolidin-1-yl)-8-chloro-1-cyclopropyl-6-fluoro-1H-quinazoline-2,4-dione;
3-Amino-7-(3-aminopyrrolidin-1-yl)-8-chloro-6-fluoro-1-isopropyl-1H-quinazoline-2,4-dione;
3-Amino-7-(3-aminopyrrolin-1-yl)-1-sec-butyl-8-chloro-6-fluoro-1H-quinazoline-2,4-dione,
3-Amino-7-[3-aminopyrrolidin-1-yl]-1-cyclopropyl-6-fluoro-8-methoxy-1H-quinazoline-2,4-dione;
3-Amino-7-[3-aminopyrrolidin-1-yl]-8-chloro-1-cyclobutylamino-6-fluoro-1H-quinazoline-2,4-dione;
3-Amino-7-(3-aminopyrrolidin-1-yl)-1-cyclopropyl-8-fluoro-1H-quinazoline-2,4-dione;
3-Amino-7-(3-aminopyrrolidin-1-yl)-6-chloro-1-cyclopropyl-8-fluoro-1H-quinazoline-2,4-dione;
3-Amino-7-((S)-3-aminopyrrolidin-1-yl)-1-cyclopropylmethyl-8-fluoro-1H-quinazoline-2,4-dione;
3-Amino-7-[(R)-3-(1-amino-1-methylethyl)pyrrolidin-1-yl]-1-cyclopropylmethyl-8-fluoro-1H-quinazoline-2,4-dione;
3-Amino-7-((S)-3-aminopyrrolidin-1-yl)-1-ethyl-8-fluoro-1H-quinazoline-2,4-dione;
3-Amino-1-ethyl-6-fluoro-7-[(R)-3-(1-amino-1-methylethyl)-pyrrolidin-1-yl]-1H-quinazoline-2,4-dione;
3-Amino-7-((S)-3-aminopyrrolidin-1-yl)-1-cyclopropyl-6-fluoro-1H-quinazoline-2,4-dione;
3-Amino-7-(3-aminopyrrolidin-1-yl)-1-cyclopropyl-6-fluoro-8-methyl-1H-quinazoline-2,4-dione;
3-Amino-7-(3-aminomethylpyrrolidin-1-yl)-1-cyclopropyl-6-fluoro-8-methyl-1H-quinazoline-2,4-dione;
3-Amino-7-(3-aminopyrrolidin-1-yl)-1-cyclopropyl-8-fluoro-6-methoxy-1H-quinazoline-2,4-dione;
3-Amino-7-(3-aminomethylpyrrolidin-1-yl)-1-cyclopropyl-6-fluoro-8-methoxy-1H-quinazoline-2,4-dione;
3-Amino-7-(3-aminopyrrolidin-1-yl)-1-cyclopropyl-8-ethoxy-6-fluoro-1H-quinazoline-2,4-dione;
3-Amino-7-(3-aminopyrrolidin-1-yl)-1-cyclopropyl-6-fluoro-2,4-dioxo-1,2,3,4-tetrahydroquinazoline-8-carbonitrile;
3-Amino-8-chloro-1-cyclopropyl-6-fluoro-7-(3-[1,2,3-triazol]-1-yl-pyrrolidin-1-yl)-1H-quinazoline-2,4-dione;
3-Amino-7-[(S)-3-((R)-1-aminoethyl)pyrrolidin-1-yl]-1-cyclopropyl-6-fluoro-8-methoxy-1H-quinazoline-2,4-dione;
3-Amino-7-[(S)-3-((S)-1-aminoethyl)pyrrolidin-1-yl]-1-cyclopropyl-6-fluoro-8-methoxy-1H-quinazoline-2,4-dione;

3-Amino-7-[(S)-3-((R)-1-aminoethyl)pyrrolidin-1-yl]-1-cyclopropyl-6-fluoro-8-methyl-1H-quinazoline-2,4-dione;

3-Amino-7-[(S)-3-((S)-1-aminoethyl)pyrrolidin-1-yl]-1-cyclopropyl-6-fluoro-8-methyl-1H-quinazoline-2,4-dione;

5-Amino-9-((S)-3-aminopyrrolidin-1-yl)-8-fluoro-3-methyl-2,3-dihydro-1-oxa-3a,5-diazaphenalene-4,6-dione;

5-Amino-9-[(R)-3-((S)-1-aminoethyl)pyrrolidin-1-yl]-8-fluoro-3-methyl-2,3-dihydro-1-oxa-3a,5-diazaphenalene-4,6-dione;

2-Amino-8-((S)-3-aminopyrrolidin-1-yl)-9-fluoro-5-methyl-6,7-dihydro-5H-pyrido[3,2,1-ij]quinazoline-1,3-dione;

2-Amino-8-[(R)-3-((S)-1-aminoethyl)pyrrolidin-1-yl]-9-fluoro-5-methyl-6,7-dihydro-5H-pyrido [3,2,1-ij] quinazoline-1,3-dione;

3-Amino-7-((S)-3-aminopyrrolidin-1-yl)-1-cyclopropyl-6-fluoro-1H-pyrido[2,3-d]pyrimidine-2,4-dione;

3-Amino-7-(6-amino-3-azabicyclo[3.1.0]hex-3-yl)-1-cyclopropyl-6-fluoro-1H-pyrido[2,3-d]pyrimidine-2,4-dione;

3-Amino-7-(3-aminomethyl-3-methylpyrrolidin-1-yl)-1-cyclopropyl-6-fluoro-1H-pyrido[2,3-d]pyrimidine-2,4-dione;

3-Amino-1-cyclopropyl-6-fluoro-7-(octahydropyrrolo[3,4-c]pyridin-2-yl)-1H-pyrido[2,3-d]pyrimidine-2,4-dione;

3-Amino-1-cyclopropyl-6-fluoro-7-(octahydropyrrolo[3,4-b]pyridin-2-yl)-1H-pyrido [2,3-d]pyrimidine-2,4-dione;

3-Amino-7-[(R)-3-(1-amino-1-methylethyl)pyrrolidin-1-yl]-1-cyclopropyl-6-fluoro-1H-pyrido[2,3-d]pyrimidine-2,4-dione;

3-Amino-7-(3-aminomethylpiperidin-1-yl)-1-cyclopropyl-6-fluoro-1H-pyrido[2,3-d]pyrimidine-2,4-dione;

trans-3-Amino-7-(3-aminomethyl-4-trifluoromethylpyrrolidin-1-yl)-1-cyclopropyl-6-fluoro-1H-pyrido[2,3-d]pyrimidine-2,4-dione;

3-Amino-1-cyclopropyl-6-fluoro-7-[(R)-3-((R)-1-methylamino-ethyl)pyrrolidin-1-yl]-1H-pyrido[2,3-d]pyrimidine-2,4-dione;

3-Amino-7-[(R)-3-((S)-1-aminoethyl)pyrrolidin-1-yl]-1-cyclopropyl-6-fluoro-1H-pyrido[2,3-d]pyrimidine-2,4-dione;

3-Amino-7-[3-(1-aminopropyl)pyrrolidin-1-yl]-1-cyclopropyl-6-fluoro-8-methyl-1H-quinazoline-2,4-dione;

3-Amino-1-cyclopropyl-6-fluoro-8-methyl-7-[(R)-3-((S)-1-methylaminoethyl)pyrrolidin-1-yl]-1H-quinazoline-2,4-dione;

3-Amino-7-[7-(1-aminoethyl)-5-azaspiro[2.4]hept-5-yl]-1-cyclopropyl-6-fluoro-8-methyl-1H-quinazoline-2,4-dione;

1-(3-Amino-8-chloro-1-cyclopropyl-6-fluoro-2,4-dioxo-1,2,3,4-tetrahydroquinazolin-7-yl)piperidine-3-carboxylic acid amide;

3-Amino-[7-trans-3-aminomethyl-4-trifluoromethylpyrrolidin-1-yl]-8-chloro-1-cyclopropyl-6-fluoro-1H-quinazoline-2,4-dione;

3-Amino-8-chloro-1-cyclopropyl-6-fluoro-7-{3-[(2,2,2-trifluoro-ethylamino)methyl]pyrrolidin-1-yl}-1H-quinazoline-2,4-dione;

3-Amino-8-chloro-1-cyclopropyl-6-fluoro-7-(5-methylhexahydro-pyrrolo[3,4-c]pyrrol-2-yl)-1H-quinazoline-2,4-dione;

3-Amino-8-chloro-1-cyclopropyl-7-(2,7-diazaspiro[4.4]non-2-yl)-6-fluoro-1H-quinazoline-2,4-dione;

3-Amino-7-(3-aminomethyl-3-benzylpyrrolidin-1-yl)-8-chloro-1-cyclopropyl-6-fluoro-1H-quinazoline-2,4-dione;

3-Amino-7-[(R)-3-((S)-1-aminoethyl)pyrrolidin-1-yl]-8-chloro-1-cyclopropyl-6-fluoro-1H-quinazoline-2,4-dione;

3-Amino-8-chloro-1-cyclopropyl-6-fluoro-7-(3-hydroxyimino-pyrrolidin-1-yl)-1H-quinazoline-2,4-dione;

3-Amino-7-[trans-3-amino-4-trifluoromethylpyrrolidin-1-yl]-8-chloro-1-cyclopropyl-6-fluoro-1H-quinazoline-2,4-dione;

3-Amino-8-chloro-1-cyclopropyl-6-fluoro-7-[(R)-3-(S)-1-methylaminoethyl)pyrrolidin-1-yl]-1H-quinazoline-2,4-dione;

3-Amino-7-(trans-3-amino-4-phenylpyrrolidin-1-yl)-8-chloro-1-cyclopropyl-6-fluoro-1H-quinazoline-2,4-dione;

3-Amino-7-[trans-3-amino-4-(4-hydroxyphenyl)pyrrolidin-1-yl]-8-chloro-1-cyclopropyl-6-fluoro-1H-quinazoline-2,4-dione;

N-[1-(3-Amino-8-chloro-1-cyclopropyl-6-fluoro-2,4-dioxo-1,2,3,4-tetrahydroquinazolin-7-yl)pyrrolidin-3-ylmethyl] methanesulfonamide;

3-Amino-7-(3-aminomethylpiperidin-1-yl)-8-chloro-1-cyclopropyl-6-fluoro-1H-quinazoline-2,4-dione;

3-Amino-8-chloro-1-cyclopropyl-6-fluoro-7-[3-(isopropylamino-methyl)pyrrolidin-1-yl]-1H-quinazoline-2,4-dione;

3-Amino-7-(3-aminomethylpyrrolidin-1-yl)-6,8-dichloro-1-cyclopropyl-1H-quinazoline-2,4-dione;

N-[1-(3-Amino-8-chloro-1-cyclopropyl-6-fluoro-2,4-dioxo-1,2,3,4-tetrahydroquinazolin-7-yl)pyrrolidin-3-ylmethyl] methanesulfonamide;

3-Amino-7-[(R)-3-(S)-(1-aminoethyl)pyrrolidin-1-yl]-1-cyclopropyl-6-fluoro-8-methyl-1H-quinazoline-2,4-dione;

3-Amino-7-[(R)-3-(1-amino-1-methylethyl)pyrrolidin-1-yl]-1-cyclopropyl-6-fluoro-8-methyl-1H-quinazoline-2,4-dione;

3-Amino-7-[3-(1-aminoethyl)-3-methoxypyrrolidin-1-yl]-1-cyclopropyl-6-fluoro-8-methyl-1H-quinazoline-2,4-dione;

3-Amino-7-[3-(1-aminoethyl)-3-fluoropyrrolidin-1-yl]-1-cyclopropyl-6-fluoro-8-methoxy-1H-quinazoline-2,4-dione;

3-Amino-7-(3-aminopyrrolidin-1-yl)-1-cyclopropyl-6-fluoro-5-methyl-1H-quinazoline-2,4-dione;

3-Amino-7-[(R)-3-(S)-(1-aminoethyl)pyrrolidin-1-yl]-1-cyclopropyl-6-fluoro-5-methyl-1H-quinazoline-2,4-dione;

3-Amino-7-(3-aminomethyl-3-methoxymethylpyrrolidin-1-yl)-1-cyclopropyl-6-fluoro-8-methyl-1H-quinazoline-2,4-dione;

3-Amino-7-(3-aminomethyl-3-fluoromethylpyrrolidin-1-yl)-1-cyclopropyl-6-fluoro-1H-quinazoline-2,4-dione;

3-Amino-7-(trans-3-aminomethyl-4-trifluoromethylpyrrolidin-1-yl)-1-cyclopropyl-6-fluoro-8-methoxy-1H-quinazoline-2,4-dione;

3-Amino-7-[3-(1-aminoethyl)piperidin-1-yl]-1-cyclopropyl-6-fluoro-8-methoxy-1H-quinazoline-2,4-dione;

3-Amino-7-[3-(aminoethyl)piperidin-1-yl]-1-cyclopropyl-6-fluoro-8-methyl-1H-quinazoline-2,4-dione;

3-Amino-7-[4-(1-aminoethyl)-3,3-dimethylpyrrolidin-1-yl]-1-cyclopropyl-6-fluoro-8-methoxy-1H-quinazoline-2,4-dione;

3-Amino-7-[4-(1-aminoethyl)-3,3-dimethylpyrrolidin-1-yl]-1-cyclopropyl-6-fluoro-8-methyl-1H-quinazoline-2,4-dione;

3-Amino-7-(3-amino-3-phenylpyrrolidin-1-yl)-1-cyclopropyl-6-fluoro-8-methyl-1H-quinazoline-2,4-dione;

3-Amino-7-[3-(1-aminoethyl)-4-methylpyrrolidin-1-yl]-1-cyclopropyl-6-fluoro-8-methyl-1H-quinazoline-2,4-dione;
3-Amino-7-(3-aminomethyl-3-phenylpyrrolidin-1-yl)-1-cyclopropyl-6-fluoro-8-methyl-1H-quinazoline-2,4-dione;
3-Amino-7-(7-aminomethyl-5-azaspiro[2,4]hept-5-yl)-1-cyclopropyl-6-fluoro-8-methyl-1H-quinazoline-2,4-dione;
3-Amino-7-(7-aminomethyl-5-azaspiro[2,4]hept-5-yl)-1-cyclopropyl-6-fluoro-8-methoxy-1H-quinazoline-2,4-dione;
3-Amino-7-(3-aminomethyl-3-hydroxypyrrolidin-1-yl)-1-cyclopropyl-6-fluoro-8-methoxy-1H-quinazoline-2,4-dione;
3-Amino-7-(3-aminomethylpiperidin-1-yl)-1-cyclopropyl-6-fluoro-8-methyl-1H-quinazoline-2,4-dione;
3-Amino-7-(3-amino-4-methoxypyrrolidin-1-yl)-1-cyclopropyl-6-fluoro-8-methyl-1H-quinazoline-2,4-dione;
3-Amino-7-(3-amino-4-methoxypyrrolidin-1-yl)-1-cyclopropyl-6-fluoro-8-methoxy-1H-quinazoline-2,4-dione;
3-Amino-7-(3-amino-4-fluoropyrrolidin-1-yl)-1-cyclopropyl-6-fluoro-8-methoxy-1H-quinazoline-2,4-dione;
3-Amino-7-(3-aminomethyl-3-methylpyrrolidin-1-yl)-1-cyclopropyl-6-fluoro-8-methyl-1H-quinazoline-2,4-dione;
3-Amino-7-[(R)-3 (-((S)-1-aminoethyl)pyrrolidin-1-yl]-1-cyclopropyl-8-ethyl-6-fluoro-1H-quinazoline-2,4-dione;
1-(3-Amino-1-cyclopropyl-6-fluoro-8-methoxy-2,4-dioxo-1,2,3,4-tetrahydroquinazolin-7-yl)pyrrolidine-3-carboxylic acid trifluoroacetate;
1-(3-Amino-1-cyclopropyl-6-fluoro-8-methyl-2,4-dioxo-1,2,3,4-tetrahydroquinazolin-7-yl)pyrrolidine-3-carboxylic acid trifluoroacetate;
3-Amino-7-(1-aminomethyl-3-azabicyclo[3.1.0]hex-3-yl)-1-cyclopropyl-6-fluoro-8-methoxy-1H-quinazoline-2,4-dione;
3-Amino-7-(1-aminomethyl-3-azabicyclo[3.1.0]hex-3-yl)-1-cyclopropyl-6-fluoro-8-methyl-1H-quinazoline-2,4-dione;
3-Amino-7-[(S)-3-((R)-1-aminoethyl)pyrrolidin-1-yl]-1-cyclopropyl-6-fluoro-8-methoxy-1H-quinazoline-2,4-dione;
3-Amino-7-[(S)-3-((R)-1-aminoethyl)pyrrolidin-1-yl]-1-cyclopropyl-6-fluoro-8-methyl-1H-quinazoline-2,4-dione;
3-Amino-1-cyclopropyl-6-fluoro-8-methyl-7-(octahydropyrrolo[3,4-b]pyridin-6-yl)-1H-quinazoline-2,4-dione;
3-Amino-7-(trans-3-aminomethyl-4-methylpyrrolidin-1-yl)-8-chloro-1-cyclopropyl-6-fluoro-1H-quinazoline-2,4-dione;
3-Amino-7-(trans-3-aminomethyl-4-methylpyrrolidin-1-yl)-1-cyclopropyl-6-fluoro-8-methoxy-1H-quinazoline-2,4-dione;
3-Amino-7-(trans-3-aminomethyl-4-methylpyrrolidin-1-yl)-1-cyclopropyl-6-fluoro-8-methyl-1H-quinazoline-2,4-dione;
3-Amino-7-(trans-3-amino-4-methylpyrrolidin-1-yl)-1-cyclopropyl-6-fluoro-8-methoxy-1H-quinazoline-2,4-dione;
3-Amino-7-(3-aminomethylmorpholin-1-yl)-1-cyclopropyl-6-fluoro-8-methoxy-1H-quinazoline-2,4-dione;
3-Amino-7-(3-aminomethylpiperidin-1-yl)-1-cyclopropyl-6-fluoro-8-methoxy-1H-quinazoline-2,4-dione;
3-Amino-7-[3-(1-aminoethyl)-4-methylpyrrolidin-1-yl]-1-cyclopropyl-6-fluoro-8-methoxy-1H-quinazoline-2,4-dione;
3-Amino-7-(3-amino-3-phenylpyrrolidin-1-yl)-8-chloro-1-cyclopropyl-6-fluoro-1H-quinazoline-2,4-dione;
3-Amino-7-(3-amino-3-methylpyrrolidin-1-yl)-1-cyclopropyl-6-fluoro-8-methyl-1H-quinazoline-2,4-dione;
3-Amino-1-cyclopropyl-6-fluoro-8-methyl-7-pyrrolidin-1yl-1H-quinazoline-2,4-dione;
3-Amino-1-cyclopropyl-6-fluoro-8-methoxy-7-pyrrolidin-1yl-1H-quinazoline-2,4-dione;
3-Amino-1-cyclopropyl-6-fluoro-7-[3-(1-hydroxy-1-methylethyl)-pyrrolidin-1-yl]-8-methyl-1H-quinazoline-2,4-dione;
3-Amino-1-cyclopropyl-6-fluoro-7-[3-(1-hydroxy-1-methylethyl)-pyrrolidin-1-yl]-8-methoxy-1H-quinazoline-2,4-dione;
3-Amino-1-cyclopropyl-6-fluoro-5-methyl-7-[(R)-3-((S)-1-methylaminoethyl)pyrrolidin-1-yl]-1H-quinazoline-2,4-dione;
(S)-1-[(R)-1-(3-Amino-1-cyclopropyl-7-[3-(1-ethylaminoethyl)pyrrolidin-1-yl]-6-fluoro-8-methoxy-1H-quinazoline-2,4-dione;
3-Amino-1-cyclopropyl-7-[(R)-3-((S)-1-ethylaminoethyl)pyrrolidin-1-yl]-6-fluoro-8-methyl-1H-quinazoline-2,4-dione;
3-Amino-7-(6-amino-1-methyl-3-azabicyclo[3.2.0]hept-3-yl)-1-cyclopropyl-6-fluoro-8-methoxy-1H-quinazoline-2,4-dione;
3-Amino-7-(4-aminomethylpiperidin-1-yl)-1-cyclopropyl-6-fluoro-8-methoxy-1H-quinazoline-2,4-dione;
3-Amino-7-(3-aminomethylazetidin-1-yl)-1-cyclopropyl-6-fluoro-8-methoxy-1H-quinazoline-2,4-dione;
cis-3-Amino-7-(3-aminomethyl-4-fluoropyrrolidin-1-yl)-1-cyclopropyl-6-fluoro-8-methoxy-1H-quinazoline-2,4-dione;
trans-3-Amino-7-(3-aminomethyl-4-fluoropyrrolidin-1-yl)-1-cyclopropyl-6-fluoro-8-methoxy-1H-quinazoline-2,4-dione;
3-Amino-7-(1-amino-5-azaspiro [2.4]hept-5-yl)-1-cyclopropyl-6-fluoro-8-methoxy-1H-quinazoline-2,4-dione;
3-Amino-7-(3-aminomethyloctahydroisoindol-2-yl)-1-cyclopropyl-6-fluoro-8-methoxy-1H-quinazoline-2,4-dione;
3-Amino-7-(3-aminomethyloctahydroisoindol-2-yl)-1-cyclopropyl-6-fluoro-8-methyl-1H-quinazoline-2,4-dione;
3-Amino-7-[(R)-3-((S)-1-aminoethylpyrrolidin-1-yl]-1-cyclopropyl-6-fluoro-8-methoxy-1H-quinazoline-2,4-dione;
3-Amino-7-(6-amino-3-azabicyclo[3.1.0]hex-3-yl)-1-cyclopropyl-6-fluoro-8-methyl-1H-quinazoline-2,4-dione;
3-Amino-7-[3-(1-amino-1-methylethyl)pyrrolidin-1-yl]-1-cyclopropyl-6-fluoro-8-methoxy-1H-quinazoline-2,4-dione;
3-Amino-1-cyclopropyl-6-fluoro-7-[3-(isopropylaminomethyl) pyrrolidin-1-yl]-8-methoxy-1H-quinazoline-2,4-dione;
3-Amino-1-cyclopropyl-6-fluoro-8-methoxy-7-[(4aS,7aS)-octahydropyrrolo[3,4-b]pyridin-6-yl-1H-quinazoline-2,4-dione;
3-Amino-7-(3-amino-4-fluoromethylpyrrolidin-1-yl)-1-cyclopropyl-6-fluoro-8-methoxy-1H-quinazoline-2,4-dione;
3-Amino-7-(3-aminomethyl-3-methylpyrrolidin-1-yl)-1-cyclopropyl-6-fluoro-8-methoxy-1H-quinazoline-2,4-dione;
3-Amino-7-(4-aminopiperidin-1-yl)-1-cyclopropyl-6-fluoro-8-methoxy-1H-quinazoline-2,4-dione;
3-Amino-7-(3-aminopiperidin-1-yl)-1-cyclopropyl-6-fluoro-8-methoxy-1H-quinazoline-2,4-dione;

3-Amino-1-cyclopropyl-6-fluoro-8-methoxy-7-[(R)-3-((S)-1-methylaminoethyl)pyrrolidin-1-yl]-1H-quinazoline-2,4-dione;

3-Amino-7-(3-aminoazetidin-1-yl)-1-cyclopropyl-6-fluoro-8-methoxy-1H-quinazoline-2,4-dione;

3-Amino-7-[(3R,4S)-3-((S)-1-aminoethyl)-4-fluoropyrrolidin-1-yl]-1-cyclopropyl-6-fluoro-8-methyl-1H-quinazoline-2,4-dione;

3-Amino-7-[(3R,4S)-3-((S)-1-aminoethyl)-4-fluoropyrrolidin-1-yl]-1-cyclopropyl-8-methyl-1H-quinazoline-2,4-dione;

3-Amino-7-[(3R,4R)-3-(R)-1-aminoethyl)-4-fluoropyrrolidin-1-yl]-1-cyclopropyl-6-fluoro-8-methyl-1H-quinazoline-2,4-dione;

3-Amino-7-[(3R,4R)-3-((R)-1-aminoethyl)-4-fluoropyrrolidin-1-yl]-1-cyclopropyl-8-methyl-1H-quinazoline-2,4-dione;

3-Amino-7-[(3R,4S)-3-(-1-amino-1-methylethyl)-4-fluoropyrrolidin-1-yl]-1-cyclopropyl-6-fluoro-8-methyl-1H-quinazoline-2,4-dione;

3-Amino-7-[(3R,4S)-3-(-1-amino-1-methylethyl)-4-fluoropyrrolidin-1-yl]-1-cyclopropyl-8-methyl-1H-quinazoline-2,4-dione;

3-Amino-7-[(3R,4R)-3-(-1-amino-1-methylethyl)-4-fluoropyrrolidin-1-yl]-1-cyclopropyl-6-fluoro-8-methyl-1H-quinazoline-2,4-dione;

3-Amino-7-[(3R,4R)-3-(-1-amino-1-methylethyl)-4-fluoropyrrolidin-1-yl]-1-cyclopropyl-8-methyl-1H-quinazoline-2,4-dione;

3-Amino-7-[(3R,4S)-3-((R)-1-amino-2-methoxyethyl)-4-fluoropyrrolidin-1-yl]-1-cyclopropyl-6-fluoro-8-methyl-1H-quinazoline-2,4-dione;

3-Amino-7-[(3R,4S)-3-((R)-1-amino-2-methoxyethyl)-4-fluoropyrrolidin-1-yl]-1-cyclopropyl-8-methyl-1H-quinazoline-2,4-dione;

3-Amino-7-[(3R,4R)-3-((S)-1-amino-2-methoxyethyl)-4-fluoropyrrolidin-1-yl]-1-cyclopropyl-6-fluoro-8-methyl-1H-quinazoline-2,4-dione;

3-Amino-7-[(3R,4R)-3-((S)-1-amino-2-methoxyethyl)-4-fluoropyrrolidin-1-yl]-1-cyclopropyl-8-methyl-1H-quinazoline-2,4-dione;

3-Amino-7-[(3R,4S)-3-((R)-1-amino-2-methoxyethyl)-4-methylpyrrolidin-1-yl]-1-cyclopropyl-6-fluoro-8-methyl-1H-quinazoline-2,4-dione;

3-Amino-7-[(3R,4S)-3-((R)-1-amino-2-methoxyethyl)-4-methylpyrrolidin-1-yl]-1-cyclopropyl-8-methyl-1H-quinazoline-2,4-dione;

3-Amino-7-[(3R,4R)-3-((S)-1-amino-2-methoxyethyl)-4-methylpyrrolidin-1-yl]-1-cyclopropyl-6-fluoro-8-methyl-1H-quinazoline-2,4-dione;

3-Amino-7-[(3R,4R)-3-((S)-1-amino-2-methoxyethyl)-4-methylpyrrolidin-1-yl]-1-cyclopropyl-8-methyl-1H-quinazoline-2,4-dione;

3-Amino-7-[(R)-4-((R)-1-amino-2-methoxyethyl)-3,3-dimethylpyrrolidin-1-yl]-1-cyclopropyl-6-fluoro-8-methyl-1H-quinazoline-2,4-dione;

3-Amino-7-[(R)-4-(R)-1-amino-2-methoxyethyl)-3,3-dimethylpyrrolidin-1-yl]-1-cyclopropyl-8-methyl-1H-quinazoline-2,4-dione;

3-Amino-7-[(R)-4-((S)-1-amino-2-methoxyethyl)-3,3-dimethylpyrrolidin-1-yl]-1-cyclopropyl-6-fluoro-8-methyl-1H-quinazoline-2,4-dione;

3-Amino-7-[(R)-4-(S)-1-amino-2-methoxyethyl)-3,3-dimethylpyrrolidin-1-yl]-1-cyclopropyl-8-methyl-1H-quinazoline-2,4-dione;

3-Amino-7-[(R)-3-((R)-1-amino-2-phenoxyethyl)pyrrolidin-1-yl]-1-cyclopropyl-6-fluoro-8-methyl-1H-quinazoline-2,4-dione;

3-Amino-7-[(R)-3-(R)-1-amino-2-phenoxyethyl)pyrrolidin-1-yl]-1-cyclopropyl-8-methyl-1H-quinazoline-2,4-dione;

3-Amino-7-[(3R,4S)-3-((R)-1-amino-2-phenoxyethyl)-4-methylpyrrolidin-1-yl]-1-cyclopropyl-6-fluoro-8-methyl-1H-quinazoline-2,4-dione;

3-Amino-7-[(3R,4S)-3-((R)-1-amino-2-phenoxyethyl)-4-methylpyrrolidin-1-yl]-1-cyclopropyl-8-methyl-1H-quinazoline-2,4-dione;

3-Amino-7-[(3R,4S)-3-((R)-1-amino-2-phenoxyethyl)-4-fluoropyrrolidin-1-yl]-1-cyclopropyl-6-fluoro-8-methyl-1H-quinazoline-2,4-dione;

3-Amino-7-[(3R,4S)-3-((R)-1-amino-2-phenoxyethyl)-4-fluoropyrrolidin-1-yl]-1-cyclopropyl-8-methyl-1H-quinazoline-2,4-dione;

3-Amino-7-[(R)-3-((S)-1-amino-2-phenoxyethyl)pyrrolidin-1-yl]-1-cyclopropyl-6-fluoro-8-methyl-1H-quinazoline-2,4-dione;

3-Amino-7-[(R)-3-((S)-1-amino-2-phenoxyethyl)pyrrolidin-1-yl]-1-cyclopropyl-8-methyl-1H-quinazoline-2,4-dione;

3-Amino-7-[(3R,4S)-3-((S)-1-amino-2-phenoxyethyl)-4-methylpyrrolidin-1-yl]-1-cyclopropyl-6-fluoro-8-methyl-1H-quinazoline-2,4-dione;

3-Amino-7-[(3R,4S)-3-((S)-1-amino-2-phenoxyethyl)-4-methylpyrrolidin-1-yl]-1-cyclopropyl-8-methyl-1H-quinazoline-2,4-dione;

3-Amino-7-[(3R,4S)-3-((S)-1-amino-2-phenoxyethyl)-4-fluoropyrrolidin-1-yl]-1-cyclopropyl-6-fluoro-8-methyl-1H-quinazoline-2,4-dione;

3-Amino-7-[(3R,4S)-3-((S)-1-amino-2-phenoxyethyl)-4-fluoropyrrolidin-1-yl]-1-cyclopropyl-8-methyl-1H-quinazoline-2,4-dione;

3-Amino-7-[(R)-4-((R)-1-amino-2-phenoxyethyl)-3,3-dimethylpyrrolidin-1-yl]-1-cyclopropyl-6-fluoro-8-methyl-1H-quinazoline-2,4-dione;

3-Amino-7-[(R)-4-((R)-1-amino-2-phenoxyethyl)-3,3-dimethylpyrrolidin-1-yl]-1-cyclopropyl-8-methyl-1H-quinazoline-2,4-dione;

3-Amino-7-[(R)-4-((S)-1-amino-2-phenoxyethyl)-3,3-dimethylpyrrolidin-1-yl]-1-cyclopropyl-6-fluoro-8-methyl-1H-quinazoline-2,4-dione; 3-Amino-7-[(R)-4-((S)-1-amino-2-phenoxyethyl)-3,3-dimethylpyrrolidin-1-yl]-1-cyclopropyl-8-methyl-1H-quinazoline-2,4-dione;

3-Amino-7-[(R)-3-((S)-1-amino-2-ethoxyethyl)pyrrolidin-1-yl]-1-cyclopropyl-6-fluoro-8-methyl-1H-quinazoline-2,4-dione;

3-Amino-7-[(R)-3-((S)-1-amino-2-ethoxyethyl)pyrrolidin-1-yl]-1-cyclopropyl-8-methyl-1H-quinazoline-2,4-dione;

3-Amino-7-[(R)-3-((R)-1-amino-2-ethoxyethyl)pyrrolidin-1-yl]-1-cyclopropyl-6-fluoro-8-methyl-1H-quinazoline-2,4-dione;

3-Amino-7-[(R)-3-((R)-1-amino-2-ethoxyethyl)pyrrolidin-1-yl]-1-cyclopropyl-8-methyl-1H-quinazoline-2,4-dione;

3-Amino-7-[(3R,4S)-3-((R)-1-amino-2-ethoxyethyl)-4-methylpyrrolidin-1-yl]-1-cyclopropyl-6-fluoro-8-methyl-1H-quinazoline-2,4-dione;

3-Amino-7-[(3R,4S)-3-((R)-1-amino-2-ethoxyethyl)-4-methylpyrrolidin-1-yl]-1-cyclopropyl-8-methyl-1H-quinazoline-2,4-dione;

3-Amino-7-[(3R,4S)-3-((R)-1-amino-2-ethoxyethyl)-4-fluoropyrrolidin-1-yl]-1-cyclopropyl-6-fluoro-8-methyl-1H-quinazoline-2,4-dione;

3-Amino-7-[(3R,4S)-3-((R)-1-amino-2-ethoxyethyl)-4-fluoropyrrolidin-1-yl]-1-cyclopropyl-8-methyl-1H-quinazoline-2,4-dione;

3-Amino-7-[(R)-4-((R)-1-amino-2-ethoxyethyl)-3,3-dimethylpyrrolidin-1-yl]-1-cyclopropyl-6-fluoro-8-methyl-1H-quinazoline-2,4-dione;

3-Amino-7-[(R)-4-((R)-1-amino-2-ethoxyethyl)-3,3-dimethylpyrrolidin-1-yl]-1-cyclopropyl-8-methyl-1H-quinazoline-2,4-dione;

3-Amino-7-[(3R,4R)-3-((S)-1-amino-2-ethoxyethyl)-4-methylpyrrolidin-1-yl]-1-cyclopropyl-6-fluoro-8-methyl-1H-quinazoline-2,4-dione;

3-Amino-7-[(3R,4R)-3-((S)-1-amino-2-ethoxyethyl)-4-methylpyrrolidin-1-yl]-1-cyclopropyl-8-methyl-1H-quinazoline-2,4-dione;

3-Amino-7-[(3R,4R)-3-((S)-1-amino-2-ethoxyethyl)-4-fluoropyrrolidin-1-yl]-1-cyclopropyl-6-fluoro-8-methyl-1H-quinazoline-2,4-dione;

3-Amino-7-[(3R,4R)-3-((S)-1-amino-2-ethoxyethyl)-4-fluoropyrrolidin-1-yl]-1-cyclopropyl-8-methyl-1H-quinazoline-2,4-dione;

3-Amino-7-[(R)-3-((S)-1-amino-3-methoxypropyl)pyrrolidin-1-yl]-1-cyclopropyl-6-fluoro-8-methyl-1H-quinazoline-2,4-dione;

3-Amino-7-[(R)-3-((S)-1-amino-3-methoxypropyl)pyrrolidin-1-yl]-1-cyclopropyl-8-methyl-1H-quinazoline-2,4-dione;

3-Amino-7-[(3R,4S)-3-((S)-1-amino-3-methoxypropyl)-4-methylpyrrolidin-1-yl]-1-cyclopropyl-6-fluoro-8-methyl-1H-quinazoline-2,4-dione;

3-Amino-7-[(3R,4S)-3-((S)-1-amino-3-methoxypropyl)-4-methylpyrrolidin-1-yl]-1-cyclopropyl-8-methyl-1H-quinazoline-2,4-dione;

3-Amino-7-[(3R,4S)-3-((S)-1-amino-3-methoxypropyl)-4-fluoropyrrolidin-1-yl]-1-cyclopropyl-6-fluoro-8-methyl-1H-quinazoline-2,4-dione;

3-Amino-7-[(3R,4S)-3-((S)-1-amino-3-methoxypropyl)-4-fluoropyrrolidin-1-yl]-1-cyclopropyl-8-methyl-1H-quinazoline-2,4-dione;

3-Amino-7-[(R)-3-((R)-1-amino-3-methoxypropyl)pyrrolidin-1-yl]-1-cyclopropyl-6-fluoro-8-methyl-1H-quinazoline-2,4-dione;

3-Amino-7-[(R)-3-((R)-1-amino-3-methoxypropyl)pyrrolidin-1-yl]-1-cyclopropyl-8-methyl-1H-quinazoline-2,4-dione;

3-Amino-7-[(3R,4R)-3-((R)-1-amino-3-methoxypropyl)-4-methylpyrrolidin-1-yl]-1-cyclopropyl-6-fluoro-8-methyl-1H-quinazoline-2,4-dione;

3-Amino-7-[(3R,4R)-3-((R)-1-amino-3-methoxypropyl)-4-methylpyrrolidin-1-yl]-1-cyclopropyl-8-methyl-1H-quinazoline-2,4-dione;

3-Amino-7-[(3R,4R)-3-((R)-1-amino-3-methoxypropyl)-4-fluoropyrrolidin-1-yl]-1-cyclopropyl-6-fluoro-8-methyl-1H-quinazoline-2,4-dione;

3-Amino-7-[(3R,4R)-3-((R)-1-amino-3-methoxypropyl)-4-fluoropyrrolidin-1-yl]-1-cyclopropyl-8-methyl-1H-quinazoline-2,4-dione;

{(R)-2-Amino-2-[(R)-1-(3-amino-1-cyclopropyl-6-fluoro-8-methyl-2,4-dioxo-1,2,3,4-tetrahydroquinazolin-7-yl)pyrrolidin-3-yl]ethyl}urea;

{(R)-2-Amino-2-[(R)-1-(3-amino-1-cyclopropyl-8-methyl-2,4-dioxo-1,2,3,4-tetrahydroquinazolin-7-yl)pyrrolidin-3-yl]ethyl}urea;

{(S)-2-Amino-2-[(R)-1-(3-amino-1-cyclopropyl-6-fluoro-8-methyl-2,4-dioxo-1,2,3,4-tetrahydroquinazolin-7-yl)pyrrolidin-3-yl]ethyl}urea;

{(S)-2-Amino-2-[(R)-1-(3-amino-1-cyclopropyl-8-methyl-2,4-dioxo-1,2,3,4-tetrahydroquinazolin-7-yl)pyrrolidin-3-yl]ethyl}urea;

{(R)-2-Amino-2-[(3R,4S)-1-(3-amino-1-cyclopropyl-6-fluoro-8-methyl-2,4-dioxo-1,2,3,4-tetrahydroquinazolin-7-yl)-4-methylpyrrolidin-3-yl]ethyl}urea;

{(R)-2-Amino-2-[(3R,4S)-1-(3-amino-1-cyclopropyl-8-methyl-2,4-dioxo-1,2,3,4-tetrahydroquinazolin-7-yl)-4-methylpyrrolidin-3-yl]ethyl}urea;

{(S)-2-Amino-2-[(3R,4R)-1-(3-amino-1-cyclopropyl-6-fluoro-8-methyl-2,4-dioxo-1,2,3,4-tetrahydroquinazolin-7-yl)-4-methylpyrrolidin-3-yl]ethyl}urea;

{(S)-2-Amino-2-[(3R,4R)-1-(3-amino-1-cyclopropyl-8-methyl-2,4-dioxo-1,2,3,4-tetrahydroquinazolin-7-yl)-4-methylpyrrolidin-3-yl]ethyl}urea;

{2-Amino-2-[(1-(3-amino-1-cyclopropyl-6-fluoro-8-methyl-2,4-dioxo-1,2,3,4-tetrahydroquinazolin-7-yl)-4-fluoropyrrolidin-3-yl]ethyl}urea;

{2-Amino-2-[(1-(3-amino-1-cyclopropyl-8-methyl-2,4-dioxo-1,2,3,4-tetrahydroquinazolin-7-yl)-4-fluoropyrrolidin-3-yl]ethyl}urea;

{2-Amino-2-[(1-(3-amino-1-cyclopropyl-6-fluoro-8-methyl-2,4-dioxo-1,2,3,4-tetrahydroquinazolin-7-yl)-4,4-dimethylpyrrolidin-3-yl]ethyl}urea;

{2-Amino-2-[(1-(3-amino-1-cyclopropyl-8-methyl-2,4-dioxo-1,2,3,4-tetrahydroquinazolin-7-yl)-4,4-dimethylpyrrolidin-3-yl]ethyl}urea;

3-Amino-7-[(3R,4S)-3-((S)-1-aminoethyl)-4-fluoropyrrolidin-1-yl]-1-cyclopropyl-6-fluoro-8-methoxy-1H-quinazoline-2,4-dione;

3-Amino-7-[(3R,4S)-3-((S)-1-aminoethyl)-4-fluoropyrrolidin-1-yl]-1-cyclopropyl-8-methoxy-1H-quinazoline-2,4-dione;

3-Amino-7-[(3R,4R)-3-(R)-1-aminoethyl)-4-fluoropyrrolidin-1-yl]-1-cyclopropyl-6-fluoro-8-methoxy-1H-quinazoline-2,4-dione;

3-Amino-7-[(3R,4R)-3-((R)-1-aminoethyl)-4-fluoropyrrolidin-1-yl]-1-cyclopropyl-8-methoxy-1H-quinazoline-2,4-dione;

3-Amino-7-[(3R,4S)-3-(-1-amino-1-methylethyl)-4-fluoropyrrolidin-1-yl]-1-cyclopropyl-6-fluoro-8-methoxy-1H-quinazoline-2,4-dione;

3-Amino-7-[(3R,4S)-3-(-1-amino-1-methylethyl)-4-fluoropyrrolidin-1-yl]-1-cyclopropyl-8-methoxy-1H-quinazoline-2,4-dione;

3-Amino-7-[(3R,4R)-3-(-1-amino-1-methylethyl)-4-fluoropyrrolidin-1-yl]-1-cyclopropyl-6-fluoro-8-methoxy-1H-quinazoline-2,4-dione;

3-Amino-7-[(3R,4R)-3-(-1-amino-1-methylethyl)-4-fluoropyrrolidin-1-yl]-1-cyclopropyl-8-methoxy-1H-quinazoline-2,4-dione;

3-Amino-7-[(3R,4S)-3-((R)-1-amino-2-methoxyethyl)-4-fluoropyrrolidin-1-yl]-1-cyclopropyl-6-fluoro-8-methoxy-1H-quinazoline-2,4-dione;

3-Amino-7-[(3R,4S)-3-((R)-1-amino-2-methoxyethyl)-4-fluoropyrrolidin-1-yl]-1-cyclopropyl-8-methoxy-1H-quinazoline-2,4-dione;

3-Amino-7-[(3R,4R)-3-((S)-1-amino-2-methoxyethyl)-4-fluoropyrrolidin-1-yl]-1-cyclopropyl-6-fluoro-8-methoxy-1H-quinazoline-2,4-dione;

3-Amino-7-[(3R,4R)-3-((S)-1-amino-2-methoxyethyl)-4-fluoropyrrolidin-1-yl]-1-cyclopropyl-8-methoxy-1H-quinazoline-2,4-dione;

3-Amino-7-[(3R,4S)-3-((R)-1-amino-2-methoxyethyl)-4-methylpyrrolidin-1-yl]-1-cyclopropyl-6-fluoro-8-methoxy-1H-quinazoline-2,4-dione;

3-Amino-7-[(3R,4S)-3-((R)-1-amino-2-methoxyethyl)-4-methylpyrrolidin-1-yl]-1-cyclopropyl-8-methoxy-1H-quinazoline-2,4-dione;
3-Amino-7-[(3R,4R)-3-((S)-1-amino-2-methoxyethyl)-4-methylpyrrolidin-1-yl]-1-cyclopropyl-6-fluoro-8-methoxy-1H-quinazoline-2,4-dione;
3-Amino-7-[(3R,4R)-3-((S)-1-amino-2-methoxyethyl)-4-methylpyrrolidin-1-yl]-1-cyclopropyl-8-methoxy-1H-quinazoline-2,4-dione;
3-Amino-7-[(R)-4-((R)-1-amino-2-methoxyethyl)-3,3-dimethylpyrrolidin-1-yl]-1-cyclopropyl-6-fluoro-8-methoxy-1H-quinazoline-2,4-dione;
3-Amino-7-[(R)-4-(R)-1-amino-2-methoxyethyl)-3,3-dimethylpyrrolidin-1-yl]-1-cyclopropyl-8-methoxy-1H-quinazoline-2,4-dione;
3-Amino-7-[(R)-4-((S)-1-amino-2-methoxyethyl)-3,3-dimethylpyrrolidin-1-yl]-1-cyclopropyl-6-fluoro-8-methoxy-1H-quinazoline-2,4-dione;
3-Amino-7-[(R)-4-(S)-1-amino-2-methoxyethyl)-3,3-dimethylpyrrolidin-1-yl]-1-cyclopropyl-8-methoxy-1H-quinazoline-2,4-dione;
3-Amino-7-[(R)-3-((R)-1-amino-2-phenoxyethyl)pyrrolidin-1-yl]-1-cyclopropyl-6-fluoro-8-methoxy-1H-quinazoline-2,4-dione;
3-Amino-7-[(R)-3-(R)-1-amino-2-phenoxyethyl)pyrrolidin-1-yl]-1-cyclopropyl-8-methoxy-1H-quinazoline-2,4-dione;
3-Amino-7-[(3R,4S)-3-((R)-1-amino-2-phenoxyethyl)-4-methylpyrrolidin-1-yl]-1-cyclopropyl-6-fluoro-8-methoxy-1H-quinazoline-2,4-dione;
3-Amino-7-[(3R,4S)-3-((R)-1-amino-2-phenoxyethyl)-4-methylpyrrolidin-1-yl]-1-cyclopropyl-8-methoxy-1H-quinazoline-2,4-dione;
3-Amino-7-[(3R,4S)-3-((R)-1-amino-2-phenoxyethyl)-4-fluoropyrrolidin-1-yl]-1-cyclopropyl-6-fluoro-8-methoxy-1H-quinazoline-2,4-dione;
3-Amino-7-[(3R,4S)-3-((R)-1-amino-2-phenoxyethyl)-4-fluoropyrrolidin-1-yl]-1-cyclopropyl-8-methoxy-1H-quinazoline-2,4-dione;
3-Amino-7-[(R)-3-((S)-1-amino-2-phenoxyethyl)pyrrolidin-1-yl]-1-cyclopropyl-6-fluoro-8-methoxy-1H-quinazoline-2,4-dione;
3-Amino-7-[(R)-3-((S)-1-amino-2-phenoxyethyl)pyrrolidin-1-yl]-1-cyclopropyl-8-methoxy-1H-quinazoline-2,4-dione;
3-Amino-7-[(3R,4S)-3-((S)-1-amino-2-phenoxyethyl)-4-methylpyrrolidin-1-yl]-1-cyclopropyl-6-fluoro-8-methoxy-1H-quinazoline-2,4-dione;
3-Amino-7-[(3R,4S)-3-((S)-1-amino-2-phenoxyethyl)-4-methylpyrrolidin-1-yl]-1-cyclopropyl-8-methoxy-1H-quinazoline-2,4-dione;
3-Amino-7-[(3R,4S)-3-((S)-1-amino-2-phenoxyethyl)-4-fluoropyrrolidin-1-yl]-1-cyclopropyl-6-fluoro-8-methoxy-1H-quinazoline-2,4-dione;
3-Amino-7-[(3R,4S)-3-((S)-1-amino-2-phenoxyethyl)-4-fluoropyrrolidin-1-yl]-1-cyclopropyl-8-methoxy-1H-quinazoline-2,4-dione,
3-Amino-7-[(R)-4-((R)-1-amino-2-phenoxyethyl)-3,3-dimethylpyrrolidin-1-yl]-1-cyclopropyl-6-fluoro-8-methooxy-1H-quinazoline-2,4-dione;
3-Amino-7-[(R)-4-((R)-1-amino-2-phenoxyethyl)-3,3-dimethylpyrrolidin-1-yl]-1-cyclopropyl-8-methoxy-1H-quinazoline-2,4-dione;
3-Amino-7-[(R)-4-((S)-1-amino-2-phenoxyethyl)-3,3-dimethylpyrrolidin-1-yl]-1-cyclopropyl-6-fluoro-8-methoxy-1H-quinazoline-2,4-dione;
3-Amino-7-[(R)-4-((S)-1-amino-2-phenoxyethyl)-3,3-dimethylpyrrolidin-1-yl]-1-cyclopropyl-8-methoxy-1H-quinazoline-2,4-dione;
3-Amino-7-[(R)-3-((S)-1-amino-2-ethoxyethyl)pyrrolidin-1-yl]-1-cyclopropyl-6-fluoro-8-methoxy-1H-quinazoline-2,4-dione;
3-Amino-7-[(R)-3-((S)-1-amino-2-ethoxyethyl)pyrrolidin-1-yl]-1-cyclopropyl-8-methoxy-1H-quinazoline-2,4-dione;
3-Amino-7-[(R)-3-((R)-1-amino-2-ethoxyethyl)pyrrolidin-1-yl]-1-cyclopropyl-6-fluoro-8-methoxy-1H-quinazoline-2,4-dione;
3-Amino-7-[(R)-3-((R)-1-amino-2-ethoxyethyl)pyrrolidin-1-yl]-1-cyclopropyl-8-methoxy-1H-quinazoline-2,4-dione;
3-Amino-7-[(3R,4S)-3-((R)-1-amino-2-ethoxyethyl)-4-methylpyrrolidin-1-yl]-1-cyclopropyl-6-fluoro-8-methoxy-1H-quinazoline-2,4-dione;
3-Amino-7-[(3R,4S)-3-((R)-1-amino-2-ethoxyethyl)-4-methylpyrrolidin-1-yl]-1-cyclopropyl-8-methoxy-1H-quinazoline-2,4-dione;
3-Amino-7-[(3R,4S)-3-((R)-1-amino-2-ethoxyethyl)-4-fluoropyrrolidin-1-yl]-1-cyclopropyl-6-fluoro-8-methoxy-1H-quinazoline-2,4-dione;
3-Amino-7-[(3R,4S)-3-((R)-1-amino-2-ethoxyethyl)-4-fluoropyrrolidin-1-yl]-1-cyclopropyl-8-methoxy-1H-quinazoline-2,4-dione;
3-Amino-7-[(R)-4-((R)-1-amino-2-ethoxyethyl)-3,3-dimethylpyrrolidin-1-yl]-1-cyclopropyl-6-fluoro-8-methoxy-1H-quinazoline-2,4-dione;
3-Amino-7-[(R)-4-((R)-1-amino-2-ethoxyethyl)-3,3-dimethylpyrrolidin-1-yl]-1-cyclopropyl-8-methooxy-1H-quinazoline-2,4-dione;
3-Amino-7-[(3R,4R)-3-((S)-1-amino-2-ethoxyethyl)-4-methylpyrrolidin-1-yl]-1-cyclopropyl-6-fluoro-8-methoxy-1H-quinazoline-2,4-dione;
3-Amino-7-[(3R,4R)-3-((S)-1-amino-2-ethoxyethyl)-4-methylpyrrolidin-1-yl]-1-cyclopropyl-8-methoxy-1H-quinazoline-2,4-dione;
3-Amino-7-[(3R,4R)-3-((S)-1-amino-2-ethoxyethyl)-4-fluoropyrrolidin-1-yl]-1-cyclopropyl-6-fluoro-8-methoxy-1H-quinazoline-2,4-dione;
3-Amino-7-[(3R,4R)-3-((S)-1-amino-2-ethoxyethyl)-4-fluoropyrrolidin-1-yl]-1-cyclopropyl-8-methoxy-1H-quinazoline-2,4-dione;
3-Amino-7-[(R)-3-((S)-1-amino-3-methoxypropyl)pyrrolidin-1-yl]-1-cyclopropyl-6-fluoro-8-methoxy-1H-quinazoline-2,4-dione;
3-Amino-7-[(R)-3-((S)-1-amino-3-methoxypropyl)pyrrolidin-1-yl]-1-cyclopropyl-8-methoxy-1H-quinazoline-2,4-dione;
3-Amino-7-[(3R,4S)-3-((S)-1-amino-3-methoxypropyl)-4-methylpyrrolidin-1-yl]-1-cyclopropyl-6-fluoro-8-methoxy-1H-quinazoline-2,4-dione;
3-Amino-7-[(3R,4S)-3-((S)-1-amino-3-methoxypropyl)-4-methylpyrrolidin-1-yl]-1-cyclopropyl-8-methoxy-1H-quinazoline-2,4-dione;
3-Amino-7-[(3R,4S)-3-((S)-1-amino-3-methoxypropyl)-4-fluoropyrrolidin-1-yl]-1-cyclopropyl-6-fluoro-8-methoxy-1H-quinazoline-2,4-dione;
3-Amino-7-[(3R,4S)-3-((S)-1-amino-3-methoxypropyl)-4-fluoropyrrolidin-1-yl]-1-cyclopropyl-8-methoxy-1H-quinazoline-2,4-dione;
3-Amino-7-[(R)-3-((R)-1-amino-3-methoxypropyl)pyrrolidin-1-yl]-1-cyclopropyl-6-fluoro-8-methoxy-1H-quinazoline-2,4-dione;

3-Amino-7-[(R)-3-((R)-1-amino-3-methoxypropyl)pyrrolidin-1-yl]-1-cyclopropyl-8-methoxy-1H-quinazoline-2,4-dione;

3-Amino-7-[(3R,4R)-3-((R)-1-amino-3-methoxypropyl)-4-methylpyrrolidin-1-yl]-1-cyclopropyl-6-fluoro-8-methoxy-1H-quinazoline-2,4-dione;

3-Amino-7-[(3R,4R)-3-((R)-1-amino-3-methoxypropyl)-4-methylpyrrolidin-1-yl]-1-cyclopropyl-8-methoxy-1H-quinazoline-2,4-dione;

3-Amino-7-[(3R,4R)-3-((R)-1-amino-3-methoxypropyl)-4-fluoropyrrolidin-1-yl]-1-cyclopropyl-6-fluoro-8-methoxy-1H-quinazoline-2,4-dione;

-Amino-7-[(3R,4R)-3-((R)-1-amino-3-methoxypropyl)-4-fluoropyrrolidin-1-yl]-1-cyclopropyl-8-methoxy-1H-quinazoline-2,4-dione;

{(R)-2-Amino-2-[(R)-1-(3-amino-1-cyclopropyl-6-fluoro-8-methoxy-2,4-dioxo-1,2,3,4-tetrahydroquinazolin-7-yl)pyrrolidin-3-yl]ethyl}urea;

{(R)-2-Amino-2-[(R)-1-(3-amino-1-cyclopropyl-8-methoxy-2,4-dioxo-1,2,3,4-tetrahydroquinazolin-7-yl)pyrrolidin-3-yl]ethyl}urea;

{(S)-2-Amino-2-[(R)-1-(3-amino-1-cyclopropyl-6-fluoro-8-methoxy-2,4-dioxo-1,2,3,4-tetrahydroquinazolin-7-yl)pyrrolidin-3-yl]ethyl}urea;

{(S)-2-Amino-2-[(R)-1-(3-amino-1-cyclopropyl-8-methoxy-2,4-dioxo-1,2,3,4-tetrahydroquinazolin-7-yl)pyrrolidin-3-yl]ethyl}urea;

{(R)-2-Amino-2-[(3R,4S)-1-(3-amino-1-cyclopropyl-6-fluoro-8-methoxy-2,4-dioxo-1,2,3,4-tetrahydroquinazolin-7-yl)-4-methylpyrrolidin-3-yl]ethyl}urea;

{(R)-2-Amino-2-[(3R,4S)-1-(3-amino-1-cyclopropyl-8-methoxy-2,4-dioxo-1,2,3,4-tetrahydroquinazolin-7-yl)-4-methylpyrrolidin-3-yl]ethyl}urea;

{(S)-2-Amino-2-[(3R,4R)-1-(3-amino-1-cyclopropyl-6-fluoro-8-methoxy-2,4-dioxo-1,2,3,4-tetrahydroquinazolin-7-yl)-4-methylpyrrolidin-3-yl]ethyl}urea;

{(S)-2-Amino-2-[(3R,4R)-1-(3-amino-1-cyclopropyl-8-methoxy-2,4-dioxo-1,2,3,4-tetrahydroquinazolin-7-yl)-4-methylpyrrolidin-3-yl]ethyl}urea;

{2-Amino-2-[(1-(3-amino-1-cyclopropyl-6-fluoro-8-methoxy-2,4-dioxo-1,2,3,4-tetrahydroquinazolin-7-yl)-4-fluoropyrrolidin-3-yl]ethyl}urea;

{2-Amino-2-[(1-(3-amino-1-cyclopropyl-8-methoxy-2,4-dioxo-1,2,3,4-tetrahydroquinazolin-7-yl)-4-fluoropyrrolidin-3-yl]ethyl}urea;

{2-Amino-2-[(1-(3-amino-1-cyclopropyl-6-fluoro-8-methoxy-2,4-dioxo-1,2,3,4-tetrahydroquinazolin-7-yl)-4,4-dimethylpyrrolidin-3-yl]ethyl}urea;

{2-Amino-2-[(1-(3-amino-1-cyclopropyl-8-methoxy-2,4-dioxo-1,2,3,4-tetrahydroquinazolin-7-yl)-4,4-dimethylpyrrolidin-3-yl]ethyl}urea;

3-Amino-7-[3-(1-aminoethyl)-4-fluoropyrrolidin-1-yl]-1-cyclopropyl-8-methyl-1H-pyrido [4,3-d]pyrimidine-2,4-dione;

3-Amino-7-[3-(1-amino-1-methylethyl)-4-fluoropyrrolidin-1-yl]-1-cyclopropyl-8-methyl-1H-pyrido[4,3-d]pyrimidine-2,4-dione;

3-Amino-7-[3-(1-amino-2-methoxyethyl)-4-fluoropyrrolidin-1-yl]-1-cyclopropyl-8-methyl-1H-pyrido [4,3-d]pyrimidine-2,4-dione;

3-Amino-7-[3-(1-amino-2-methoxyethyl)-4-methylpyrrolidin-1-yl]-1-cyclopropyl-8-methyl-1H-pyrido[4,3-d]pyrimidine-2,4-dione;

3-Amino-7-[4-(1-amino-2-methoxyethyl)-3,3-dimethylpyrrolidin-1-yl]-1-cyclopropyl-8-methyl-1H-pyrido[4,3-d]pyrimidine-2,4-dione;

3-Amino-7-[3-(1-amino-2-phenoxyethyl)-pyrrolidin-1-yl]-1-cyclopropyl-8-methyl-1H-pyrido[4,3-d]pyrimidine-2,4-dione;

3-Amino-7-[3-(1-amino-2-phenoxyethyl)-4-methylpyrrolidin-1-yl]-1-cyclopropyl-8-methyl-1H-pyrido[4,3-d]pyrimidine-2,4-dione;

3-Amino-7-[3-(1-amino-2-phenoxyethyl)-4-fluoropyrrolidin-1-yl]-1-cyclopropyl-8-methyl-1H-pyrido[4,3-d]pyrimidine-2,4-dione;

3-Amino-7-[4-(1-amino-2-phenoxyethyl)-3,3-dimethylpyrrolidin-1-yl]-1-cyclopropyl-8-methyl-1H-pyrido[4,3-d]pyrimidine-2,4-dione;

3-Amino-7-[3-(1-amino-2-ethoxyethyl)pyrrolidin-1-yl]-1-cyclopropyl-8-methyl-1H-pyrido[4,3-d]pyrimidine-2,4-dione;

3-Amino-7-[3-(1-amino-2-ethoxyethyl)-4-methylpyrrolidin-1-yl]-1-cyclopropyl-8-methyl-1H-pyrido[4,3-d]pyrimidine-2,4-dione;

3-Amino-7-[3-(1-amino-2-ethoxyethyl)-4-fluoropyrrolidin-1-yl]-1-cyclopropyl-8-methyl-1H-pyrido[4,3-d]pyrimidine-2,4-dione;

3-Amino-7-[3-(1-amino-2-ethoxyethyl)-4,4-dimethylpyrrolidin-1-yl]-1-cyclopropyl-8-methyl-1H-pyrido[4,3-d]pyrimidine-2,4-dione;

3-Amino-7-[3-(1-amino-2-methoxypropyl)pyrrolidin-1-yl]-1-cyclopropyl-8-methyl-1H-pyrido[4,3-d]pyrimidine-2,4-dione;

3-Amino-7-[3-(1-amino-2-methoxypropyl)-4-methylpyrrolidin-1-yl]-1-cyclopropyl-8-methyl-1H-pyrido[4,3-d]pyrimidine-2,4-dione;

3-Amino-7-[3-(1-amino-2-methoxypropyl)-4-fluoropyrrolidin-1-yl]-1-cyclopropyl-8-methyl-1H-pyrido[4,3-d]pyrimidine-2,4-dione;

{2-Amino-2-[1-(3-amino-1-cyclopropyl-8-methyl-2,4-dioxo-1,2,3,4-tetrahydropyrido[4,3-d]pyrimidin-7-yl)pyrrolidin-3-yl]ethylurea;

{2-Amino-2-[1-(3-amino-1-cyclopropyl-8-methyl-2,4-dioxo-1,2,3,4-tetrahydropyrido[4,3-d]pyrimidin-7-yl)-4-methylpyrrolidin-3-yl]ethylurea;

{2-Amino-2-[1-(3-amino-1-cyclopropyl-8-methyl-2,4-dioxo-1,2,3,4-tetrahydropyrido[4,3-d]pyrimidin-7-yl)-4-fluoropyrrolidin-3-yl]ethylurea;

{2-Amino-2-[1-(3-amino-1-cyclopropyl-8-methyl-2,4-dioxo-1,2,3,4-tetrahydropyrido[4,3-d]pyrimidin-7-yl)-4,4-dimethylpyrrolidin-3-yl]ethylurea;

3-Amino-7-[3-(1-aminoethyl)-4-fluoropyrrolidin-1-yl]-1-cyclopropyl-6-fluoro-8-methyl-1H-pyrido[3,2-d]pyrimidine-2,4-dione;

3-Amino-7-[3-(1-aminoethyl)-4-fluoropyrrolidin-1-yl]-1-cyclopropyl-8-methyl-1H-pyrido[3,2-d]pyrimidine-2,4-dione;

3-Amino-7-[3-(1-amino-1-methylethyl)-4-fluoropyrrolidin-1-yl]-1-cyclopropyl-6-fluoro-8-methyl-1H-pyrido[3,2-d]pyrimidine-2,4-dione, 3-Amino-7-[3-(1-amino-1-methylethyl)-4-fluoropyrrolidin-1-yl]-1-cyclopropyl-8-methyl-1H-pyrido[3,2-d]pyrimidine-2,4-dione;

3-Amino-7-[3-(1-amino-2-methoxyethyl)-4-fluoropyrrolidin-1-yl]-1-cyclopropyl-6-fluoro-8-methyl-1H-pyrido[3,2-d]pyrimidine-2,4-dione;

3-Amino-7-[3-(1-amino-2-methoxyethyl)-4-fluoropyrrolidin-1-yl]-1-cyclopropyl-8-methyl-1H-pyrido[3,2-d]pyrimidine-2,4-dione;

3-Amino-7-[3-(1-amino-2-methoxyethyl)-4-methylpyrrolidin-1-yl]-1-cyclopropyl-6-fluoro-8-methyl-1H-pyrido[3,2-d]pyrimidine-2,4-dione;

3-Amino-7-[3-(1-amino-2-methoxyethyl)-4-methylpyrrolidin-1-yl]-1-cyclopropyl-8-methyl-1H-pyrido[3,2-d]pyrimidine-2,4-dione;
3-Amino-7-[4-(1-amino-2-methoxyethyl)-3,3-dimethylpyrrolidin-1-yl]-1-cyclopropyl-6-fluoro-8-methyl-1H-pyrido[3,2-d]pyrimidine-2,4-dione;
3-Amino-7-[4-(1-amino-2-methoxyethyl)-3,3-dimethylpyrrolidin-1-yl]-1-cyclopropyl-8-methyl-1H-pyrido[3,2-d]pyrimidine-2,4-dione;
3-Amino-7-[3-(1-amino-2-phenoxyethyl)pyrrolidin-1-yl]-1-cyclopropyl-6-fluoro-8-methyl-1H-pyrido[3,2-d]pyrimidine-2,4-dione;
3-Amino-7-[3-(1-amino-2-phenoxyethyl)pyrrolidin-1-yl]-1-cyclopropyl-8-methyl-1H-pyrido[3,2-d]pyrimidine-2,4-dione;
3-Amino-7-[3-(1-amino-2-phenoxyethyl)-4-methylpyrrolidin-1-yl]-1-cyclopropyl-6-fluoro-8-methyl-1H-pyrido[3,2-d]pyrimidine-2,4-dione;
3-Amino-7-[3-(1-amino-2-phenoxyethyl)-4-methylpyrrolidin-1-yl]-1-cyclopropyl-8-methyl-1H-pyrido[3,2-d]pyrimidine-2,4-dione;
3-Amino-7-[3-(1-amino-2-phenoxyethyl)-4-fluoropyrrolidin-1-yl]-1-cyclopropyl-6-fluoro-8-methyl-1H-pyrido[3,2-d]pyrimidine-2,4-dione;
3-Amino-7-[3-(1-amino-2-phenoxyethyl)-4-fluoropyrrolidin-1-yl]-1-cyclopropyl-8-methyl-1H-pyrido[3,2-d]pyrimidine-2,4-dione;
3-Amino-7-[4-(1-amino-2-phenoxyethyl)-3,3-dimethylpyrrolidin-1-yl]-1-cyclopropyl-6-fluoro-8-methyl-1H-pyrido[3,2-d]pyrimidine-2,4-dione;
3-Amino-7-[4-(1-amino-2-phenoxyethyl)-3,3-dimethylpyrrolidin-1-yl]-1-cyclopropyl-8-methyl-1H-pyrido[3,2-d]pyrimidine-2,4-dione;
3-Amino-7-[3-(1-amino-2-ethoxyethyl)pyrrolidin-1-yl]-1-cyclopropyl-6-fluoro-8-methyl-1H-pyrido[3,2-d]pyrimidine-2,4-dione;
3-Amino-7-[3-(1-amino-2-ethoxyethyl)pyrrolidin-1-yl]-1-cyclopropyl-8-methyl-1H-pyrido[3,2-d]pyrimidine-2,4-dione;
3-Amino-7-[3-(1-amino-2-ethoxyethyl)-4-methylpyrrolidin-1-yl]-1-cyclopropyl-6-fluoro-8-methyl-1H-pyrido[3,2-d]pyrimidine-2,4-dione;
3-Amino-7-[3-(1-amino-2-ethoxyethyl)-4-methylpyrrolidin-1-yl]-1-cyclopropyl-8-methyl-1H-pyrido[3,2-d]pyrimidine-2,4-dione;
3-Amino-7-[3-(1-amino-2-ethoxyethyl)-4-fluoropyrrolidin-1-yl]-1-cyclopropyl-6-fluoro-8-methyl-1H-pyrido [3,2-d]pyrimidine-2,4-dione;
3-Amino-7-[3-(1-amino-2-ethoxyethyl)-4-fluoropyrrolidin-1-yl]-1-cyclopropyl-8-methyl-1H-pyrido[3,2-d]pyrimidine-2,4-dione;
3-Amino-7-[3-(1-amino-2-ethoxyethyl)-4,4-dimethylpyrrolidin-1-yl]-1-cyclopropyl-6-fluoro-8-methyl-1H-pyrido[3,2-d]pyrimidine-2,4-dione;
3-Amino-7-[3-(1-amino-2-ethoxyethyl)-4,4-dimethylpyrrolidin-1-yl]-1-cyclopropyl-8-methyl-1H-pyrido[3,2-d]pyrimidine-2,4-dione;
3-Amino-7-[3-(1-amino-2-methoxypropyl)pyrrolidin-1-yl]-1-cyclopropyl-6-fluoro-8-methyl-1H-pyrido[3,2-d]pyrimidine-2,4-dione;
3-Amino-7-[3-(1-amino-2-methoxypropyl)pyrrolidin-1-yl]-1-cyclopropyl-8-methyl-1H-pyrido[3,2-d]pyrimidine-2,4-dione;
3-Amino-7-[3-(1-amino-2-methoxypropyl)-4-methylpyrrolidin-1-yl]-1-cyclopropyl-6-fluoro-8-methyl-1H-pyrido[3,2-d]pyrimidine-2,4-dione;
3-Amino-7-[3-(1-amino-2-methoxypropyl)-4-methylpyrrolidin-1-yl]-1-cyclopropyl-8-methyl-1H-pyrido[3,2-d]pyrimidine-2,4-dione;
3-Amino-7-[3-(1 amino-2-methoxypropyl)-4-fluoropyrrolidin-1-yl]-1-cyclopropyl-6-fluoro-8-methyl-1H-pyrido[3,2-d]pyrimidine-2,4-dione;
3-Amino-7-[3-(1-amino-2-methoxypropyl)-4-fluoropyrrolidin-1-yl]-1 cyclopropyl-8-methyl-1H-pyrido[3,2-d]pyrimidine-2,4-dione;
{2-Amino-2-[1-(3-amino-1-cyclopropyl-6-fluoro-8-methyl-2,4-dioxo-1,2,3,4-tetrahydropyrido[3,2-d]pyrimidin-7-yl)pyrrolidin-3-yl]ethyl}urea;
{2-Amino-2-[1-(3-amino-1-cyclopropyl-8-methyl-2,4-dioxo-1,2,3,4-tetrahydropyrido[3,2-d]pyrimidin-7-yl)pyrrolidin-3-yl]ethyl}urea;
{2-Amino-2-[1-(3-amino-1-cyclopropyl-6-fluoro-8-methyl-2,4-dioxo-1,2,3,4-tetrahydropyrido[3,2-d]pyrimidin-7-yl)-4-methylpyrrolidin-3-yl]ethyl}urea;
{2-Amino-2-[1-(3-amino-1-cyclopropyl-8-methyl-2,4-dioxo-1,2,3,4-tetrahydropyrido[3,2-d]pyrimidin-7-yl)-4-methylpyrrolidin-3-yl]ethyl}urea;
{2-Amino-2-[1-(3-amino-1-cyclopropyl-6-fluoro-8-methyl-2,4-dioxo-1,2,3,4-tetrahydropyrido[3,2-d]pyrimidin-7-yl)-4-fluoropyrrolidin-3-yl]ethyl}urea;
{2-Amino-2-[1-(3-amino-1-cyclopropyl-8-methyl-2,4-dioxo-1,2,3,4-tetrahydropyrido[3,2-d]pyrimidin-7-yl)-4-fluoropyrrolidin-3-yl]ethyl}urea;
{2-Amino-2-[1-(3-amino-1-cyclopropyl-6-fluoro-8-methyl-2,4-dioxo-1,2,3,4-tetrahydropyrido[3,2-d]pyrimidin-7-yl)-4,4-dimethylpyrrolidin-3-yl]ethyl}urea;
{2-Amino-2-[1-(3-amino-1-cyclopropyl-8-methyl-2,4-dioxo-1,2,3,4-tetrahydropyrido[3,2-d]pyrimidin-7-yl)-4,4-dimethylpyrrolidin-3-yl]ethyl}urea;
3-Amino-7-(3-aminomethylphenyl)-8-chloro-1-cyclopropyl-6-fluoro-1H-quinazoline-2,4-dione;
3-Amino-7-(3-aminomethylphenyl)-8-methyl-1-cyclopropyl-6-fluoro-1H-quinazoline-2,4-dione;
3-Amino-7-(3-aminomethylphenyl)-8-methoxy-1-cyclopropyl-6-fluoro-1H-quinazoline-2,4-dione;
3-Amino-7-(3-aminomethylphenyl)-8-chloro-1-cyclopropyl-1H-quinazoline-2,4-dione;
3-Amino-7-(3-aminomethylphenyl)-8-methyl-1-cyclopropyl-1H-quinazoline-2,4-dione;
3-Amino-7-(3-aminomethylphenyl)-8-methoxy-1-cyclopropyl-1H-quinazoline-2,4-dione;
3-Amino-7-(2-aminomethylthiazol-4-yl)-8-chloro-1-cyclopropyl-6-fluoro-1H-quinazoline-2,4-dione;
3-Amino-7-(2-aminomethylthiazol-4-yl)-8-methyl-1-cyclopropyl-6-fluoro-1H-quinazoline-2,4-dione;
3-Amino-7-(2-aminomethylthiazol-4-yl)-8-methoxy-1-cyclopropyl-6-fluoro-1H-quinazoline-2,4-dione;
3-Amino-7-(2-aminomethylthiazol-4-yl)-8-chloro-1-cyclopropyl-1H-quinazoline-2,4-dione;
3-Amino-7-(2-aminomethylthiazol-4-yl)-8-methyl-1-cyclopropyl-1H-quinazoline-2,4-dione;
3-Amino-7-(2-aminomethylthiazol-4-yl)-8-methoxy-1-cyclopropyl-1H-quinazoline-2,4-dione;
3-Amino-7-[2-(1-aminoethyl)thiazol-4-yl]-8-chloro-1-cyclopropyl-6-fluoro-1H-quinazoline-2,4-dione;
3-Amino-7-[2-(1-aminoethyl)thiazol-4-yl]-8-methyl-1-cyclopropyl-6-fluoro-1H-quinazoline-2,4-dione;
3-Amino-7-[2-(1-aminoethyl)thiazol-4-yl]-8-methoxy-1-cyclopropyl-6-fluoro-1H-quinazoline-2,4-dione;
3-Amino-7-[2-(1-aminoethyl)thiazol-4-yl]-8-chloro-1-cyclopropyl-6H-quinazoline-2,4-dione;
3-Amino-7-[2-(1-aminoethyl)thiazol-4-yl]-8-methyl-1-cyclopropyl-1H-quinazoline-2,4-dione;

3-Amino-7-[2-(1-aminoethyl)thiazol-4-yl)-8-methoxy-1-cyclopropyl-1H-quinazoline-2,4-dione;
3-Amino-7-(5-aminomethylthiophen-3-yl)-8-chloro-1-cyclopropyl-6-fluoro-1H-quinazoline-2,4-dione;
3-Amino-7-(5-aminomethylthiophen-3-yl)-8-methyl-1-cyclopropyl-6-fluoro-1H-quinazoline-2,4-dione;
3-Amino-7-(5-aminomethylthiophen-3-yl)-8-methoxy-1-cyclopropyl-6-fluoro-1H-quinazoline-2,4-dione;
3-Amino-7-(5-aminomethylthiophen-3-yl)-8-chloro-1-cyclopropyl-1H-quinazoline-2,4-dione;
3-Amino-7-(5-aminomethylthiophen-3-yl)-8-methyl-1-cyclopropyl-1H-quinazoline-2,4-dione;
3-Amino-7-(5-aminomethylthiophen-3-yl)-8-methoxy-1-cyclopropyl-1H-quinazoline-2,4-dione;
3-Amino-7-(4-aminomethyl-3,3-difluoropyrrolidin-1-yl)-8-chloro-1-cyclopropyl-6-fluoro-1H-quinazoline-2,4-dione;
3-Amino-7-(4-aminomethyl-3,3-difluoropyrrolidin-1-yl)-8-methyl-1-cyclopropyl-6-fluoro-1H-quinazoline-2,4-dione;
3-Amino-7-(4-aminomethyl-3,3-difluoropyrrolidin-1-yl)-8-methoxy-1-cyclopropyl-6-fluoro-1H-quinazoline-2,4-dione;
3-Amino-7-(4-aminomethyl-3,3-difluoropyrrolidin-1-yl)-8-chloro-1-cyclopropyl-1H-quinazolin-2,4-dione;
3-Amino-7-(4-aminomethyl-3,3-difluoropyrrolidin-1-yl)-8-methyl-1-cyclopropyl-1H-quinazoline-2,4-dione
3-Amino-7-(4-aminomethyl-3,3-difluoropyrrolidin-1-yl)-8-methoxy-1-cyclopropyl-1H-quinazoline-2,4-dione;
3-Amino-7-(4-(1-aminoethyl)-3,3-difluoropyrrolidin-1-yl)-8-chloro-1-cyclopropyl-6-fluoro-1H-quinazoline-2,4-dione;
3-Amino-7-(4-(1-aminoethyl)-3,3-difluoropyrrolidin-1-yl)-8-methyl-1-cyclopropyl-6-fluoro-1H-quinazoline-2,4-dione;
3-Amino-7-(4-(1-aminoethyl)-3,3-difluoropyrrolidin-1-yl)-8-methoxy-1-cyclopropyl-6-fluoro-1H-quinazoline-2,4-dione;
3-Amino-7-(4-(1-aminoethyl)-3,3-difluoropyrrolidin-1-yl)-8-chloro-1-cyclopropyl-1H-quinazoline-2,4-dione;
3-Amino-7-(4-(1-aminoethyl)-3,3-difluoropyrrolidin-1-yl)-8-methyl-1-cyclopropyl-1H-quinazoline-2,4-dione;
3-Amino-7-(4-(1-aminoethyl)-3,3-difluoropyrrolidin-1-yl)-8-methoxy-1-cyclopropyl-1H-quinazoline-2,4-dione;
3-Amino-7-(4-(1-amino-1-methylethyl)-3,3-difluoropyrrolidin-1-yl)-8-chloro-1-cyclopropyl-6-fluoro-1H-quinazoline-2,4-dione;
3-Amino-7-(4-(1-amino-1-methylethyl)-3,3-difluoropyrrolidin-1-yl)-8-methyl-1-cyclopropyl-6-fluoro-1H-quinazoline-2,4-dione;
3-Amino-7-(4-(1-amino-1-methylethyl)-3,3-difluoropyrrolidin-1-yl)-8-methoxy-1-cyclopropyl-6-fluoro-1H-quinazoline-2,4-dione;
3-Amino-7-(4-(1-amino-1-methylethyl)-3,3-difluoropyrrolidin-1-yl)-8-chloro-1-cyclopropyl-1H-quinazoline-2,4-dione;
3-Amino-7-(4-(1-amino-1-methylethyl)-3,3-difluoropyrrolidin-1-yl)-8-methyl-1-cyclopropyl-1H-quinazoline-2,4-dione;
3-Amino-7-(4-(1-amino-1-methylethyl)-3,3-difluoropyrrolidin-1-yl)-8-methoxy-1-cyclopropyl-1H-quinazoline-2,4-dione;
3-Amino-7-(3-(1-aminoethyl)pyrrolidin-1-yl)-1-cyclopropyl-6-fluoro-5,8-dimethyl-1H-quinazoline-2,4-dione;
3-Amino-7-(3-(1-aminoethyl)pyrrolidin-1-yl)-1-cyclopropyl-5,8-dimethyl-1H-quinazoline-2,4-dione;
3-Amino-7-(3-(1-aminoethyl)pyrrolidin-1-yl)-1-cyclopropyl-6-fluoro-8-methoxy-5-methyl-1H-quinazoline-2,4-dione;
3-Amino-7-(3-(1-aminoethyl)pyrrolidin-1-yl)-1-cyclopropyl-8-methoxy-5-methyl-1H-quinazoline-2,4-dione;
3,8-Diamino-7-[3-(1-aminoethyl)pyrrolidin-1-yl]-1-cyclopropyl-6-fluoro-5-methyl-1H-quinazoline-2,4-dione; and
3,8-Diamino-7-[3-(1-aminoethyl)pyrrolidin-1-yl]-1-cyclopropyl-5-methyl-1H-quinazoline-2,4-dione.

A further embodiment of the invention is a pharmaceutical composition comprising a compound of Formula I together with an excipient, carrier, or diluent. Preferred compositions will have a compound of Formulas II, III, IV, V, VI, or VII mixed with an excipient, carrier, or diluent.

Still another embodiment of the invention is a method of treating bacterial infections in mammals comprising administering an antibacterial effective amount of a compound of Formula I. Preferred methods comprise administering a compound of Formulas II, III, IV, V, VI, or VII.

Another embodiment is a method of preventing or eliminating bacterial growth on surfaces comprising applying to the surface an antibacterially effective amount of a compound of Formulas I–VII.

DETAILED DESCRIPTION

All references cited herein, including patents, are incorporated herein by reference.

The terms used in this specification and the appended claims have the following meanings. The term "halo" means chloro, bromo, fluoro, and iodo.

The term "alkyl" means a straight or branched hydrocarbon radical having from 1 to 12 carbon atoms and includes, for example, methyl, ethyl, n-propyl, isopropyl, n-butyl, sec-butyl, isobutyl, tert-butyl, n-pentyl, n-hexyl, n-heptyl, n-octyl, 2-isopropylheptyl, 3-n-butyloctyl, n-nonyl, n-decyl, undecyl, and dodecyl.

Preferred alkyl groups are $C_1$–$C_6$ alkyl such as methyl, isopropyl, neopentyl, and 1-methylpentyl.

The term "$C_2$–$C_{12}$ alkenyl" means a straight or branched hydrocarbon radical having from 1 to 3 double bonds. Examples include ethenyl, 2-propen-1-yl, 1,3-butadien-1-yl, 3-hexen-1-yl, 5-octen-2-yl, 2-isopropyl-3,5-octadien-1-yl, cis-3-hexen-1-yl, and trans-2-hepten-1-yl. Preferred alkenyl groups include $C_2$–$C_6$ alkenyls such as ethenyl, 2-propen-1-yl, 2-buten-1-yl, and 3-penten-1-yl.

The term "$C_2$–$C_{12}$ alkynyl" means a straight or branched hydrocarbon radical having from 1 to 3 triple-bonds. Examples include ethynyl, propynyl, 3-butyn-1-yl, 4-hexyn-1-yl, 5-octyn-3-yl, 4,6-octadiyn-1-yl, 4-decyn-1-yl, and 1,1-dimethyl-5-decyn-1-yl. Preferred alkynyl groups are $C_2$–$C_6$ alkynyls such as ethynyl, propynyl, 3-butyn-1-yl, and 5-hexyn-1-yl.

The alkyl, alkenyl, and alkynyl groups can be substituted with 1 to 3 groups selected from halo, hydroxy, cyano, $C_1$–$C_6$ alkoxy, nitro, amino, $C_1$–$C_6$ alkylamino, di-$C_1$–$C_6$ alkylamino, carboxy, $C_1$–$C_6$ alkoxycarbonyl, aminocarbonyl, halo-dihalo and trihalomethyl, thiol, alkylsulfanyl, alkylsulfinyl, and aminosulfonyl. Examples of substituted alkyl groups include fluoromethyl, tribromomethyl, hydroxymethyl, 3-methoxypropyl, 3-carboxypentyl, 3,5-dibromo-6-aminocarbonyldecyl, and 4-ethylsulfinyloctyl. Examples of substituted alkenyl groups include 2-bromoethenyl, 1-amino-2-propen-1-yl, 3-hydroxypent-2-en-1-yl, 4-methoxycarbonyl-hex-2-en-1-yl, and 2-nitro-3-bromo-4- iodo-oct-5-en-1-yl. Typical substituted alkynyl groups include 2-hydroxyethynyl, 3-dimethylamino-hex-5-yn-1-yl, and 2-cyano-hept-3-yn-1-yl.

The term "cycloalkyl" means a hydrocarbon ring which contains from 3 to 12 carbon atoms, for example, cyclopropyl, cyclobutyl, cyclopentyl, cyclohexyl, decalinyl, norpinanyl, and adamantyl. Where possible, the cycloalkyl group may contain double bonds, for example, 3-cyclohexen-1-yl. The cycloalkyl ring may be unsubstituted or substituted by 1 to 3 substituents selected from alkyl, alkoxy, thioalkoxy, hydroxy, thiol, nitro, halogen, amino, alkyl and dialkylamino, formyl, carboxyl, CN, —NH—CO—R', —CO—NHR'—, —CO$_2$R', —COR', aryl, or heteroaryl, wherein alkyl, aryl, and heteroaryl are as defined herein. Examples of substituted cycloalkyl groups include fluorocyclopropyl, 2-iodocyclobutyl, 2,3-dimethylcyclopentyl, 2,2-dimethoxycyclohexyl, and 3-phenylcyclopentyl.

The term "heterocyclic" means a cyclic or fused bicyclic or polycyclic ring system having from 3 to 12 ring atoms, with from 1 to 5 being heteroatoms selected from N, O, and S. The heterocyclic groups can be substituted with 1 to 3 of the substituents listed above for the cycloalkyl groups. Examples of heterocyclic groups include cyclic ethers (oxiranes) such as ethyleneoxide, tetrahydrofuran, dioxane, and substituted cyclic ethers, wherein the substituents are those described above for the alkyl and cycloalkyl groups. Typical substituted cyclic ethers include propyleneoxide, phenyloxirane (styrene oxide), cis-2-butene-oxide (2,3-dimethyloxirane), 3-chlorotetrahydrofuran, 2,6-dimethyl-1,4-dioxane, and the like. Heterocycles containing nitrogen are groups such as pyrrolidine, piperidine, piperazine, tetrahydrotriazine, tetrahydropyrazole, and substituted groups such as 3-aminopyrrolidine, 4-methylpiperazin-1-yl, and the like. Typical sulfur containing heterocycles include tetrahydrothiophene, dihydro-1,3-dithiol-2-yl, and hexahydrothiepin-4-yl. Other commonly employed heterocycles include dihydro-oxathiol-4-yl, tetrahydro-oxazolyl, tetrahydro-oxadiazolyl, tetrahydro-dioxazolyl, tetrahydro-oxathiazolyl, hexahydrotriazinyl, tetrahydro-oxazinyl, morpholinyl, thiomorpholinyl, tetrahydropyrimidinyl, dioxolinyl, octahydrobenzofuranyl, octahydrobenzimidazolyl, and octahydrobenzothiazolyl. For heterocycles containing sulfur, the oxidized sulfur heterocycles containing SO or SO$_2$ groups are also included. Examples include the sulfoxide and sulfone forms of tetrahydrothiophene.

The term "aryl" means a cyclic or polycyclic aromatic ring having from 5 to 12 carbon atoms, and being unsubstituted or substituted with up to 3 of the substituent groups recited above for alkyl, alkenyl, and alkynyl. Examples of aryl groups include phenyl, 2,6-dichlorophenyl, 3-methoxyphenyl, naphthyl, 4-thionaphthyl, tetralinyl, anthracinyl, phenanthrenyl, benzonaphthenyl, fluorenyl, 2-acetamidofluoren-9-yl, and 4'-bromobiphenyl.

The term "heteroaryl" means an aromatic cyclic or polycyclic ring system having from 1 to 4 heteroatoms selected from N, O, and S. Typical heteroaryl groups include 2- or 3-thienyl, 2- or 3-furanyl, 2- or 3-pyrrolyl, 2-, 4-, or 5-imidazolyl, 3-, 4-, or 5-pyrazolyl, 2-, 4-, or 5-thiazolyl, 3-, 4-, or 5-isothiazolyl, 2-, 4-, or 5-oxazolyl, 3-, 4-, or 5-isoxazolyl, 3- or 5-1,2,4-triazolyl, 4- or 5-1,2,3-triazolyl, tetrazolyl, 2-, 3-, or 4-pyridinyl, 3-, 4-, or 5-pyridazinyl, 2-pyrazinyl, 2-, 4-, or 5-pyrimidinyl, 2-, 3-, 4-, 5-, 6-, 7-, or 8-quinolinyl, 1-, 3-, 4-, 5-, 6-, 7-, or 8-isoquinolinyl, 2-, 3-, 4-, 5-, 6-, or 7-indolyl, 2-, 3-, 4-, 5-, 6-, or 7-benzo[b]thienyl, 2-, 4-, 5-, 6-, or 7-benzoxazolyl, 2-, 4-, 5-, 6-, or 7-benzimidazolyl, 2-, 4-, 5-, 6-, or 7-benzothiazolyl. The heteroaryl groups may be unsubstituted or substituted by 1 to 3 substituents selected from those described above for alkyl, alkenyl, and alkynyl, for example, cyanothienyl and formylpyrrolyl.

Preferred aromatic fused heterocyclic rings of from 8 to 10 atoms include but are not limited to 2-, 3-, 4-, 5-, 6-, 7-, or 8-quinolinyl, 1-, 3-, 4-, 5-, 6-, 7-, or 8-isoquinolinyl, 2-, 3-, 4-, 5-, 6-, or 7-indolyl, 2-, 3-, 4-, 5-, 6-, or 7-benzo[b]thienyl, 2-, 4-, 5-, 6-, or 7-benzoxazolyl, 2-, 4-, 5-, 6-, or 7-benzimidazolyl, 2-, 4-, 5-, 6-, or 7-benzothiazolyl.

Preferred compounds of the invention have Formula I wherein R$_7$ is a heterocyclic or heteroaryl group such as those described above. Such heterocyclic and heteroaryl groups will be referred to herein generically as

.

Further examples of typical heterocycles, fused heterocycles, and heteroaryl groups that are preferred as R$_7$ substituents are listed below in Table A.

TABLE A

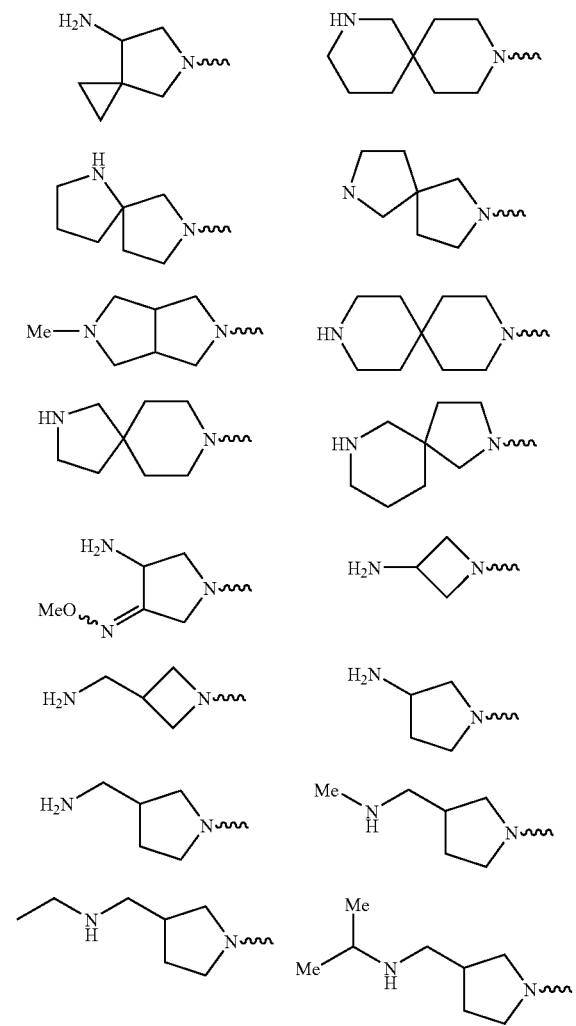

TABLE A-continued
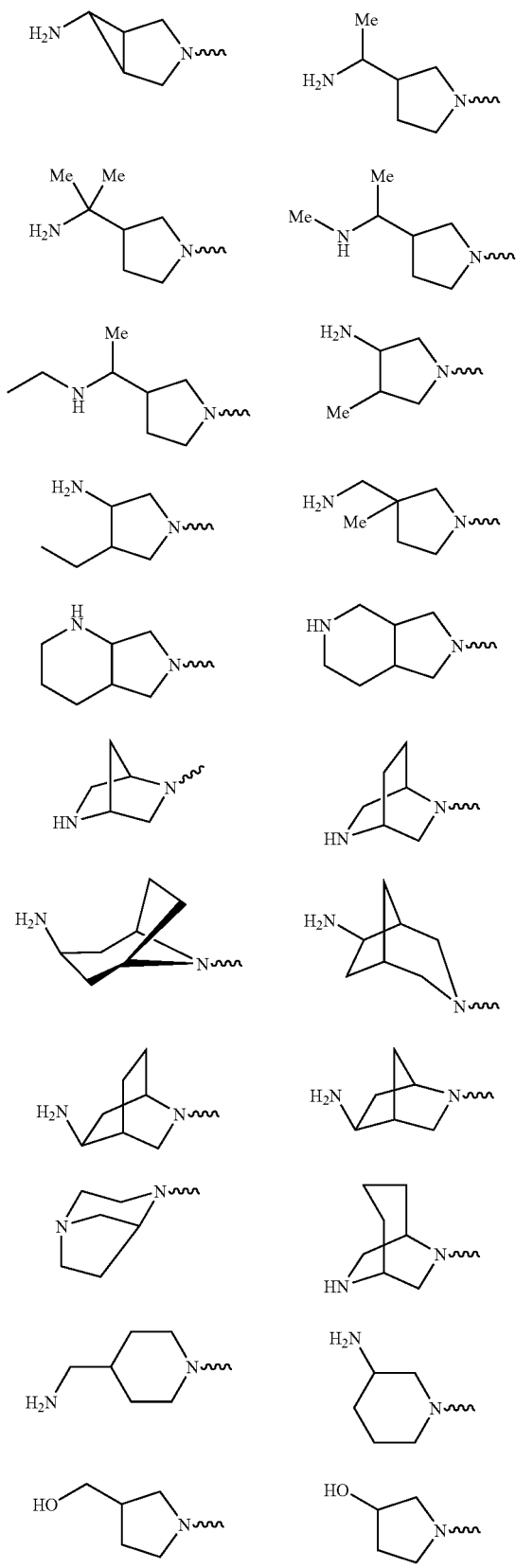
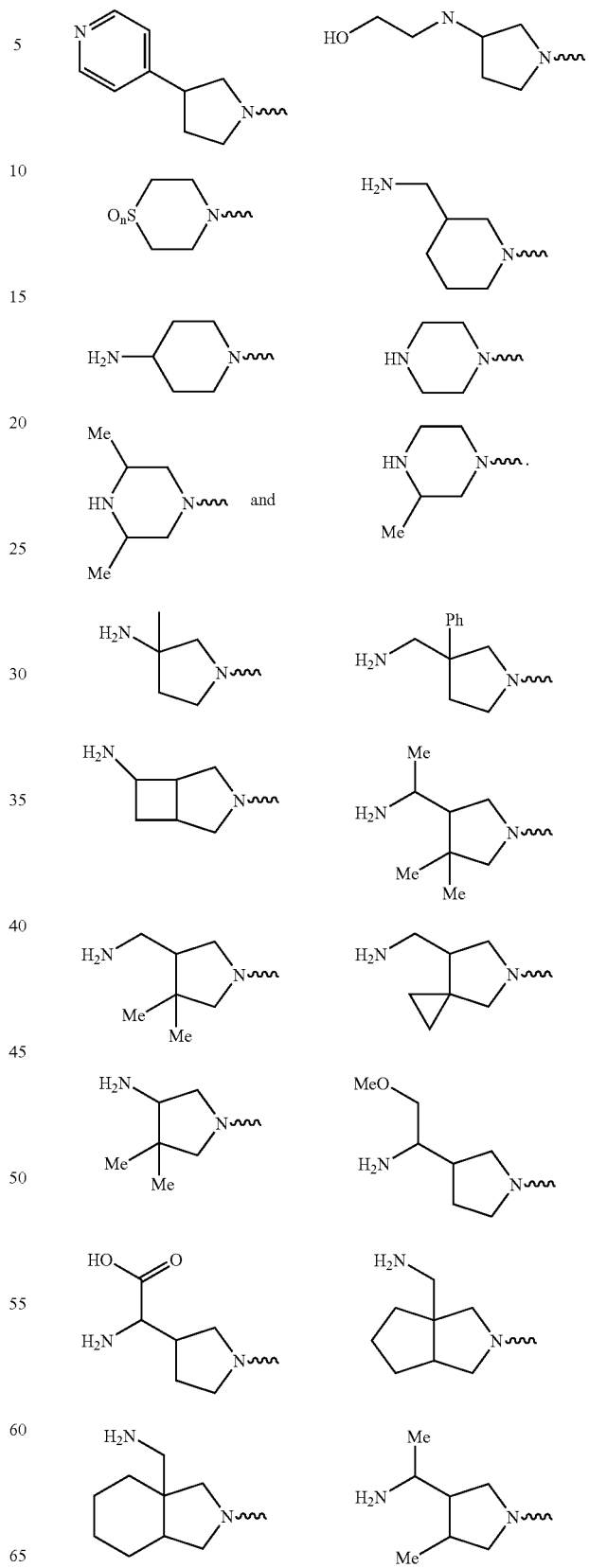

TABLE A-continued
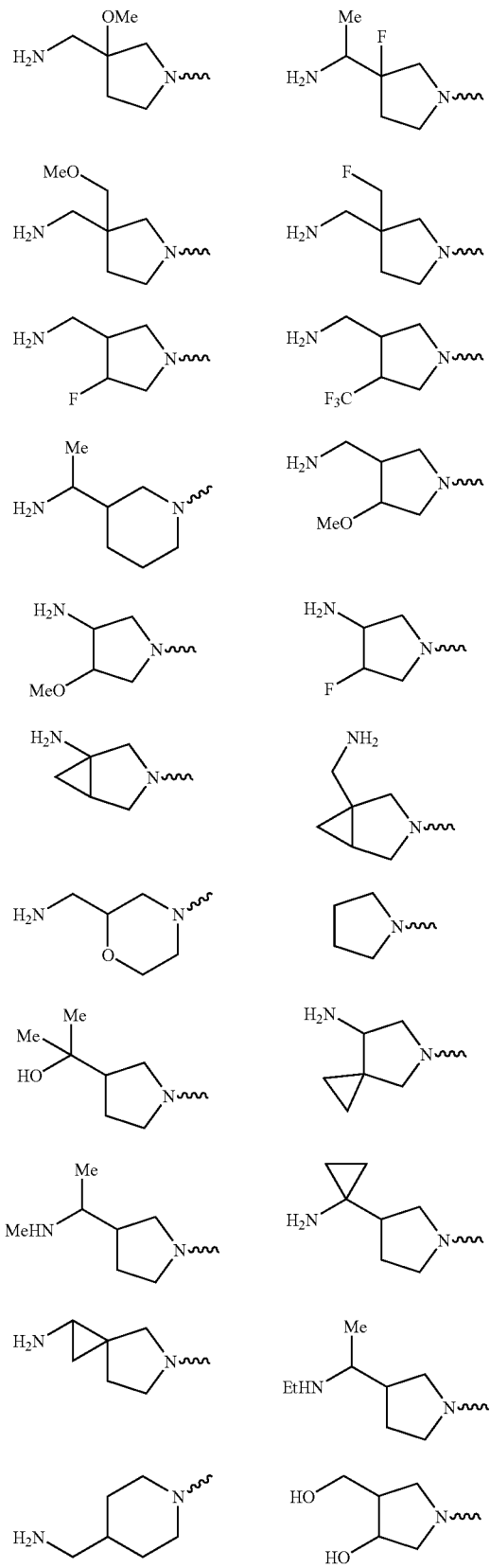
TABLE A-continued
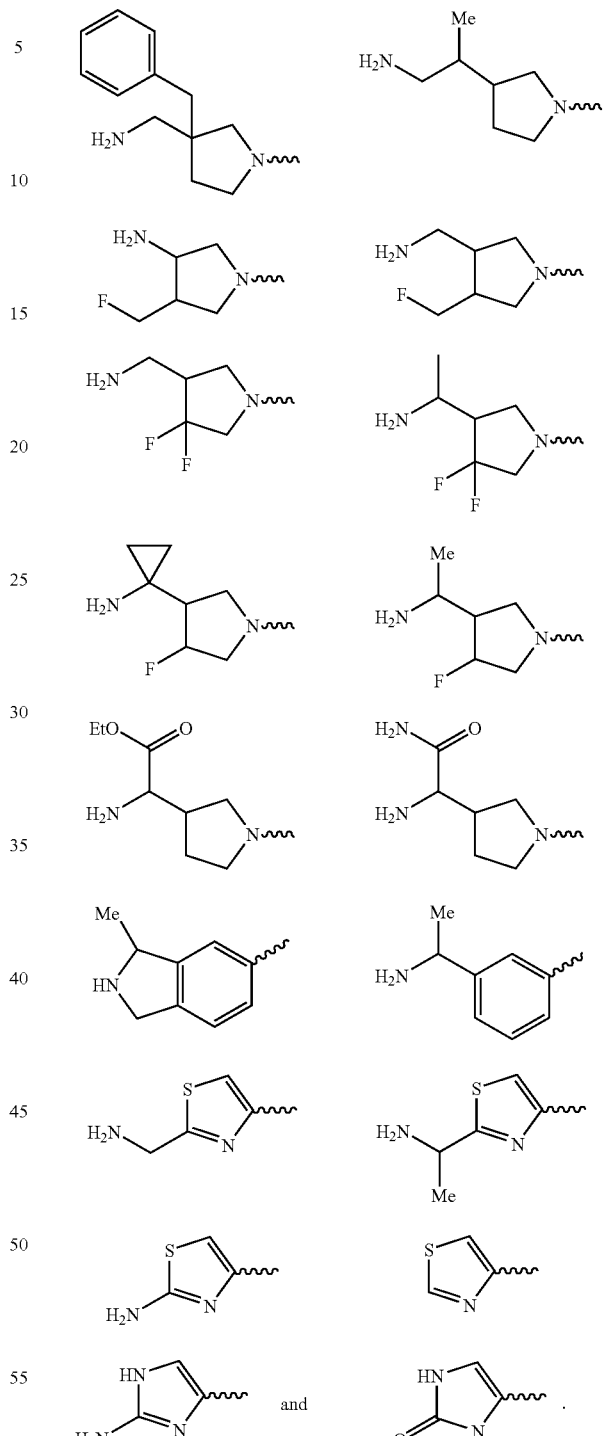
The foregoing groups are especially preferred as $R_7$ side chains on the quinazoline ring system. The heterocycles and heteroaryl groups such as those depicted above are known in the quinolone art and are prepared by literature methods such as *J. Med. Chem.*, 1992;35:1764; *J. Med. Chem.*, 1996;39:3070; *Synlett.*, 1996:1097; and *J. Med. Chem.*, 1986;29:445. Any of the primary or secondary amines shown as substituents on the heteroaryl or heterocyclic groups may be substituted by alkyl, such as methyl, ethyl, isopropyl, and the like.

Some of the compounds of Formula I are capable of forming pharmaceutically acceptable acid addition and/or base salts. All of these forms are within the scope of the present invention and are prepared by art recognized methods. For example, an acid addition salt is prepared by contacting the free base form of the invention compound with a sufficient amount of the desired acid to produce the salt in the conventional manner. Pharmaceutically acceptable acid addition salts of the compounds of Formula I include salts derived from inorganic acids such as hydrochloric, nitric, phosphoric, sulfuric, hydrobromic, hydriodic, hydrofluoric, phosphorous, and the like, as well as the salts derived from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, acetate, trifluoroacetate, propionate, caprylate, isobutyrate, oxalate, malonate, succinate suberate, sebacate, fumarate, maleate, mandelate, benzoate, chlorobenzoate, methylbenzoate, dinitrobenzoate, phthalate, benzensulfonate, toluenesulfonate, phenylacetate, citrate, lactate, tartrate, methanesulfonate, and the like. Also contemplated are salts of amino acids such as arginate and the like, as well as gluconate and galacturonate. All such salts are readily prepared, for example as described by Berge S. M. et al., "Pharmaceutical Salts," *Journal of Pharmaceutical Science,* 1977;66:1–19.

Pharmaceutically acceptable base addition salts are formed with metals or amines, such as alkali and alkaline earth metals or organic amines, when compounds of Formula I have an acidic group such as carboxy. The base addition salts of acidic invention compounds are prepared by contacting the free acid form with a sufficient amount of the desired base to produce the salt in the conventional manner. Typical bases include sodium hydroxide, calcium oxide, diethylamine, and pyridine. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge S. M., supra., 1977).

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

Certain of the compounds of the present invention possess one or more chiral centers. Each center may exist in the R or S configuration. The present invention includes all diastereomeric, enantiomeric, and epimeric forms, as well as the appropriate mixtures thereof. Additionally, the compounds of the present invention may exist as geometric isomers. The present invention includes all cis, trans, syn, anti, entgegen (E), and zusammen (Z) isomers, as well as the mixtures thereof.

Structures of representative compounds of the invention are shown below in Table 1.

TABLE 1

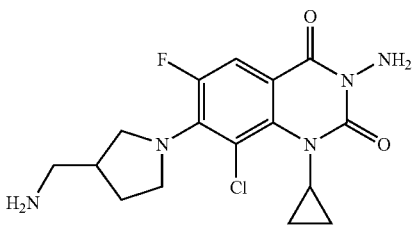

1

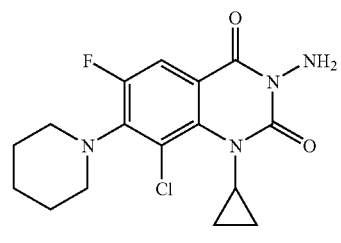

2

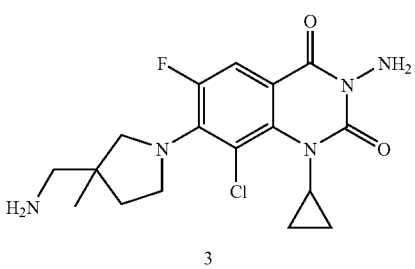

3

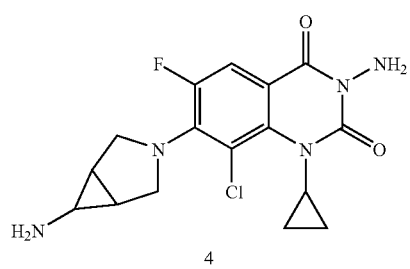

4

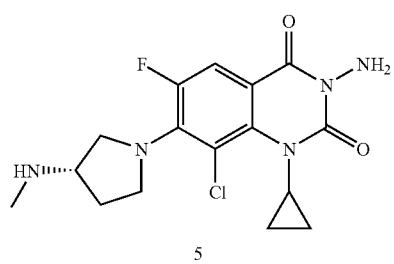

5

TABLE 1-continued
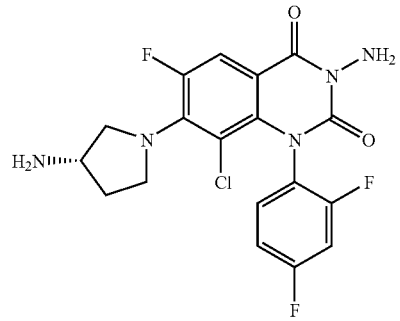
6
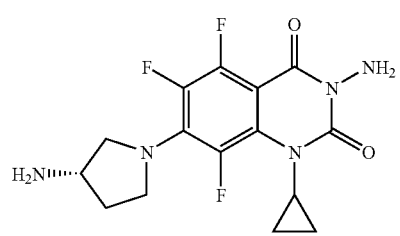
9
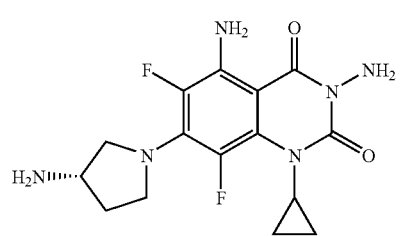
11
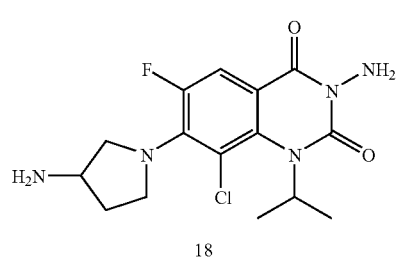
18
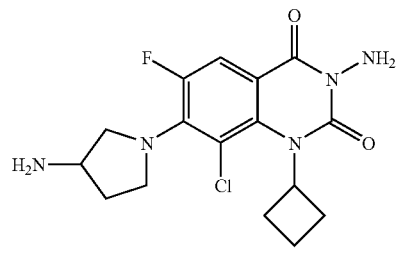
21
TABLE 1-continued
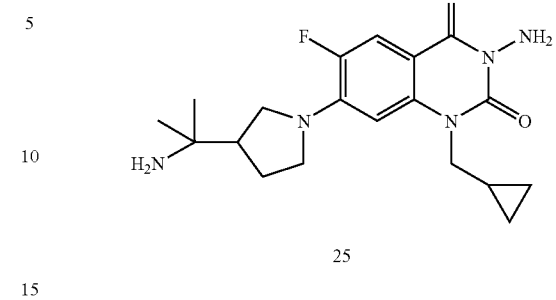
25
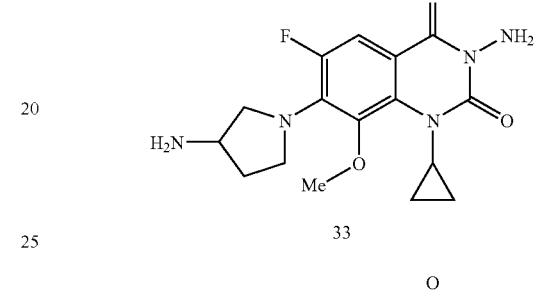
33
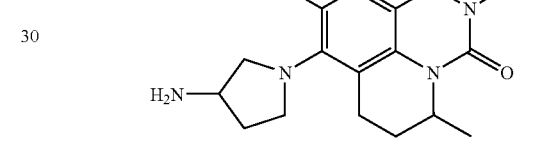
42
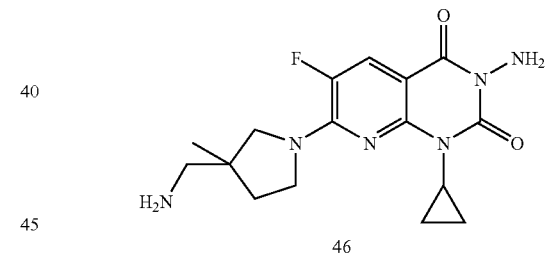
46
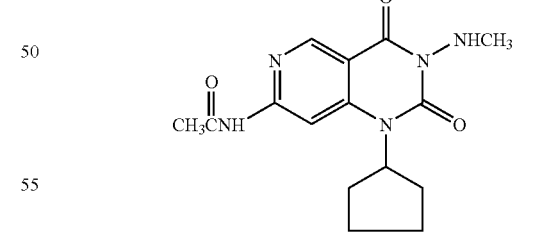
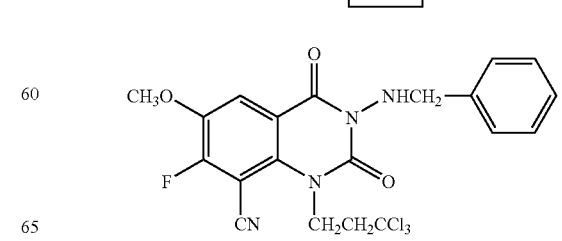

TABLE 1-continued

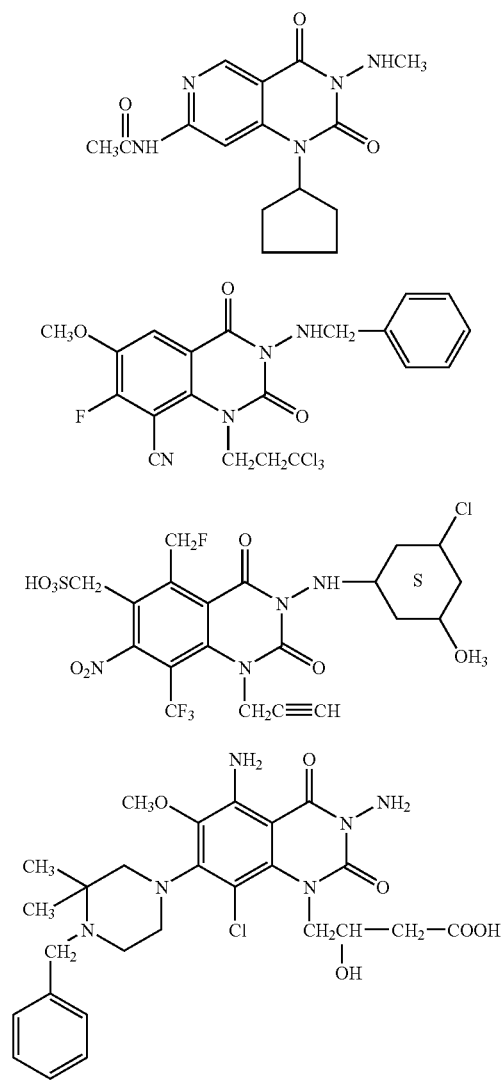

The compounds of Formula I can be prepared utilizing standard synthetic methodology well-known to those skilled in the art of organic chemistry. Many of the compounds have reactive functional groups that generally need to be derivatized with a protecting group in order to avoid unwanted side reactions. For example, functional groups such as alcohols, acid groups, and amines generally are protected while a reaction is carried out at a different site in the molecule, and then the protecting group is subsequently removed following the desired chemical transformation. The use of such protecting groups is standard in organic chemistry synthesis, as described, for example, in T. W. Green and P. G. Wuts, *Protective Groups in Organic Synthesis*, $2^{nd}$ edition, New York City: John Wiley & Sons, 1991. Thus, for example, protecting groups such as the following may be utilized to protect suitable amino, hydroxyl, and other groups of related reactivity: carboxylic acyl groups, such as formyl, acetyl, trifluoroacetyl; alkoxycarbonyl groups, such as ethoxycarbonyl, t-butoxyCarbonyl (BOC), β, β, β-trichloroethoxycarbonyl (TCEC), β-iodoethoxycarbonyl; aryloxycarbonyl groups, such as benzyloxycarbonyl, p-methoxybenzyloxycarbonyl, phenoxycarbonyl; trialkyl silyl groups, such as trimethylsilyl and t-butyldimethylsilyl (TBDMS); and groups such as trityl, tetrahydropyranyl, vinyloxycarbonyl, o-nitrophenylsulfenyl, diphenylphosphinyl, p-toluenesulfonyl, and benzyl may all be utilized. The protecting group may be removed, after completion of the synthetic reaction of interest, by procedures known to those skilled in the art. For example, a BOC group may be removed by acidolysis, a trityl group by acidolysis or hydrogenolysis, TBDMS by treatment with fluoride ions, and TCEC by treatment with zinc.

Illustrations of typical preparations of compounds of the present invention having Formula I are shown in Schemes 1–22. Typical heterocyclic and aromatic side chains defined by $R_7$ in Formula I are prepared as described in Schemes A1–A8. All of the 3-aminoquinazoline-2,4-diones of the invention may be prepared from appropriately substituted benzoic acid starting materials. Protecting groups (referred to in the schemes as "Pro") may be used when appropriate throughout many of the schemes. Although specifically noted in certain schemes, the appropriate use and choice of protecting groups is well-known by those skilled in the art, and is not limited to the specific illustrations shown below. It should also be understood that such protecting groups not only serve to protect chemically reactive sites, but also to enhance solubility or otherwise change physical properties of the underlying invention compound. A number of general reactions such as oxidations and reductions are not shown in detail in the schemes, but can be carried out by standard methods well-known to those skilled in the art. In general, the starting materials used in the following schemes are obtained from commercial sources, or are readily prepared by standard methods. All cited published articles, patents, books, and the like are incorporated herein by reference.

As shown in Scheme 1, a difluoro substituted benzoic acid is reacted with oxalyl chloride or an equivalent acylating reagent (such as an acid anhydride), and the acid halide or anhydride is reacted with an alcohol (ZOH) to afford the respective ester (Z is $C_1$–$C_6$ alkyl such as methyl, ethyl, isopropyl, etc.). The ester is reacted with an amine, for example, a heterocyclic amine, to produce the desired 4-heterocyclic phenyl derivative. Alternatively, carbocycles and aryls may also be introduced at this 4-position using palladium catalyzed couplings of tin or boronate carbocycles and aryls, with starting materials containing a Br, I, or triflate at the 4-position as described by Suzuki A., *Pure Appl. Chem.*, 1994; 66(2):213–222 and Stille J. K., *Angew. Chem.* 1986; 98(6):504–519.

Reaction of the 2-fluoro benzoic acid analog with a primary amine $R_1NH_2$ affords the corresponding 2-amino benzoic acid ester. The ester group is readily hydrolyzed by reaction with an acid such as hydrochloric acid or a base such as sodium hydroxide to give the corresponding polysubstituted 2-amino benzoic acid. The acid is then coupled to an appropriately protected hydrazine to provide the corresponding amide, which in turn is cyclized to generate the quinazoline-2,4-dione by treatment with, for example, phosgene. At this point, the protecting group may be removed to give the free amine A of Formula I, which can represent a final product of the invention, and which can be further derivatized, if desired, for instance by alkylation with $R_3Cl$.

Alternatively, the quinazoline-2,4-dione may also be metallated at low temperatures with bases such as, for example, NaH, KH, and lithium diisopropylamine, and then alkylated or acylated to provide the corresponding N-protected-mono-substituted ($R_3$) amine. The protecting group (Pro) of the N-protected-mono-substituted amine is removed by conventional methods such as hydrogenation, treatment with acid or base, or metal catalysis to afford invention compound C.

If $R_5$ is a leaving group such as F, it is activated towards displacement with a nucleophile HY-Pro' where Y is N or O and Pro' is a protecting group such as trimethylsilyl. Other $R_5$ groups such as chlorine, bromine, or sulfonyl are also good leaving groups. The displacement generally is carried out in a solvent such as ethanol, DMSO, DMF, THF, and at a temperature of about 0° C. to 120° C.

The protecting groups (Pro) may be selectively removed by hydrogenation, acid or base treatment, metal catalysis, or such other standard methods. When Pro is benzyl, the benzyl may be removed with Pd/C and hydrogen. A t-butyl carbamate group may be removed by alcoholic HCl, TFA, or TFA in dichloromethane, ethyl acetate or diethyl ether. Allylic carbamates may be removed by $PhSiH_3$ and Pd catalyst. Solvents such as alcohol, THF, alcohol/THF, alcohol/THF/DMF, diethyl ether, etc. are generally employed in such protecting group cleavage reactions.

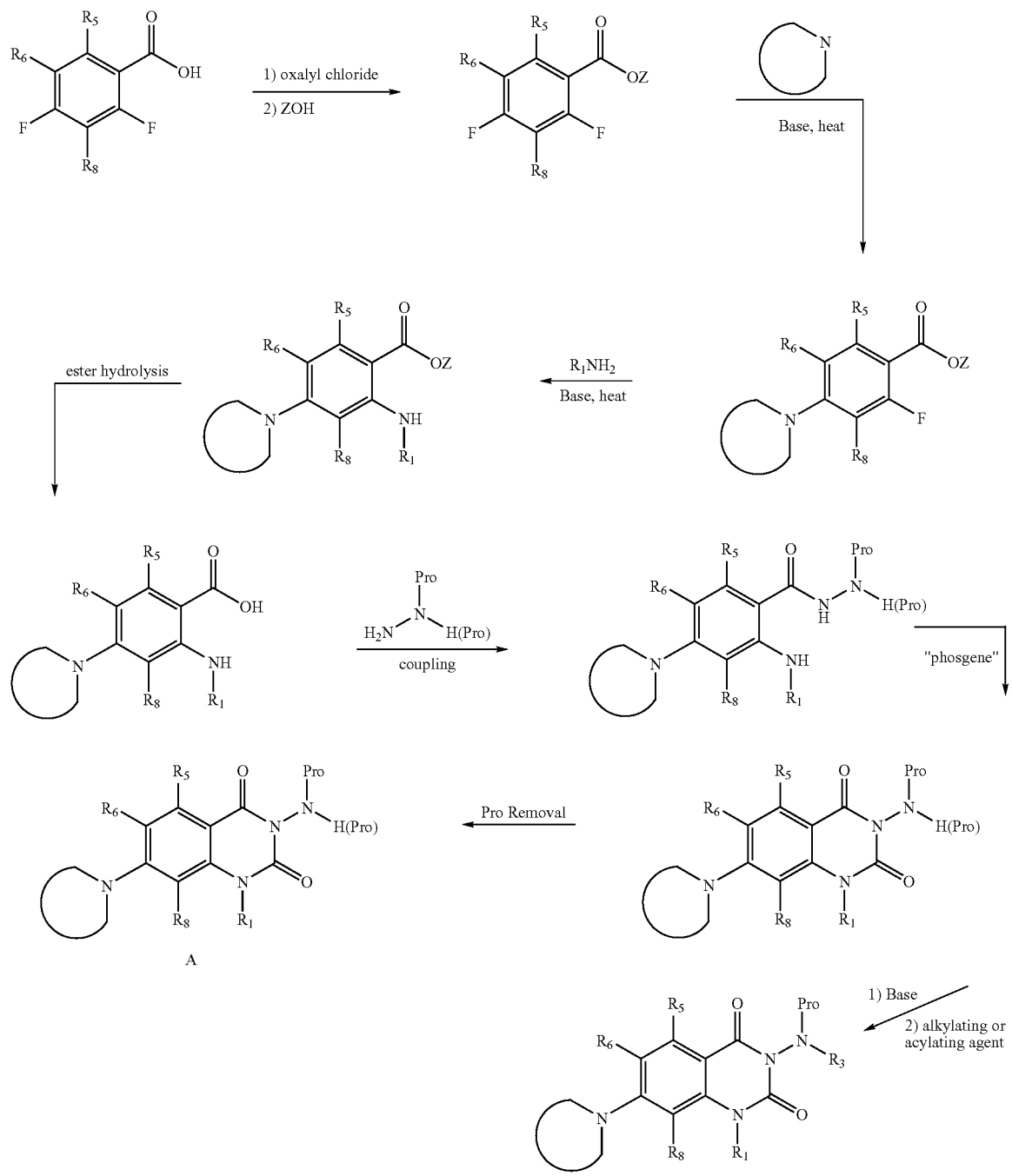

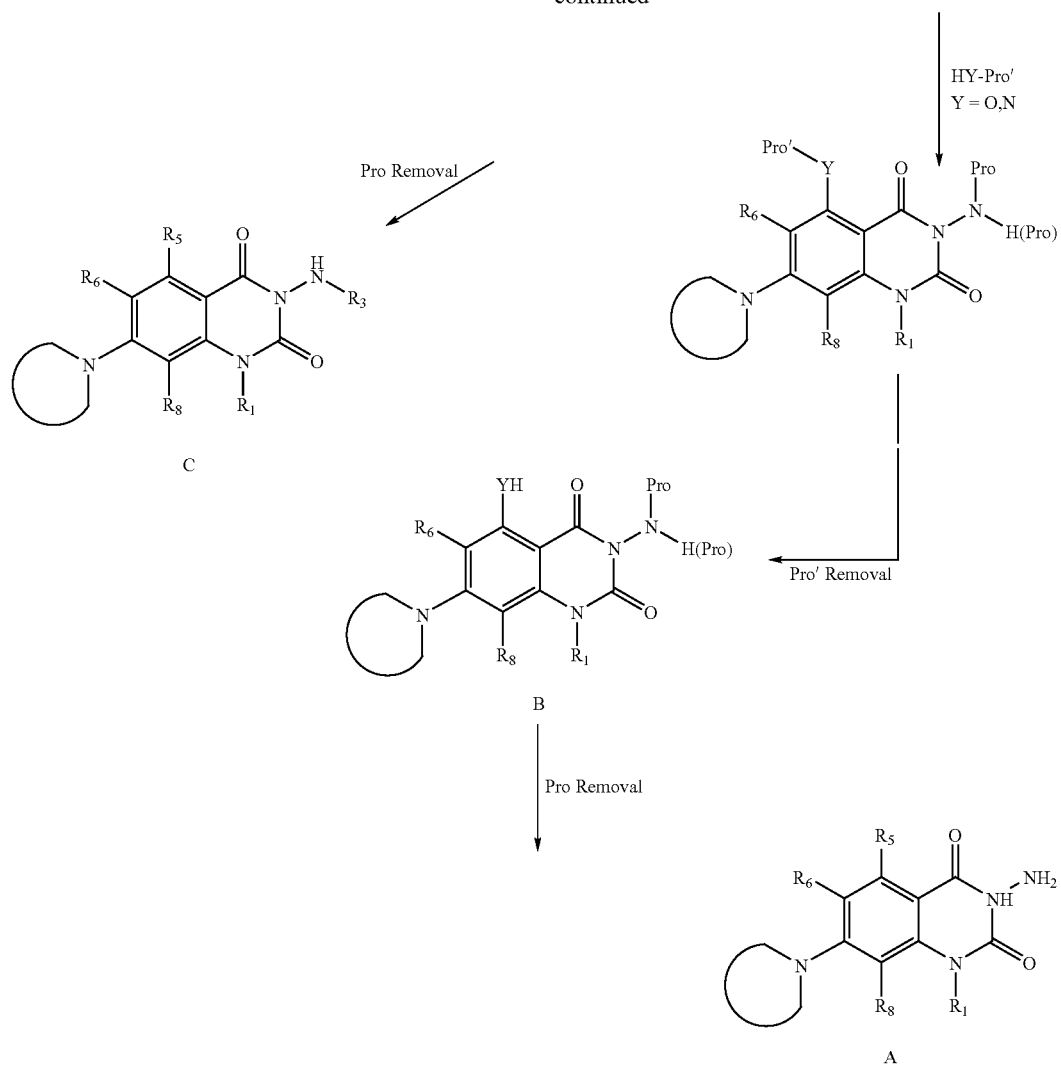

In Scheme 2, an ortho-aminobenzoic acid is utilized as the starting material, and is alkylated on the amino group. For example, when $R_1$ is cyclopropyl, the alkylation is carried out according to the method of Gillaspy (*Tetrahedon Letters*, 1995:7399) to provide the cyclopropyl amine. When $R_1$ is phenyl or substituted phenyl, the respective amine is prepared from the ortho-fluorobenzoic acid using a base, such as, lithium diisopropylamide or Li-hexamethyl disilazide, and the appropriate aryl amine ($R_1NH_2$). When $R_1$ is any alkyl group, such as t-butyl or isopropyl, the $R_1$ can be introduced by reacting the amine and ortho halo benzoic acid with a Cu catalyst such as copper, bronze, or cupric acetate in the presence of a base such as potassium acetate, triethylamine, or pyridine.

The resulting $R_1$-substituted amino benzoic acid is then coupled to an appropriately protected hydrazine to provide the corresponding benzamide using methods described in the literature. The corresponding amide can be further reacted, if $R_7$ is a leaving group such as fluoro, with various heterocyclic amines (e.g., piperidine or pyrrolidine) to form the desired 4-heterocyclic benzamide derivative. Alternatively, carbocycles and aryls (e.g., cyclobutyl or phenyl) may also be introduced at this 4-position using palladium catalyzed couplings of tin or boronate carbocycles and aryls, if the starting material contains a Br, I, or triflate at the 4-position.

The 4-substituted benzamide derivative is then cyclized to generate the quinazoline-2,4-dione by reaction with carbonyldiimidazole (CDI), phosgene, triphosgene or the like in ethereal solvents such as diethyl ether, chlorinated hydrocarbons such as dichloromethane, or aromatic hydrocarbons such as toluene, in the presence of a base such as triethylamine or $NaHCO_3$.

Alternatively, the corresponding amide is first cyclized and then the $R_7$ halo group is displaced by reaction with a carbocyclic amine

to afford the same product. Deprotection by conventional methods provides the invention compound A.

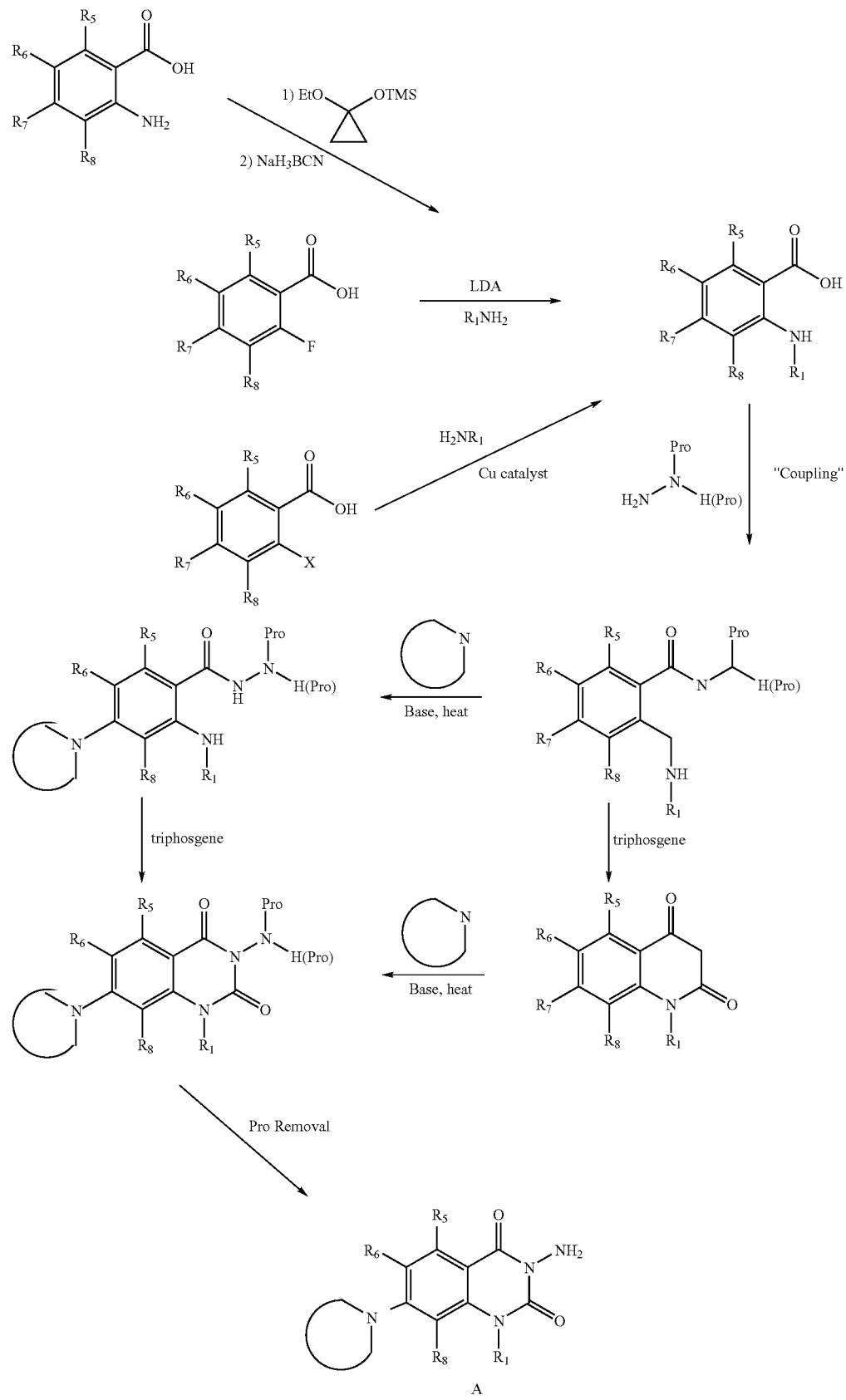

Scheme 3 illustrates alkylation at the 1-position of a 3-aminoquinazolin-2,4-dione to provide invention compounds wherein $R_1$ is alkyl. A 2-aminobenzoic acid is reacted with an N,N-diprotected hydrazine such as dibenzyl hydrazine ($H_2N$—$NBn_2$) to provide the corresponding N-protected amide. This intermediate can then be reacted with phosgene or phosgene/base in an ethereal solvent, or with a phosgene equivalent such as triphosgene in a chlorinated hydrocarbon such as dichloromethane, to give the quinazoline-2,4-dione. The alkylation of the quinazoline-2,4-dione to provide a 1-alkylated-quinazoline-2,4-dione is accomplished by reaction with an alkyl halide as described by Bouzard, supra., 1990. Typically, such reactions are carried out in THF, ether, DMSO, an alkanol, or DMF, and in the presence of a base. Typical alkyl halides ($R_1X$ where X is halo) include ethyl iodide, ethyl bromide, cyclopropyl iodide, n-decyl bromide, and the like. Typical bases include sodium hydride, potassium carbonate, and the like. Conversion of the 1-alkylated-quinazoline-2,4-dione to other invention compounds (and removal of protecting groups such as benzyl Bn) can be carried out according to Scheme 1, for example, to give the corresponding 1-alkyl ($R_1$=alkyl) 3-amino ($NH_2$) compounds such as A.

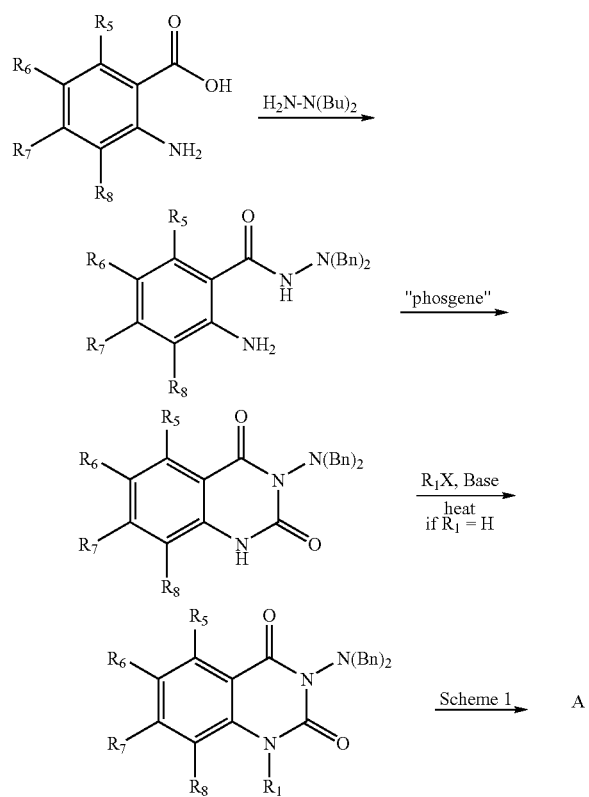

Displacement of leaving groups located at the 7-position of the quinazolin (e.g., $R_7$=halo) as shown in Schemes 1 and 2 is not limited to nitrogen heterocycles. Other nucleophiles (Nu) such as $CH_3O$—, $N_3$—, R'R"NH, R'—$NH_2$, and R'S— (where R' and R" are defined above) also displace a leaving group such as F, Cl, or $NO_2$ at the 7-position as shown in Scheme 4. When the leaving group is a triflate or higher halide, organo tin reagents or organoboronates may be used with palladium catalysts to deliver a carbon nucleophile. The methodology shown in Scheme 4 follows that of Stille et al., *Angew. Chem. Int. Ed. Eng.,* 1986; 25:508 and is exemplified by Mitchell (*Synthesis*, 1992:803).

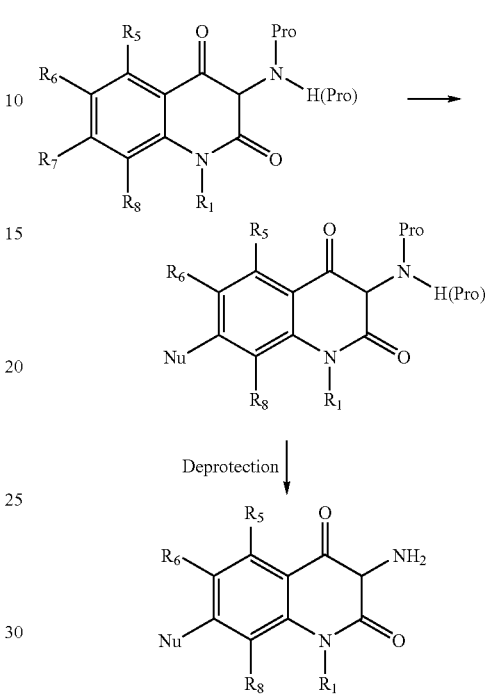

All of the chemistry depicted and described in Schemes 1 to 4 is applicable to make compounds of Formula I wherein J and K both are carbon, or where one or both of J and K are N. When either J or K is nitrogen, the displacement reactions described above is even more facile than when J and K are carbon.

Compounds of the invention where J and/or K of Formula I are nitrogen may be prepared by the Schemes 1, 2, 3, and 4, or by routes which take advantage of the activation of leaving groups ortho and para to the J and/or K nitrogen atom. Such routes will systematically introduce $R_7$ and $R_1$ groups as desired. This methodology also applies to cases in Formula I where K—$R_8$ is C—H or C—F and J—$R_6$ is C—F. Such systematic substitutions are illustrated in Scheme 5. For example, a pyridine amide has leaving groups such as halo on both sides of the nitrogen. Such groups are generally chlorine, but fluorine, alkylthiol, and sulfoxides such as methyl sulfoxides are also good leaving groups for such compounds. These leaving groups may be sequentially displaced based on reactivity. In Scheme 5, where J=N or J—$R_6$=CF, the 4-chloro (para to the aminocarbonyl group) is displaced preferentially (relative to the 2-chloro group) using a nucleophilic amine such as diethylamine, pyrrolidine, methylpiperazine, and the like to give the corresponding amino substituted analog. This analog is then reacted with $R_1NH_2$ to displace the second leaving group (e.g., the 2-chloro group). The resulting 2,6-disubstituted-pyridylamide is then reacted with CDI, phosgene, or other phosgene equivalents to form the cyclized quinazoline product. Amination at the 3-position NH is achieved by reaction with any number of aminating reagents such as ammonia and N-alkylamines, for example, as described by Kloetzer (*Sci. Pharm.,* 1984; 52:46–50) to give the corresponding invention compound.

Scheme 5

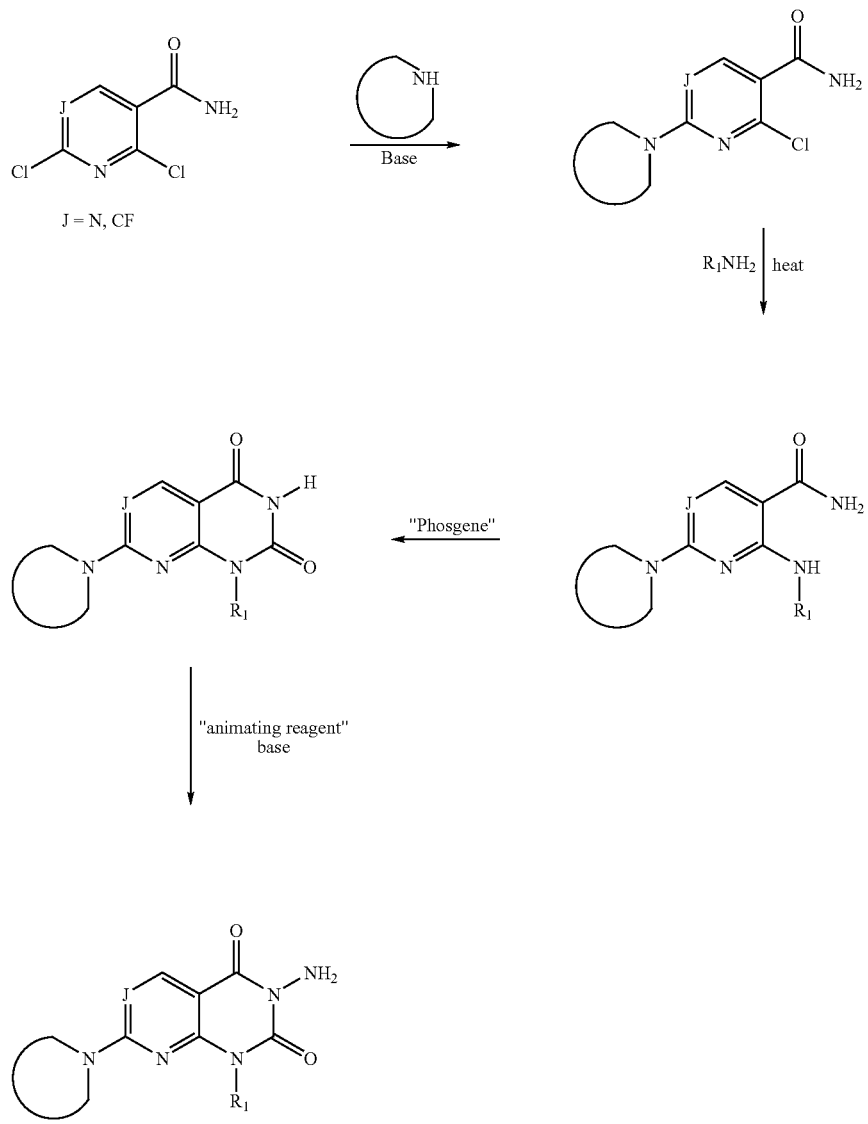

Tricyclic compounds (i.e., where $R_1$ and $R_8$ in Formula I are taken together with the atoms to which they are attached to form a ring) can be prepared according to Schemes 6 and 7. Schemes 6 and 7 differ in the introduction of the $R_1$ substitutions in Structures B and C wherein $R_1=R_1'$ and $R_1$ is as defined above for Formula I and $R_1'$ is alkyl, alkenyl, alkynyl, aryl, cycloalkyl, heteroaryl, and the like. In Scheme 6, the ortho-fluoro nitro compound (other leaving groups such as chlorine, bromine, and sulfonyl may also be employed in place of fluoro) is displaced by the α-nucleophile substituted ester (where Q is a nucleophile Nu such as methyl or methoxy). The nitro group is then reduced using, for example, Raney Ni, $H_2$ over Pd/C, or an active metal in acid such as iron or tin in HCl or acetic acid. The newly formed amine readily cyclizes with the ester (other acid analogs may be employed such as thioesters, amides, and the like). The cyclized product is then reduced with hydride reducing agents such as $LiAlH_4$ and the like to produce the dihydroquinoline derivative, which in turn is reacted with chloral hydrate and then an acid to form the dione ring. The dione ring is subsequently opened using, for example, sodium hydroxide and hydrogen peroxide to give the benzoic acid. The 3-aminoquinazolinedione ring is then prepared using the chemistry described in Schemes 2, 3, or 5 to give the invention compound B, where $R_3'$ is alkyl, alkenyl, cycloalkyl, aryl, and heteroaryl.

Scheme 6

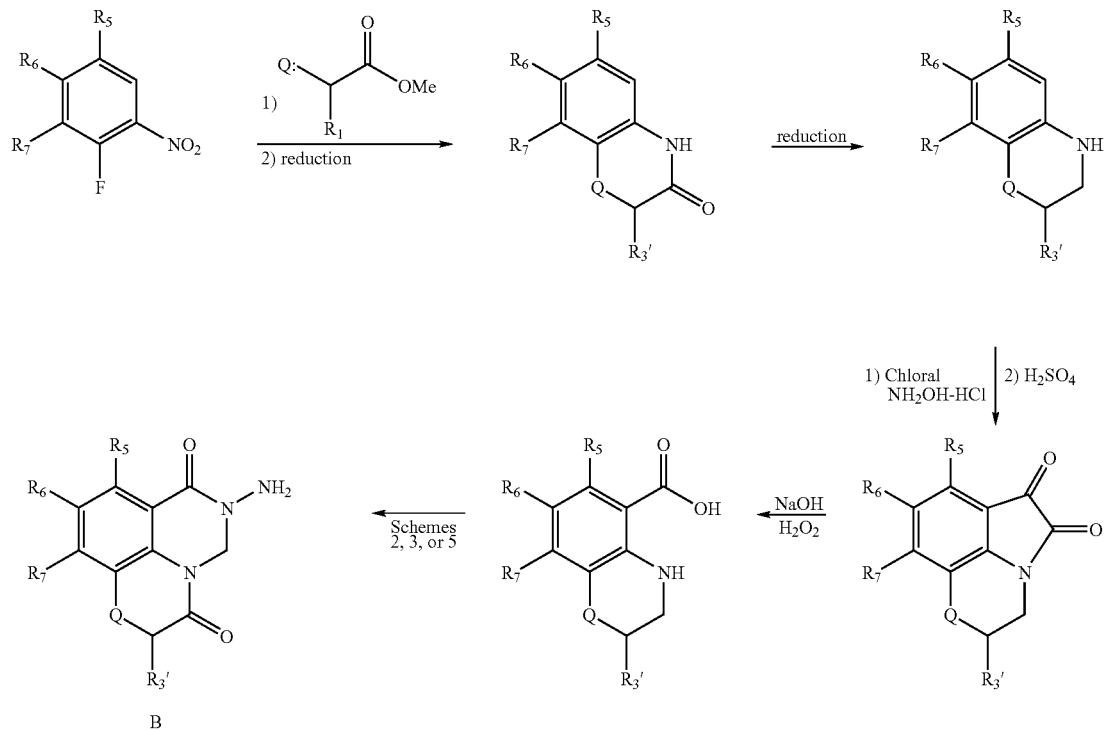

In a similar series of reactions depicted in Scheme 7, the ortho-fluoro nitro compound is reacted with an α-nucleophile substituted ketone, and the resulting product is likewise reduced. In this sequence, the resulting aniline forms a cyclic imine, which is further reduced with $H_2$ on Pd/C or by chemical hydride reducing agents such as sodium borohydride or sodium cyanoborohydride to give the dihydroquinoline. Such reductive aminations are well-known in the art and are typically performed in THF, alcohol, water alcohol mixtures, or in water DMF mixtures. The remaining steps to produce C follow those of Scheme 6. When the C-7 substituent is a leaving group (e.g., $R_7$=halo), compounds B and C may be further reacted with nucleophiles (such as pyrrolidine or piperidine) to give compounds of Formula I as in the previous schemes.

Scheme 7

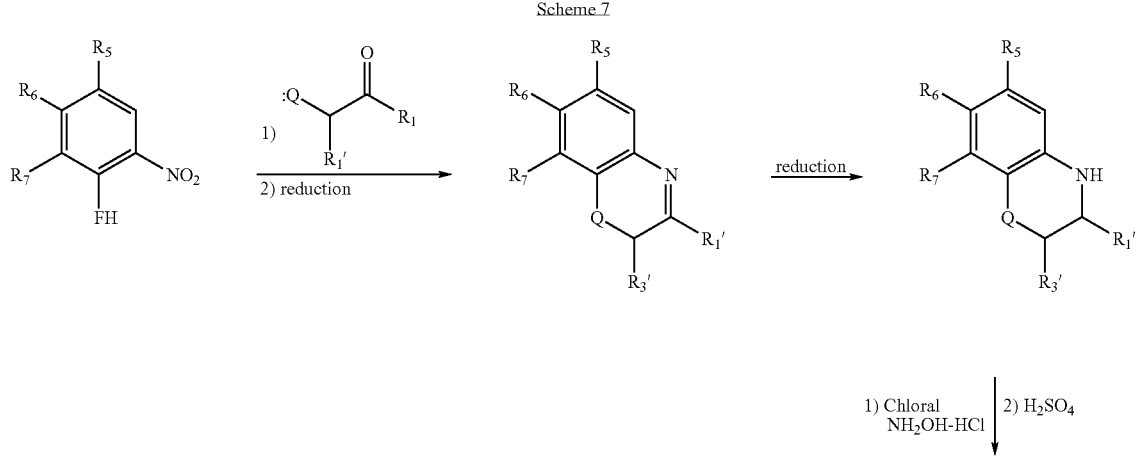

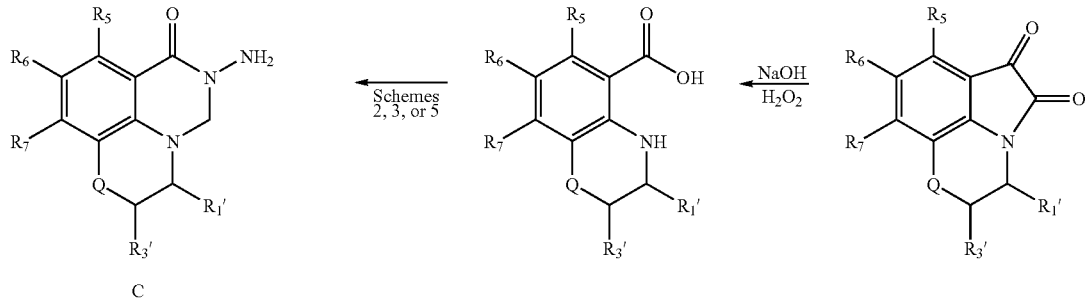

In Scheme 8, the target tricylic compounds as C are prepared in a slightly different manner. In this case, the nucleophile Q (such as hydroxymethyl) is attached to the phenyl ring of the starting aniline, and a leaving group L (such as halo) is attached alpha to the ketone reactant. The nucleophile may be activated with bases such as sodium hydride or potassium hydride, triethylamine or 1,8-diazabicyclo[5.4.0]-undec-7-ene (DBU), or sodium, potassium, or cesium carbonate to displace the leaving group L. In this sequence, the resulting aniline forms a cyclic imine, which is further reduced with $H_2$ on Pd/C or by chemical hydride reducing agents such as sodium borohydride or sodium cyanoborohydride to give a dihydroquinoline. Such reductive aminations are well-known in the art and are typically performed in THF, alcohol, water alcohol mixtures, or in water DMF mixtures. The dihydroquinoline intermediate is reacted with chloral hydrate, and then an acid to form the dione ring. The dione ring is subsequently opened by reaction with a base, for example sodium hydroxide and hydrogen peroxide, to give the benzoic acid. The 3-aminoquinazolindione ring is then prepared by first forming an ester on the benzoic acid as in Scheme 2, followed by reaction of the benzoic acid ester with chlorosulfonylisocyanate or the like at temperatures of 0° C. and below, followed by treatment with a base such as triethylamine or diisopropylethylamine. Amination can then be carried out in the same manner as described in Scheme 5 to provide compounds of structure C. When $R_7$ is a leaving group such as Cl or F, the invention compounds of structures B (in Scheme 6) and D (in Scheme 8) can be prepared by coupling to the $R_7$ side chain, e.g., various heterocyclic amines

to produce the desired derivatives. Alternatively, carbocycles and aryls may also be introduced as $R_7$ side chains using palladium catalyzed couplings with tin or bornate carbocycles and aryls, for example when $R_7$ is a Br, I, or triflate.

Scheme 8

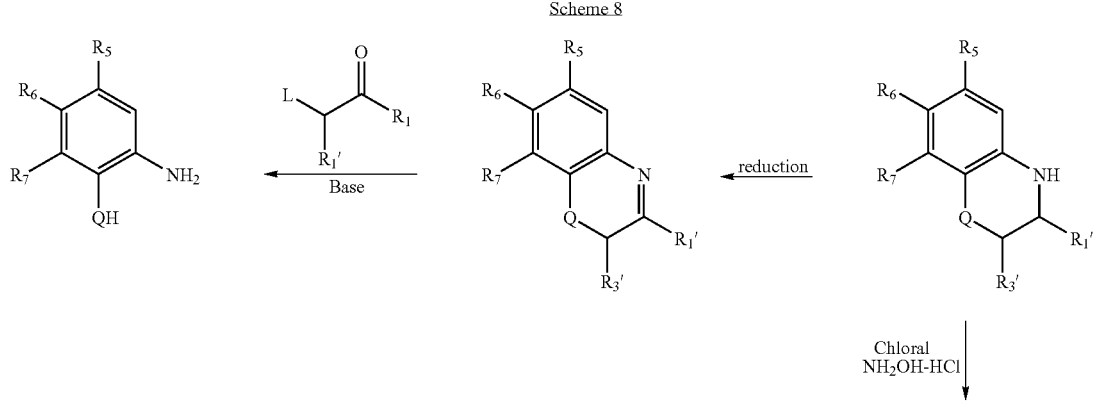

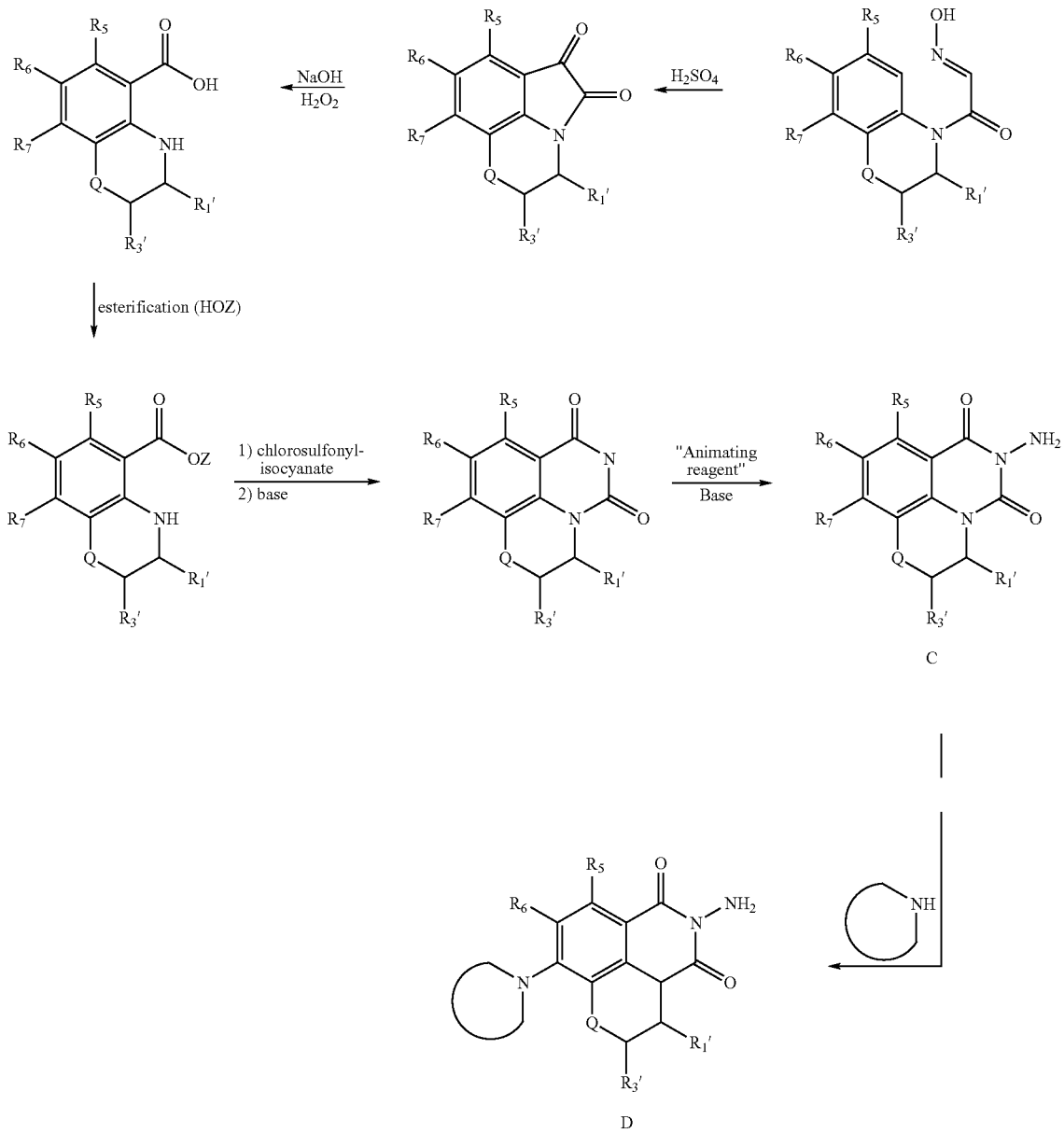

It should be noted from Schemes 6, 7, and 8 that $R_1'$ and $R_3'$ will form chiral centers, giving R and S enantiomers and diastereomers. Such enantiomers or diastereomers may be separated, if desired, at any stage by chiral HPLC, or by other conventional resolution techniques. Resolution of the precursor benzoic acid may also be accomplished by fractional crystallization using mandelic acid, tartaric acid, or other chiral, optically pure acid bearing resolving agents. Chiral amides may also be prepared from the benzoic acids using chiral amines such as camphorsulfonamide, benzylamine, or the like. The isomers can then be separated and the chiral amide hydrolyzed as desired.

Scheme 9 illustrates synthesis of compounds of Formula I wherein one or both of $R_6$ and $R_8$ are halo via halogenation.

The halogenation is carried out on a 2-aminobenzoic acid where one or both of $R_6$ and $R_8$ is hydrogen. If both $R_6$ and $R_8$ in the benzoic acid are H, then halogenation can be accomplished at both positions selectively or simultaneously. Thus, for example, chlorination at $R_6$ or $R_8$ is achieved by reaction of the benzoic acid with N-chlorosuccinamide, t-butylhypochlorite, chlorine gas, and the like. Similarly, bromination at $R_6$ and $R_8$ can also be accomplished by reaction of the benzoic acid with $Br_2$, N-bromosuccinimide, and the like. Such halogenations are well-known in the art. Halogenation provides the respective mono- or dihalo compound. The halogenated benzoic acid can be further reacted as shown in Schemes 1 and 2 to provide the quinazoline-2,4-diones of Formula I.

Scheme 9

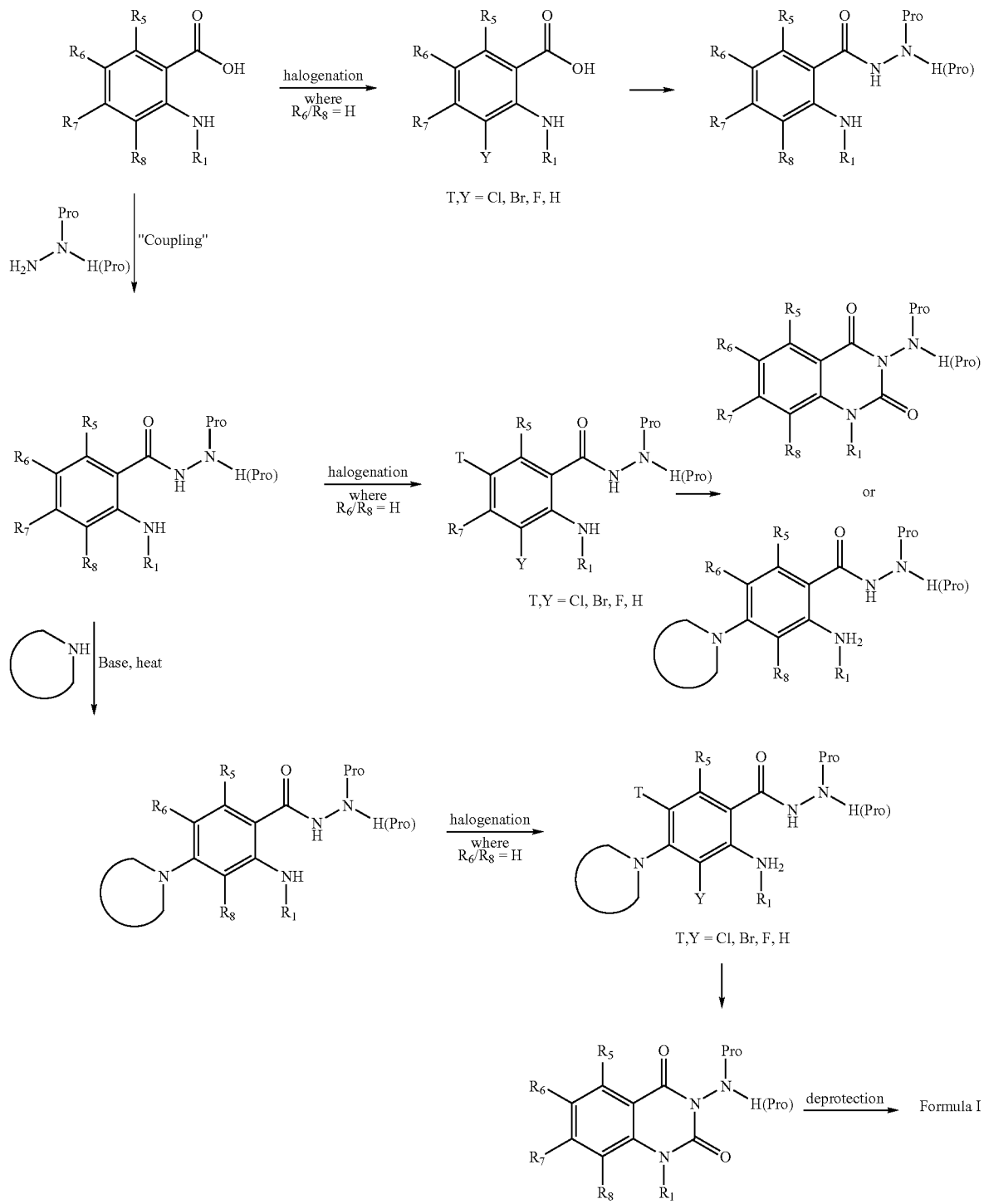

In Scheme 10, compounds where $R_8$ is H are halogenated as described in Scheme 9 to provide the corresponding 3-halo-2-aminobenzoic acid (Y=halo). This intermediate can then be diazotized by reaction of the 2-amino group with sodium nitrite or t-butyl nitrite, which is then converted to a 2-halobenzoic acid in the presence of an appropriate sodium, potassium, or copper salt such as sodium iodide, potassium chloride, and the like. The resulting 2,3-dihalobenzoic acid (where X and Y both are halo) is then converted to the 3-halo-2-aminobenzoic acid by reaction with an amine $R_1NH_2$ in the presence of a copper catalyst. The 3-halo-2-aminobenzoic acid is converted to an amide and cyclized to the corresponding 8-halo-3-amino-quinazolin-2,4-dione, as illustrated in Scheme 2.

Scheme 10

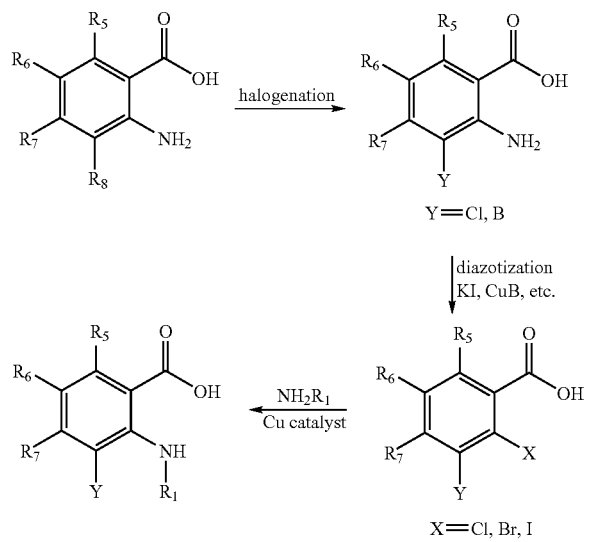

Compounds of Formula I wherein $R_6$ and/or $R_8$ is halo such as chloro or bromo are readily dehalogenated by reaction with metal catalysts under hydrogen pressure (Scheme 11). Suitable catalysts include the many variations of Pd on carbon, Raney nickel, or other reagents that are well-known to effect such dehalogenation.

Scheme 11

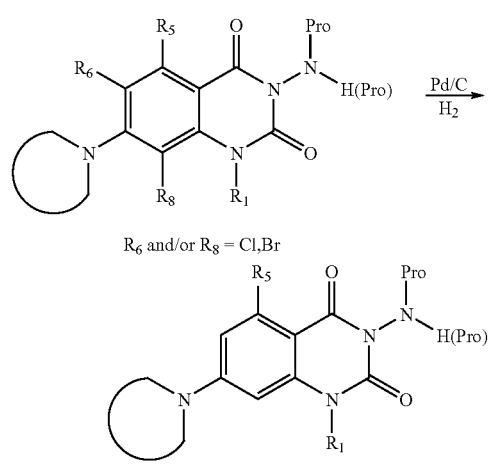

Compounds of Formula I wherein $R_6$ and/or $R_8$ are hydrogen can be halogenated to give the mono- or dihalo compound (e.g., $R_6$ or $R_8$=Cl or Br). The invention compounds are preferably prepared by first halogenating a benzoic acid derivative, and then cyclizing the halogenated benzoate (Scheme 12). If both $R_6$ and $R_8$ are H, then halogenation can be accomplished at both positions selectively or simultaneously. Halogenations can be carried out as described above for Scheme 10. The resulting compound is then converted to the 2-substituted-aminobenzoic acid as depicted in Scheme 1, which is subsequently cyclized and aminated.

Scheme 12

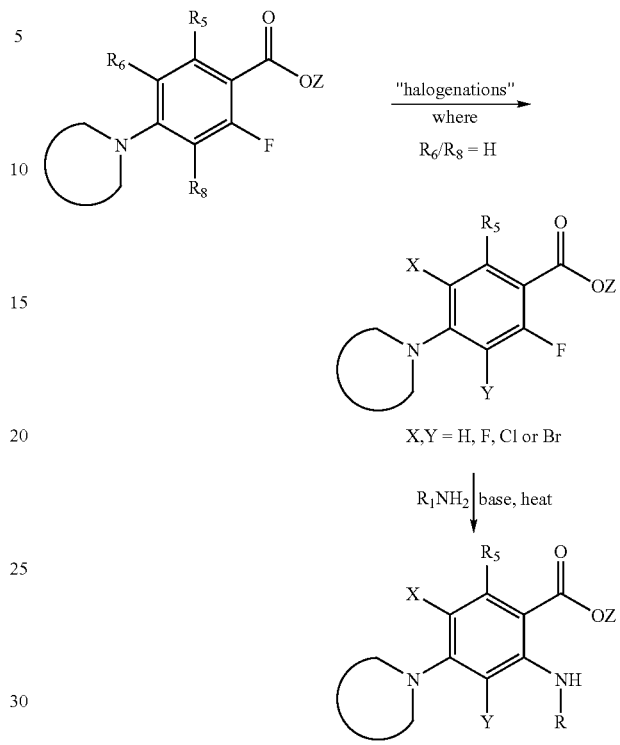

Z is an ester forming group such as alkyl or benzyl.

Invention compounds of Formula I can also be prepared as shown in Scheme 13. Substituted benzoic acids can be converted into esters (where Z is an ester forming group such as alkyl or benzyl) by a number of methods known by those skilled in the art. The ester is reacted with an isocyanate such as trimethylsilylisocyanate, chlorosulfanyl isocyanate, and chlorocarbonyl isocyanate, followed by treatment with a base such as triethylamine, sodium t-butoxide or the like, to provide a quinazoline-2,4-dione. The quinazoline-2,4-dione can be aminated by reaction with an aminating agent such as ammonia as described in Scheme 5 to generate the corresponding 3-aminoquinazoline-2,4-dione. This compound may be further reacted, when $R_7$ is a leaving group such as fluoro, with various heterocyclic amines. Again, carbocycles and aryls may also be introduced at $R_7$ if $R_7$ is a Br, I, or triflate, using palladium catalyzed couplings of tin or boronate carbocycles and aryls. Removal of any protecting groups (Pro) by normal means provides invention compounds such as A, as described above in Scheme 1.

Scheme 13

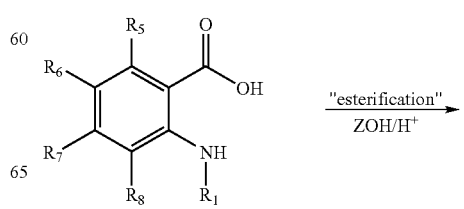

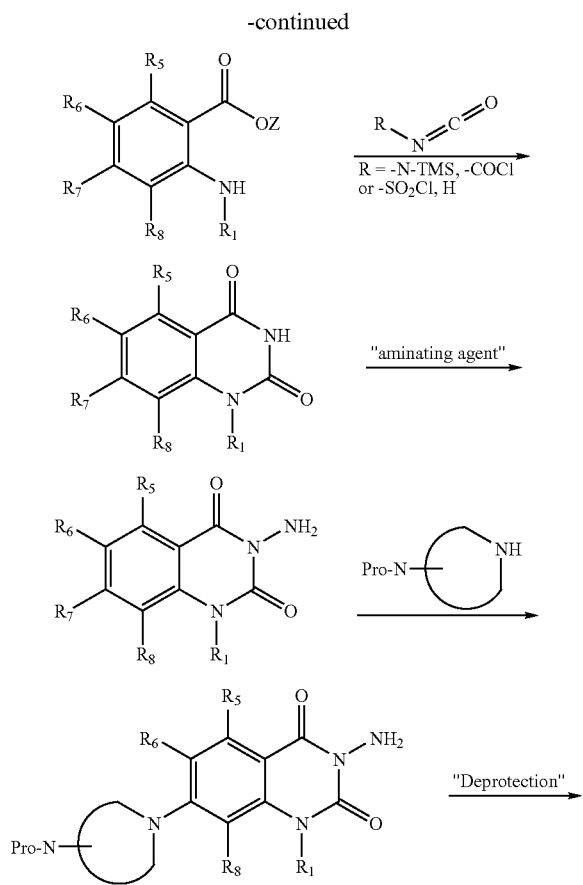

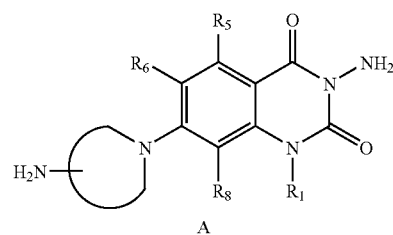

Invention compounds of Formula I having a cyano substituent can be prepared as shown in Scheme 14. For example, a benzoic acid wherein $R_8$ is hydrogen can be metallated with a strong base such as lithium hexamethyldisilazane or lithium diisopropylamine. The resulting metallated intermediate can then be quenched with dimethylformamide or an equivalent to provide an aldehyde. The aldehyde can be converted to an oxime by reaction with an alkoxy amine (other electrophiles such as alkyl halides, activated amides, esters and halide sources such as 1,2-dichloro-tetrafluoroethane may also be employed to provide other benzoic acid derivatives that can be used as defined in Schemes 1, 2, 13, and 15). The oxime is converted into a cyano group under the cyclization conditions required to form the quinazolinedione ring system (e.g., reaction with phosgene) as described in Schemes 1, 12, and 13. Deprotection provides invention compounds where $R_8$ is —CN.

Scheme 14

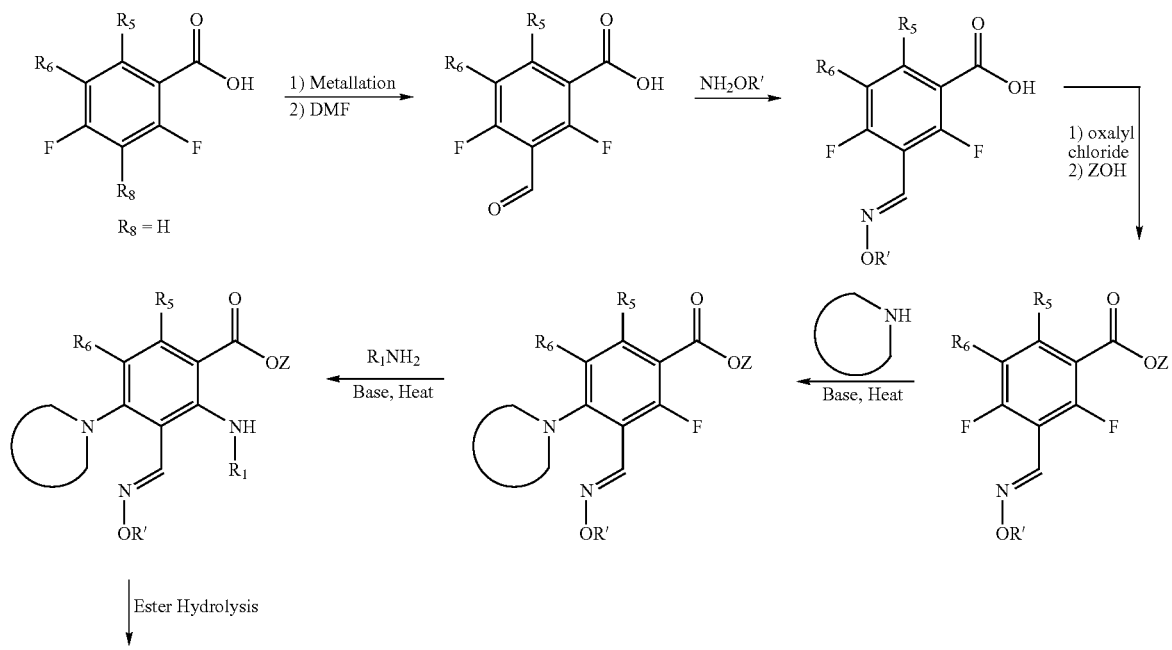

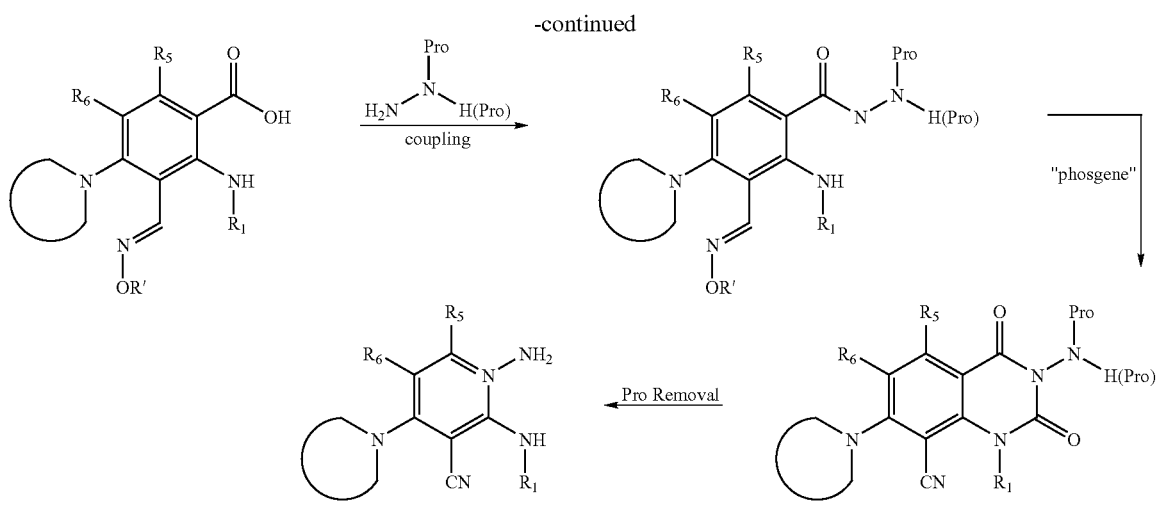

Another alternative for preparing invention compounds is illustrated in Scheme 15. Appropriately substituted benzoic acids can be converted into benzamides by any number of methods as described above. A benzamide can then be treated with oxalyl chloride in a chlorinated solvent such as dichloroethane or an equivalent to provide an isocyanate. The isocyanate is reacted with a substituted primary amine to give a benzoyl substituted urea. This intermediate can be cyclized to form a quinazolinedione ring system by reaction with sodium hydride, potassium hexamethyldisilazane or other non-nucleophilic bases, generally in a solvent such as tetrahydrofuran (THF)/dimethylformamide, THF with 18-crown-6, THF/dioxane, THF/glyme, THF/diglyme, dimethoxyethane/toluene or an equivalent. The quinazo- linedione can then be aminated by reaction with any number of aminating reagents as described by Kloetzer (*Sci. Pharm.*, 1984; 52:46–50). The resulting 3-aminoquinazolinedione ring system can then be readily coupled with an appropriately substituted heterocyclic amine (such as those noted above in Table A) by reaction in the presence of a base such as triethyl amine, diisopropylethyl amine, tetramethyl guanidine, and the like in solvents such as dimethyl sulfoxide, dimethylformamide, dimethylacetamide, sulfolane or the equivalent. Any protecting group associated with the heterocyclic amine side chain is then removed by methods known to those skilled in the art to provide invention compounds having Structure A.

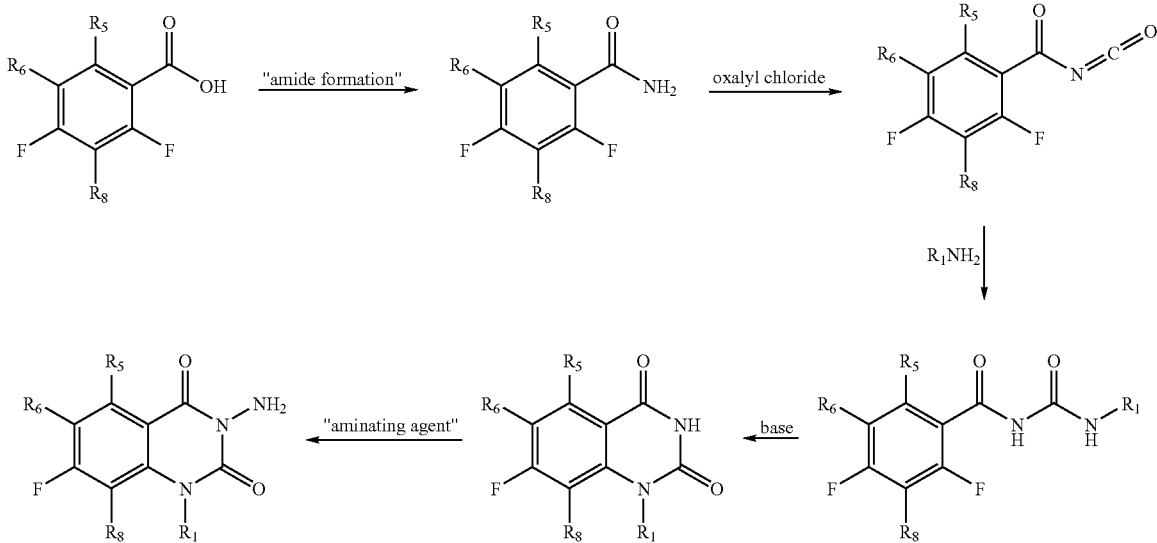

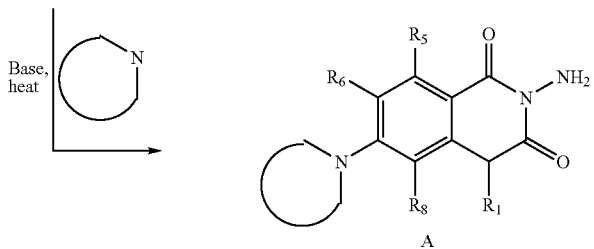

Tricyclic compounds (i.e., where $R_1$ and $R_8$, together with the atoms to which they are attached, form a carbocyclic ring in invention compounds of Formula I) can be prepared according to Scheme 16 where a palladium mediated carbon monoxide insertion on a quinoline (X=Br, I, or triflate) under well-precedented conditions gives rise to an ester. The quinoline ring can then be hydrogenated to provide a tetrahydroquinoline by standard hydrogenation conditions. The remainder of Scheme 16 follows that of Scheme 8 to provide invention compounds such as G, substituted with a displaceable substituent at $R_7$ (e.g., halo). These compounds may be further reacted with nucleophiles such as amines from Table A to give compounds of Formula I.

Compounds of Formula I where K is N may be prepared by the routes shown in Schemes 1, 2, 3, 4, and 6, or by routes such as the one illustrated in Scheme 17, which follows closely the chemistry shown in Scheme 15. The leaving groups (e.g. halo) ortho and para to the carboxyl group of the pyridyl starting material are highly activated. The two leaving groups ortho to the pyridine nitrogen are generally chlorine, but fluorine, alkylthiol, and sulfoxides such as methylsulfoxide are also good leaving groups for such compounds. The urea intermediate readily cyclizes to the 7-halo-quinazolinedione. Amination at the 3-position gives an invention compound that is an important intermediate due to the good leaving group at the 7-position ($R_7$=halo), which is readily displaced by reaction with an amine

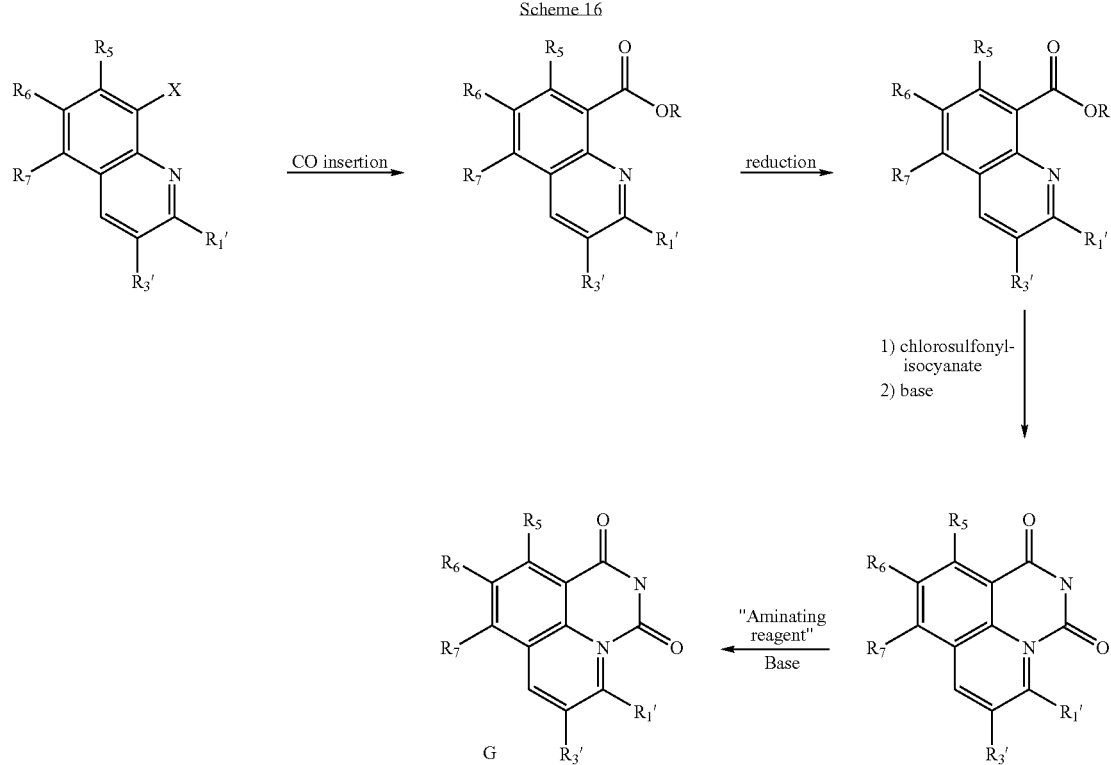

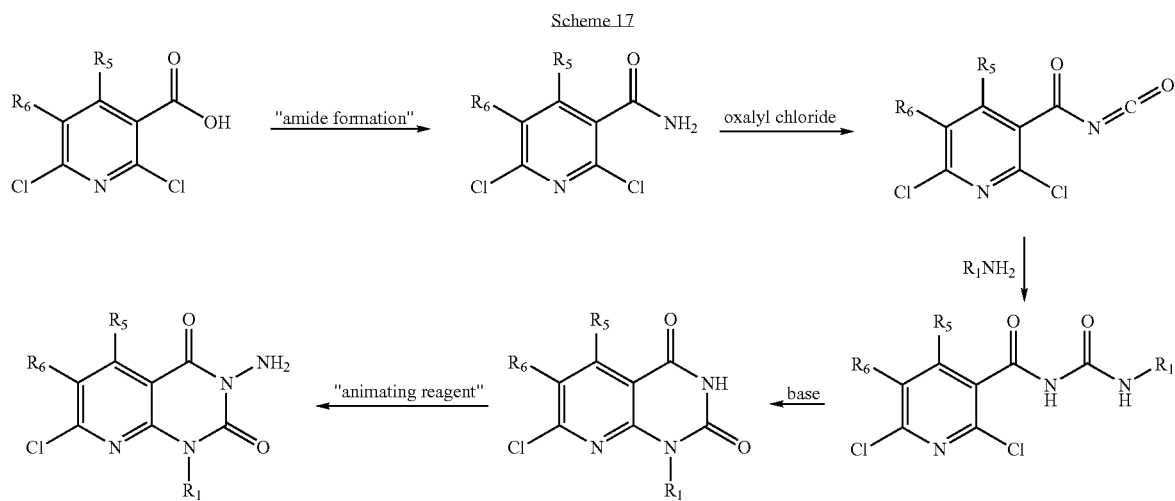

Scheme 17

Scheme 18 illustrates the synthesis of benzoic acid starting materials that have a bromo for $R_7$. A difluoro substituted benzoic acid is converted to an ester by first reaction with oxalyl chloride or an equivalent reagent (including acid anhydride), and the acid halide or anhydride is reacted with an alkanol to afford the respective ester (Z=methyl, ethyl, isopropyl, etc.). The ester is then reacted with 4-methoxybenzylamine or an equivalent to produce the desired 4-substituted benzoic acid derivative. This intermediate is reacted with triethylsilane and trifluoroacetic acid in a chlorinated solvent such as dichloromethane or an equivalent to provide an aniline derivative. Alternatively, one skilled in the art might also employ transition metal catalysis. The resulting aniline is then subjected to diazotization and converted to a bromide by treatment with cuprous bromide. The ester is then hydrolyzed by well-known methods to the desired benzoic acid, which can be used as a starting material as illustrated in Scheme 20 below.

-continued

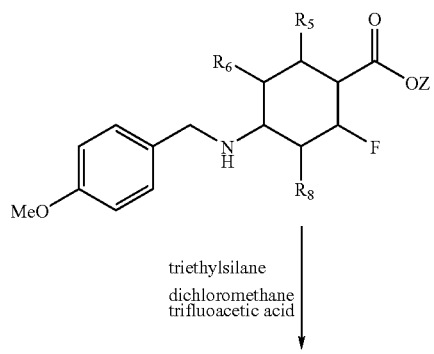

Scheme 18

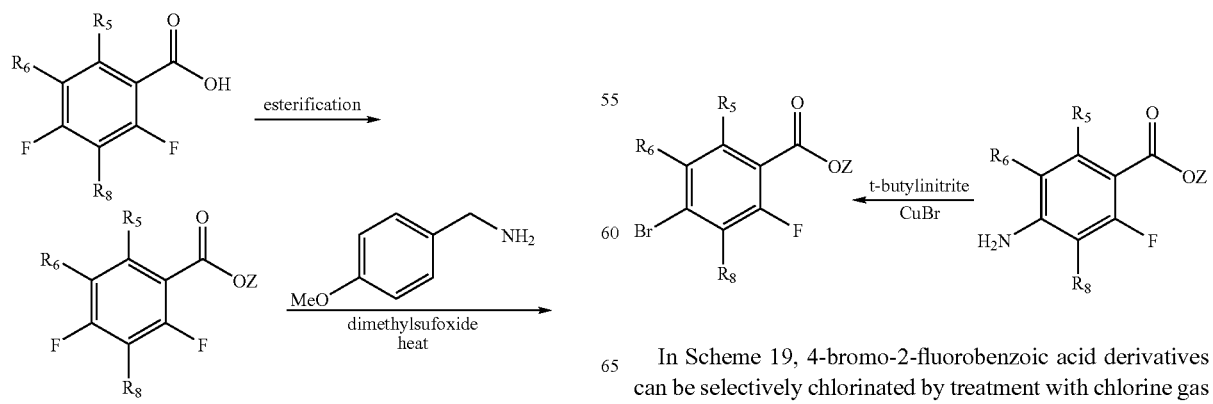

In Scheme 19, 4-bromo-2-fluorobenzoic acid derivatives can be selectively chlorinated by treatment with chlorine gas in chlorosulfonic acid at a temperature of 40° C.–100° C.

Scheme 19

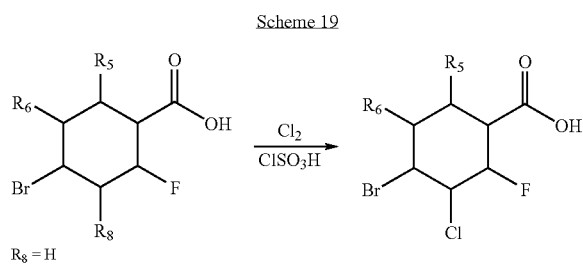

Scheme 20 illustrates use of 4-bromobenzoic acids as starting materials to make invention compounds wherein $R_7$ is aryl. The 4-bromobenzoic acids are converted into benzamides by any number of methods known in the art. A benzamide is reacted with oxalyl chloride in a chlorinated solvent such as dichloroethane or an equivalent to provide an isocyanate. The isocyanate is reacted with a substituted primary amine to give a benzoyl substituted urea. This intermediate can be cyclized to form a quinazolinedione ring system by reaction with sodium hydride, potassium hexamethyldisilazane or other non-nucleophilic bases in tetrahydrofuran/dimethylformamide, tetrahydrofuran with 18-crown-6, toluene/dioxane, tetrahydrofuran/glyme, tetrahydrofuran/diglyme, glyme/toluene or an equivalent. The quinazolinedione can then be aminated with a number of aminating reagents as described in Scheme 15. The resulting 3-aminoquinazolinedione ring system can then be readily coupled with a stannane or boronic acid derivative of a substituted aryl such as phenyl or substituted aromatic heterocycle (Ar).

Alternatively, the 3-position amine can be protected with a protecting group such as a tert-butyl carbamate or trifluoroacetamide. Protecting groups of these types are well known in the art. The 3-derivatized aminoquinazolinedione ring system can then be coupled via palladium catalysis with an aromatic (Ar) stannane or boronic acid.

Each of the outlined routes, upon deprotection by standard procedures, provides invention compounds of Formula I where $R_7$ is aryl such as phenyl or substituted phenyl, or heteroaryl such as pyridyl or substituted pyridyl.

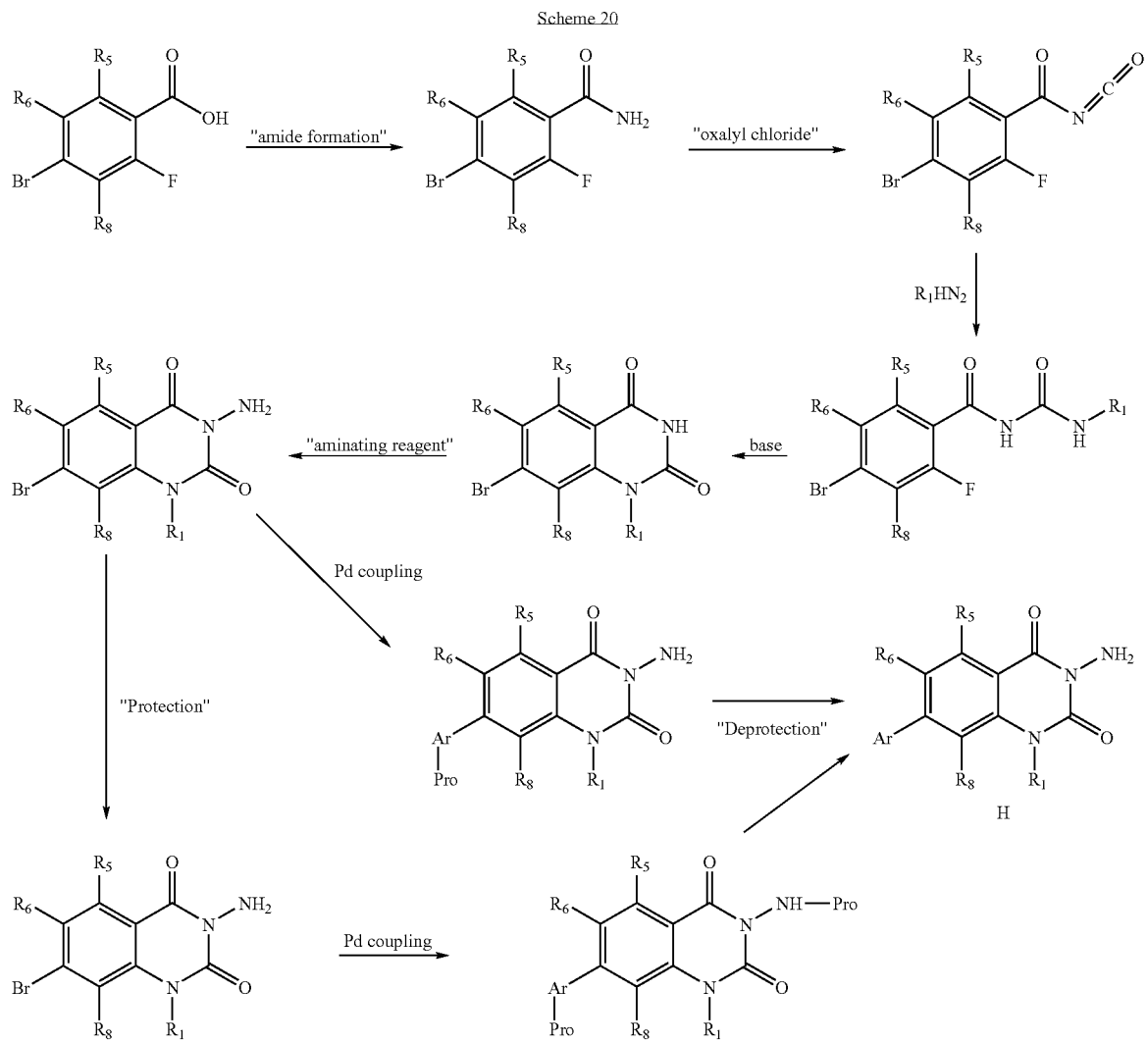

Scheme 20

Compounds of Formula I wherein $R_7$ is a heteroaryl group (such as those in Table A) are alternatively prepared as illustrated in Scheme 21, where $R_7$ is a substituted thiazole. A 3-protected 3-amino-7-bromoquinazolinedione from Scheme 20 is reacted with 1-tributyl-ethoxyvinyltin in the presence of a palladium catalyst. The resulting 7-substituted adduct is reacted with a brominating reagent such as n-bromosuccinimide and the like in tetrahydrofuran/$H_2O$ to provide an bromoketone at the quinazolinedione 7-position. Reaction of this intermediate with a thioamide (or thiourea) in a polar solvent such as dimethyl formamide, dimethylacetamide, or ethanol, and at an elevated temperature of about 80° C. to 120° C., effects cyclization to form a thiazolyl group. Deprotection by known methods can then be applied to provide invention compounds of Formula I wherein $R_7$ is the heteroaryl, optionally substituted with T, which is H, alkyl, substituted alkyl, $NH_2$, NH-allyl and N-dialkyl.

Alternatively, 7-aromatic or heterocyclic aromatic compounds of Formula I are prepared as shown in Scheme 22. A 4-bromo-2-fluorobenzoic acid (Schemes 18 or 19) is first esterified (Z is alkyl or benzyl), and the ester is reacted with a substituted primary amine ($R_1NH_2$) in dimethylsulfoxide (DMSO) at elevated temperature of about 100° C. to provide an anthranilic ester. The resulting aniline is then reacted with an appropriately protected hydrazine to provide the corresponding amide, for example as described in Scheme 1. The resulting amido aniline is then cyclized by reaction with phosgene, CDI, or the like to generate the quinazoline-2,4-dione. The cyclization typically is carried out in a solvent, such as ethereal solvents, chlorinated hydrocarbons such as chloroform, or aromatic hydrocarbons such as toluene, and in the presence of a base such as triethylamine or $NaHCO_3$. The quinazolin-2,4-dione ring system is then further modified as described in Scheme 20 to provide the desired 7-aryl (Ar) compound of Formula I.

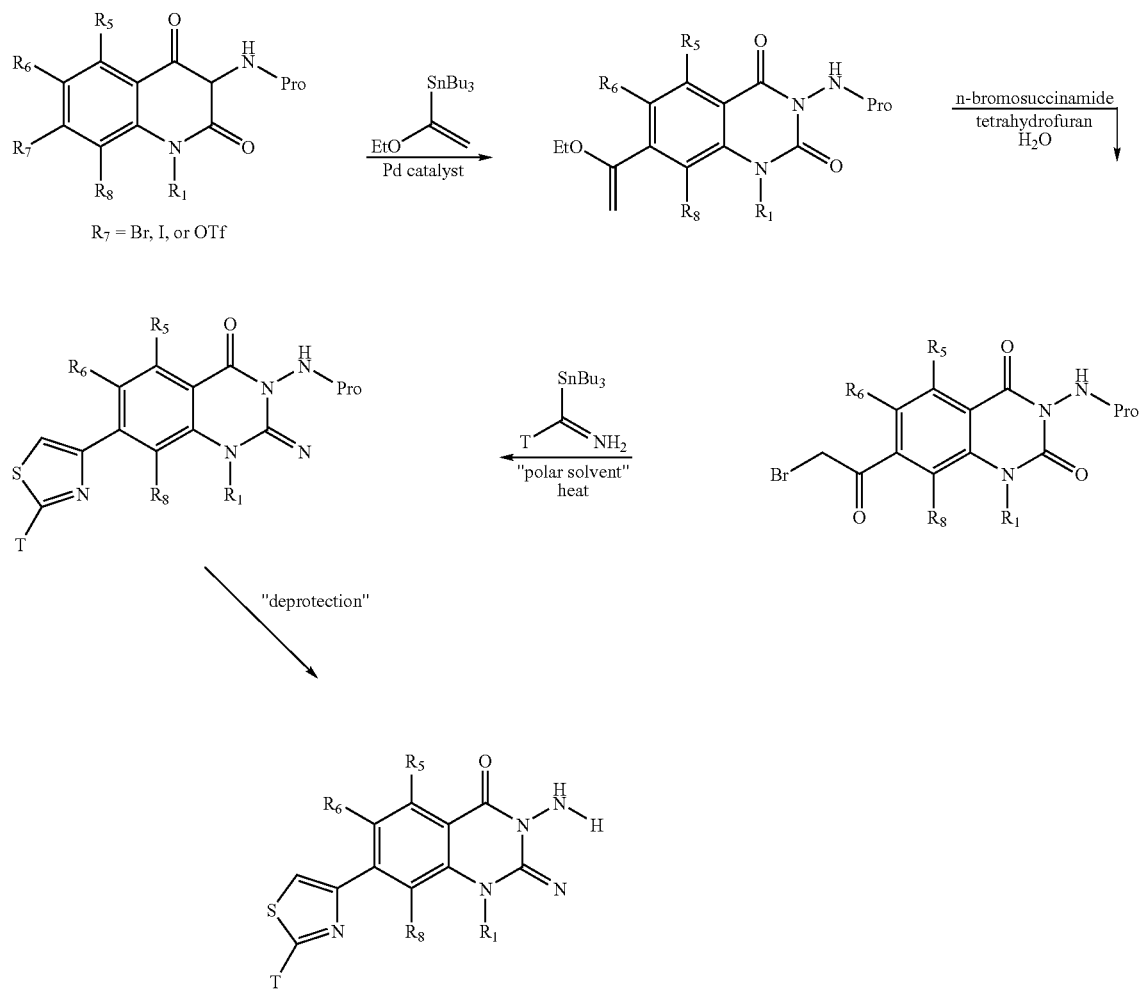

Scheme 21

Scheme 22

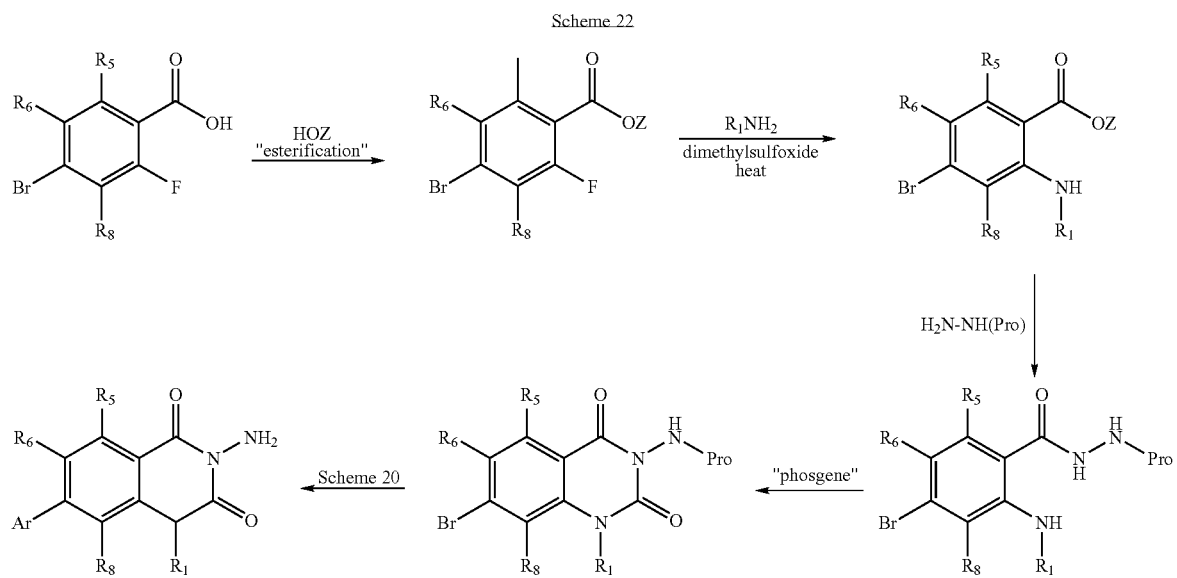

As noted above, $R_7$ in Formula I is referred to as the "side chain" of the 3-aminoquinazolin-2,4-dione nucleus. The $R_7$ side chains are any of those typically found on the quinolone antibiotics. Most of the $R_7$ side chain reactants that are required to make the Formula I compounds are readily available from commercial sources. Typical $R_7$ side chains are shown in Table A above.

The synthesis of the $R_7$ side chains can be accomplished by standard synthetic methods, for example as shown in the following schemes or as found in the literature. Those of ordinary skill in the art will be able to make any of the starting materials required to prepare the invention compounds, although most are available from commercial sources. The following schemes are provided to illustrate the synthesis of typical $R_7$ side chain reactants.

Scheme A1 illustrates the synthesis of typical pyrrolidines, which are preferred side chains ($R_7$) for invention compounds of Formula I. In Scheme A1, appropriately activated enones can undergo [3+2]cycloadditions under the conditions described by Tsuge et al. (Recent advances in azomethine ylid chemistry. In: Advances in Heterocyclic Chemistry [Katritsky A., ed.] San Diego: Academic Press, 231–349). These reactions are carried out in a chlorinated hydrocarbon solvent such as dichloromethane, chloroform, or dichloroethane and the like, and in the presence of a catalytic acid such as trifluoacetic acid, to provide substituted pyrrolidines (wherein $S_1$, $S_2$, $S_3$, and $S_4$ independently are alkyl, substituted alkyl, aryl, amino, alkyl and dialkylamino). These intermediates can then be treated with hydroxylamine or any O-alkylated or arylated hydroxylamine under a variety of conditions known to those skilled in the art to provide oximated substituted pyrrolidines. The oximes are reduced to amines with lithium aluminum hydride, diisobutylaluminum hydride borane, or by selective catalytic hydrogenation. The resulting primary amines can then be protected using a number of methods as described in "Protecting Groups in Organic Synthesis" by Theodora Green (supra). The benzylic pyrrolidine can then be deprotected by hydrogenation, and the resulting pyrrolidine used in the preparation of 7-cyclic amino substituted 3-aminoquinazolinediones of Formula I as shown in the schemes above.

Scheme A1

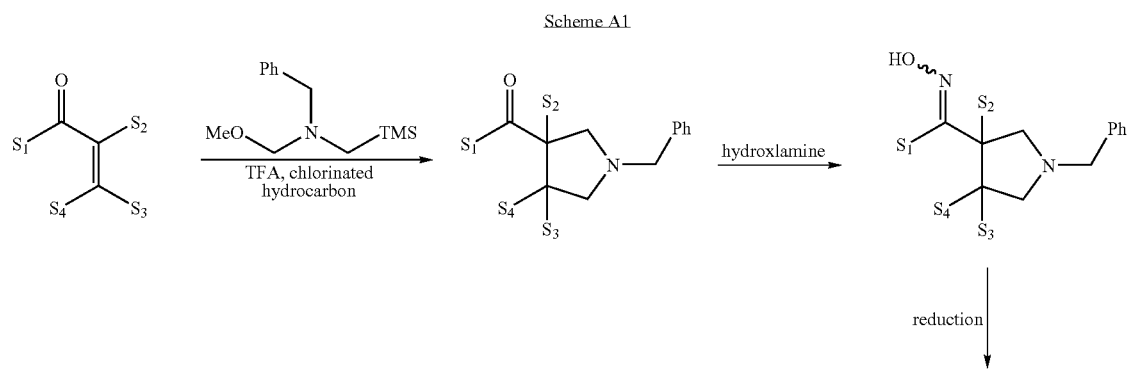

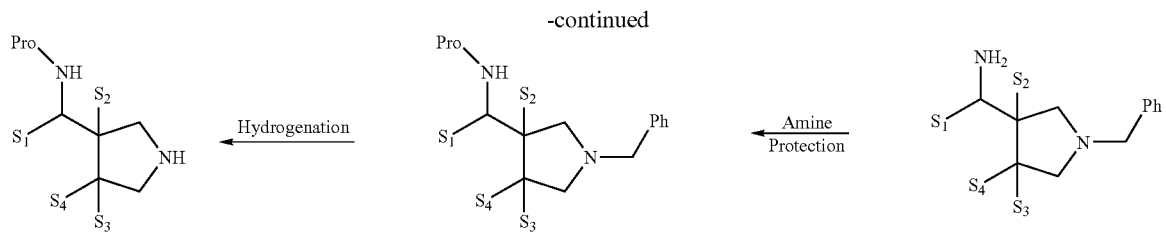

In Scheme A2, enoates (or vinylogous nitrites) may also be used in [3+2]cycloadditions to provide 3- and 4-substituted pyrrolidines. The ester (or nitrite) functionality can then be treated directly with alkyl lithium reagents at low temperature (0° C.) in ether to provide $S_1$ substituted ketones, or the ester (Z is alkyl or benzyl) can be hydrolyzed under conditions usually employed by those skilled in the art to provide carboxylic acids. This intermediate can then be transformed into an acid chloride with oxalyl chloride and catalytic dimethyl formamide in solvents such as dichloromethane or chloroform or into an activated amide (Singh J., Satyamurthi N., Aidhen I., Singh J., *Prakt. Chem.* [Weinheim, Ger.], 2000; 342(4):340–347). An acid chloride can be converted into a ketone using organocopper reagents (Lipshutz B. H., Sengupta S., *Org. React.* [N.Y.], 1992; 41:135–631), and Weinreb amides can be converted into ketones according to the methods described by Weinreb (*Tetrahedron Lett.*, 1981; 22(39):3815–3818) using organo Grignard reagents. The resulting ketones can then be converted into pyrrolidines (optionally substituted with $S_2$, $S_3$, and $S_4$) as described in Scheme A1. As noted above, pyrrolidines and substituted pyrrolidines are preferred $R_7$ groups in Formula I.

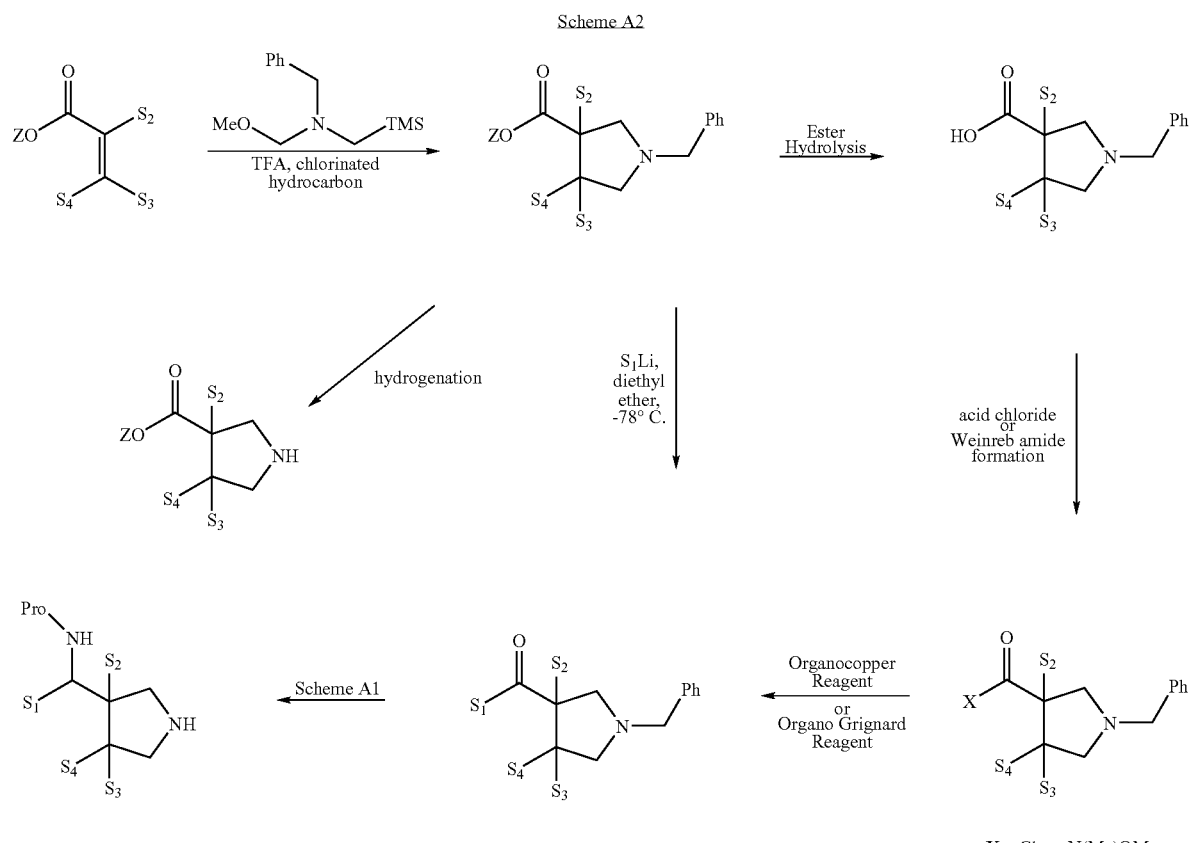

In Scheme A3, 3-carboxylic acid N-benzyl substituted pyrrolidines (Scheme A2) can be converted into amides by a number of methods well-known to those who practice the art of organic synthesis. The amides can then be treated with lithium aluminum hydride in an ethereal solvent such as diethyl ether or tetrahydrofuran or the like to provide amines that can be protected as described in Scheme A1. Hydrogenation with palladium catalysis provides an appropriately substituted pyrrolidine ($S_2$, $S_3$, $S_4$ are independently alkyl, lower alkyl, aryl, etc.).

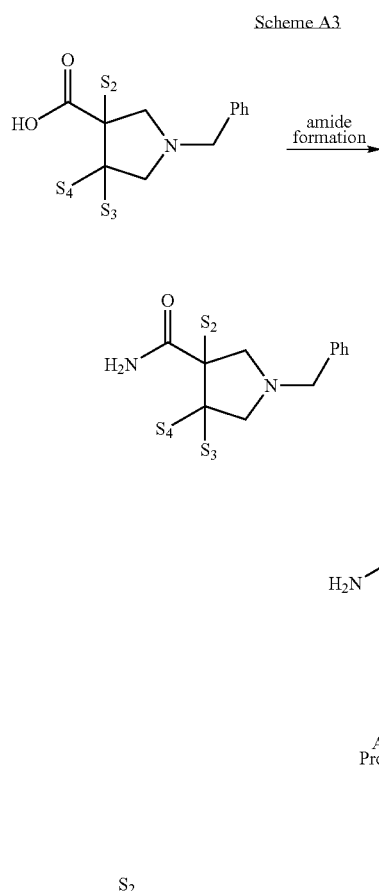

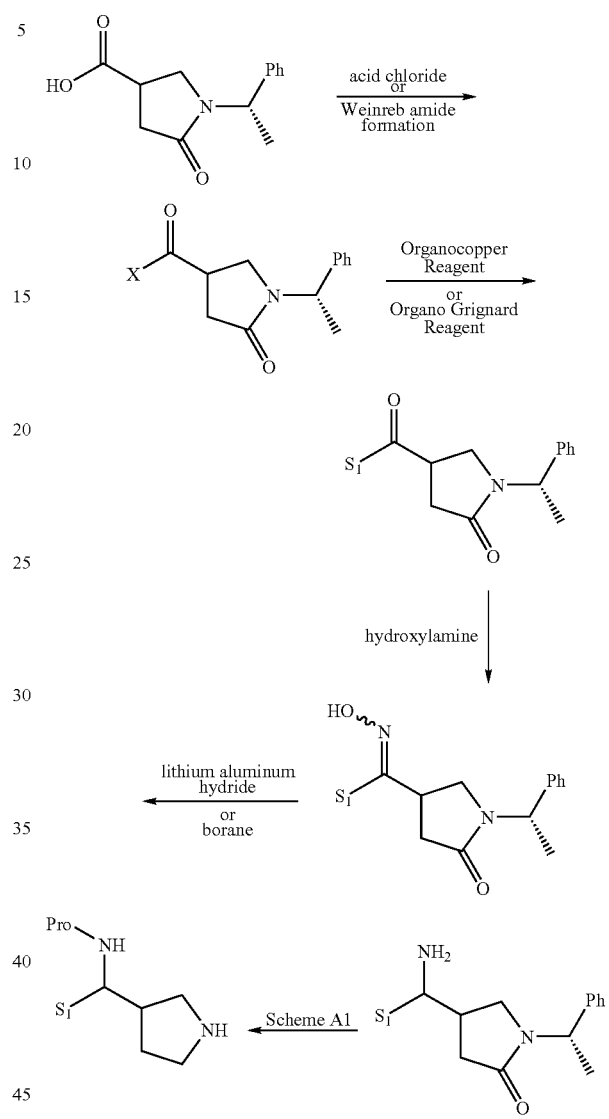

In Scheme A4, a 3-carboxypyrrolidinone (Culbertson T. P., Domagala J. M., Nichols J. B., Priebe S., Skeean R. W., *J. Med. Chem.*, 1987; 30(10):1711–1715) can be converted into an acid chloride or Weinreb amide in the same fashion as that defined in Scheme A3. The acid chlorides are reacted with an organocopper reagent or an organo Grignard reagent (for a Weinreb amide) to provide a ketone that can be manipulated as described in Scheme A1 to provide an appropriately substituted pyrrolidine with a variety of substitutions at $S_1$ (alkyl, lower alkyl, substituted alkyl, aryl). The use of S-methylbenzyl (or R-methylbenzyl) as a protecting group for the pyrrolidine nitrogen allows for the separation of enantiomers and diastereomers at any step in the reaction sequence.

In Scheme A5, carboxybenzyl protected 3-pyrrolidinone is reacted with a Wittig salt in the presence of sodium hydride or an equivalent in dimethylsulfoxide or any polar aprotic solvent to give an olefin. The resulting olefin is oxidized with 3-chloroperoxybenzoic acid in dichloromethane or other suitable chlorinated hydrocarbon to provide an epoxide. The epoxide is reacted with ammonium hydroxide in methanol, ethanol, dimethylformamide, dimethylacetamide or the like to generate an aminoalcohol. Methylation of the tertiary hydroxyl group can then be carried out by formation of a Schiff-base, followed by alkoxide formation with sodium hydride and treatment with iodomethane. Hydrolysis of the Schiff-base under standard conditions liberates the amine. Reaction of the amine with di-tert-butyldicarbonate in methanol, followed by hydrogenation via palladium catalysis provides $R_7$ side chains ($S_1$ is alkyl, lower alkyl, and aryl) that can be used in the synthesis of compounds of Formula I.

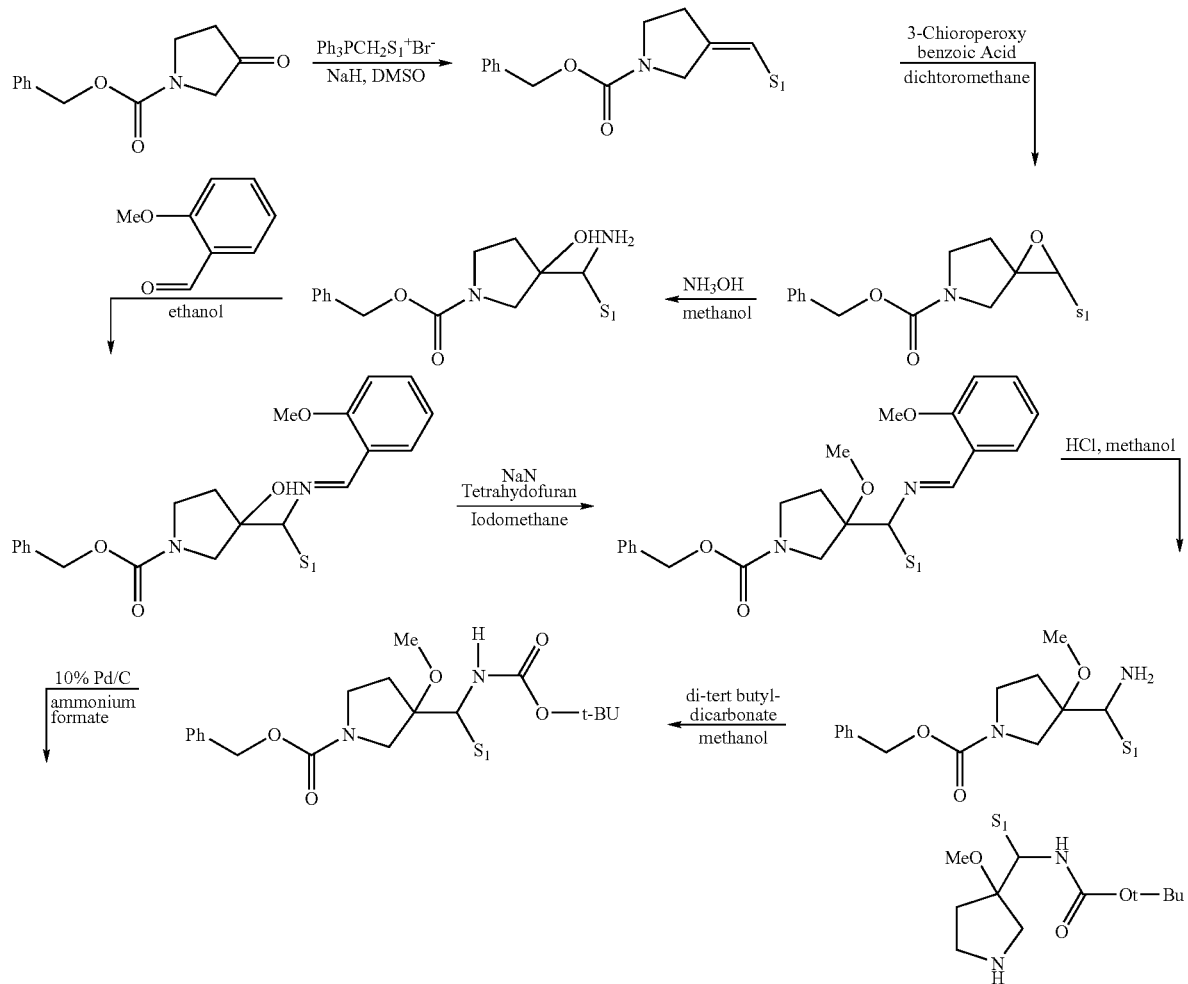

In Scheme A6, the aminoalcohol intermediate described in Scheme A5 is reacted with di-tert-butyldicarbonate in methanol to produce the N-protected intermediate. Other amine protection strategies familiar to those skilled in the art can also be utilized. Hydrogenation under palladium catalysis provides substituted pyrrolidine $R_7$ side chains that are used in the synthesis of compounds of Formula I.

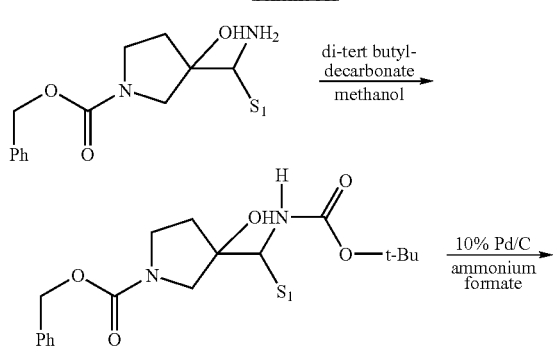

-continued

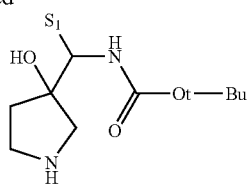

In Scheme A7, an epoxide intermediate (Scheme A5) is selectively opened with hydrofluoric acid in pyridine, and the resulting secondary alcohol is reacted with methanesulfonylchloride, or an equivalent sulfonating reagent, in dichloromethane or another chlorinated hydrocarbon and triethylamine. Other appropriate bases include diisopropylethylamine, pyridine, collidine, n-methylmorpholine, and the like. The mesylate is then displaced by reaction with sodium azide, and the azide is reduced with Raney nickel under hydrogen pressure in methanol. Such transformations are well-precedented in the art. The resulting amine is then treated with di-tert-butyldicarbonate in methanol as shown in Schemes A4–A6, and the product is hydrogenated to provide the $R_7$ side chain as shown above.

Scheme A7

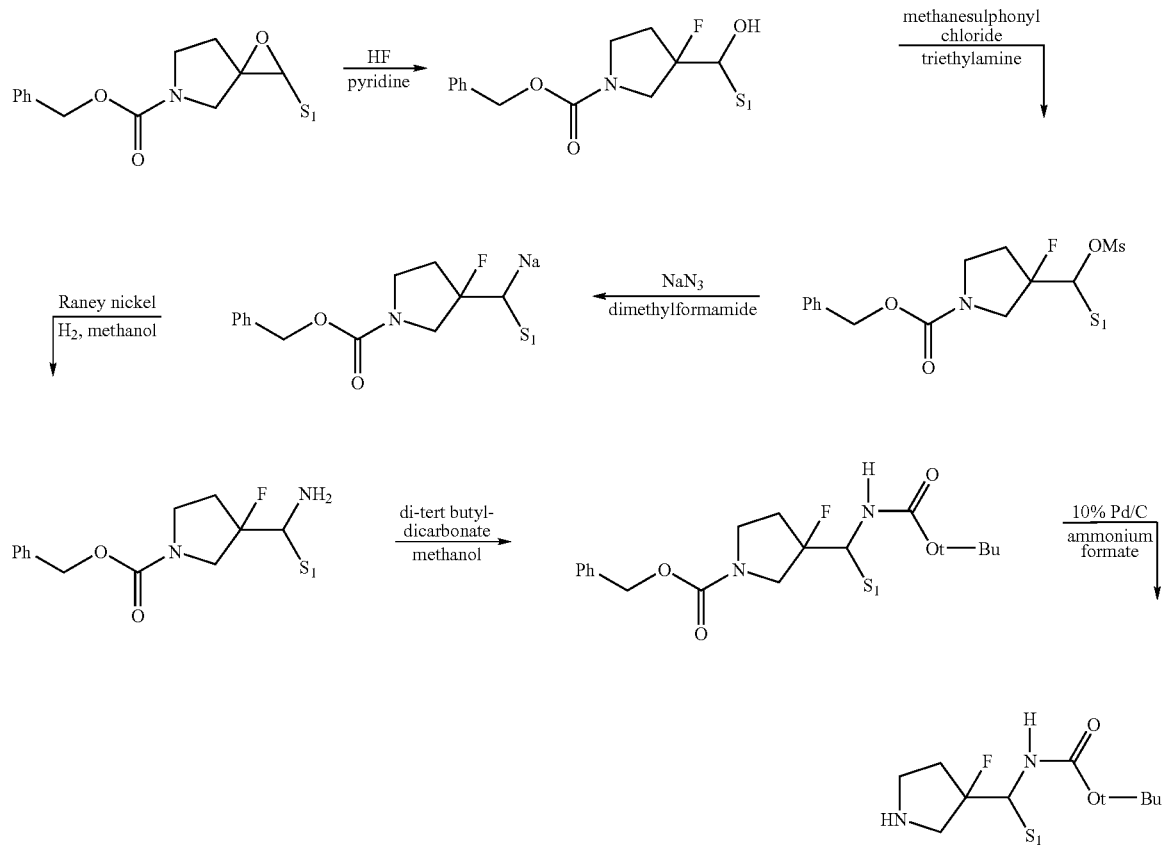

The synthesis of 3-substituted piperidines is demonstrated in Scheme A8. Esterification and alkylation of 3-piperidine carboxylic acid is simultaneously accomplished by treatment with a benzylbromide in a polar solvent such as dimethylformamide or dimethylsulfoxide and a base such as potassium carbonate ($K_2CO_3$) or an equivalent. The ester is then hydrolyzed, and the resulting carboxylic acid is converted to a methyl ketone by treatment with methyllithium at low temperature (0° C.). This intermediate is then converted to an oxime by a number of methods known by those skilled in the art. The oxime is reduced with lithium aluminum hydride in tetrahydrofuran to provide an amine. The amine is reacted with di-tert-butyldicarbonate in dichloromethane and triethylamine as a base. As shown in Schemes A4–A6, the product is then hydrogenated to provide the $R_7$ side chain.

Scheme A8

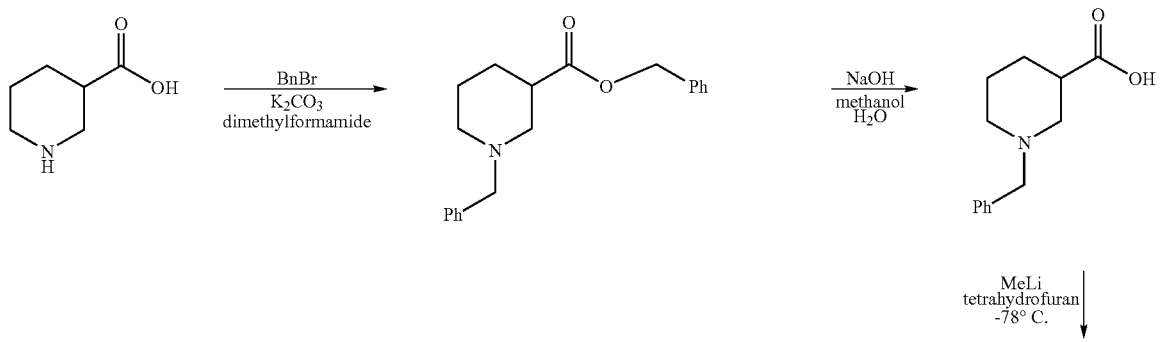

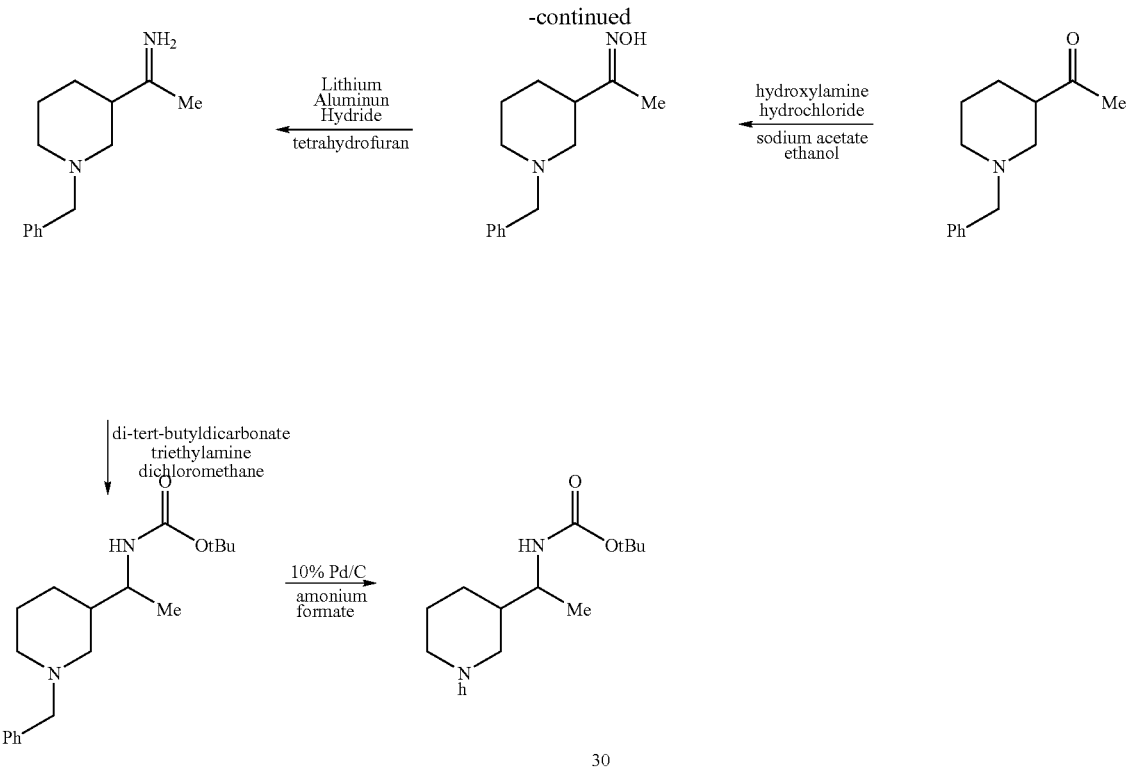

It should be recognized from Schemes A1–A8 that substitutions on ring systems such as a pyrrolidine, piperazine, or piperidine ring will form chiral centers giving R and S enantiomers and diastereomers. Such enantiomers or diastereomers may be separated, if desired, by chiral HPLC at any stage. Resolution of any of the intermediates may be performed with techniques of fractional crystallization using mandelic acid, tartaric acid, or other chiral, optically pure acid resolving agents. Chiral benzylic amines can be used in the preparation of starting materials for the above schemes, and chiral amides may also be prepared using chiral acids, such as mandelic acid and the like. The isomers can then be separated and the chiral amine can be hydrogenated, or the chiral amide can be hydrolyzed.

The synthesis of invention compounds of Formula I is further illustrated by the following detailed examples. The examples are not to be construed as limiting the invention in scope or spirit to the specific procedures described. The starting materials and various intermediates utilized in the following examples may be obtained from commercial sources, or are readily prepared from commercially available organic compounds, using well-known synthetic methods.

EXAMPLE 1

Synthesis of Benzoates (a) 2,3,4,5-Tetrafluorobenzoic acid ethyl ester

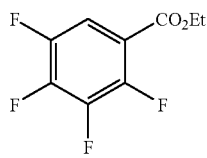

A solution of 2,3,4,5-tetrafluorobenzoic acid (4.68 g, 24.1 mmol) in dichloromethane (50 mL) at 0° C. is treated with oxalyl chloride (11.5 mL, 132 mmol) followed by N,N-dimethylformamide (4 drops). The mixture is stirred at 0° C. for 5 minutes and then at room temperature for 1.5 hours. The mixture is concentrated to dryness and subsequently co-evaporated from benzene. The resulting acid chloride is diluted with dichloromethane (50 mL), cooled to 0° C., and anhydrous ethanol (15.0 mL, 256 mmol) is added dropwise. The resulting solution is stirred at room temperature for 4.5 hours, then poured into saturated $NaHCO_3$ and extracted with chloroform. The combined organic extracts are washed with brine, dried over $Na_2SO_4$, filtered, and concentrated under vacuum to afford the title compound (5.37 g). $^1H$ NMR ($CDCl_3$): δ 7.67–7.55 (m, 1H), 4.42 (q, 2H), 1.41 (t, 3H).

(b) 2,3,4,6-Tetrafluorobenzoic acid ethyl ester

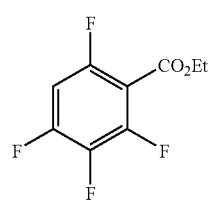

2,3,4,6-Tetrafluorobenzoic acid (4.8 g, 24.7 mmol) in dichloromethane (80 mL) is cooled to 0° C. under a nitrogen atmosphere and treated with oxalyl chloride (11.2 mL, 128 mmol) followed by anhydrous N,N-dimethylformamide (2 drops). The mixture is warmed to room temperature and stirred for 2 hours. The solution is co-evaporated with benzene to yield an oil that is taken up in dichloromethane (80 mL), cooled to 0° C. under an inert atmosphere, and treated with anhydrous ethanol (15 mL, 258 mmol). After 5 hours at room temperature, the solution is poured into saturated NaHCO$_3$ and extracted with chloroform. The organic phase is washed with brine, dried over Na$_2$SO$_4$, filtered, and concentrated under vacuum to provide the title compound (3.3 g). This material is used without further purification. $^1$H NMR (CDCl$_3$): δ 6.93–6.75 (m, 1H), 4.42 (q, 2H), 1.39 (t, 3H).

(c) 3-Chloro-2,4,5-trifluorobenzoic acid ethyl ester

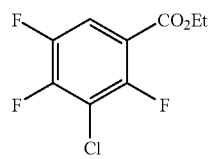

To a solution of 3-chloro-2,4,5-trifluorobenzoic acid (Example 20, 4.90 g, 23.3 mmol) in dichloromethane (50 mL) is added oxalyl chloride (5.1 mL, 58.2 mmol) and N,N-dimethylformamide (1 drop). After 45 minutes, the reaction mixture is concentrated under vacuum. The resulting residue is dissolved in dichloromethane (50 mL) and treated with ethanol (10 mL, 172 mmol). After 30 minutes, the reaction mixture is diluted with dichloromethane and washed with saturated NaHCO$_3$, water, and brine. The organic layer is dried over MgSO$_4$, filtered, and the filtrate is concentrated to afford the title compound (5.59 g). $^1$H NMR (CDCl$_3$): δ 7.76–7.68 (m, 1H), 4.40 (q, 2H), 1.39 (t, 3H).

(d) 2,3,4,5,6-Pentafluorobenzoic acid benzyl ester

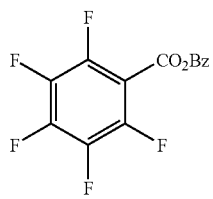

A solution of 2,3,4,5,6-pentafluorobenzoic acid (15.25 g, 71.9 mmol), 4-dimethylaminopyridine (4.4 g, 36.0 mmol) and benzyl alcohol (7.4 mL, 71.5 mmol) in dichloromethane (150 mL) is cooled to 0° C. under an inert atmosphere. 1-[3-(Dimethylamino)propyl]-3-ethyl carbodiimide hydrochloride (16.7 g, 87.1 mmol) is added and the mixture stirred at 0° C. for 2 hours. The mixture is warmed to ambient temperature, stirred for 24 hours, and then poured into brine. The mixture is extracted with chloroform and the organic phase washed with NaHCO$_3$, dried over Na$_2$SO$_4$, filtered and concentrated under vacuum to yield the title compound as a white solid (16.7 g). This material is used without further purification. $^1$H NMR (CDCl$_3$): δ 7.49–7.27 (m, 5H), 5.40 (s, 2H).

(e) 2,4,5-Trifluorobenzoic acid ethyl ester

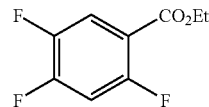

To a solution of 2,4,5-trifluorobenzoic acid (10.85 g, 61.6 mmol) in dichloromethane (100 mL) is added oxalyl chloride (13.5 mL, 154 mmol) and N,N-dimethylformamide (1 drop). After 45 minutes, the reaction mixture is concentrated under vacuum. The resulting residue is dissolved in dichloromethane (100 mL), and to this solution is added ethanol (18 mL, 310 mmol). After 30 minutes, the reaction mixture is diluted with dichloromethane and washed with saturated NaHCO$_3$, water, and brine. The organic layer is dried over MgSO$_4$, filtered, and the filtrate is concentrated to afford the title compound as an oil (12.23 g). $^1$H NMR(CDCl$_3$): δ 7.85–7.73 (m, 1H), 7.06–6.94 (m, 1H), 4.38 (q, 2H), 1.38 (t, 3H).

(f) 2,4,5-Trifluoro-3-methoxybenzoic acid ethyl ester

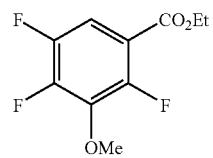

A solution of 2,4,5-trifluoro-3-methoxybenzoic acid (2.513 g, 12.19 mmol) in dichloromethane (50 mL) at 0° C. is treated with oxalyl chloride (5.4 mL, 61.9 mmol) followed by N,N-dimethylformamide (4 drops). The mixture is stirred at 0° C. for 5 minutes and then at room temperature for 2.5 hours. The mixture is concentrated to near dryness and then co-evaporated from benzene. The resulting acid chloride is diluted with dichloromethane (50 mL), cooled to 0° C., and then anhydrous ethanol (7.30 mL, 124 mmol) is added dropwise. The resulting solution is stirred at room temperature for 4.5 hours, poured into saturated NaHCO$_3$ solution, and extracted with dichloromethane. The combined organic extracts are washed with brine, dried over Na$_2$SO$_4$, filtered, and concentrated under vacuum to afford the title compound as a light yellow liquid (2.82 g). $^1$H NMR (CDCl$_3$): δ 7.47 (ddd, 1H), 4.39 (q, 2H), 4.05 (s, 3H), 1.40 (t, 3H).

(g) 2,3,4-Trifluorobenzoic acid ethyl ester

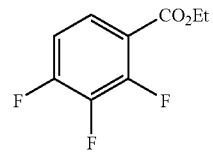

To a solution of 2,3,4-trifluorobenzoic acid (10.85 g, 61.6 mmol) in dichloromethane (100 mL) is added oxalyl chloride (13.5 mL, 154 mmol) and N,N-dimethylformamide (3 drops). After 45 minutes, the reaction mixture is concentrated under vacuum. The resulting residue is dissolved in dichloromethane (100 mL) and to this solution is added ethanol (18 mL, 310 mmol). After 30 minutes, the reaction mixture is diluted with dichloromethane and washed with saturated NaHCO$_3$, water, and brine. The organic layer is dried over MgSO$_4$, filtered, and the filtrate is concentrated to afford the title compound as an oil (12.23 g). $^1$H NMR (CDCl$_3$): δ 7.93–7.67 (m, 1H), 7.09–6.96 (m, 1H), 4.39 (q, 2H), 1.40 (t, 3H).

(h) 2,3,4-Trifluoro-5-methoxybenzoic acid ethyl ester

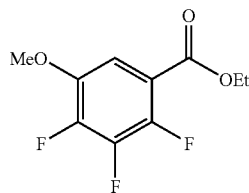

A solution of 2,3,4-trifluoro-5-methoxybenzoic acid (Hayashi et al., *Bull. Chem. Soc. Jap.*, 1972; 45(9):2909–2914, 3.443 g, 16.7 mmol) in dichloromethane (100 mL) at 0° C. is treated with oxalyl chloride (7 mL, 80 mmol) followed by N,N-dimethylformamide (4 drops). The mixture is stirred at room temperature for 3.5 hours, concentrated to near dryness, and co-evaporated with benzene. The acid chloride is then diluted with dichloromethane, cooled to 0° C., and treated with absolute ethanol (10 mL, 170 mmol). The resulting solution is stirred at room temperature for 20 hours, poured into saturated NaHCO$_3$ solution, and extracted with dichloromethane. The organic extracts are washed with brine, dried over Na$_2$SO$_4$, filtered, and concentrated under vacuum to afford the title compound (3.785 g). $^1$H NMR (200 MHz, CDCl$_3$): δ 7.36–7.29 (m, 1H), 4.42 (q, 2H), 3.93 (s, 3H), 1.44 (t, 3H).

(i) 2,4,5-Trifluoro-3-methylbenzoic acid ethyl ester

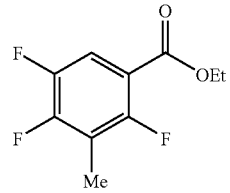

A solution of 3-methyl-2,4,5-trifluorobenzoic acid (Shimizu T., Asai T., Kumai S., Jpn. Kokai Tokkyo Koho (1997) Japanese Appl. JP 95-219069, 4.3 g, 22.6 mmol) in dichloromethane (100 mL) at 0° C. is treated with oxalyl chloride (4.2 g, 33 mmol) followed by N,N-dimethylformamide (2 drops). The mixture is stirred at room temperature for 3 hours, concentrated and dried in vacuo. The acid chloride is diluted with dichloromethane, cooled to 0° C., and treated with absolute ethanol (10 mL, 170 mmol). The resulting solution is stirred at room temperature for 20 hours, poured into saturated NaHCO$_3$ solution and extracted with dichloromethane. The organic extracts are washed with brine, dried over Na$_2$SO$_4$, filtered, and concentrated under vacuum to afford the title compound (3.8 g). $^1$H NMR (200 MHz, CDCl$_3$): δ 7.67–7.26 (m, 1H), 4.44 (q, 2H), 2.27 (dd, 3H), 1.42 (t, 3H).

(j) 3-(Benzyloxyiminomethyl)-2,4,5-trifluorobenzoic acid ethyl ester

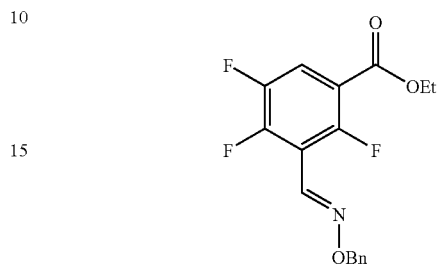

2,4,5-Trifluoro-3-formylbenzoic acid (Horiuchi N., Yonezawa T., Chiba K., Yoshida H., PCT Int. Appl. [1999] WO 97-JP2918), (5.70 g, 27.9 mmol), triethylamine (11 mL, 78.9 mmol), O-benzylhydroxylamine hydrochloride (4.47 g, 28.0 mmol) and anhydrous tetrahydrofuran (150 mL) are stirred at room temperature for 50 hours. The mixture is poured into brine and the pH adjusted to 5.5–6.0 using 1.0 M hydrochloric acid. The mixture is extracted with ethyl acetate. The organic phase is dried over Na$_2$SO$_4$, filtered, and concentrated in vacuo to provide 3-(benzyloxyiminomethyl)-2,4,5-trifluorobenzoic acid (8.63 g), which is used without further purification. $^1$H NMR (200 MHz, CDCl$_3$): δ 9.82–9.18 (bs, 1H), 8.24 (s, 1H), 7.94–7.68 (m, 1H), 7.55–7.23 (m, 5H), 5.23 (d, 2H). MS (EI, M−1) m/z 308.

3-(Benzyloxyiminomethyl)-2,4,5-trifluorobenzoic acid (0.117 g, 0.378 mmol), 4-dimethylaminopyridine (0.023 g, 0.189 mmol), anhydrous ethanol (0.030 mL, 0.517 mmol) are mixed in dichloromethane (6 mL), cooled to 0° C., and treated with 1-ethyl-3-(3-dimethylaminopropyl)carbodiimide hydrochloride (0.082 g, 0.427 mmol). After 2 hours at 0° C. and room temperature for 21 hours, the solvents are evaporated. The residue is dissolved in chloroform, washed with saturated NaHCO$_3$ and brine, dried over Na$_2$SO$_4$, filtered, and concentrated in vacuo. Purification by chromatography (1:8 ethyl acetate/hexanes) provided the title compound (0.068 g). $^1$H NMR (200 MHz, CDCl$_3$): δ 8.27 (s, 1H), 7.87–7.66 (m, 1H), 7.49–7.28 (m, 5H), 5.27 (s, 2H), 4.48–4.29 (q, 2H), 1.46–1.31 (t, 3H).

EXAMPLE 2

Synthesis of 4-Heterocyclic Benzoates

General Procedure

A mixture of 4-fluoro substituted benzoic acid ester (1 eq.), substituted pyrrolidine (1.3–2.5 eq.), and triethylamine (2–10 eq.) in N,N-dimethylacetamide or acetonitrile is heated to 50° C.–100° C. for 15 to 60 hours. The solution is then concentrated to near dryness, poured into saturated NaHCO$_3$ solution, and extracted with ethyl acetate. The combined organic extracts are washed with brine, dried over Na$_2$SO$_4$, filtered, and concentrated in vacuo. The resulting residue is purified by column chromatography (ethyl acetate/hexanes) to afford 4-pyrrolidinyl substituted benzoic acid esters.

85

(a) 4-[(S)-3-tert-Butoxycarbonylaminopyrrolidin-1-yl]-2,3,5-trifluorobenzoic acid ethyl ester

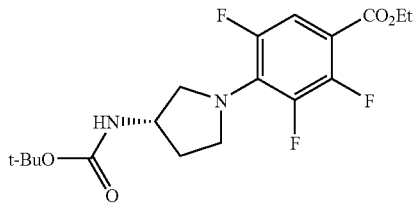

A solution of 2,3,4,5-tetrafluorobenzoic acid ethyl ester (Example 1a, 4.03 g, 18.1 mmol), (S)-pyrrolidin-3-ylcarbamic acid tert-butyl ester (4.02 g, 21.6 mmol) (Sanchez J. P., Domagala J. M., Heifetz C. L., Priebe S. R., Sesnie J. A., Trehan A. K., *J. Med. Chem.*, 1992; 35(10):1764–1773), and triethylamine (18.0 mL, 129 mmol) in acetonitrile (50 mL) is heated at 50° C. under a nitrogen atmosphere for 4.5 hours. The yellow solution is concentrated in vacuo and poured into a saturated NaHCO$_3$ solution. The mixture is then extracted with chloroform, and the combined organic extracts are washed with brine, dried with Na$_2$SO$_4$, filtered, and concentrated in vacuo. The resulting residue is then purified by flash column chromatography (1:7 ethyl acetate/hexanes) to afford the title compound (5.24 g). $^1$H NMR (CDCl$_3$): δ 7.35 (ddd, 1H), 4.70–4.65 (bs, 1H), 4.42–4.20 (m, 3H), 3.90–3.62 (m, 3H), 3.58–3.42 (m, 1H), 2.28–2.03 (m, 1H), 1.99–1.80 (m, 1H), 1.46 (s, 9H), 1.37 (t, 3H).

(b) 4-[(S)-3-tert-Butoxycarbonylaminopyrrolodin-1-yl]-2,3,6-trifluorobenzoic acid ethyl ester

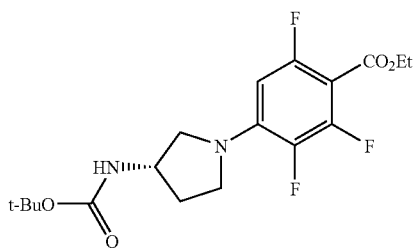

A solution of 2,3,4,6-tetrafluorobenzoic acid ethyl ester (Example 1b, 5.1 g, 22.9 mmol), triethylamine (22 mL, 157 mmol), and (S)-pyrrolidin-3-ylcarbamic acid tert-butyl ester (5.2 g, 27.9 mmol) in acetonitrile (60 mL) is stirred at room temperature for 64 hours. The mixture is concentrated in vacuo and the residue dissolved in chloroform, washed with NaHCO$_3$ and then brine, dried over Na$_2$SO$_4$, filtered, and concentrated under vacuum to afford a solid. The solid is purified by column chromatography (1:1:7 ethyl acetate/chloroform/hexanes) to afford the title compound (6.21 g). $^1$H NMR (CDCl$_3$): δ 6.07 (ddd, 1H), 4.78–4.63 (bd, 1H), 4.49–4.22 (m, 3H), 3.80–3.68 (m, 1H), 3.66–3.28 (m, 3H), 2.33–2.13 (m, 1H), 2.04–1.83 (m, 1H), 1.45 (s, 9H), 1.36 (t, 3H).

86

(c) 4-[(S)-3-tert-Butoxycarbonylaminopyrrolidin-1-yl]-3-chloro-2,5-difluorobenzoic acid ethyl ester

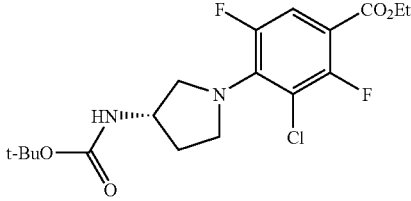

To a solution of 3-chloro-2,4,5-trifluorobenzoic acid ethyl ester (Example 1c, 5.50 g, 23.05 mmol) in acetonitrile (25 mL) is added triethylamine (6.43 mL, 46.1 mmol) and (S)-pyrrolidin-3-ylcarbamic acid tert-butyl ester (4.72 g, 25.4 mmol). After 48 hours, the mixture is diluted with ethyl acetate and washed with saturated NaHCO$_3$, water, and brine. The organic layer is dried over MgSO$_4$, filtered, and the filtrate is concentrated to afford the title compound (9.34 g). MS CI: m/z 405 (MH$^+$).

(d) 4-[(S)-3-(tert-Butoxycarbonylamino)pyrrolidin-1-yl]-2,3,5,6-tetrafluorobenzoic acid benzyl ester

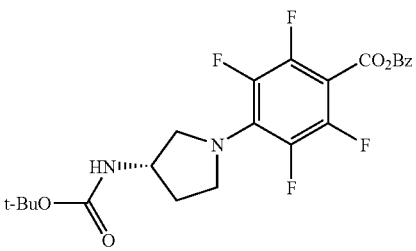

A solution of 2,3,4,5,6-pentafluorobenzoic acid benzyl ester (Example 1d, 8.05 g, 26.6 mmol), triethylamine (26 mL, 186 mmol), and (S)-pyrrolidin-3-yl-carbamic acid tert-butyl ester (5.6 g, 30 mmol) in acetonitrile (150 mL) is stirred at room temperature for 24 hours. The solvent is removed under vacuum and the residue dissolved in chloroform, washed with NaHCO$_3$ and then brine, dried over Na$_2$SO$_4$, filtered, and concentrated in vacuo to afford a solid. The solid is then purified by column chromatography (1:1:6 ethyl acetate/chloroform/hexanes) to yield the title compound as a solid (7.92 g). $^1$H NMR (CDCl$_3$): δ 7.48–7.30 (m, 5H), 5.35 (s, 2H), 4.77–4.50 (m, 1H), 4.37–4.19 (m, 1H), 4.01–3.63 (m, 3H), 3.59–3.46 (m, 1H), 2.29–2.09 (m, 1H), 2.01–1.82 (m, 1H), 1.45 (s, 9H).

(e) 4-(Pyrrolidin-1-yl)-2,5-difluorobenzoic acid ethyl ester

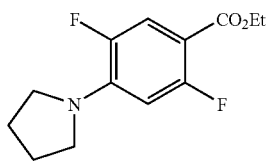

87

To a solution of 2,4,5-trifluorobenzoic acid ethyl ester (Example 1e, 4.32 g, 21.2 mmol) in acetonitrile (25 mL) is added triethylamine (5.9 mL, 42.3 mmol) and pyrrolidine (2.2 mL, 25.4 mmol). After 24 hours, the reaction mixture is diluted with ethyl acetate and washed with saturated NaHCO₃, water, and brine. The organic layer is dried over MgSO₄, filtered, and the filtrate is concentrated to afford the title compound as an oil (5.25 g). MS CI: m/z 256 (MH⁺).

(f) 4-[3-(tert-Butoxycarbonylamino)pyrrolidin-1-yl]-2,5-difluoro-3-methoxybenzoic acid ethyl ester

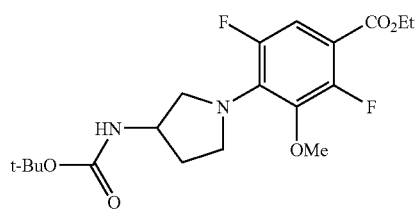

A solution of 2,4,5-trifluoro-3-methoxybenzoic acid ethyl ester (Example 1f, 2.821 g, 12.05 mmol), pyrrolidin-3-ylcarbamic acid tert-butyl ester (3.310 g, 17.77 mmol), and triethylamine (9.13 g, 12.6 mL, 90.23 mmol) in acetonitrile (50 mL) is heated at 40° C. under nitrogen for 2 days. The yellow solution is concentrated to near dryness and poured into saturated NaHCO₃ solution and extracted with dichloromethane. The combined organic extracts are washed with brine, dried over Na₂SO₄, filtered, and concentrated under vacuum. The resulting residue is purified by flash column chromatography (1:7 ethyl acetate/hexanes) to afford the title compound as a yellow solid (3.743 g). MS EI: m/z 401 (MH⁺).

(g) 4-[3-tert-Butoxycarbonylaminopyrrolidin-1-yl]-3-chloro-2,5-difluorobenzoic acid ethyl ester

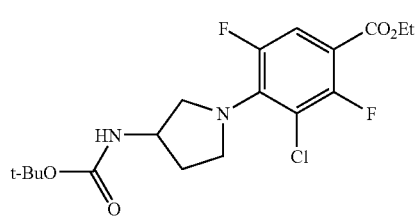

To a solution of 3-chloro-2,4,5-tri-fluorobenzoic acid ethyl ester (Example 1c, 5.50 g, 23.05 mmol) in acetonitrile (25 mL) is added triethylamine (6.43 mL, 46.1 mmol) and pyrrolidin-3-ylcarbamic acid tert-butyl ester (4.72 g, 25.4 mmol). After 48 hours, the mixture is diluted with ethyl acetate and washed with saturated NaHCO₃, water, and brine. The organic layer is dried over MgSO₄, filtered, and the filtrate is concentrated to afford the title compound (9.2 g). MS CI: m/z 405 (MH⁺).

88

4-[3-(tert-Butoxycarbonylamino)pyrrolidin-1-yl]-2,3-difluorobenzoic acid ethyl ester

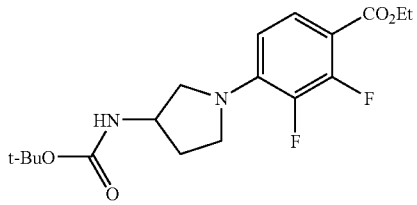

A solution of 2,3,4-trifluorobenzoic acid ethyl ester (Example 1g, 3.70 g, 18.1 mmol), pyrrolidin-3-ylcarbamic acid tert-butyl ester (4.02 g, 21.6 mmol), and triethylamine (18.0 mL, 129 mmol) in acetonitrile (50 mL) is heated at 50° C. under nitrogen atmosphere for 4.5 hours. The solution is concentrated in vacuo and poured into a saturated NaHCO₃ solution. The mixture is then extracted with chloroform, and the combined organic extracts are washed with brine, dried with Na₂SO₄, filtered, and the mixture concentrated in vacuo. The resulting residue is then purified by column chromatography (1:7 ethyl acetate/hexanes) to afford the title compound (4.70 g). $^1$H NMR (CDCl₃): δ 7.59–7.49 (m, 1H), 6.35–6.26 (m, 1H), 4.88–4.84 (bd, 1H), 4.39–4.28 (m, 3H), 3.81–3.50 (m, 3H), 3.48–3.34 (m, 1H), 2.32–2.15 (m, 1H), 2.02–1.76 (m, 1H), 1.45 (s, 9H), 1.40 (t, 3H).

(i) 4-(3-tert-Butoxycarbonylaminopyrrolidin-1-yl)-2,5-difluorobenzoic acid ethyl ester

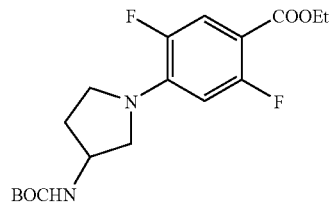

To a solution of 2,4,5-trifluorobenzoic acid ethyl ester (Example 1e, 14.8 g, 72.4 mmol) in acetonitrile (225 mL) is added triethylamine (65 mL, 466 mmol) and pyrrolidin-3-ylcarbamic acid tert-butyl ester (16.07 g, 86.2 mmol). After 45 hours, the reaction mixture is diluted with ethyl acetate and washed with saturated NaHCO₃, water, and brine. The organic layer is dried over MgSO₄, filtered, and the filtrate is concentrated to afford an oil. The resulting residue is purified by flash chromatography (1:5 ethyl acetate/hexanes) to afford the title compound. MS (ES, M+1) m/z 371, mp 98–100° C.

The following compounds are synthesized according to general procedures described in Examples 2a–i above.

(k) 4-(3-tert-Butoxycarbonylaminopyrrolidin-1-yl)-2,5-difluoro-3-methylbenzoic acid ethyl ester (MS ES, MH⁺) m/z 385) using 2,4,5-trifluoro-3-methylbenzoic acid ethyl ester (Example 1i) and pyrrolidin-3-ylcarbamic acid tert-butyl ester.

(l) 4-[3-(tert-Butoxycarbonylaminomethyl)pyrrolidin-1-yl]-2,5-difluoro-3-methylbenzoic acid ethyl ester (MS ES, MH⁺) m/z 399) using 2,4,5-trifluoro-3-methylbenzoic acid ethyl ester (Example 1i) and 3-(tert-butoxycarbonylaminomethyl)pyrrolidine (Rogers D. H., Saunders J., Williams J. P., DE 19955794).

(m) 4-(3-tert-Butoxycarbonylaminopyrrolidin-1-yl)-2,3-difluoro-5-methoxybenzoic acid ethyl ester (MS ES, MH+) m/z 401) using 2,3,4-trifluoro-5-methoxybenzoic acid ethyl ester (Example 1h) and pyrrolidin-3-ylcarbamic acid tert-butyl ester.

(n) 4-[3-(tert-Butoxycarbonylaminomethyl)pyrrolidin-1-yl]-2,5-difluoro-3-methoxybenzoic acid ethyl ester (MS ES, MH+) m/z 415) using 2,4,5-trifluoro-3-methoxybenzoic acid ethyl ester (Example 1f) and 3-(tert-butoxycarbonylaminomethyl)pyrrolidine (Rogers D. H., Saunders J., Williams J. P., DE 19955794).

(o) 4-(3-tert-Butoxycarbonylaminopyrrolidin-1-yl)-3-ethoxy-2,5-difluorobenzoic acid ethyl ester. (1H NMR (200 MHz, CDCl3): δ 7.31 (dd, 1H), 4.71 (bs, 1H), 4.34–3.4 (m, 9H), 2.23–1.81 (m, 2H), 1.45 (s, 9H), 1.37 (t, 3H), 1.33 (t, 3H); ((MS ES, MH+) m/z 415.) using 3-ethoxy-2,5-difluorobenzoic acid ethyl ester (Sanchez J. P., Gogliotti R. D., Domagala J. M., Gracheck S. J., Huband M. D., Sesnie J. A., Cohen M. A., Shapiro M. A., *J. Med. Chem.,* 1995; 38(22): 4478–4487) and pyrrolidin-3-ylcarbamic acid tert-butyl ester.

(p) 3-(Benzyloxyiminomethyl)-4-(3-tert-butoxycarbonylaminopyrrolidin-1-yl)-2,5-difluorobenzoic acid ethyl ester (MS ES, MH+) m/z 504) using 3-(benzyloxyiminomethyl)-2,4,5-trifluorobenzoic acid ethyl ester (Example 1j) and pyrrolidin-3-ylcarbamic acid tert-butyl ester.

(q) 3-Chloro-2,5-difluoro-4-(3-[1,2,3]-triazol-1-ylpyrrolidin-1-yl)benzoic acid ethyl ester (1H NMR (200 MHz, CDCl3): δ 7.79 (s, 1H), 7.65 (s, 1H), 7.41–7.51 (m, 1H), 5.40–5.30 (m, 1H), 4.34–4.24 (q, 2H), 4.13–3.45 (m, 4H), 2.65–2.50 (m, 1H), 2.43–2.28 (m, 1H), 1.34–1.27 (t, 3H)) using 3-chloro-2,4,5-trifluorobenzoic acid ethyl ester (Example 1c) and 1-pyrrolidin-3-yl-1H-[1,2,3]triazole (Singh R., Singh I. P., Thomas G., Singh M. P., Micetich R. G., Fahti-Afshar R., Doerksen T. R., PCT Int. Appl., 1992, WO 9210492 A1).

EXAMPLE 3

Synthesis of 2-Substituted-Amino Benzoates

General Procedure

A solution of 4-(pyrrolidin-1-yl)-2-fluorobenzoic acid ethyl esters (Example 2) and cyclopropylamine (10–15 eq.) in dimethyl sulfoxide and triethylamine (2–5 eq.) is heated in a sealed glass tube for 3 days at 140° C. Compressed air is blown into the mixture to remove excess cyclopropylamine. The resulting solution is concentrated under vacuum and purified by column chromatography (ethyl acetate/hexanes) to afford 4-(substituted pyrrolidin-1-yl)-2-cyclopropylamino-benzoic acid esters.

(a) 4-[(S)-3-tert-Butoxycarbonylaminopyrrolidin-1-yl]-2-cyclopropylamino-3,5-difluorobenzoic acid ethyl ester

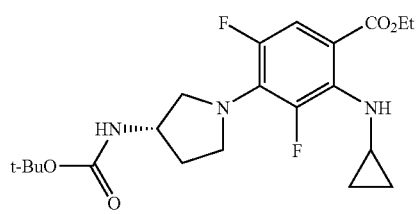

A solution of 4-[(S)-3-(tert-butoxycarbonylamino)pyrrolidin-1-yl]-2,3,5-trifluorobenzoic acid ethyl ester (Example 2a, 1.95 g, 5.01 mmol) and cyclopropylamine (14.0 mL, 201 mmol) in dimethyl sulfoxide (5 mL) is heated in a sealed glass tube for 44.5 hours at 100° C. Compressed air is blown into the black solution to remove excess cyclopropylamine. The solution is concentrated under high vacuum and purified by flash column chromatography (1:9 ethyl acetate/hexanes) to afford the title compound (1.77 g). 1H NMR (CDCl3): δ 7.32 (dd, 1H), 4.81–4.67 (bs, 1H), 4.35–4.16 (m, 3H), 3.95–3.40 (m, 4H), 2.92–2.80 (m, 1H), 2.25–2.08 (m, 1H), 1.97–1.77 (m, 1H), 1.46 (s, 9H), 1.34 (t, 3H), 0.72–0.63 (m, 2H), 0.57–0.49 (m, 2H).

(b) 4-[(S)-3-tert-Butoxycarbonylaminopyrrolidin-1-yl]-2-cyclopropylamino-3,6-difluorobenzoic acid ethyl ester

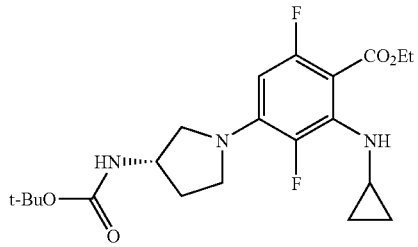

A solution of 4-[(S)-3-(tert-butoxycarbonylamino)pyrrolidin-1-yl]-2,3,6-trifluorobenzoic acid ethyl ester (Example 2b, 5.4 g, 13.9 mmol), cyclopropylamine (40 mL, 577 mmol), and dimethyl sulfoxide (28 mL) in a sealed glass tube is heated at 100° C. for 27 hours. The excess amine is removed by blowing in compressed air before the solution is concentrated under high vacuum. The residue is then purified by column chromatography (1:1:8 ethyl acetate/chloroform/hexanes) to afford the title compound (4.80 g). 1H NMR (CDCl3): δ 7.42 (bs, 1H), 5.69 (ddd, 1H), 4.76–4.61 (m, 1H), 4.37–4.19 (m, 3H), 3.81–3.66 (m, 1H), 3.65–3.43 (m, 2H), 3.39–3.28 (m, 1H), 2.98–2.82 (m, 1H), 2.30–2.09 (m, 1H), 1.98–1.82 (m, 1H), 1.45 (s, 9H), 1.34 (t, 3H), 0.72–0.68 (m, 2H), 0.67–0.44 (m, 2H).

(c) 4-[(S)-3-tert-Butoxycarbonylaminopyrrolidin-1-yl]-3-chloro-2-cyclopropylamino-5-fluorobenzoic acid ethyl ester

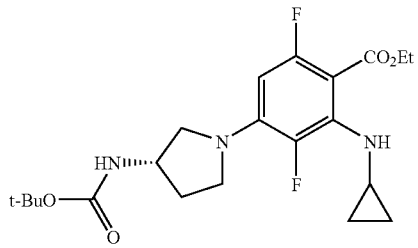

A solution of 4-[(S)-3-(tert-butoxycarbonylamino)pyrrolidin-1-yl]-3-chloro-2,5-difluorobenzoic acid ethyl ester (Example 2c, 9.34 g, 23.1 mmol), cyclopropylamine (16 mL, 228 mmol), and dimethyl sulfoxide (30 mL) is heated in a sealed tube at 110° C. for 3 days. After cooling to room temperature, the reaction mixture is diluted with ethyl acetate and washed with saturated NaHCO3, water, and brine. The organic layer is dried over MgSO4, filtered, and the filtrate is concentrated to afford a brown residue. The residue is then purified via flash column chromatography (1:1 ethyl acetate/hexanes) to afford the title compound (4.41 g). MS CI: m/z 442 (MH⁺).

(d) 4-[(S)-3-tert-Butoxycarbonylaminopyrrolidin-1-yl]-2-cyclopropylamino-3,5,6-trifluorobenzoic acid benzyl ester

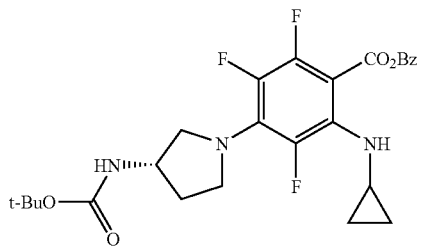

A solution of 4-[(S)-3-(tert-butoxycarbonylamino)pyrrolidin-1-yl]-2,3,5,6-tetrafluorobenzoic acid benzyl ester (Example 2d, 2.5 g, 5.3 mmol), cyclopropylamine (40 mL, 577 mmol), and dimethyl sulfoxide (20 mL) in a sealed glass tube is heated at 80° C. for 24 hours. The excess amine is removed by blowing in compressed air, and the solution is then concentrated under high vacuum. The residue is purified by column chromatography (1:1:7 ethyl acetate/chloroform/hexanes) to afford the title compound as a solid (2.31 g). ¹H NMR (CDCl₃): δ 7.47–7.27 (m, 5H), 7.12 (bs, 1H), 5.30 (s, 2H), 4.78–4.62 (m, 1H), 4.35–4.17 (m, 1H), 3.96–3.56 (m, 3H), 3.54–3.39 (m, 1H), 2.91–2.73 (m, 1H), 2.24–2.02 (m, 1H), 1.96–1.77 (m, 1H), 1.45 (s, 9H), 0.69–0.56 (m, 2H), 0.53–0.40 (m, 2H).

(e) 2-Cyclopropylamino-5-fluoro-4-pyrrolindin-1-ylbenzoic acid ethyl ester

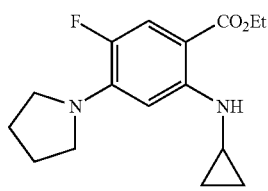

4-(Pyrrolidin-1-yl)-2,5-difluorobenzoic acid ethyl ester (Example 2e, 5.25 g, 20.6 mmol) and cyclopropylamine (30 mL, 428 mmol) are stirred in dimethyl sulfoxide (30 mL) at 110° C. for 3 days in a sealed tube. After cooling to room temperature, the reaction mixture is diluted with ethyl acetate and washed with saturated NaHCO₃, water, and brine. The organic layer is dried over MgSO₄, filtered, and the filtrate concentrated to afford a brown residue. The residue is purified via flash column chromatography (1:9 hexanes/dichloromethane) to afford the title compound as a solid (5.39 g). MS CI: m/z 293 (MH⁺).

(f) 4-[3-(tert-Butoxycarbonylamino)pyrrolidin-1-yl]-5-fluoro-2-isopropylaminobenzoic acid ethyl ester

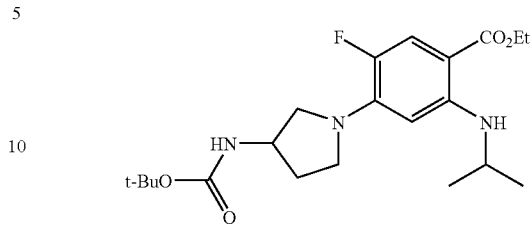

4-[3-(tert-Butoxycarbonylamino)-pyrrolidin-1-yl]-2,5-difluorobenzoic acid ethyl ester (Example 2j, 5.4 g, 13.9 mmol), isopropylamine (40 mL, 469 mmol), and dimethyl sulfoxide (25 mL) are heated at 100° C. for 4 days in a sealed glass tube. The excess amine is removed by blowing in compressed air. The residue is filtered and concentrated under vacuum to a thick oil. Purification by column chromatography (1:1:7 ethyl acetate/chloroform/hexanes) to provide the title compound as a solid (1.6 g). MS: m/z 410 (MH⁺).

(g) 4-[(S)-3-(tert-butoxycarbonylamino)pyrrolidin-1-yl]-2-sec-butylamino-3-chloro-5-fluorobenzoic acid ethyl ester

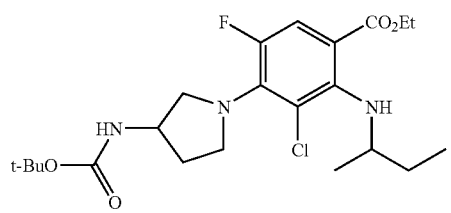

4-[(S)-3-(tert-Butoxycarbonylamino)pyrrolidin-1-yl]-3-chloro-2,5-difluorobenzoic acid ethyl ester (Example 2c, 1.95 g, 4.81 mmol), sec-butylamine (30 mL, 296 mmol), and dimethyl sulfoxide (20 mL) are heated in a sealed glass tube at 110° C. for 24 hours. The reaction mixture is evaporated, and purification by column chromatography (1:8, ethyl acetate/hexanes) provides the title compound as a yellow syrup (3.69 g). MS EI: m/z 458 (MH⁺).

(h) 4-[3-tert-butoxycarbonylamino)pyrrolidin-1-yl]-2-cyclopropylamino-5-fluoro-3-methoxybenzoic acid ethyl ester

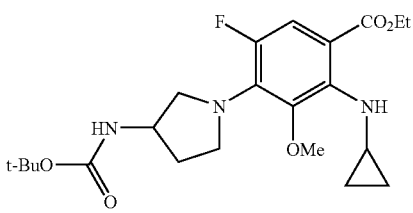

A solution of 4-[3-(tert-butoxycarbonylamino)pyrrolidin-1-yl]-2,5-difluoro-3-methoxybenzoic acid ethyl ester (Example 2f, 3.087 g, 7.71 mmol) and cyclopropylamine (12.0 mL, 172 mmol) in dimethyl sulfoxide (5 mL) is heated in a sealed glass tube for 3 days at 110° C. Compressed air is blown into the black solution to remove excess cyclopropylamine. The solution is concentrated under vacuum and purified by flash column chromatography (1:5 ethyl acetate/hexanes) to afford the title compound as a yellow solid (0.875 g). $^1$H NMR (CDCl$_3$): δ 7.33 (d, 1H), 7.15 (bs, 1H), 4.78–4.65 (m, 1H), 4.33–4.15 (m, 3H), 3.92–3.50 (m, 3H), 3.55 (s, 3H), 3.45–3.34 (m, 1H), 3.02–2.89 (m, 1H), 2.28–2.09 (m, 1H), 1.93–1.77 (m, 1H), 1.46 (s, 9H), 1.34 (t, 3H), 0.7–0.59 (m, 2H), 0.49–0.42 (m, 2H).

(i) 4-[3-tert-Butoxycarbonylamino)pyrrolidin-1-yl]-2-cyclobutylamino-5-fluorobenzoic acid ethyl ester

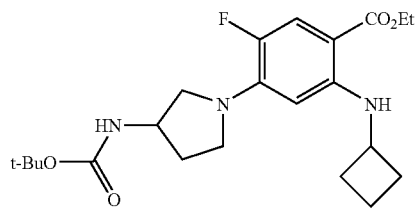

A solution of 4-[3-(tert-butoxycarbonylamino)pyrrolidin-1-yl]-2,5-difluorobenzoic acid ethyl ester (2j, 3.059 g, 8.26 mmol) and cyclobutylamine (15.0 mL, 175 mmol) in dimethyl sulfoxide (20 mL) is heated in a sealed vessel for 4 days at 110° C. Compressed air is blown into the black solution to remove excess cyclobutylamine. The solution is concentrated under vacuum and purified by flash column chromatography (1:5 ethyl acetate/hexanes) to afford the title compound as a yellow solid (1.715 g). $^1$H NMR (CDCl$_3$): δ 7.67 (bs, 1H), 7.48 (d, 1H), 5.54 (d, 1H), 4.77–4.64 (bs, 1H), 4.38–4.18 (m, 3H), 3.97–3.85 (m, 1H), 3.80–3.42 (m, 3H), 3.41–3.30 (m, 1H), 2.50–2.32 (m, 2H), 2.28–2.12 (m, 1H), 2.05–1.70 (m, 5H), 1.46 (s, 9H), 1.35 (t, 3H).

(j) 4-[3-(tert-Butoxycarbonylamino)pyrrolidin-1-yl]-2-cyclopropylamino-3-fluorobenzoic acid ethyl ester

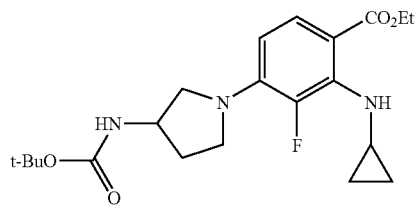

A solution of 4-[3-(tert-butoxycarbonylamino)pyrrolidin-1-yl]-2,3-difluorobenzoic acid ethyl ester (Example 2h, 1.85 g, 5.01 mmol) and cyclopropylamine (14.0 mL, 201 mmol) in N,N-dimethylacetamide (5 mL) is heated in a sealed glass tube for 48 hours at 100° C. The solution is then concentrated under high vacuum and purified by column chromatography (1:9 ethyl acetate/hexanes) to afford the title compound (1.57 g). $^1$H NMR (CDCl$_3$): δ 7.59 (bs, 1H), 7.57 (dd, 1H), 6.00 (dd, 1H), 4.82–4.68 (bd, 1H), 4.39–4.18 (m, 3H), 3.80–3.49 (m, 3H), 3.41–3.30 (m, 1H), 3.00–2.88 (m, 1H), 2.31–2.11 (m, 1H), 2.00–1.85 (m, 1H), 1.45 (s, 9H), 1.37 (t, 3H), 0.73–0.50 (m, 4H).

(k) 4-[3-(tert-Butoxycarbonylamino)pyrrolidin-1-yl]-5-chloro-2-cyclopropylamino-3-fluorobenzoic acid ethyl ester

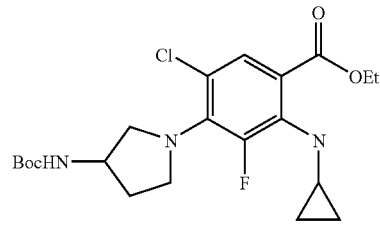

A solution of 4-[3-(tert-butoxycarbonylamino)pyrrolidin-1-yl]-5-chloro-2,3-difluorobenzoic acid ethyl ester (Example 21, 3.75 g, 9.3 mmol) and cyclopropylamine (14.0 mL, 201 mmol) in N,N-dimethylacetamide (5 mL) is heated in a sealed glass tube for 48 hours at 100° C. The solution is then concentrated under high vacuum and purified by column chromatography (1:9 ethyl acetate/hexanes) to afford the title compound (2.0 g). $^1$H NMR (CDCl$_3$): δ 7.64 (d, 1H), 7.56 (bs, 1H), 4.98–4.90 (bd, 1H), 4.40–4.20 (m, 3H), 3.78–3.63 (m, 4H), 2.97–2.83 (m, 1H), 2.35–2.21 (m, 1H), 1.93–1.81 (m, 1H), 1.46 (s, 9H), 1.38 (t, 3H), 0.75–0.61 (m, 2H), 0.57–0.50 (m, 2H).

The following compounds are synthesized according to general procedures Examples 3a–k described above.

(l) 4-(3-tert-Butoxycarbonylaminopyrrolidin-1-yl)-2-cyclopropylamino-5-fluoro-3-methylbenzoic acid ethyl ester ([MS ES, MH$^+$] m/z 422) using 4-(3-tert-butoxycarbonylaminopyrrolidin-1-yl)-2,5-difluoro-3-methyl-benzoic acid ethyl ester (Example 2k).

(m) 4-[3-(tert-Butoxycarbonylaminomethyl)pyrrolidin-1-yl]-2-cyclopropylamino-5-fluoro-3-methylbenzoic acid ethyl ester. ([MS ES, M+1] m/z 436) using 4-[3-(tert-butoxycarbonylaminomethyl)-pyrrolidin-1-yl]-2,5-difluoro-3-methylbenzoic acid ethyl ester (Example 2l).

(n) 4-(3-tert-Butoxycarbonylaminopyrrolidin-1-yl)-2-cyclopropylamino-3-fluoro-5-methoxybenzoic acid ethyl ester. ([MS ES, M+1] m/z 439) using 4-(3-tert-butoxycarbonylaminopyrrolidin-1-yl)-2,3-difluoro-5-methoxybenzoic acid ethyl ester (Example 2m).

(o) 4-[3-(tert-Butoxycarbonylaminomethyl)pyrrolidin-1-yl]-2-cyclopropylamino-5-fluoro-3-methoxybenzoic acid ethyl ester ([MS ES, MH$^+$] m/z 453) using 4-[3-(tert-butoxycarbonylaminomethyl)-pyrrolidin-1-yl]-2,5-difluoro-3-methoxybenzoic acid ethyl ester (Example 2n)

(p) 4-(3-tert-Butoxycarbonylaminopyrrolidin-1-yl)-2-cyclopropylamino-3-ethoxy-5-fluorobenzoic acid ethyl ester ([MS ES, MH$^+$] m/z 452). using 4-(3-tert-butoxycarbonylaminopyrrolidin-1-yl)-3-ethoxy-2,5-difluorobenzoic acid ethyl ester (Example 2o).

(q) 3-(Benzyloxyiminomethyl)-4-(3-tert-butoxycarbonylaminopyrrolidin-1-yl)-2-cyclopropylamino-5-fluorobenzoic acid ethyl ([MS ES, MH$^+$] m/z 541) using 3-(benzyloxyiminomethyl)-4-(3-tert-butoxycarbonylaminopyrrolidin-1-yl)-2,5-difluorobenzoic acid ethyl ester (Example 2p).

(r) 3-Chloro-2-cyclopropylamino-5-fluoro-4-(3-[1,2,3]-triazol-1-yl-pyrrolidin-1-yl)benzoic acid ethyl ester ($^1$H NMR (200 MHz, CDCl$_3$): δ 8.00 (s, 1H), 7.73 (s, 1H), 7.52 (d, 1H), 7.19 (bs, 1H), 5.53–5.39 (m, 1H), 4.36–4.21 (q, 2H), 4.14–4.01 (m, 1H), 3.98–3.83 (m, 1H), 2.71–2.58 (m, H), 2.43–2.29 (m, H), 1.41–1.28 (t, 3H), 0.73–0.59 (m, 2H), 0.52–0.37 (m, 2H)) using 3-chloro-2,5-difluoro-4-(3-[1,2,3]-triazol-1-yl-pyrrolidin-1-yl)benzoic acid ethyl ester (Example 2q)

EXAMPLE 4

Ester Hydrolysis

General Procedure

A solution of 4-(substituted-pyrrolidin-1-yl)-2-cyclopropylaminobenzoic acid ester (Example 3) and aqueous sodium hydroxide (10–20 eq., 1.0N) in tetrahydrofuran and methanol is heated for 16 to 24 hours at 70° C. The solution is cooled, diluted with water, and partially concentrated under vacuum. The resulting solution is acidified to pH 6 with aqueous 1.0N hydrochloric acid, then the pH is adjusted to pH 7–8 with 5% NaHCO$_3$ solution and extracted with ethyl acetate. The combined organic extracts are dried over Na$_2$SO$_4$, filtered, and concentrated in vacuo to afford 4-(substituted-pyrrolidin-1-yl)-2-cyclopropylaminobenzoic acid.

(a) 4-[(S)-3-tert-Butoxycarbonylaminopyrrolidin-1-yl]-2-cyclopropylamino-3,5-difluorobenzoic acid

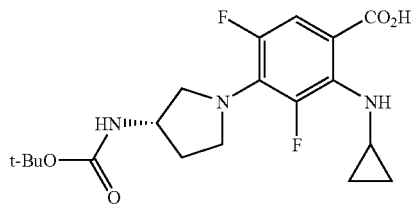

A solution of 4-[(S)-3-tert-butoxycarbonylamino)pyrrolidin-1-yl]-2-cyclopropylamino-3,5-difluorobenzoic acid ethyl ester (Example 3a, 1.40 g, 3.29 mmol) and aqueous sodium hydroxide (1.33 N, 15.0 mL, 20.0 mmol) in tetrahydrofuran (20 mL) and methanol (50 mL) is heated for 3 hours at 50° C. The solution is cooled, diluted with water, and partially concentrated in vacuo. The resulting solution is acidified to pH 6 with aqueous 1N hydrochloric acid, and then the pH is adjusted to pH 7–8 with 5% NaHCO$_3$ and extracted with chloroform. The combined organic extracts are dried over Na$_2$SO$_4$, filtered, and concentrated to give the title compound as a pale yellow solid (1.31 g). $^1$H NMR (DMSO-d$_6$): δ 12.65 (bs, 1H), 7.48 (bs, 1H), 7.27–7.14 (m, 2H), 4.08–3.92 (m, 1H), 3.85–3.45 (m, 3H), 3.45–3.29 (m, 1H), 2.86–2.74 (m, 1H), 2.10–1.91 (m, 1H), 1.89–1.72 (m, 1H), 1.39 (s, 9H), 0.71–0.60 (m, 2H), 0.47–0.38 (m, 2H).

(b) 4-[(S)-3-tert-Butoxycarbonylaminopyrridin-1-yl]-2-cyclopropylamino-3,6-difluorobenzoic acid

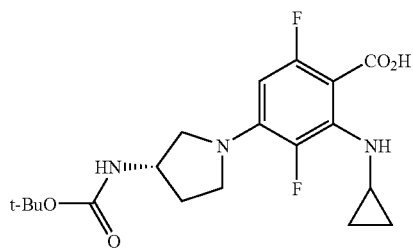

A solution of 4-[(S)-3-tert-butoxycarbonylamino)pyrrolidin-1-yl]-2-cyclopropylamino-3,6-difluorobenzoic acid ethyl ester (Example 3b, 1.45 g, 3.40 mmol) and aqueous sodium hydroxide (1.33N, 17.0 mL, 22.6 mmol) in tetrahydrofuran (20 mL) and methanol (50 mL) is heated for 21 hours at 50° C. The solution is cooled, diluted with water, and then partially concentrated in vacuo. The resulting solution is acidified to pH 6 with aqueous 1N hydrochloric acid, and then the pH is adjusted to pH 7–8 with 5% NaHCO$_3$ and extracted with ethyl acetate three times. The combined organic extracts are dried over Na$_2$SO$_4$, filtered, and concentrated under vacuum to give the title compound as a pale green solid (1.33 g). $^1$H NMR (DMSO-d$_6$): δ 7.21 (bd, 1H), 5.83 (dd, 1H), 4.12–3.98 (m, 1H), 3.75–3.20 (m, 5H), 2.88–2.78 (m, 1H), 2.14–1.96 (m, 1H), 1.90–1.73 (m, 1H), 1.39 (s, 9H), 0.69–0.59 (m, 2H), 0.45–0.36 (m, 2H).

(c) 4-[(S)-3-tert-Butoxycarbonylaminopyrrolidin-1-yl]-3-chloro-2-cyclopropylamino-5-fluoro-benzoic acid

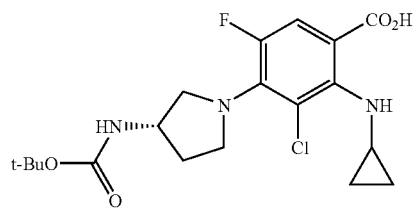

To a solution of 4-[(S)-3-(tert-butoxycarbonylamino)pyrrolidin-1-yl]-3-chloro-2-cyclopropylamino-5-fluorobenzoic acid ethyl ester (Example 3c, 2.90 g, 6.56 mmol) in methanol (30 mL) and tetrahydrofuran (30 mL) is added a 1N solution of sodium hydroxide (50 mL). The reaction mixture is stirred at 80° C. for 20 hours, cooled to room temperature, and diluted with ethyl acetate. The organic layer is washed with 1N hydrochloric acid, water, and brine. The organic layer is dried over MgSO$_4$, filtered, and filtrate concentrated to the title compound as a solid (2.74 g). MS CI: m/z 414 (MH$^+$).

(d) 4-[(S)-3-tert-Butoxycarbonylaminopyrrolidin-1-yl]-2-cyclopropylamino-3,5,6-trifluorobenzoic acid

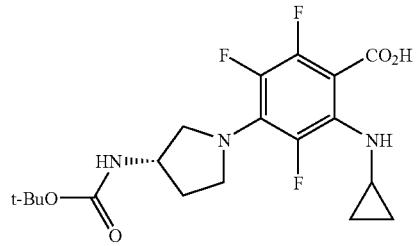

A solution of benzyl 4-[(S)-3-(tert-butoxycarbonylamino)pyrrolidin-1-yl]-2-cyclopropylamino-3,5,6-trifluorobenzoate (Example 3d, 3.68 g, 7.31 mmol), 1.0 M NaOH (75 mL), methanol (50 mL), and tetrahydrofuran (50 mL) is heated at 50° C. for 24 hours. The mixture is partially concentrated under vacuum and then extracted with dichloromethane. The aqueous phase is brought to pH 7.5 using 1.0 M HCl and extracted with ethyl acetate. The combined ethyl acetate extracts are dried over Na$_2$SO$_4$, filtered, and concentrated under vacuum to afford 4-[(S)-3-tert-butoxycarbonylamino-pyrridin-1-yl]-2-cyclopropylamino-3,5,6-trifluoro-benzoic acid as a solid (2.9 g). This material is used without further purification. ¹H NMR (DMSO-d₆): δ 7.19 (bd, 1H), 4.12–3.95 (m, 1H), 3.83–3.52 (m, 3H), 3.48–3.33 (m, 1H), 2.83–2.69 (m, 1H), 2.10–1.94 (m, 1H), 1.89–1.72 (m, 1H), 1.49 (s, 9H), 0.70–0.56 (m, 2H), 0.44–0.33 (m, 2H).

(e) 2-Cyclopropylamino-5-fluoro-4-pyrrolidin-1-ylbenzoic acid

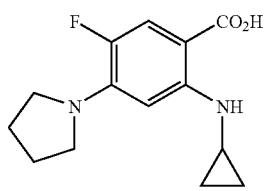

To a solution of 4-(pyrrolidin-1-yl)-2-cyclopropylamino-5-fluorobenzoic acid ethyl ester (Example 3e, 3.10 g, 10.4 mmol) in methanol (50 mL) and tetrahydrofuran (20 mL) is added 1N solution of sodium hydroxide (35 mL). The reaction mixture is stirred at 80° C. for 20 hours, cooled to room temperature, and diluted with ethyl acetate. The organic layer is washed with 1N hydrochloric acid, water, and brine. The organic layer is dried over MgSO₄, filtered, and the filtrate concentrated to afford the title compound as a solid (2.47 g). MS CI: m/z 263 (M⁺).

4-[3-tert-Butoxycarbonylamino)pyrrolidin-1-yl]-5-fluoro-2-isopropylaminobenzoic acid

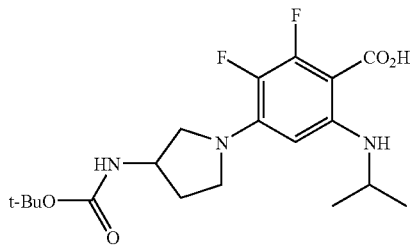

A solution of 4-[3-(tert-butoxycarbonylamino)pyrrolidin-1-yl]-5-fluoro-2-isopropylaminobenzoic acid ethyl ester (Example 3f, 1.5 g, 3.40 mmol), aqueous 1 M sodium hydroxide (50 mL), tetrahydrofuran (40 mL), and methanol (40 mL) are heated for 25 hours at 70° C. The solution is cooled, diluted with water, and then partially concentrated. The resulting solution is acidified to pH 7–8 with aqueous 1.0 M hydrochloric acid and extracted with ethyl acetate. The combined organic extracts are dried over Na₂SO₄, filtered, and concentrated under vacuum to give the title compound as a solid (1.25 g). MS EI: m/z 380 (M⁺).

(g) 4-[3-(tert-Butoxycarbonylamino)pyrrolidin-1-yl]-2-sec-butylamino-3-chloro-5-fluorobenzoic acid

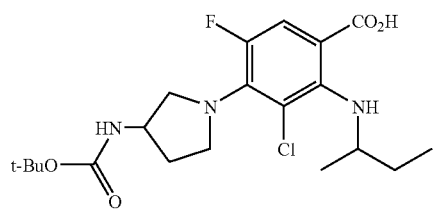

A solution of 4-[3-tert-butoxycarbonylamino)pyrrolidin-1-yl]-2-sec-butylamino-3-chloro-5-fluorobenzoic acid ethyl ester (Example 3g, 3.57 g, 7.79 mmol), 1.0N sodium hydroxide (50 mL), and methanol (80 mL) are heated at 80° C. for 16.5 hours. The mixture is partially evaporated, diluted with water (150 mL), and the pH adjusted to 7.0–8.0 using 1.0 M hydrochloric acid. The mixture is extracted with ethyl acetate, dried over Na₂SO₄, and concentrated under vacuum to give the title compound as an off-white solid (3.26 g) which is used without further purification. MS EI: m/z 430 (M⁺).

(h) 4-[3-tert-Butoxycarbonylamino)pyrrolidin-1-yl]-2-cyclopropylamino-5-fluoro-3-methoxybenzoic acid

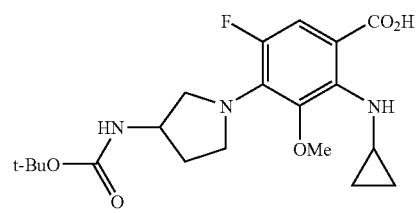

A solution of 4-[3-tert-butoxycarbonylamino)pyrrolidin-1-yl]-2-cyclopropylamino-5-fluoro-3-methoxybenzoic acid ethyl ester (Example 3h, 0.173 g, 0.395 mmol) and aqueous sodium hydroxide (1.33N, 2.0 mL, 2.66 mmol) in tetrahydrofuran (10 mL) and methanol (30 mL) is heated for 22 hours at 70° C. The solution is cooled, diluted with water, and partially concentrated under vacuum. The resulting solution is acidified to pH 6 with aqueous 1N hydrochloric acid, and then the pH is adjusted to pH 7–8 with 5% NaHCO₃ solution and extracted with ethyl acetate. The combined organic extracts are dried over Na₂SO₄, filtered, and concentrated in vacuo to afford the title compound as a yellow solid (0.160 g). ¹H NMR (CDCl₃): δ 7.46 (d, 1H), 4.80–4.69 (bs, 1H), 4.33–4.18 (m, 1H), 3.90–3.45 (m, 3H), 3.62 (s, 3H), 3.43–3.32 (m, 1H), 2.91–2.80 (m, 1H), 2.28–2.10 (m, 1H), 1.96–1.78 (m, 1H), 1.46 (s, 9H), 0.63–0.52 (m, 4H).

(i) 4-[3-tert-Butoxycarbonylamino)pyrrolidin-1-yl]-2-cyclobutylamino-5-fluorobenzoic acid

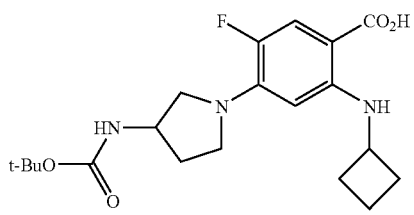

A solution of 4-[3-tert-butoxycarbonylamino)pyrrolidin-1-yl]-2-cyclobutylamino-5-fluorobenzoic acid ethyl ester (Example 3i, 1.51 g, 3.58 mmol) and aqueous sodium hydroxide (1.33N, 20.0 mL, 26.6 mmol) in tetrahydrofuran (15 mL) and methanol (40 mL) is refluxed for 19 hours. The solution is cooled, diluted with water, and partially concentrated under vacuum. The resulting solution is acidified to pH 6 with aqueous 1.0N hydrochloric acid, and then the pH is adjusted to pH 7–8 with 5% NaHCO$_3$ solution and extracted with ethyl acetate. The combined organic extracts are dried over Na$_2$SO$_4$, filtered, and concentrated under vacuum to afford the title compound as a yellow solid (1.353 g). MS EI: m/z 394 (MH$^+$).

(j) 4-[3-(tert-Butoxycarbonylamino)pyrrolidin-1-yl]-2-cyclopropylamino-3-fluorobenzoic acid

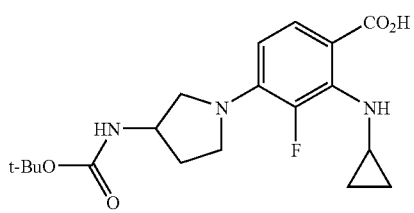

A solution of 4-[3-(tert-butoxycarbonylamino)pyrrolidin-1-yl]-2-cyclopropylamino-3-fluorobenzoic acid ethyl ester (Example 3j, 1.34 g, 3.29 mmol) and aqueous sodium hydroxide (2N, 20 mL) in tetrahydrofuran (20 mL) and methanol (20 mL) is refluxed for 1 hour. The solution is partially concentrated in vacuo, then acidified to pH 6 and extracted with chloroform. The combined organic extracts are dried over Na$_2$SO$_4$, filtered, and concentrated to give the title compound (1.40 g). $^1$H NMR (CDCl$_3$): δ 7.59 (dd, 1H), 6.06 (dd, 1H), 4.80–4.70 (bd, 1H), 4.38–4.22 (m, 1H), 3.79–3.50 (m, 3H), 3.47–3.35 (m, 1H), 2.98–2.87 (m, 1H), 2.30–2.14 (m, 1H), 1.97–1.84 (m, 1H), 1.46 (s, 9H), 0.69–0.54 (m, 4H).

(k) 4-[3-(tert-Butoxycarbonylamino)pyrrolidin-1-yl]-5-chloro-2-cyclopropylamino-3-fluorobenzoic acid

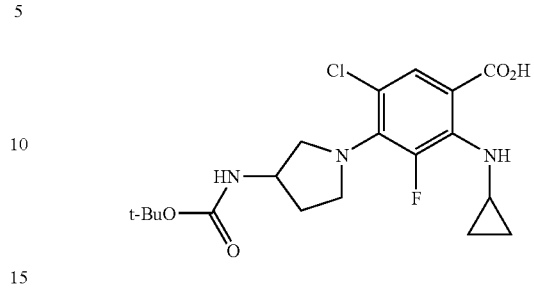

A solution of 4-[3-(tert-butoxycarbonylamino)pyrrolidin-1-yl]-5-chloro-2-cyclopropylamino-3-fluorobenzoic acid ethyl ester (Example 3k, 2.00 g, 4.50 mmol) and aqueous sodium hydroxide (2.0N, 20 mL) in tetrahydrofuran (20 mL), and methanol (20 mL) is refluxed for 1 hour. The solution is partially concentrated in vacuo, acidified to pH 6, and extracted with chloroform. The combined organic extracts are dried over Na$_2$SO$_4$, filtered, and concentrated to give the title compound (1.70 g). $^1$H NMR (CDCl$_3$): δ 7.71 (d, 1H), 4.91–4.82 (bd, 1H), 4.40–4.25 (m, 1H), 3.77–3.69 (m, 2H), 3.53–3.34 (m, 2H), 3.00–2.88 (m, 1H), 2.24–2.15 (m, 1H), 1.90–1.80 (m, 1H), 1.46 (s, 9H), 0.72–0.54 (m, 4H).

The following compounds are synthesized according to general procedures of Examples 4a–k.

(l) 4-(3-tert-Butoxycarbonylaminopyrrolidin-1-yl)-2-cyclopropylamino-5-fluoro-3-methylbenzoic acid ([MS ES, MH$^+$] m/z 394.) using 4-(3-tert-butoxycarbonylaminopyrrolidin-1-yl)-2-cyclopropylamino-5-fluoro-3-methylbenzoic acid ethyl ester (Example 3l).

(m) 4-[3-(tert-Butoxycarbonylaminomethyl)pyrrolidin-1-yl]-2-cyclopropylamino-5-fluoro-3-methylbenzoic acid ([MS ES, M+1] m/z 408) using 4-[3-(tert-butoxycarbonylaminomethyl)pyrrolidin-1-yl]-2-cyclopropylamino-5-fluoro-3-methylbenzoic acid ethyl ester (Example 3m).

(n) 4-(3-tert-Butoxycarbonylaminopyrrolidin-1-yl)-2-cyclopropylamino-3-fluoro-5-methoxybenzoic acid ($^1$H NMR (200 MHz, CDCl$_3$): δ 12.50 (bs, 1H), 7.18–7.09 (m, 1H), 7.07 (d, 1H), 4.07–3.90 (m, 1H), 3.80–3.50 (m, 2H), 3.66 (s, 3H), 3.42–3.29 (m, 2H), 2.88–2.71 (m, 1H), 2.10–1.91 (m, 1H), 1.86–1.67 (m, 1H), 1.39 (s, 9H), 0.70–0.57 (m, 2H), 0.46–0.32 (m, 2H)) using 4-(3-tert-butoxycarbonylaminopyrrolidin-1-yl)-2-cyclopropylamino-3-fluoro-5-methoxybenzoic acid ethyl ester (Example 3n).

(o) 4-[3-(tert-Butoxycarbonylaminomethyl)pyrrolidin-1-yl]-2-cyclopropylamino-5-fluoro-3-methoxybenzoic acid. ([MS ES, M+1] m/z 424) using 4-[3-(tert-butoxycarbonylaminomethyl)pyrrolidin-1-yl]-2-cyclopropylamino-5-fluoro-3-methoxybenzoic acid ethyl ester (Example 3o)

(p) 4-(3-tert-Butoxycarbonylaminopyrrolidin-1-yl)-2-cyclopropylamino-3-ethoxy-5-fluorobenzoic acid ([MS ES, MH$^+$] m/z 424) using 4-(3-tert-butoxycarbonylaminopyrrolidin-1-yl)-2-cyclopropylamino-3-ethoxy-5-fluorobenzoic acid ethyl ester (Example 3p).

(q) 3-(Benzyloxyiminomethyl)-4-(3-tert-butoxycarbonylaminopyrrolidin-1-yl)-2-cyclopropylamino-5-fluorobenzoic acid (MS ES: m/z 513 (MH$^+$]) using 3-(benzyloxyiminomethyl)-4-(3-tert-butoxycarbonylamino-pyrrolidin-1-yl)-2-cyclopropylamino-5-fluorobenzoic acid ethyl ester (Example 3q)

(r) 3-Chloro-2-cyclopropylamino-5-fluoro-4-(3-[1,2,3-triazol]-1-yl-pyrrolidin-1-yl)benzoic acid ($^1$H NMR (200 MHz, CDCl$_3$): δ 8.50 (bs, 1H), 8.03 (s, 1H), 7.72 (s, 1H), 7.60 (d, 1H), 7, 5.54–5.39 (m, 1H), 4.13–3.97 (m, 1H), 3.92–3.85 (m, 1H), 3.68–3.63 (m, 1H), 3.54–3.42 (m, 1H), 3.10–3.00 (m, 1H), 2.78–2.60 (m, 1H), 2.39–2.33 (m, 1H), 0.70–0.58 (m, 2H), 0.58–0.46 (m, 2H)) using 3-chloro-2-cyclopropylamino-5-fluoro-4-(3-[1,2,3-triazol]-1-yl-pyrrolidin-1-yl)benzoic acid ethyl ester (Example 3r).

EXAMPLE 5

Synthesis of N-Substituted Anthranilic Acids

2-Cyclopropylamino-4,5-difluorobenzoic acid

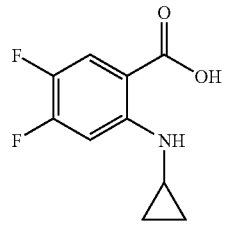

To a solution of 4,5-difluoroanthranilic acid (1.13 g, 6.53 mmol) in anhydrous methanol (40 mL) is added molecular sieves (3 Å), acetic acid (3.70 mL, 65.3 mmol) and [(1-ethoxycyclopropyl)oxy]trimethylsilane (5.25 mL, 26.11 mmol). After 30 minutes, sodium cyanoborohydride (2.08 g, 32.64 mmol) is added, and the reaction mixture is heated to reflux. After 16 hours, the reaction is cooled to room temperature, filtered, washed with methanol, and the combined filtrate concentrated under vacuum to afford a viscous oil. The resulting oil is dissolved in ethyl acetate and washed with 1.0 M hydrochloric acid, water, and brine. The organic layer is dried over MgSO$_4$, filtered, and the filtrate is concentrated under vacuum to afford as a beige solid (1.32 g). MS CI: m/z 212 (M$^+$).

(b) 5-Chloro-2-cyclopropylamino-4-fluorobenzoic acid

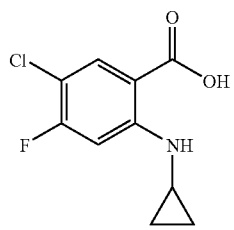

To a solution of 4,5-difluoroanthranilic acid (1.20 g, 6.37 mmol) in anhydrous methanol (50 mL) is added molecular sieves (3 Å), acetic acid (3.70 mL, 65.3 mmol), and [(1-ethoxycyclopropyl)oxy]trimethylsilane (5.12 mL, 25.5 mmol). After 30 minutes, sodium cyanoborohydride (2.03 g, 31.9 mmol) is added, and the reaction mixture is heated to reflux. After 16 hours, the reaction is cooled to room temperature, filtered, washed with methanol, and the combined filtrate concentrated under vacuum to afford a viscous oil. The resulting oil is dissolved in ethyl acetate and washed with 1.0 M hydrochloric acid, water, and brine. The organic layer is dried over MgSO$_4$, filtered, and the filtrate is concentrated under vacuum to afford as a beige solid (1.78 g). MS CI: m/e 228 (M$^+$).

(c) 2-(2,4-Difluoroanilino)-4,5-difluorobenzoic acid

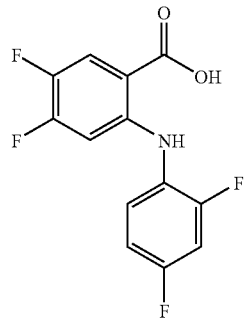

Lithium diisopropylamide is generated at –5° C. by combining diisopropylamine (7.2 mL, 51 mmol) and n-butyllithium (33 mL, 53 mmol) in anhydrous tetrahydrofuran (150 mL) under an inert atmosphere. After 0.5 hour, the solution is cooled to –78° C. and 2,4-difluoroaniline (3.46 mL, 34 mmol) is added and stirred for 2 hours. 2,4,5-Trifluorobenzoic acid (3.0 g, 17 mmol) is added, and the mixture is subsequently allowed to warm to room temperature over 18 hours. A saturated solution of hydrogen chloride/dioxane (10 MIL) is added, and after 1 hour, the mixture is concentrated to a solid. The solid is dissolved in chloroform and washed with 1.0 M hydrochloric acid, water, and brine. The solution is dried, concentrated in vacuo, and purified by column chromatography (3:1 ethyl acetate/hexanes) to give 2-(2,4-difluoroanilino)-4,5-difluorobenzoic acid as a solid (2.18 g). $^1$H NMR (CDCl$_3$): δ 8.95 (bs, 1H), 7.80–7.75 (m, 2H), 7.50–6.85 (m, 3H), 6.62–6.40 (m, 1H). MS EI: m/z 286 (M$^+$).

(d) 3-Chloro-2-cyclopropylamino-4,5-difluorobenzoic acid

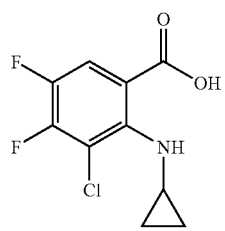

In a sealed tube a mixture of 2-bromo-3-chloro-4,5-difluorobenzoic acid (Example 20, 7.96 g, 29.3 mmol), cyclopropyl amine (4.20 mL, 58.7 mmol), potassium acetate (5.77 g, 58.6 mmol), cupric acetate monohydrate (0.50 g, 2.5 mmol), and triethylamine (4.9 mL, 35.19 mmol) in isopropyl alcohol is stirred at 80° C. After 16 hours, the reaction mixture is concentrated under vacuum, and the resulting residue is dissolved in ethyl acetate. The organic layer is washed with 1.0 M hydrochloric acid, water, and brine. The organic layer is dried over MgSO₄ and filtered. The filtrate is concentrated under vacuum and purified via flash column chromatography (5% isopropyl alcohol/1% formic acid/94% dichloromethane) to afford the title compound (4.62 g). MS CI: m/z 248 (MH⁺).

EXAMPLE 6

Synthesis of Hydrazinecarboxylic t-Butyl Esters (2-Cyclopropylamino-4,5-difluorobenzoyl)hydrazinecarboxylic acid tert-butyl ester

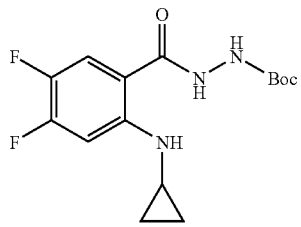

To a solution of 2-cyclopropylamino-4,5-difluorobenzoic acid (Example 5) (1.32 g, 6.19 mmol) and tert-butyl carbazate (1.30 g, 9.75 mmol) in dichloromethane (30 mL) is added 1-ethyl-3-(3-dimethylaminopropyl)-carbodiimide (1.87 g, 9.75 mmol). After 16 hours, the reaction mixture is diluted with dichloromethane and washed with saturated NaHCO₃, water, and brine. The organic layer is dried over MgSO₄ and filtered. The filtrate is concentrated under vacuum and purified via flash column chromatography (1:2 ethyl acetate/hexanes) to afford N₂-(2-cyclopropylamino-4,5-difluorobenzoyl)hydrazinecarboxylic acid tert-butyl ester as a solid (1.65 g). MS EI: m/z 328 (M⁺).

(b) [2-(2,4-Difluoroanilino)-4,5-difluorobenzoyl]hydrazinecarboxylic acid tert-butyl ester

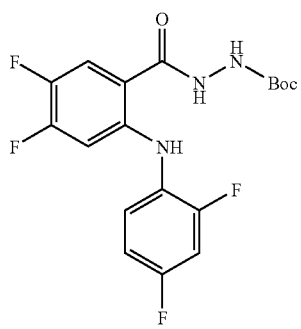

To a solution of 2-(2,4-difluoroanilino)-4,5-difluorobenzoic acid (Example 5, 2.18 g, 7.6 mmol) and tert-butyl carbazate (1.57 g, 11.8 mmol) in dichloromethane (30 mL) is added 1-ethyl-3-(3-dimethylaminopropyl)-carbodiimide (2.25 g, 11.77 mmol). After stirring for 16 hours at room temperature, the reaction mixture is diluted with dichloromethane and then washed with saturated NaHCO₃, water, and brine. The organic layer is dried over Na₂SO₄, concentrated under vacuum, and purified via column chromatography (1:3 ethyl acetate/hexanes) to afford [2-(2,4-difluoroanilino)-4,5-difluorobenzoyl]-hydrazinecarboxylic acid tert-butyl ester as a solid (2.20 g). MS EI: m/z 400 (M⁺).

(c) (3-Chloro-2-cyclopropylamino-4,5-difluorobenzoyl)-hydrazinecarboxylic acid tert-butyl ester

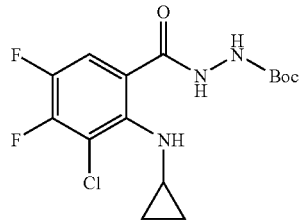

To a solution of 3-chloro-2-cyclopropylamino-4,5-difluorobenzoic acid (Example 5d, 2.09 g, 8.45 mmol) in dichloromethane (30 mL) is added tert-butyl carbazate (1.67 g, 12.7 mmol) and 1-ethyl-3-(3-dimethylaminopropyl)-carbodiimide (2.43 g, 12.7 mmol). After 16 hours, the reaction mixture is diluted with dichloromethane and washed with saturated NaHCO₃, water, and brine. The organic layer is dried over MgSO₄ and filtered. The filtrate is concentrated under vacuum and purified via flash column chromatography (1:2 ethyl acetate/hexanes) to afford the title compound (1.93 g). MS EI: m/z 360 (M⁺).

(d) (5-Chloro-2-cyclopropylamino-4-fluorobenzoyl)-hydrazinecarboxylic acid tert-butyl ester

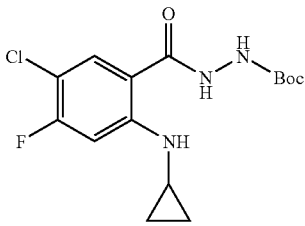

To a solution of 5-chloro-2-cyclopropylamino-4-fluorobenzoic acid (Example 5, 1.48 g, 6.46 mmol) in dichloromethane (50 mL) is added tert-butyl carbazate (1.28 g, 9.69 mmol) and 1-ethyl-3-(3-dimethylaminopropyl)carbodiimide (1.86 g, 9.69 mmol). After 16 hours, the reaction mixture is diluted with dichloromethane and washed with saturated NaHCO₃, water, and brine. The organic layer is dried over MgSO₄ and filtered. The filtrate is concentrated under vacuum and purified via flash column chromatography (1:2 ethyl acetate/hexanes) to afford (3-chloro-2-cyclopropylamino-4,5-difluorobenzoyl)hydrazinecarboxylic acid tert-butyl ester as a solid (1.04 g). MS CI: m/e 344 (M⁺+1).

EXAMPLE 7

Synthesis of 4-Heterocyclic-benzoylhydrazinecarboxylic acid t-butyl esters

General Procedure A

A solution of a substituted benzoylhydrazinecarboxylic acid tert-butyl ester from Example 6 (where $R_7$=F), heterocyclic amine (2 eq.), and triethylamine (10 eq.) is stirred in dimethyl sulfoxide or N,N-dimethylformamide (6 mL) at 120° C. in a sealed tube for 16 hours. After cooling to room temperature, the reaction mixture is diluted with ethyl acetate and washed with saturated NaHCO$_3$, water, and brine. The organic layer is dried over MgSO$_4$, filtered, and the filtrate concentrated to afford a brown residue. Trituration with diethyl ether or purification via flash column chromatography (ethyl acetate/hexanes) yields the product.

General Procedure B

To a suspension of a benzoic acid of Example 4 (3.30 mmol) and tert-butyl carbazate (1.5 eq.) in anhydrous dichloromethane is added 1-[3-(dimethylamino)propyl]-3-ethylcarbodiimide hydrochloride (1.5 eq.). The mixture is stirred at room temperature for 20 hours, poured into saturated NaHCO$_3$, and extracted with dichloromethane. The combined organic extracts are washed with brine, dried over Na$_2$SO$_4$, filtered, and concentrated in vacuo. Purification by flash column chromatography (ethyl acetate/hexanes) afford the title compounds.

The following compounds are synthesized according to General Procedures A or B above:

(a) N'-{4-[3-(tert-Butoxycarbonylaminomethyl)pyrrolidin-1-yl]-2-cyclopropylamino-5-fluorobenzoyl}hydrazinecarboxylic acid tert-butyl ester (MS CI: m/z 508 (MH$^+$)) using (2-cyclopropylamino-4,5-difluorobenzoyl)-hydrazinecarboxylic acid tert-butyl ester (Example 6a) and 3-(tert-butoxycarbonylaminomethyl)pyrrolidine (General Method A).

(b) N'-4-[4-(tert-Butoxycarbonylpiperazin-1-yl)-2-cyclopropylamino-5-fluorobenzoyl]hydrazinecarboxylic acid tert-butyl ester (MS CI: m/z 494 (MH$^+$)) using (2-cyclopropylamino-4,5-difluorobenzoyl)-hydrazinecarboxylic acid tert-butyl ester (Example 6a) and 4-tert-butoxycarbonylpiperazine (General Method A).

(c) N'-{4-[3-(tert-Butoxycarbonylaminomethyl)-3-methylpyrrolidin-1-yl]-2-cyclopropylamino-5-fluorobenzoyl}hydrazinecarboxylic acid tert-butyl ester (MS CI: m/z 522 (MH$^+$)) using (2-cyclopropylamino-4,5-difluorobenzoyl)-hydrazinecarboxylic acid tert-butyl ester (Example 6a) and 3-(tert-butoxycarbonylaminomethyl)-3-methylpyrrolidine (Sanchez J. P., Bridges A. J., Bucsh R., Domagala J. M., Gogliotti R. D., Hagen S. E., Heifetz C. L., Joannides E. T., Sesnie J. C., et al. *J. Med. Chem.*, 1992; 35(2):361–367) (General Method A).

(d) N'-[4-(6-tert-Butoxycarbonylamino-3-azabicyclo[3.1.0]hex-3-yl)-2-cyclopropylamino-5-fluorobenzoyl]hydrazinecarboxylic acid tert-butyl ester (MS CI: m/z 506 (MH$^+$)) using (2-cyclopropylamino-4,5-difluorobenzoyl)-hydrazinecarboxylic acid tert-butyl ester (Example 6a) and (3-azabicyclo[3.1.0]hex-6-yl)carbamic acid tert-butyl ester (Brighty K. E., 1991, EP 413455] (General Method A).

(e) N'-{4-[(S)-3-(tert-Butoxycarbonyl-N-methylamino)pyrrolidin-1-yl]-2-cyclopropylamino-5-fluorobenzoyl}hydrazinecarboxylic acid tert-butyl ester (MS CI: m/z 508 (MH$^+$)) using (2-cyclopropylamino-4,5-difluorobenzoyl)-hydrazinecarboxylic acid tert-butyl ester (Example 6a) and (S)-3-(tert-butoxycarbonyl-N-methylamino)pyrrolidine (Chu D. T., Li Q., Cooper C. S., Fung A. K. L., Lee C. M., Plattner J. J., PCT Int. Appl., 1995:255. WO 9510519) (General Method A).

(f) N'-{4-[(S)-3-(tert-Butoxycarbonylamino)pyrrolidin-1-yl]-2-(2,4-difluoroanilino)-5-fluorobenzoyl}hydrazinecarboxylic acid tert-butyl ester (MS CI: m/z 566 (MH$^+$)) using [2-(2,4-difluoroanilino)-4,5-difluorobenzoyl]-hydrazinecarboxylic acid tert-butyl ester (Example 6b) and (S)-pyrrolidin-3-ylcarbamic acid tert-butyl ester (General Method A).

(g) N'-{4-[(S)-3-tert-Butoxycarbonylamino)pyrrolidin-1-yl]-2-cyclopropylamino-3,5-difluorobenzoyl}hydrazinecarboxylic acid tert-butyl ester MS CI: m/z 538 (MH$^+$) using 4-[(S)-3-tert-butoxycarbonylaminopyrrolidin-1-yl]-2-cyclopropylamino-3,5-difluorobenzoic (Example 4a) (General Method B).

(h) N'-{4-[(S)-3-tert-Butoxycarbonylamino)pyrrolidin-1-yl]-2-cyclopropylamino-3,6-difluorobenzoyl}hydrazinecarboxylic acid tert-butyl ester ($^1$H NMR (CDCl$_3$): δ 8.08 (bs, 2H), 6.50 (bs, 1H), 5.70 (dd, 1H), 4.76–4.68 (m, 1H), 4.37–4.23 (m, 1H), 3.78–3.68 (m, 1H), 3.65–3.42 (m, 2H), 3.40–3.30 (m, 1H), 2.96–2.83 (m, 1H), 2.28–2.14 (m, 1H), 2.00–1.84 (m, 1H), 1.49 (s, 9H), 1.46 (s, 9H), 0.68–0.61 (m, 2H), 0.58–0.48 (m, 2H)) using 4-[(S)-3-tert-butoxycarbonylaminopyrrolidin-1-yl]-2-cyclopropylamino-3,6-difluorobenzoic acid (Example 4b) (General Method B).

(i) N'-{4-[(S)-3-(tert-Butoxycarbonylamino)pyrrolidin-1-yl]-2-cyclopropylamino-3,5,6-trifluorobenzoyl}hydrazine carboxylic acid tert-butyl ester ($^1$H NMR (CDCl$_3$), δ 8.04 (bd, 1H), 7.55 (bs, 1H), 6.52 (bs, 1H), 4.79–4.67 (m, 1H), 4.37–4.19 (m, 1H), 3.97–3.55 (m, 3H), 3.53–3.40 (m, 1H), 2.90–2.75 (m, 1H), 2.29–2.06 (m, 1H), 1.96–1.75 (m, 1H), 1.49 (s, 9H), 1.46 (s, 9H), 0.69–0.57 (m, 2H), 0.54–0.43 (m, 2H)) using 4-[(S)-3-tert-butoxycarbonylaminopyrrolidin-1-yl]-2-cyclopropylamino-3,5,6-trifluorobenzoic acid (Example 4d) (General Method B).

(j) N'-{4-[(S)-3-(tert-Butoxycarbonylamino)pyrrolidin-1-yl]-3-chloro-2-cyclopropylamino-5-fluorobenzoyl}hydrazinecarboxylic tert-butyl ester (MS CI: m/z 528 (MH$^+$)) using 4-[(S)-3-tert-butoxycarbonylaminopyrrolidin-1-yl]-3-chloro-2-cyclopropylamino-5-fluorobenzoic acid (Example 4c) (General Method B).

(k) N'-[(S)-4-(7-tert-Butoxycarbonylamino-5-azaspiro[2.4]hept-5-yl)-2-cyclopropylamino-5-fluorobenzoyl]hydrazinecarboxylic acid tert-butyl ester (MS CI: m/z 520 (MH$^+$)) using (2-cyclopropylamino-4,5-difluorobenzoyl)-hydrazinecarboxylic acid tert-butyl ester (Example 6a) and (5-azaspiro[2,4]hept-7-yl)carbamic acid tert-butyl ester (General Method A).

(l) N'-{4-[(R)-3-(1-tert-Butoxycarbonylamino-1-methylethyl)pyrrolidin-1-yl]-3-chloro-2-cyclopropylamino-5-fluorobenzoyl}hydrazinecarboxylic acid tert-butyl ester (MS CI: m/z 570 (MH$^+$)) using (3-chloro-2-cyclopropylamino-4,5-difluorobenzoyl)-hydrazinecarboxylic acid tert-butyl ester (Example 6c) and [(R)-3-(1-tert-butoxycarbonylamino-1-methylethyl)pyrrolidine (Fedij V., Lenoir E. A., III, Suto M. J., Zeller J. R., Wemple J., *Tetrahedron: Asymmetry*, 1994; 5[7]:1131–1134) (General Method A).

(m) N'-[4-(Pyrrolidin-1-yl)-2-cyclopropylamino-5-fluorobenzoyl]-hydrazinecarboxylic tert-butyl ester (MS CI: m/z 379 (MH$^+$)) using 2-cyclopropylamino-5-fluoro-4-pyrrolidin-1-ylbenzoic acid (Example 4e) (General Method B).

(n) N'-{4-[3-(tert-Butoxycarbonylamino)pyrrolidin-1-yl]-5-fluoro-2-isopropylaminobenzoyl}hydrazine carboxylic acid tert-butyl ester (MS EI: m/z 496 (MH$^+$)) using 4-[3-tert-butoxycarbonylamino)pyrrolidin-1-yl]-5-fluoro-2-isopropylaminobenzoic acid (Example 4f) (General Method B).

(o) N'-{4-[3-(tert-Butoxycarbonylamino)pyrrolidin-1-yl]-2-sec-butylamino-3-chloro-5-fluorobenzoyl}hydrazinecarboxylic acid tert-butyl ester (MS EI: m/z 544 (MH$^+$)) using 4-[3-(tert-butoxycarbonylamino)pyrrolidin-1-yl]-2-sec-butylamino-3-chloro-5-fluorobenzoic acid (Example 4g) (General Method B).

(p) N'-{4-[3-tert-Butoxycarbonylamino)pyrrolidin-1-yl]-2-cyclopropylamino-5-fluoro-3-methoxybenzoyl}hydrazinecarboxylic acid tert-butyl ester (MS EI: m/z 524 (MH$^+$)) using 4-[3-tert-butoxycarbonylamino)-pyrrolidin-1-yl]-2-cyclopropylamino-5-fluoro-3-methoxybenzoic acid (Example 4h) (General Method B).

(q) N'-{4-[3-(tert-Butoxycarbonylamino)pyrrolidin-1-yl]-2-cyclobutylamino-5-fluorobenzoyl}hydrazinecarboxylic acid tert-butyl ester (MS EI: m/z 394 (M$^+$)) using 4-[3-tert-butoxycarbonylamino)pyrrolidin-1-yl]-2-cyclobutylamino-5-fluorobenzoic acid (Example 4i) (General Method B).

(r) N'-{4-[3-(tert-Butoxycarbonylamino)pyrrolidin-1-yl]-2-cyclopropylamino-3-fluorobenzoyl}hydrazinecarboxylic acid tert-butyl ester (MS EI: m/z 494 (MH$^+$)) using 4-[3-(tert-butoxycarbonylamino)pyrrolidin-1-yl]-2-cyclopropylamino-3-fluorobenzoic acid (Example 4j) (General Method B).

(s) N'-{4-[3-(tert-Butoxycarbonylamino)pyrrolidin-1-yl]-5-chloro-2-cyclopropylamino-3-fluorobenzoyl}hydrazinecarboxylic acid tert-butyl ester ($^1$H NMR (CDCl$_3$): δ 8.77 (bs, 1H), 7.35 (d, 1H), 6.82 (bs, 1H), 6.55 (bs, 1H), 5.01–4.97 (m, 1H), 4.29 (bs, 1H), 3.74–3.57 (m, 2H), 3.41–3.24 (m, 2H), 2.84–2.75 (m, 1H), 2.33–2.16 (m, 1H), 1.92–1.72 (m, 1H), 1.47 (s, 9H), 1.45 (s, 9H), 0.69–0.62 (m, 2H), 0.60–0.50 (m, 2H)) using 4-[3-(tert-butoxycarbonylamino)pyrrolidin-1-yl]-5-chloro-2-cyclopropylamino-3-fluorobenzoic acid (Example 4k) (General Method B).

(t) N'-[4-(3-tert-Butoxycarbonylaminopyrrolidin-1-yl)-2-cyclopropylamino-5-fluoro-3-methylbenzoyl]hydrazinecarboxylic acid tert-butyl ester ([MS ES, MH+] m/z 508) using 4-(3-tert-butoxycarbonylaminopyrrolidin-1-yl)-2-cyclopropylamino-5-fluoro-3-methylbenzoic acid (Example 4l) (General Method B).

(u) N'-{4-[3-(tert-Butoxycarbonylaminomethyl)pyrrolidin-1-yl]-2-cyclopropylamino-5-fluoro-3-methylbenzoyl}hydrazinecarboxylic acid tert-butyl ester ([MS ES, MH$^+$] m/z 522) using 4-[3-(tert-butoxycarbonylaminomethyl)-pyrrolidin-1-yl]-2-cyclopropylamino-5-fluoro-31-methylbenzoic acid (Example 4m) (General Method B).

(v) N'-[4-(3-tert-Butoxycarbonylaminopyrrolidin-1-yl)-2-cyclopropylamino-3-fluoro-5-methoxybenzoyl]hydrazinecarboxylic acid tert-butyl ester. ([MS ES, MH$^+$] m/z 525) using 4-(3-tert-butoxycarbonylamino-pyrrolidin-1-yl)-2-cyclopropylamino-3-fluoro-5-methoxybenzoic acid (Example 4n) (General Method B).

(w) N'-{4-[3-(tert-Butoxycarbonylaminomethyl)pyrrolidin-1-yl]-2-cyclopropylamino-5-fluoro-3-methoxybenzoyl}hydrazinecarboxylic acid tert-butyl ester ([MS ES, MH$_2^{+2}$] m/z 539) using 4-[3-(tert-butoxycarbonylamino-methyl)pyrrolidin-1-yl]-2-cyclopropylamino-5-fluoro-3-methoxybenzoic acid (Example 4o) (General Method B).

(x) N'-[3-(Benzyloxyiminomethyl)-4-(3-tert-butoxycarbonylamino-pyrrolidin-1-yl)-2-cyclopropylamino-5-fluorobenzoyl]hydrazinecarboxylic acid tert-butyl ester. ([MS ES, MH$^+$] m/z 627) using 3-(benzyloxyiminomethyl)-4-(3-tert-butoxycarbonylaminopyrrolidin-1-yl)-2-cyclopropylamino-5-fluorobenzoic acid (Example 4q) (General Method B)

(y) N'-[3-Chloro-2-cyclopropylamino-5-fluoro-4-(3-[1,2,3-triazol]-1-yl-pyrrolidin-1-yl)benzoyl]hydrazinecarboxylic acid tert-butyl ester ($^1$H NMR (200 MHz, CDCl$_3$): δ 9.90 (bs, 1H), 7.97 (s, 1H), 7.72 (s, 1H), 7.52 (d, 1H), 7.17 (bs, 1H), 5.51–5.41 (m, 1H), 4.59 (bs, 1H), 4.06–3.95 (m, 1H), 3.87–3.74 (m, 1H), 3.61–3.55 (m, 1H), 3.48–3.36 (m, 1H), 2.97–2.90 (m, 1H), 2.77–2.59 (m, 1H) 2.42–2.31 (m, 1H), 1.46 (s, 9H), 0.68–0.50 (m, 4H)) using 3-chloro-2-cyclopropylamino-5-fluoro-4-(3-[1,2,3-triazol]-1-ylpyrrolidin-1-yl)benzoic acid (Example 4r) (General Method B).

(z) N-(1-{4-[3-(tert-Butoxycarbonylaminomethyl)-piperidin-1-yl]-2-cyclopropylamino-5-fluorophenyl}methanoyl)hydrazinecarboxylic acid tert-butyl ester (MS CI: m/e 522 (MH+)) from piperidin-3-ylmethylcarbamic acid tert-butyl ester (Hilpert K., Ackermann J., Banner D. W., Gast A., Gubernator K., Hadvary P., Labler L., Mueller K., Schmid G., et al., *J. Med. Chem.*, 1994; 37[23]:3889–3901) and (2-Cyclopropylamino-4,5-difluorobenzoyl)-hydrazinecarboxylic acid tert-butyl ester (Example 6a) (General Method A).

(aa) N-[1-(4-{3-[(tert-Butoxycarbonylisopropylamino)-methyl]-pyrrolidin-1-yl}-2-cyclopropylamino-5-fluorophenyl)methanoyl]-hydrazinecarboxylic acid tert-butyl ester (MS CI: m/e 550 (MH+)) using isopropylpyrrolidin-3-ylmethylamine (Mich T. F., Culbertson T. P., U.S. Pat. No. 4,550,103) and (2-cyclopropylamino-4,5-difluorobenzoyl)-hydrazinecarboxylic acid tert-butyl ester (Example 6a) (General Method B).

(bb) N'-(1-{4-[3-(tert-Butoxycarbonylaminomethyl)pyrrolidin-1-yl]-5-chloro-2-cyclopropylaminophenyl}methanoyl)hydrazinecarboxylic acid tert-butyl ester (MS CI: m/e 524 [M$^+$+1]) using (3-chloro-2-cyclopropylamino-4,5-difluorobenzoyl)hydrazinecarboxylic acid tert-butyl ester (Example 6c) and 3-(tert-butoxycarbonylaminomethyl)pyrrolidine (General Method A).

(cc) N'-[4-(3-tert-Butoxycarbonylaminopyrrolidin-1-yl)-2-cyclopropylamino-3-ethoxy-5-fluorobenzoyl]hydrazinecarboxylic acid tert-butyl ester (MS ES: m/z 537 (MH$^+$)) from (4-(3-tert-butoxycarbonylamino-pyrrolidin-1-yl)-2-cyclopropylamino-3-ethoxy-5-fluorobenzoic acid (Example 4p) (General Method A).

EXAMPLE 8

Synthesis of (2,4-dioxo-1,4-dihydro-2H-quinazolin-3-yl)carbamic acid tert-butyl esters General Method A To a solution of a benzoylhydrazinecarboxylic acid tert-butyl ester (from Example 7 (0.435 mmol) in tetrahydrofuran (15 mL) is added potassium carbonate (0.300 g, 2.18 mmol) and triphosgene (0.167 g, 0.566 mmol). The reaction mixture is refluxed for 90 minutes, cooled to room temperature, and diluted with ethyl acetate. The organic layer is washed with water and brine, then dried over MgSO$_4$, and filtered. The filtrate is concentrated under vacuum and purified by flash column chromatography (ethyl acetate/hexanes) to afford the title compounds.

General Method B

A solution of (2,4-dioxo-1,4-dihydro-2H-quinazolin-3-yl) carbamic acid tert-butyl ester (such as, for example, Example 14), pyrrolidine side chain (2 eq.), and triethylamine (10 eq.) are stirred in dimethyl sulfoxide or acetonitrile (3 mL) at 80° C. for 48 hours. After cooling to room temperature, the reaction mixture is diluted with ethyl acetate and washed with saturated NaHCO$_3$, water, and brine. The organic layer is dried over MgSO$_4$, filtered, and concentrated. The resulting residue is purified via flash column chromatography (ethyl acetate/hexanes) to afford the title compounds General Method C To a solution of a C-6- and/or C-8-halogenated-(2,4-dioxo-1,4-dihydro-2H-quinazolin-3-yl)carbamic acid tert-butyl ester in ethanol and tetrahydrofuran is added triethylamine and 20% palladium on carbon. Hydrogen is introduced to the reaction mixture at high pressure for several days, then the reaction mixture is filtered through Celite, washed with ethanol, and the combined filtrate concentrated in vacuo and purified via flash column chromatography (ethyl acetate/hexanes) to afford the title compounds.

General Method D

A suspension of benzoylhydrazinecarboxylic acid tert-butyl ester (from Example 7) and triethylamine (10 eq.) are stirred in anhydrous tetrahydrofuran for 5 minutes. Phosgene (20% solution in toluene, 2 eq.) is added in one portion to the suspension. The reaction mixture is heated at 60° C. for 4.5 hours, cooled to room temperature, poured into saturated NaHCO$_3$ solution, and extracted with chloroform. The combined organic extracts are washed with water, brine, and then dried over Na$_2$SO$_4$, filtered, and concentrated under vacuum. The resulting residue is purified by flash column chromatography (1:1 ethyl acetate/hexanes) to afford the title compounds.

General Method E

An appropriately substituted pyrrolidine (1.5–2 eq.), a 3-dibenzylamino-6, 7-difluoro-1-substituted-1H-quinazoline-2,4-dione (Example 16) (1 eq.), and triethylamine (10 eq.) are combined in acetonitrile and heated to reflux for 72 hours. The solution is cooled, concentrated, and re-dissolved in chloroform. The organic solution is washed with 1.0 N hydrochloric acid, saturated NaHCO$_3$, brine, and dried over magnesium sulfate. The solution is concentrated to give the title compounds.

General Method F

A solution of (2,4-dioxo-1,4-dihydro-2H-quinazolin-3-yl) carbamic acid tert-butyl ester (such as, for example, Example 14), pyrrolidine side chain (2 eq.), and triethylamine (10 eq.) are stirred in dimethyl sulfoxide or acetonitrile (3 mL) at 80° C. for 20 to 40 hours. After cooling to room temperature, the reaction mixture is diluted with ethyl acetate and washed with saturated NaHCO$_3$, water, and brine. The organic layer is dried over MgSO$_4$, filtered, and concentrated. The resulting residue is redissolved in methylene chloride and then treated with di-tert-butyl dicarbonate (2 eq). After 1 hour, the reaction mixture is concentrated and the product purified via flash column chromatography (ethylacetate/hexanes) to afford the title compounds.

The following compounds are synthesized according to General Procedures A–F of Example 8:

(a) {7-[3-(tert-Butoxycarbonylaminomethyl)pyrrolidin-1-yl]-8-chloro-1-cyclopropyl-6-fluoro-2,4-dioxo-1,4-dihydro-2H-quinazolin-3-yl}carbamic acid tert-butyl ester (MS CI: m/z 568 (MH+)) from N'-{4-[3-(tert-butoxycarbonylaminomethyl)pyrrolidin-1-yl]-3-chloro-2-cyclopropylamino-5-fluorobenzoyl}hydrazinecarboxylic acid tert-butyl ester (Example 18a) (General Method A)

(b) 7-[4-(tert-Butoxycarbonylpiperazin-1-yl)-8-chloro-1-cyclopropyl-6-fluoro-2,4-dioxo-1,4-dihydro-2H-quinazolin-3-yl]carbamic acid tert-butyl ester (MS CI: m/z 554 (MH+)) from N'-4-[4-(tert-butoxycarbonylpiperazin-1-yl)-3-chloro-2-cyclopropylamino-5-fluorobenzoyl]hydrazinecarboxylic acid tert-butyl ester (Example 18b) (General Method A).

(c) {7-[3-(tert-Butoxycarbonylaminomethyl)-3-methylpyrrolidin-1-yl]-8-chloro-1-cyclopropyl-6-fluoro-2,4-dioxo-1,4-dihydro-2H-quinazolin-3-yl}carbamic acid tert-butyl ester (MS CI: m/z 582 (MH+)) from N'-{4-[3-(tert-butoxycarbonylaminomethyl)-3-methylpyrrolidin-1-yl]-3-chloro-2-cyclopropylamino-5-fluorobenzoyl}hydrazinecarboxylic acid tert-butyl ester (Example 18c) (General Method A).

(d) [7-(6-tert-Butoxycarbonylamino-3-azabicyclo[3.1.0]hex-3-yl)-8-chloro-1-cyclopropyl-6-fluoro-2,4-dioxo-1,4-dihydro-2H-quinazolin-3-yl]-carbamic acid tert-butyl ester (MS CI: m/z 566 (MH$^+$)) from N'-[4-(6-tert-Butoxycarbonylamino-3-azabicyclo [3.1.0]hex-3-yl)-3-chloro-2-cyclopropylamino-5-fluorobenzoyl]hydrazinecarboxylic acid tert-butyl ester (Example 18d) (General Method A).

(e) {7-[(S)-3-(tert-Butoxycarbonyl-N-methylamino)pyrrolidin-1-yl]-8-chloro-1-cyclopropyl-6-fluoro-2,4-dioxo-1,4-dihydro-2H-quinazolin-3-yl}-carbamic acid tert-butyl ester (MS CI: m/z 568 (MH$^+$)) from N'-{4-[(S)-3-(tert-butoxycarbonyl-N-methylamino)pyrrolidin-1-yl]-3-chloro-2-cyclopropylamino-5-fluoro-benzoyl}hydrazinecarboxylic acid tert-butyl ester (Example 18e) (General Method A).

(f) {7-[(S)-3-(tert-Butoxycarbonylamino)pyrrolidin-1-yl]-8-chloro-1-(2,4-difluoroanilino)-6-fluoro-1,4-dihydro-2,4-dioxo-2H-quinazolin-3-yl}-carbamic acid tert-butyl ester ($^1$H NMR (CDCl$_3$): δ 7.45–7.38 (m, 1H), 6.97–6.81 (m, 1H), 6.73–6.66 (m, 1H), 6.54–6.42 (m, 1H), 4.90–4.81 (bs, 1H), 4.31–4.21 (bs, 1H), 3.86–3.36 (m, 4H), 2.32–2.04 (m, 1H), 1.96–1.84 (m, 1H), 1.61 (s, 9H), 1.45 (s, 9H)) from N'-{4-[(S)-3-(tert-butoxycarbonyl-N-amino)-pyrrolidin-1-yl]-3-chloro-2-(2,4-difluoroanilino)-5-fluorobenzoyl}-hydrazinecarboxylic acid tert-butyl ester (Example 18f) (General Method A).

(g) 7-[(S)-3-(tert-Butoxycarbonylamino)pyrrolidin-1-yl-1-cyclopropylamino-6,8-difluoro-1,4-dihydro-2,4-dioxo-2H-quinazolin-3-yl}-carbamic acid tert-butyl ester ($^1$H NMR (CDCl$_3$): δ 7.54 (dd, 1H), 6.67 (bs, 1H), 4.79–4.68 (bs, 1H), 4.39–4.23 (m, 1H), 4.10–3.65 (m, 3H), 3.58–3.45 (m, 1H), 3.37–3.25 (m, 1H), 2.30–2.11 (m, 1H), 2.03–1.86 (m, 1H), 1.50 (s, 9H), 1.47 (s, 9H), 1.20–1.12 (m, 2H), 0.83–0.74 (bs, 2H)) from N'-{4-[(S)-3-tert-butoxycarbonylamino)pyrrolidin-1-yl]-2-cyclopropylamino-3,5-difluorobenzoyl}-hydrazinecarboxylic acid tert-butyl ester (Example 5g) (General Method A).

(h) {7-[(S)-3-(tert-Butoxycarbonylamino)pyrrolidin-1-yl]-1-cyclopropylamino-5,8-difluoro-1,4-dihydro-2,4-dioxo-2H-quinazolin-3-yl}-carbamic acid tert-butyl ester (MS CI: m/z 538 (M$^+$)) from N'-{4-[(S)-3-tert-butoxycarbonylamino)pyrrolidin-1-yl]-2-cyclopropylamino-3,6-difluorobenzoyl}-hydrazinecarboxylic acid tert-butyl ester (Example 5h) (General Method A).

(i) {7-[(S)-3-(tert-Butoxycarbonylamino)pyrrolidin-1-yl]-1-cyclopropyl-1,4-dihydro-2,4-dioxo-5,6,8-trifluoro-2H-quinazolin-3-yl-3-carbamic acid tert-butyl ester (MS CI: m/z 556 (MH$^+$)) from N'-{4-[(S)-3-(tert-butoxycarbonylamino)pyrrolidin-1-yl]-2-cyclopropylamino-3,5,6-trifluorobenzoyl}hydrazine carboxylic acid tert-butyl ester (Example 5i) (General Method A)

(j) {7-[3-(tert-Butoxycarbonylpyrrolidin-1-yl]-8-chloro-1-cyclopropyl-6-fluoro-2,4-dioxo-1,4-dihydro-2H-quinazolin-3-yl}carbamic acid tert-butyl ester (MS CI: m/z 552 (MH$^+$)) from N'-{4-[(S)-3-(tert-butoxycarbonylamino) pyrrolidin-1-yl]-3-chloro-2-cyclopropylamino-5-fluorobenzoyl}hydrazinecarboxylic tert-butyl ester (Example 5j) (General Method A).

(k) [7-(3-Hydroxymethylpyrrolidin-1-yl)-8-chloro-1-cyclopropyl-6-fluoro-2,4-dioxo-1,4-dihydro-2H-quinazolin-3-yl]carbamic acid tert-butyl ester (MS CI: m/z 467 (MH$^+$)) from (8-chloro-1-cyclopropyl-6,7-difluoro-2,4-dioxo-1,4-

(l) {7-[3-(tert-Butoxycarbonylaminoethyl)pyrrolidin-1-yl]-8-chloro-1-cyclopropyl-6-fluoro-2,4-dioxo-1,4-dihydro-2H-quinazolin-3-yl} carbamic acid tert-butyl ester (MS CI: m/z 580 (MH$^+$)) from (8-chloro-1-cyclopropyl-6,7-difluoro-2,4-dioxo-1,4-dihydro-2H-quinazolin-3-yl)carbamic acid tert-butyl ester (Example 14) and 3-(tert-butoxycarbonylaminoethyl)pyrrolidine (Antonsson K. T., Bylund R. E., Gustafsson N. D., Nilsson N. O. I. WO 9429336) (General Method B).

(m) [7-(7-tert-Butoxycarbonylamino-5-azaspiro[2.4]hept-5-yl)-8-chloro-1-cyclopropyl-6-fluoro-2,4-dioxo-1,4-dihydro-2H-quinazolin-3-yl]-carbamic acid tert-butyl ester (MS CI: m/z 580 (MH$^+$)) from N'-[(S)-4-(7-tert-butoxycarbonylamino-5-azaspiro [2.4]hept-5-yl)-3-chloro-2-cyclopropylamino-5-fluorobenzoyl]hydrazinecarboxylic acid tert-butyl ester (Example 18g) (General Method A).

(n) {7-[(R)-3-(1-tert-Butoxycarbonylamino-1-methylethyl)pyrrolidin-1-yl]-8-chloro-1-cyclopropyl-6-fluoro-2,4-dioxo-1,4-dihydro-2H-quinazolin-3-yl}carbamic acid tert-butyl ester (MS CI: m/z 596 (MH$^+$) from N'-{4-[(R)-3-(1-tert-butoxycarbonylamino-1-methylethyl)pyrrolidin-1-yl]-3-chloro-2-cyclopropylamino-5-fluorobenzoyl}hydrazinecarboxylic acid tert-butyl ester (Example 7l) (General Method A).

(o) {7-[3-(tert-Butoxycarbonylaminomethyl)pyrrolidin-1-yl]-1-cyclopropyl-6-fluoro-2,4-dioxo-1,4-dihydro-2H-quinazolin-3-yl}carbamic acid tert-butyl ester (MS CI: m/z 534 (MH$^+$)) from {7-[3-(tert-butoxycarbonylaminomethyl)pyrrolidin-1-yl]-8-chloro-1-cyclopropyl-6-fluoro-2,4-dioxo-1,4-dihydro-2H-quinazolin-3-yl}carbamic acid tert-butyl ester (Example 8a) (General Method C).

(p) [7-(Pyrrolidin-1-yl)-8-chloro-1-cyclopropyl-6-fluoro-2,4-dioxo-1,4-dihydro-2H-quinazolin-3-yl]carbamic acid tert-butyl ester (MS CI: m/z 437 (MH$^+$)) using N'-[4-(Pyrrolidin-1-yl)-3-chloro-2-cyclopropylamino-5-fluorobenzoyl]hydrazinecarboxylic tert-butyl ester (Example 18h) (General Method A).

(q) {7-[3-(tert-Butoxycarbonylamino)pyrrolidin-1-yl]-8-chloro-6-fluoro-1-isopropyl-2,4-dioxo-6-fluoro-2H-quinazolin-3-yl}carbamic acid tert-butyl ester. (MS EI: m/z 530 (M$^+$)) using N'-{4-[3-(tert-butoxycarbonylamino)-pyrrolidin-1-yl)-3-chloro-5-fluoro-2-isopropylaminobenzoyl}-hydrazinecarboxylic acid tert-butyl ester (Example 18i) (General Method A).

(r) {7-[3-(tert-Butoxycarbonylamino)pyrrolidin-1-yl]-1-sec-butyl-8-chloro-6-fluoro-2,4-dioxo-2H-quinazolin-3-yl}carbamic acid tert-butyl ester (MS EI: m/z 570 (MH$^+$)) using N'-{4-[3-(tert-butoxycarbonylamino)pyrrolidin-1-yl]-2-sec-butylamino-3-chloro-5-fluorobenzoyl}hydrazinecarboxylic acid tert-butyl ester (Example 7o) (General Method A).

(s) {7-[3-(tert-Butoxycarbonylamino)pyrrolidin-1-yl]-1-cyclopropyl-6-fluoro-8-methoxy-2,4-dioxo-1,4-dihydro-2H-quinazolin-3-yl}carbamic acid tert-butyl ester (MS EI: m/z 550 (MH$^+$)) using N'-{4-[3-tert-butoxycarbonylamino)pyrrolidin-1-yl]-2-cyclopropylamino-5-fluoro-3-methoxybenzoyl}hydrazinecarboxylic acid tert-butyl ester (Example 7p) (General Method D).

(t) {7-[3-(tert-Butoxycarbonylamino)pyrrolidin-1-yl]-8-chloro-1-cyclobutylamino-6-fluoro-2,4-dioxo-1,4-dihydro-2H-quinazolin-3-yl}carbamic acid tert-butyl ester (MS EI: m/z 568 (MH$^+$)) using N'-{4-[3-(tert-butoxycarbonylamino)pyrrolidin-1-yl]-2-cyclobutylamino-5-fluorobenzoyl}-hydrazinecarboxylic acid tert-butyl ester (Example 7q) (General Method A).

(u) {7-[3-(tert-Butoxycarbonylamino)pyrrolidin-1-yl]-1-cyclopropyl-8-fluoro-2,4-dioxo-1,4-dihydro-2H-quinazolin-3-yl}carbamic acid tert-butyl ester (MS EI: m/z 520 (MH$^+$)) using N'-{4-[3-(tert-butoxycarbonylamino)pyrrolidin-1-yl]-2-cyclopropylamino-3-fluorobenzoyl}hydrazinecarboxylic acid tert-butyl ester (Example 7r) (General Method D).

(v) {7-[3-(tert-Butoxycarbonylamino)pyrrolidin-1-yl]-6-chloro-1-cyclopropyl-8-fluoro-2,4-dioxo-1,4-dihydro-2H-quinazolin-3-yl}carbamic acid tert-butyl ester ($^1$H NMR (CDCl$_3$): δ 7.36 (d, 1H), 6.64 (bs, 1H), 4.86–4.80 (bd, 1H), 4.31–4.25 (m, 1H), 3.81–3.66 (m, 2H), 3.51–3.31 (m, 2H), 3.02–2.97 (m, 1H), 2.32–2.22 (m, 1H), 1.95–1.85 (m, 1H), 1.63 (s, 9H), 1.46 (s, 9H), 0.77–0.73 (m, 2H), 0.63–0.57 (bs, 2H)) using N'-{4-[3-(tert-butoxycarbonylamino)pyrrolidin-1-yl]-5-chloro-2-cyclopropylamino-3-fluorobenzoyl}hydrazinecarboxylic acid tert-butyl ester (Example 7s) (General Method D).

(w) [(S)-1-(1-Cyclopropylmethyl-3-dibenzylamino-6-fluoro-2,4-dioxo-1,2,3,4-tetrahydroquinazolin-7-yl)pyrrolidin-3-yl]carbamic acid tert-butyl ester (MS CI, m/z 614 (MH$^+$)) using 3-dibenzylamino-6,7-difluoro-1-cyclopropylmethyl-1H-quinazoline-2,4-dione (Example 17a) and (S)-pyrrolidin-3-ylcarbamic acid tert-butyl ester (General Method E).

(x) {1-[(R)-1-(Cyclopropylmethyl-3-dibenzylamino-6-fluoro-2,4-dioxo-1,2,3,4-tetrahydroquinazolin-7-yl)pyrrolidin-3-yl]-1-methylethyl}carbamic acid tert-butyl ester (MS CI: m/z 656 (MH$^+$)) using 3-dibenzylamino-6,7-difluoro-1-cyclopropylmethyl-1H-quinazoline-2,4-dione (Example 17a) and (R)-3-(1-tert-butoxycarbonylamino-1-methylethyl)pyrrolidine (General Method E).

(y) [(S)-1-(3-Dibenzylamino-1-ethyl-6-fluoro-2,4-dioxo-1,2,3,4-tetrahydroquinazolin-7-yl)pyrrolidin-3-yl]carbamic acid tert-butyl ester (mp 104–106° C., MS CI: m/z 588 (MH$^+$)) using 3-dibenzylamino-6,7-difluoro-1-ethyl-1H-quinazoline-2,4-dione (Example 17b) and (S)-pyrrolidin-3-ylcarbamic acid tert-butyl ester (General Method E).

(z) [(R)-1-(3-Dibenzylamino-1-ethyl-6-fluoro-2,4-dioxo-1,2,3,4-tetrahydro-quinazolin-7-yl)-1-methyl-1-pyrrolidin-3-ylethyl]carbamic acid tert-butyl ester (MS CI: m/z 630 (MH$^+$)) using 3-dibenzylamino-6,7-difluoro-1-ethyl-1H-quinazoline-2,4-dione (Example 17b) and (R)-(1-tert-butoxycarbonylamino-1-methylethyl)pyrrolidine (General Method E).

(aa) [7-(3-tert-Butoxycarbonylaminopyrrolidin-1-yl)-1-cyclopropyl-6-fluoro-8-methyl-2,4-dioxo-1,4-dihydro-2H-quinazolin-3-yl]carbamic acid tert-butyl ester ([MS ES, MH$^+$] m/z 534) using N'-[4-(3-tert-butoxycarbonylamino-pyrrolidin-1-yl)-2-cyclopropylamino-5-fluoro-3-methylbenzoyl]-hydrazinecarboxylic acid tert-butyl ester (Example 7t) (General Method D).

(bb) {7-[3-(tert-Butoxycarbonylaminomethyl)pyrrolidin-1-yl]-1-cyclopropyl-6-fluoro-8-methyl-2,4-dioxo-1,4-dihydro-2H-quinazolin-3-yl}-carbamic acid tert-butyl ester (MS ES, MH$^+$) m/z 548)) using N'-{4-[3-(tert-butoxycarbonylaminomethyl)pyrrolidin-1-yl]-2-cyclopropylamino-5-fluoro-3-methylbenzoyl}hydrazinecarboxylic acid tert-butyl ester (Example 7u) (General Method D.

(cc) [7-(3-tert-Butoxycarbonylaminopyrrolidin-1-yl)-1-cyclopropyl-8-fluoro-6-methoxy-2,4-dioxo-1,4-dihydro-2H-quinazolin-3-yl]carbamic acid tert-butyl ester ([MS ES, MH$_2^+$] m/z 551) using N'-[4-(3-tert-butoxycarbonylaminopyrrolidin-1-yl)-2-cyclopropylamino-3-fluoro-5-methoxybenzoyl]-hydrazinecarboxylic acid tert-butyl ester (Example 7v) (General Method D).

(dd) {7-[3-(tert-Butoxycarbonylaminomethyl)pyrrolidin-1-yl]-1-cyclopropyl-6-fluoro-8-methoxy-2,4-dioxo-1,4-dihydro-2H-quinazolin-3-yl}-carbamic acid tert-butyl ester ([MS ES, $MH_2^{+2}$] m/z 565) using N'-{4-[3-(tert-butoxycarbonylaminomethyl)pyrrolidin-1-yl]-2-cyclopropylamino-5-fluoro-3-methoxybenzoyl}hydrazinecarboxylic acid tert-butyl ester (Example 7w) (General Method D).

(ee) [7-(3-tert-Butoxycarbonylaminopyrrolidin-1-yl)-1-cyclopropyl-8-ethoxy-6-fluoro-2,4-dioxo-1,4-dihydro-2H-quinazolin-3-yl]carbamic acid tert-butyl ester ([MS ES, $MH_2^{+2}$] m/z 565) from N'-[4-(3-tert-butoxycarbonylaminopyrrolidin-1-yl)-2-cyclopropylamino-3-ethoxy-5-fluorobenzoyl]-hydrazinecarboxylic acid tert-butyl ester (Example 7 cc) (General Method A).

(ff) [7-(3-tert-Butoxycarbonylaminopyrrolidin-1-yl)-8-cyano-1-cyclopropyl-6-fluoro-2,4-dioxo-1,4-dihydro-2H-quinazolin-3-yl]carbamic acid tert-butyl ester ([MS ES, $MH^+$] m/z 545) from N'-[3-(benzyloxyiminomethyl)-4-(3-tert-butoxycarbonylaminopyrrolidin-1-yl)-2-cyclopropylamino-5-fluoro-benzoyl]hydrazinecarboxylic acid tert-butyl ester (Example 7x) (General Method A).

(gg) [8-Chloro-1-cyclopropyl-6-fluoro-2,4-dioxo-7-(3-[1,2,3-triazol]-1-yl-pyrrolidin-1-yl)-1,4-dihydro-2H-quinazolin-3-yl]carbamic acid tert-butyl ester ($^1$H NMR (200 MHz, CDCl$_3$): δ 7.96 (s, 1H), 7.74 (s, 1H), 7.29 (d, H), 6.26 (bs, 1H), 5.51–5.39 (m, 1H), 4.17–4.07 (m, 1H), 3.99–3.88 (m, 1H), 3.71–3.66 (m, 1H), 3.57–3.45 (m, 1H), 3.15–3.05 (m, 1H), 2.74–2.60 (m, 1H), 2.44–2.32 (m, 1H), 1.64 (s, 9H), 0.76–0.49 (m, 4H)) from N'-[3-chloro-2-cyclopropylamino-5-fluoro-4-(3-[1,2,3-triazol]-1-yl-pyrrolidin-1-yl)benzoyl]hydrazinecarboxylic acid tert-butyl ester (Example 7y) (General Method A).

(hh) [7-(3-Carbamoylpiperidin-1-yl)-8-chloro-1-cyclopropyl-6-fluoro-2,4-dioxo-1,4-dihydro-2H-quinazolin-3-yl]carbamic acid tert-butyl ester (MS CI: m/z 496 ($MH^+$)) from (8-chloro-1-cyclopropyl-6,7-difluoro-2,4-dioxo-1,4-dihydro-2H-quinazolin-3-yl)carbamic acid tert-butyl ester (Example 14) and 3-carbamoyl-piperidine (General Method B).

(ii) {7-[(trans-3-(tert-Butoxycarbonylaminomethyl)-4-trifluoromethyl-pyrrolidin-1-yl]-8-chloro-1-cyclopropyl-6-fluoro-2,4-dioxo-1,4-dihydro-2H-quinazolin-3-yl}carbamic acid tert-butyl ester (MS CI: m/z 635 ($M^+$)) from (8-chloro-1-cyclopropyl-6,7-difluoro-2,4-dioxo-1,4-dihydro-2H-quinazolin-3-yl)-carbamic acid tert-butyl ester (Example 14) and trans-3-(tert-butoxycarbonylaminomethyl)-4-trifluoromethylpyrrolidine (Li Q., Wang W., Berst K. B., Claiborne A., Hasvold L., Raye K., Tufano M., et al., *J. Med. Chem. Lett.*, 1998; 8[15]:1953–1958) (General Method B).

(jj) 8-Chloro-1-cyclopropyl-6-fluoro-2,4-dioxo-7-{3-[(2,2,2-trifluoro-ethylamino)methyl]pyrrolidin-1-yl}-1,4-dihydro-2H-quinazolin-3-yl)carbamic acid tert-butyl ester (MS CI: m/z 548 ($M^+$)) using (8-chloro-1-cyclopropyl-6,7-difluoro-2,4-dioxo-1,4-dihydro-2H-quinazolin-3-yl)carbamic acid tert-butyl ester (Example 14) and {3-[(2,2,2-trifluoroethylamino)methyl]pyrrolidin-1-yl}carbamic acid tert-butyl ester (Domagala J. M., Mich T. F., Sanchez J. P. U.S. Pat. No. 5,097,032) (General Method B).

(kk) [8-Chloro-1-cyclopropyl-6-fluoro-7-(5-methyl-hexahydro-pyrrolo[3,4-c]pyrrol-2-yl)-2,4-dioxo-1,4-dihydro-2H-quinazolin-3-yl]carbamic acid tert-butyl ester (MS CI: m/z 494 ($MH^+$)) using (8-chloro-1-cyclopropyl-6,7-difluoro-2,4-dioxo-1,4-dihydro-2H-quinazolin-3-yl)carbamic acid tert-butyl ester (Example 14) and 5-methyloctahydropyrrolo[3,4-c]pyrrole (Ohnmacht C. J. Jr., Draper C. W., Dedinas R. F., Loftus P., Wong J. J., *J. Heterocycl. Chem.*, 1983; 20[2]:321–329) (General Method B).

(ll) [8-Chloro-1-cyclopropyl-7-(2,7-diazaspiro[4.4]non-2-yl)-6-fluoro-2,4-dioxo-1,4-dihydro-2H-quinazolin-3-yl] carbamic acid tert-butyl ester (MS CI: m/z 494 ($MH^+$)) from (8-chloro-1-cyclopropyl-6,7-difluoro-2,4-dioxo-1,4-dihydro-2H-quinazolin-3-yl)carbamic acid tert-butyl ester (Example 14) and (2,7-diaza-spiro[4.4]non-2-yl)carbamic acid tert-butyl ester (Culbertson T. P., Sanchez J. P., Gambino L., Sesnie J. A., *J. Med. Chem.*, 1990; 33(8):2270–2275) (General Method B).

(mm) (7-[3-Benzyl-3-(tert-butoxycarbonylaminomethyl) pyrrolidin-1-yl]-8-chloro-1-cyclopropyl-6-fluoro-2,4-dioxo-1,4-dihydro-2H-quinazolin-3-yl}-carbamic acid tert-butyl ester (MS CI: m/z 658 ($MH^+$)) using (8-chloro-1-cyclopropyl-6,7-difluoro-2,4-dioxo-1,4-dihydro-2H-quinazolin-3-yl)carbamic acid tert-butyl ester (Example 14) and (3-benzylpyrrolidin-3-ylmethyl)carbamic acid tert-butyl ester (Example A7o) (General Method B).

(nn) {7-[(R)-3-((S)-1-tert-Butoxycarbonylaminoethyl) pyrrolidin-1-yl]-8-chloro-1-cyclopropyl-6-fluoro-2,4-dioxo-1,4-dihydro-2H-quinazolin-3-yl}-carbamic acid tert-butyl ester ((MS CI: m/z 582 ($MH^+$)) from (8-chloro-1-cyclopropyl-6,7-difluoro-2,4-dioxo-1,4-dihydro-2H-quinazolin-3-yl)carbamic acid tert-butyl ester (Example 14) and (R)-(S)-1-pyrrolidin-3-ylethyl)carbamic acid tert-butyl ester (Johnson D. R., Szoteck D. L., Domagala J. M., Stickney T. M., Michel A., Kampf J. W., *J. Heterocycl. Chem.*, 1992; 29[6]:1481–1488) (General Method B).

(oo) [8-Chloro-1-cyclopropyl-6-fluoro-7-(3-hydroxyiminopyrrolidin-yl)-2,4-dioxo-1,4-dihydro-2H-quinazolin-3-yl]carbamic acid tert-butyl ester (MS CI: m/z 469 ($MH^+$)) from (8-chloro-1-cyclopropyl-6,7-difluoro-2,4-dioxo-1,4-dihydro-2H-quinazolin-3-yl)carbamic acid tert-butyl ester (Example 14) and pyrrolidin-3-one oxime (Example A7) (General Method B).

(pp) [7-trans-(3-tert-Butoxycarbonylamino-4-trifluoromethylpyrrolidin-1-yl)-8-chloro-1-cyclopropyl-6-fluoro-2,4-dioxo-1,4-dihydro-2H-quinazolin-3-yl]-carbamic acid tert-butyl ester (MS CI: m/z 622 ($MH^+$)) from (8-chloro-1-cyclopropyl-6,7-difluoro-2,4-dioxo-1,4-dihydro-2H-quinazolin-3-yl)carbamic acid tert-butyl ester (Example 14) and trans-(4-trifluoromethylpyrrolidin-3-yl)carbamic acid tert-butyl ester (Fukui H., Shibata T., Naito T. Nakano J., Maejima T., Senda H., Iwatani W., et al., *Bioorg. Med. Chem. Lett.*, 1998; 8[20]:2833–2838) (General Method B).

(qq) (7-{(R)-3-(S)-1-(tert-Butoxycarbonylmethylamino) ethyl] pyrrolidin-1-yl}-8-chloro-1-cyclopropyl-6-fluoro-2,4-dioxo-1,4-dihydro-2H-quinazolin-3-yl)carbamic acid tert-butyl ester (MS CI: m/z 596 ($MH^+$)) from (8-chloro-1-cyclopropyl-6,7-difluoro-2,4-dioxo-1,4-dihydro-2H-quinazolin-3-yl)carbamic acid tert-butyl ester (Example 14) and (R)-3-((S)-1-methylaminoethyl)pyrrolidine (*J. Het. Chem.*, 1992; 29:1481) (General Method F).

(rr) trans-[7-((3-tert-Butoxycarbonylamino-4-phenylpyrrolidin-1-yl)-8-chloro-1-cyclopropyl-6-fluoro-2,4-dioxo-1,4-dihydro-2H-quinazolin-3-yl]carbamic acid tert-butyl ester (MS CI: m/z 630 ($MH^+$)) using (8-chloro-1-cyclopropyl-6,7-difluoro-2,4-dioxo-1,4-dihydro-2H-quinazolin-3-yl)carbamic acid tert-butyl ester (Example 14) and trans-4-phenylpyrrolidin-3-ylamine carbamic acid tert-butyl ester (Bucsh R. A., Domagala J. M., Laborde E., Sesnie J. C., *J. Med. Chem.*, 1993; 36[26]:4139–1451) (General Method B).

(ss) trans-{7-[3-tert-Butoxycarbonylamino-4-(4-hydroxyphenyl)-pyrrolidin-1-yl]-8-chloro-1-cyclopropyl-6-fluoro-2,4-dioxo-1,4-dihydro-2H-quinazolin-3-yl}-carbamic acid tert-butyl ester (MS: m/z 646 ($MH^+$)) using (8-chloro-1- cyclopropyl-6,7-difluoro-2,4-dioxo-1,4-dihydro-2H-quinazolin-3-yl)carbamic acid tert-butyl ester (Example 14) and trans-4-(4-hydroxyphenyl)-pyrrolidin-3-ylamine carbamic acid tert-butyl ester (Bucsh R. A., Domagala J. M., Laborde E., Sesnie J.C., *J. Med. Chem.*, 1993; 36[26]: 4139–4151) (General Procedure B).

(tt) {7-[3-(tert-Butoxycarbonylaminomethyl)piperidin-1-yl]-8-chloro-1-cyclopropyl-6-fluoro-2,4-dioxo-1,4-dihydro-2H-quinazolin-3-yl}carbamic acid tert-butyl ester (MS CI: m/z 580 (M$^+$)) using (8-chloro-1-cyclopropyl-6,7-difluoro-2,4-dioxo-1,4-dihydro-2H-quinazolin-3-yl)carbamic acid tert-butyl ester (Example 14) and (piperidin-3-ylmethyl)carbamic acid tert-butyl ester (General Method B).

(uu) (7-{3-[(tert-Butoxycarbonylisopropylamino)methyl]pyrrolidin-1-yl}-8-chloro-1-cyclopropyl-6-fluoro-2,4-dioxo-1,4-dihydro-2H-quinazolin-3-yl)-carbamic acid tert-butyl ester (MS CI: m/z 608 (M$^+$)) from (8-chloro-1-cyclopropyl-6,7-difluoro-2,4-dioxo-1,4-dihydro-2H-quinazolin-3-yl)carbamic acid tert-butyl ester (Example 14) and 3-(isopropylaminomethyl)pyrrolidine (Domagala et al., *J. Med. Chem.*, 1994; 3889–3901) (General Method F).

(vv) {7-[3-(tert-Butoxycarbonylaminomethyl)pyrrolidin-1-yl]-6,8-dichloro-1-cyclopropyl-2,4-dioxo-1,4-dihydro-2H-quinazolin-3-yl}carbamic acid tert-butyl ester (MS CI: m/z 584 (MH$^+$)) from (8-chloro-1-cyclopropyl-6,7-difluoro-2,4-dioxo-1,4-dihydro-2H-quinazolin-3-yl)carbamic acid tert-butyl ester (Example 14) and (pyrrolidine-3-ylmethyl)carbamic acid tert-butyl ester (General Method B).

(ww) [7-(3-tert-Butoxycarbonylamino-3-phenylpyrrolidin-1-yl)-8-chloro-1-cyclopropyl-6-fluoro-2,4-dioxo-1,4-dihydro-2H-quinazolin-3-yl]carbamic acid tert-butyl ester ($^1$H NMR (200 MHz, CDCl$_3$) δ 7.68 (d, 1H), 7.50–7.29 (m, 5H), 6.72 (s, 1H), 5.24 (s, 1H), 4.18–3.85 (m, 3H), 3.78–3.52 (m, 2H), 2.70 (s, 1H), 2.58–2.39 (m, 1H), 1.62–0.62 (m, 22H)) from (8-chloro-1-cyclopropyl-6,7-difluoro-2,4-dioxo-1,4-dihydro-2H-quinazolin-3-yl)carbamic acid tert-butyl ester (Example 14) and (3-phenylpyrrolidin-3-yl)carbamic acid tert-butyl ester (Example A30) using General Method B.

(xx) {7-[3-(tert-Butoxycarbonylaminomethyl)-4-methylpyrrolidin-1-yl]-8-chloro-1-cyclopropyl-6-fluoro-2,4-dioxo-1,4-dihydro-2H-quinazolin-3-yl}carbamic acid tert-butyl ester (MS ES: m/z 582 (MH$^+$)) from (8-chloro-1-cyclopropyl-6,7-difluoro-2,4-dioxo-1,4-dihydro-2H-quinazolin-3-yl)carbamic acid tert-butyl ester (Example 14) and trans-(4-methylpyrrolidin-3-yl)carbamic acid tert-butyl ester (Kuniyoshi M., Seigo S., Keiji H., Takayoshi I., Eur. Pat. Appl., 1987, EP 208210) using general procedure F.

EXAMPLE 9

Deprotection of Quinazolin-2,4-diones

General Method A

Hydrogen chloride gas is bubbled into diethyl ether (or dichloromethane or dichloroethane for 15 minutes. The resulting solution is then cooled to 0° C. and added to a solution of a 2,4-dioxo-1,4-dihydro-2H-quinazolin-3-yl}carbamic acid tert-butyl ester (Example 6), The reaction mixture is slowly warmed to room temperature. After 30 hours, the precipitate is filtered, washed with ether (or dichloromethane or dichloroethane) and hexanes, and dried under vacuum to afford the hydrochloride salt of the desired deprotected amine as a solid.

General Method B

A compound is dissolved in trifluoroacetic acid and stirred at 0° C. for 3 to 8 hours. The acid is removed by blowing compressed air over the solution or concentrate in vacuo. The residue is twice co-evaporated with ethanol and dried in vacuo to yield the trifluoroacetate salt of the title compound as a solid.

General Method C

A 3-dibenzylamino-6-fluoro-1-substituted-2,4-dioxo-1,2,3,4-tetrahydro-quinazolin-7-yl)pyrrolidin-3-yl]carbamic acid tert-butyl ester and 20% Pd/C (cat.) are combined in methanol and shaken under 50 psi of hydrogen for 22.5 hours. The suspension is filtered through Celite and concentrated. The residue is purified via chromatography (SiO$_2$, CHCl$_3$) to give a solid. The solid is then dissolved in methylene chloride, cooled to 0° C., and HCl gas is passed through the solution for 10 minutes. The suspension is stirred for 2 hours and concentrated to give the title compound.

General Method D

Hydrogen chloride gas is bubbled through a solution of substrate in diethyl ether, and the solution stirred for 2 hours. The solvent is removed under reduced pressure to afford the desired title compound as a solid.

General Method E

A solution of substrate in ethanol is treated with a solution of ethanol saturated with gaseous hydrogen chloride. The reaction mixture is stirred at room temperature for 18 hours, and the solvent is removed in vacuo. The residue is dissolved in water, filtered through a fiber glass pad to clarify, and lyophilized. The solid residue is triturated with ether, filtered, washed with ether and dried in vacuo.

General Method F

A solution of 3-amino-7-chloro-1-cyclopropyl-6-fluoro-1H-pyrido[2,3-d]pyrimidine-2,4-dione (Example 24b), 1.2 eq. of heterocyclic amine side chain, and 1:3 N,N-diisopropylethylamine/acetonitrile is heated at 50° C. for 18 hours. The reaction mixture is diluted with water, cooled to 0° C., and the solid is removed by filtration, washed with 50% aqueous acetonitrile, and dried in vacuo to give a solid that is dissolved in ethanol and treated with a solution of ethanol saturated with gaseous hydrogen chloride. The mixture is then stirred at room temperature for 18 hours. The solvent is removed in vacuo and the residue is triturated with ether. The solid is removed by filtration, washed with ether and dried in vacuo.

The following compounds are synthesized according to General Procedures A–F of Example 9:

(a) 3-Amino-7-(3-aminomethylpyrrolidin-1-yl)-8-chloro-1-cyclopropyl-6-fluoro-1H-quinazoline-2,4-dione hydrochloride (Compound 1) (mp 153–155° C., MS CI: m/z 368 (MH$^+$)) from 7-[3-(tert-butoxycarbonylamino-methyl)pyrrolidin-1-yl]-8-chloro-1-cyclopropyl-6-fluoro-2,4-dioxo-1,4-dihydro-2H-quinazolin-3-yl}carbamic acid tert-butyl ester (Example 8a) using General Method A.

(b) 3-Amino-8-chloro-1-cyclopropyl-6-fluoro-7-piperazin-1-yl-1H-quinazoline-2,4-dione hydrochloride (Compound 2) (mp 156–159° C., MS CI: m/z 354 (MH$^+$)) from 7-[4-(tert-butoxycarbonylpiperazin-1-yl)-8-chloro-1-cyclopropyl-6-fluoro-2,4-dioxo-1,4-dihydro-2H-quinazolin-3-yl]carbamic acid tert-butyl ester (Example 8b) using General Method A.

(c) 3-Amino-7-[3-(aminomethyl)-3-methylpyrrolidin-1-yl]-8-chloro-1-cyclopropyl-6-fluoro-1H-quinazoline-2,4-dione hydrochloride (Compound 3) (mp 166–168° C., MS CI: m/z 382 (MH$^+$)) from {7-[3-(tert-butoxycarbonylamino-methyl)-3-methylpyrrolidin-1-yl]-8-chloro-1-cyclopropyl-6-fluoro-2,4-dioxo-1,4-dihydro-2H-quinazolin-3-yl}carbamic acid tert-butyl ester (Example 8c) using General Method A.

(d) 3-Amino-7-(6-amino-3-aza-bicyclo[3.1.0]hex-3-yl)-8-chloro-1-cyclopropyl-6-fluoro-1H-quinazoline-2,4-dione hydrochloride (Compound 4) (mp 111–114° C., MS CI: m/z 366 (MH$^+$)) from [7-(6-tert-butoxycarbonylamino-3-azabicyclo[3.1.0]hex-3-yl)-8-chloro-1-cyclopropyl-6-fluoro-2,4-dioxo-1,4-dihydro-2H-quinazolin-3-yl]carbamic acid tert-butyl ester (Example 8d) using General Method A.

(e) 3-Amino-7-((S)-3-N-methylaminopyrrolidin-1-yl)-8-chloro-1-cyclopropyl-6-fluoro-1H-quinazoline-2,4-dione hydrochloride (Compound 5) (mp 118–120° C., MS CI: m/z 368 (MH$^+$)) from {7-[(S)-3-(tert-butoxycarbonyl-N-methylamino)pyrrolidin-1-yl]-8-chloro-1-cyclopropyl-6-fluoro-2,4-dioxo-1,4-dihydro-2H-quinazolin-3-yl}carbamic acid tert-butyl ester (Example 8e) using General Method A.

(f) 3-Amino-7-((S)-3-aminopyrrolidin-1-yl)-8-chloro-1-(2,4-difluoroanilino)-6-fluoro-1H-quinazoline-2,4-dione hydrochloride (Compound 6) (mp 184–186° C., MS CI: m/z 427 (MH$^+$)) from {7-[(S)-3-(tert-butoxycarbonylamino)pyrrolidin-1-yl]-8-chloro-1-(2,4-difluoroanilino)-6-fluoro-1,4-dihydro-2,4-dioxo-2H-quinazolin-3-yl}carbamic acid tert-butyl ester (Example 8f) using General Method A.

(g) 3-Amino-7-[(S)-3-aminopyrrolidin-1-yl]-1-cyclopropylamino-6,8-difluoro-1H-quinazoline-2,4-dione hydrochloride (Compound 7) (mp 288° C. (dec.), MS EI: m/z 338 (M$^+$)) from 7-[(S)-3-(tert-butoxycarbonylamino)-pyrrolidin-1-yl]-1-cyclopropylamino-6,8-difluoro-1,4-dihydro-2,4-dioxo-2H-quinazolin-3-yl}carbamic acid tert-butyl ester (Example 8g) using General Method A.

(h) 3-Amino-7-[(S)-3-aminopyrrolidin-1-yl]-1-cyclopropylamino-5,8-difluoro-1H-quinazoline-2,4-dione hydrochloride (Compound 8) (mp 338° C. (dec), MS EI: m/z 338 (M$^+$)) from {7-[(S)-3-(tert-butoxycarbonylamino)-pyrrolidin-1-yl]-1-cyclopropylamino-5,8-difluoro-1,4-dihydro-2,4-dioxo-2H-quinazolin-3-yl}carbamic acid tert-butyl ester (Example 8h) using General Method A (i) 3-Amino-7-((S)-3-aminopyrrolidin-1-yl)-1-cyclopropyl-5,6,8-trifluoro-1H-quinazoline-2,4-dione hydrochloride (Compound 9) (mp 271° C. (dec.), MS CI: m/z 356 (MH$^+$)) from {7-[(S)-3-(tert-butoxycarbonylamino)-pyrrolidin-1-yl]-1-cyclopropyl-1,4-dihydro-2,4-dioxo-5,6,8-trifluoro-2H-quinazolin-3-yl}-carbamic acid tert-butyl ester (Example 8i) using General Method A.

(j) 3-Amino-7-(3-aminopyrrolidin-1-yl)-8-chloro-1-cyclopropyl-6-fluoro-1H-quinazoline-2,4-dione hydrochloride (Compound 10) (mp 134–136° C., MS CI: m/z 354 (MH$^+$)) from {7-[3-(tert-butoxycarbonylamino)-pyrrolidin-1-yl]-8-chloro-1-cyclopropyl-6-fluoro-2,4-dioxo-1,4-dihydro-2H-quinazolin-3-yl}carbamic acid tert-butyl ester (Example 8a) using General Method A.

(k) 7-((S)-3-Aminopyrrolidin-1-yl)-1-cyclopropyl-3,5-diamino-6,8-difluoro-1H-quinazoline-2,4-dione hydrochloride (Compound 11) (mp 215–218° C. (dec.), MS EI: 352 (M$^+$)) from {5-amino-7-[(S)-3-(tert-butoxycarbonylamino)pyrrolidin-1-yl]-1-cyclopropyl-6,8-difluoro-1,4-dihydro-2,4-dioxo-2H-quinazolin-3-yl}carbamic acid tert-butyl ester (Example 12) using Method A.

(l) 3-Amino-7-(3-hydroxymethylpyrrolidin-1-yl)-8-chloro-1-cyclopropyl-6-fluoro-1H-quinazoline-2,4-dione hydrochloride (Compound 12) (mp 78–80° C., MS CI: m/z 369 (MH$^+$)) from [7-(3-hydroxymethylpyrrolidin-1-yl)-8-chloro-1-cyclopropyl-6-fluoro-2,4-dioxo-1,4-dihydro-2H-quinazolin-3-yl]carbamic acid tert-butyl ester (Example 8k) using Method A.

(m) 3-Amino-7-(3-aminoethylpyrrolidin-1-yl)-8-chloro-1-cyclopropyl-6-fluoro-1H-quinazoline-2,4-dione hydrochloride (Compound 13) (mp 158–160° C., MS CI: m/z 382 (M$^+$)) from {7-[3-(tert-butoxycarbonylamino-ethyl)pyrrolidin-1-yl]-8-chloro-1-cyclopropyl-6-fluoro-2,4-dioxo-1,4-dihydro-2H-quinazolin-3-yl}carbamic acid tert-butyl ester (Example 81) using Method A.

(n) 3-Amino-7-((S)-7-amino-5-azaspiro[2.4]hept-5-yl)-8-chloro-1-cyclopropyl-6-fluoro-1H-quinazoline-2,4-dione hydrochloride (Compound 14) (mp 177–179° C., MS CI: m/z 380 (MH$^+$) from [7-(7-tert-butoxycarbonylamino-5-azaspiro[2.4]hept-5-yl)-8-chloro-1-cyclopropyl-6-fluoro-2,4-dioxo-1,4-dihydro-2H-quinazolin-3-yl]carbamic acid tert-butyl ester (Example 8m) using General Method A.

(o) 3-Amino-7-[(R)-3-(1-amino-1-methylethyl)pyrrolidin-1-yl]-8-chloro-1-cyclopropyl-6-fluoro-1H-quinazoline-2,4-dione hydrochloride (Compound 15) (mp 117–120° C., MS CI: m/z 396 (MH$^+$)) from {7-[(R)-3-(1-tert-butoxycarbonylamino-1-methylethyl)pyrrolidin-1-yl]-8-chloro-1-cyclopropyl-6-fluoro-2,4-dioxo-1,4-dihydro-2H-quinazolin-3-yl}carbamic acid tert-butyl ester (Example 8n) using General Method A.

(p) 3-Amino-7-(3-aminomethylpyrrolidin-1-yl)-1-cyclopropyl-6-fluoro-1H-quinazoline-2,4-dione hydrochloride (Compound 16) (mp 170–172° C., MS CI: m/z 334 (MH$^+$)) from {7-[3-(tert-butoxycarbonylamino-methyl)pyrrolidin-1-yl]-1-cyclopropyl-6-fluoro-2,4-dioxo-1,4-dihydro-2H-quinazolin-3-yl}carbamic acid tert-butyl ester (Example 8o) using General Method A.

(q) 3-Amino-7-(pyrrolidin-1-yl)-8-chloro-1-cyclopropyl-6-fluoro-1H-quinazoline-2,4-dione hydrochloride (Compound 17) (mp 96–98° C., MS CI: m/z 339 (MH$^+$)) from [7-(pyrrolidin-1-yl)-8-chloro-1-cyclopropyl-6-fluoro-2,4-dioxo-1,4-dihydro-2H-quinazolin-3-yl]carbamic acid tert-butyl ester (Example 8p) using General Method A.

(r) 3-Amino-7-(3-aminopyrrolidin-1-yl)-8-chloro-6-fluoro-1-isopropyl-1H-quinazoline-2,4-dione trifluoroacetate (Compound 18) (mp 151° C., MS EI: m/z 356 (M$^+$)) from {7-[3-(tert-butoxycarbonylamino)-pyrrolidin-1-yl]-8-chloro-6-fluoro-1-isopropyl-2,4-dioxo-6-fluoro-2H-quinazolin-3-yl}carbamic acid tert-butyl ester (Example 8q) using General Method B.

(s) 3-Amino-7-(3-aminopyrrolin-1-yl)-1-sec-butyl-8-chloro-6-fluoro-1H-quinazoline-2,4-dione trifluoroacetate (Compound 19) (mp 115° C.) from {7-[3-(tert-butoxycarbonylamino)pyrrolidin-1-yl]-1-sec-butyl-8-chloro-6-fluoro-2,4-dioxo-2H-quinazolin-3-yl}carbamic acid tert-butyl ester (Example 8r) using General Method B.

(t) 3-Amino-7-[3-aminopyrrolidin-1-yl]-1-cyclopropyl-6-fluoro-8-methoxy-1H-quinazoline-2,4-dione hydrochloride (Compound 20) (mp 216–218° C., MS EI: m/z 350 (MH$^+$)) from {7-[3-(tert-butoxycarbonylamino)-pyrrolidin-1-yl]-1-cyclopropyl-6-fluoro-8-methoxy-2,4-dioxo-1,4-dihydro-2H-quinazolin-3-yl}carbamic acid tert-butyl ester (Example 8s) using Method A.

(u) 3-Amino-7-[3-aminopyrrolidin-1-yl]-8-chloro-1-cyclobutylamino-6-fluoro-1H-quinazoline-2,4-dione hydrochloride (Compound 21) (mp 205–208° C. (dec.), MS EI: m/z 368 (MH$^+$)) from {7-[3-(tert-butoxycarbonylamino)pyrrolidin-1-yl]-8-chloro-1-cyclobutylamino-6-fluoro-2,4-dioxo-1,4-dihydro-2H-quinazolin-3-yl}carbamic acid tert-butyl ester (Example 8t) using General Method A.

(v) 3-Amino-7-(3-aminopyrrolidin-1-yl)-1-cyclopropyl-8-fluoro-1H-quinazoline-2,4-dione trifluoroacetate (Compound 22) (mp 210–212° C., MS EI: m/z 320 (M+)) from {7-[3-(tert-butoxycarbonylamino)pyrrolidin-1-yl]-1-cyclopropyl-8-fluoro-2,4-dioxo-1,4-dihydro-2H-quinazolin-3-yl}carbamic acid tert-butyl ester (Example 8u) using Method A.

(w) 3-Amino-7-(3-aminopyrrolidin-1-yl)-6-chloro-1-cyclopropyl-8-fluoro-1H-quinazoline-2,4-dione trifluoroacetate (Compound 23) (mp 135–137° C., MS EI: m/z 354 (MH$^+$)) from {7-[3-(tert-butoxycarbonylamino)-pyrrolidin-1-yl]-6-chloro-1-cyclopropyl-8-fluoro-2,4-dioxo-1,4-dihydro-2H-quinazolin-3-yl}carbamic acid tert-butyl ester (Example 8v) using General Method B.

(x) 3-Amino-7-((S)-3-aminopyrrolidin-1-yl)-1-cyclopropylmethyl-8-fluoro-1H-quinazoline-2,4-dione hydrochloride (Compound 24) (mp>250° C., MS CI: m/z 334 (MH$^+$)) from [(S)-1-(1-cyclopropylmethyl-3-dibenzylamino-6-fluoro-2,4-dioxo-1,2,3,4-tetrahydroquinazolin-7-yl)pyrrolidin-3-yl]carbamic acid tert-butyl ester (Example 8w) using General Method C.

(y) 3-Amino-7-[(R)-3-(1-amino-1-methylethyl)pyrrolidin-1-yl]-1-cyclopropylmethyl-8-fluoro-1H-quinazoline-2,4-dione hydrochloride (Compound 25) (mp>250° C., MS CI: m/z 376 (MH$^+$)) from {1-[(R)-1-(cyclopropylmethyl-3-dibenzylamino-6-fluoro-2,4-dioxo-1,2,3,4-tetrahydroquinazolin-7-yl)pyrrolidin-3-yl]-1-methylethyl)carbamic acid tert-butyl ester (Example 8x) using General Method C.

(z)-3-Amino-7-((S)-3-aminopyrrolidin-1-yl)-1-ethyl-8-fluoro-1H-quinazoline-2,4-dione hydrochloride (Compound 26) (mp 248–251° C., MS CI: m/z 308 (MH$^+$)) from [(S)-1-(3-dibenzylamino-1-ethyl-6-fluoro-2,4-dioxo-1,2,3,4-tetrahydroquinazolin-7-yl)pyrrolidin-3-yl]-carbamic acid tert-butyl ester (Example 8y) using General Method C.

(aa) 3-Amino-1-ethyl-6-fluoro-7-[(R)-3-(1-amino-1-methylethyl)-pyrrolidin-1-yl]-1H-quinazoline-2,4-dione hydrochloride (Compound 27) (mp>250° C., MS CI: m/z 350 (MH$^+$)) from [(R)-1-(3-dibenzylamino-1-ethyl-6-fluoro-2,4-dioxo-1,2,3,4-tetrahydroquinazolin-7-yl)-1-methyl-1-pyrrolidin-3-ylethyl]carbamic acid tert-butyl ester (Example 8z) using Method C.

(bb) 3-Amino-7-((S)-3-aminopyrrolidin-1-yl)-1-cyclopropyl-6-fluoro-1H-quinazoline-2,4-dione hydrochloride (Compound 28) (mp>250° C., MS CI: m/z 320 (MH$^+$)) from 3-amino-{7-[(S)-3-(tert-butoxycarbonylamino)pyrrolidin-1-yl]-1-cyclopropyl-6-fluoro-1H-quinazoline-2,4-dione (Example 25) using General Method A.

(cc) 3-Amino-7-(3-aminopyrrolidin-1-yl)-1-cyclopropyl-6-fluoro-8-methyl-1H-quinazoline-2,4-dione trifluoroacetate (Compound 29) (mp 110–112° C., MS ES, MH$^+$) m/z 334) from [7-(3-tert-butoxycarbonylamino-pyrrolidin-1-yl)-1-cyclopropyl-6-fluoro-8-methyl-2,4-dioxo-1,4-dihydro-2H-quinazolin-3-yl]carbamic acid tert-butyl ester (Example 8aa) using General Method B.

(dd) 3-Amino-7-(3-aminomethylpyrrolidin-1-yl)-1-cyclopropyl-6-fluoro-8-methyl-1H-quinazoline-2,4-dione trifluoroacetate (Compound 30) (mp 82–84° C., MS ES, m/z 348 (M$^+$)) from {7-[3-(tert-butoxycarbonylaminomethyl)-pyrrolidin-1-yl]-1-cyclopropyl-6-fluoro-8-methyl-2,4-dioxo-1,4-dihydro-2H-quinazolin-3-yl}carbamic acid tert-butyl ester (Example 8bb) using General Method B.

(ee) 3-Amino-7-(3-aminopyrrolidin-1-yl)-1-cyclopropyl-8-fluoro-6-methoxy-1H-quinazoline-2,4-dione hydrochloride (Compound 31) (mp 208–210° C., MS ES, m/z 350 (MH$^+$)) from [7-(3-tert-butoxycarbonylamino-pyrrolidin-1-yl)-1-cyclopropyl-8-fluoro-6-methoxy-2,4-dioxo-1,4-dihydro-2H-quinazolin-3-yl]carbamic acid tert-butyl ester (Example 8 cc) using General Method A.

(ff) 3-Amino-7-(3-aminomethylpyrrolidin-1-yl)-1-cyclopropyl-6-fluoro-8-methoxy-1H-quinazoline-2,4-dione hydrochloride (Compound 32) (mp 180–182° C., MS ES, m/z 364 (MH$^+$)) from {7-[3-(tert-butoxycarbonylaminomethyl)pyrrolidin-1-yl]-1-cyclopropyl-6-fluoro-8-methoxy-2,4-dioxo-1,4-dihydro-2H-quinazolin-3-yl}-carbamic acid tert-butyl ester (Example 8dd) using General Method A.

(gg) 3-Amino-7-(3-aminopyrrolidin-1-yl)-1-cyclopropyl-8-ethoxy-6-fluoro-1H-quinazoline-2,4-dione hydrochloride (Compound 33) (mp 220° C., MS ES, m/z 364 (MH$^+$)) from [7-(3-tert-butoxycarbonylaminopyrrolidin-1-yl)-1-cyclopropyl-8-ethoxy-6-fluoro-2,4-dioxo-1,4-dihydro-2H-quinazolin-3-yl]carbamic acid tert-butyl ester (Example 8ee) using General Method A.

(hh) 3-Amino-7-(3-aminopyrrolidin-1-yl)-1-cyclopropyl-6-fluoro-2,4-dioxo-1,2,3,4-tetrahydroquinazoline-8-carbonitrile hydrochloride (Compound 34) (mp 277° C., MS ES, m/z 345 (MH$^+$)) from [7-(3-tert-butoxycarbonylaminopyrrolidin-1-yl)-8-cyano-1-cyclopropyl-6-fluoro-2,4-dioxo-1,4-dihydro-2H-quinazolin-3-yl]carbamic acid tert-butyl ester (Example 8ff) using General Method A.

(ii) 3-Amino-8-chloro-1-cyclopropyl-6-fluoro-7-(3-[1,2,3-triazol]-1-yl-pyrrolidin-1-yl)-1H-quinazoline-2,4-dione trifluoroacetate (Compound 35) (mp 145–147° C., MS ES, m/z 406 (MH$^+$)) from [8-chloro-1-cyclopropyl-6-fluoro-2,4-dioxo-7-(3-[1,2,3-triazol]-1-yl-pyrrolidin-1-yl)-1,4-dihydro-2H-quinazolin-3-yl]carbamic acid tert-butyl ester (Example 8gg) using General Method B.

(jj) 3-Amino-7-[(S)-3-((R)-1-aminoethyl)pyrrolidin-1-yl]-1-cyclopropyl-6-fluoro-8-methoxy-1H-quinazoline-2,4-dione hydrochloride (Compound 36), (mp 215–217° C.) from {(R)-1-[(S)-1-(3-amino-1-cyclopropyl-6-fluoro-8-methoxy-2,4-dioxo-1,2,3,4-tetrahydroquinazolin-7-yl)pyrrolidin-3-yl]ethyl}-carbamic acid tert-butyl ester (Example 28a) using General Method E.

(kk) 3-Amino-7-[(S)-3-((S)-1-aminoethyl)pyrrolidin-1-yl]-1-cyclopropyl-6-fluoro-8-methoxy-1H-quinazoline-2,4-dione hydrochloride (Compound 37) (mp 221–223° C.) from {(S)-1-[(S)-1-(3-amino-1-cyclopropyl-6-fluoro-8-methoxy-2,4-dioxo-1,2,3,4-tetrahydroquinazolin-7-yl)pyrrolidin-3-yl]ethyl}-carbamic acid tert-butyl ester (Example 28b) using General Method A.

(ll) 3-Amino-7-[(S)-3-((R)-1-aminoethyl)pyrrolidin-1-yl]-1-cyclopropyl-6-fluoro-8-methyl-1H-quinazoline-2,4-dione hydrochloride (Compound 38) (mp 197–199° C.) from {(R)-1-[(S)-1-(3-amino-1-cyclopropyl-6-fluoro-8-methyl-2,4-dioxo-1,2,3,4-tetrahydroquinazolin-7-yl]pyrrolidin-3-yl]ethyl}carbamic acid tert-butyl ester (Example 28c) using General Method E.

(mm) 3-Amino-7-[(S)-3-((S)-1-aminoethyl)pyrrolidin-1-yl]-1-cyclopropyl-6-fluoro-8-methyl-1H-quinazoline-2,4-dione hydrochloride (Compound 39) (mp 192–194° C.) from {(S)-1-[(S)-1-(3-amino-1-cyclopropyl-6-fluoro-8-methyl-2,4-dioxo-1,2,3,4-tetrahydroquinazolin-7-yl)pyrrolidin-3-yl]-ethyl}carbamic acid tert-butyl ester (Example 28d) using General Method E.

(nn) 5-Amino-9-((S)-3-aminopyrrolidin-1-yl)-8-fluoro-3-methyl-2,3-dihydro-1-oxa-3a,5-diazaphenalene-4,6-dione hydrochloride (Compound 40) (mp 202–204° C.) from [(S)-1-(5-amino-8-fluoro-3-methyl-4,6-dioxo-2,3,5,6-tetrahydro-4H-1-oxa-3a,5-diazaphenalen-9-yl)pyrrolidin-3-yl]carbamic acid tert-butyl ester (Example 28e) using General Method E.

(oo) 5-Amino-9-[(R)-3-((S)-1-aminoethyl)pyrrolidin-1-yl]-8-fluoro-3-methyl-2,3-dihydro-1-oxa-3a,5-diazaphenalene-4,6-dione hydrochloride (Compound 41) (mp 192–194° C.) from {(S)-1-[(R)-1-(5-amino-8-fluoro-3-methyl-4,6-dioxo-2,3,5,6-tetrahydro-4H-1-oxa-3a,5-diazaphenalen-9-yl)-pyrrolidin-3-yl]ethyl}carbamic acid tert-butyl ester (Example 28f) using General Method E.

(pp) 2-Amino-8-((S)-3-aminopyrrolidin-1-yl)-9-fluoro-5-methyl-6,7-dihydro-5H-pyrido[3,2,1-ij]quinazoline-1,3-dione, hydrochloride (Compound 42) (mp 202–204° C.) from [(S)-1-(2-amino-9-fluoro-5-methyl-1,3-dioxo-2,3,6,7-tetrahydro-1H,5H-pyrido[3,2,1-ij]quinazolin-8-yl)pyrrolidin-3-yl]carbamic acid tert-butyl ester (Example 28g) using General Method E.

(qq) 2-Amino-8-[(R)-3-((S)-1-aminoethyl)pyrrolidin-1-yl]-9-fluoro-5-methyl-6,7-dihydro-5H-pyrido[3,2,1-ij]quinazoline-1,3-dione hydrochloride (Compound 43) (mp 197–199° C.) from {(R)-3-[(S)-1-(2-amino-9-fluoro-5-methyl-1,3-dioxo-2,3,6,7-tetrahydro-1H,5H-pyrido[3,2,1-ij]quinazolin-8-yl)-pyrrolidin-3-yl}ethyl]carbamic acid tert-butyl ester (Example 28h) using General Method E.

(rr) 3-Amino-7-((S)-3-aminopyrrolidin-1-yl)-1-cyclopropyl-6-fluoro-1H-pyrido[2,3-d]pyrimidine-2,4-dione hydrochloride (Compound 44) (mp 213–215° C.) from [1-(3-Amino-1-cyclopropyl-6-fluoro-2,4-dioxo-1,2,3,4-tetrahydro-pyrido[2,3-d]pyrimidin-7-yl)pyrrolidin-3-yl]carbamic acid tert-butyl ester (Example 28i) using General Method E.

(ss) 3-Amino-7-(6-amino-3-azabicyclo[3.1.0]hex-3-yl)-1-cyclopropyl-6-fluoro-1H-pyrido[2,3-d]pyrimidine-2,4-dione, hydrochloride (Compound 45) (mp 268–270° C.) from 3-amino-7-chloro-1-cyclopropyl-6-fluoro-1H-pyrido[2,3-d]pyrimidine-2,4-dione (Example 24b) and 3-azabicyclo[3.1.0]hex-6-ylcarbamic acid tert-butyl ester using General Method F.

(tt) 3-Amino-7-(3-aminomethyl-3-methylpyrrolidin-1-yl)-1-cyclopropyl-6-fluoro-1H-pyrido[2,3-d]pyrimidine-2,4-dione, hydrochloride (Compound 46) (mp 187–189° C.) from 3-amino-7-chloro-1-cyclopropyl-6-fluoro-1H-pyrido[2,3-d]pyrimidine-2,4-dione (Example 24b) and [1-methyl-(3-methylpyrrolidin-3-yl)]methylcarbamic acid tert-butyl ester (*J. Med. Chem.*, 1992; 361–367) using General Method F.

(uu) 3-Amino-1-cyclopropyl-6-fluoro-7-(octahydropyrrolo[3,4-c]pyridin-2-yl)-1H-pyrido[2,3-d]pyrimidine-2,4-dione hydrochloride (Compound 47) (mp 200–203° C.) from 3-amino-7-chloro-1-cyclopropyl-6-fluoro-1H-pyrido[2,3-d]pyrimidine-2,4-dione (Example 24b) and (3aS,7aR)-octahydropyrrolo[3,4-c]pyridine-5-carboxylic acid tert-butyl ester (Example A27) using General Method F.

(vv) 3-Amino-1-cyclopropyl-6-fluoro-7-(octahydropyrrolo[3,4-b]pyridin-2-yl)-1H-pyrido[2,3-d]pyrimidine-2,4-dione hydrochloride (Compound 48) (mp 200–202° C.) from 3-amino-7-chloro-1-cyclopropyl-6-fluoro-1H-pyrido[2,3-d]pyrimidine-2,4-dione (Example 24b) and octahydropyrrolo[3,4-b]pyridine-5-carboxylic acid tert-butyl ester using General Method F.

(ww) 3-Amino-7-[(R)-3-(1-amino-1-methylethyl)pyrrolidin-1-yl]-1-cyclopropyl-6-fluoro-1H-pyrido[2,3-d]pyrimidine-2,4-dione hydrochloride (Compound 49) (mp>260° C.) from 3-amino-7-chloro-1-cyclopropyl-6-fluoro-1H-pyrido[2,3-d]pyrimidine-2,4-dione (Example 24b) and (R)-3-(1-amino-1-methylethyl)-pyrrolidine using General Method F.

(xx) 3-Amino-7-(3-aminomethylpiperidin-1-yl)-1-cyclopropyl-6-fluoro-1H-pyrido[2,3-d]pyrimidine-2,4-dione, dihydrochloride(Compound 50) (mp 152–154° C.) from 3-amino-7-chloro-1-cyclopropyl-6-fluoro-1H-pyrido [2,3-d]pyrimidine-2,4-dione (Example 24b) and (3-aminomethylpiperidin-1-yl)carbamic acid tert-butyl ester (Hilpert K. et al., *J. Med. Chem.*, 1994; 37[23]:3889–3901) using General Method F.

(yy) trans-3-Amino-7-(3-aminomethyl-4-trifluoromethylpyrrolidin-1-yl)-1-cyclopropyl-6-fluoro-1H-pyrido[2,3-d]pyrimidine-2,4-dione hydrochloride (Compound 51) (mp 214–216° C.) from 3-amino-7-chloro-1-cyclopropyl-6-fluoro-1H-pyrido[2,3-d]pyrimidine-2,4-dione (Example 24b) and 3-aminomethyl-4-trifluoromethylpyrrolidine (Li Q., Wang W., Berst K. B., Claiborne A., Hasvold L., Raye K., Tufano M., et al., *Bioorg. Med. Chem. Lett.*, 1998; 8:1953–1958) using General Method F.

(zz) 3-Amino-1-cyclopropyl-6-fluoro-7-[(R)-3-((R)-1-methylamino-ethyl)pyrrolidin-1-yl]-1H-pyrido[2,3-d]pyrimidine-2,4-dione hydrochloride (Compound 52) (mp 137–139° C.) from 3-amino-7-chloro-1-cyclopropyl-6-fluoro-1H-pyrido[2,3-d]pyrimidine-2,4-dione (Example 24b) and (R)-3-((R)-1-methylaminoethyl)pyrrolidine using General Method F.

(aaa) 3-Amino-7-[(R)-3-((S)-1-aminoethyl)pyrrolidin-1-yl]-1-cyclopropyl-6-fluoro-1H-pyrido[2,3-d]pyrimidine-2,4-dione hydrochloride (Compound 53) (mp>260° C.) from {(S)-1-[(R)-1-(3-amino-1-cyclopropyl-6-fluoro-2,4-dioxo-1,2,3,4-tetrahydropyrido[2,3-d]pyrimidin-7-yl)pyrrolidin-3-yl]-ethyl}carbamic acid tert-butyl ester (Example 28j) using General Method E.

(bbb) 3-Amino-7-[3-(1-aminopropyl)pyrrolidin-1-yl]-1-cyclopropyl-6-fluoro-8-methyl-1H-quinazoline-2,4-dione hydrochloride (Compound 54) (MS CI: m/z 376 (MH⁺)) from {1-[1-(3-amino-1-cyclopropyl-6-fluoro-8-methyl-2,4-dioxo-1,2,3,4-tetrahydroquinazolin-7-yl)pyrrolidin-3-yl]propyl}carbamic acid tert-butyl ester (Example 28ooo) using General Method E.

(ccc) 3-Amino-1-cyclopropyl-6-fluoro-8-methyl-7-[(R)-3-((S)-1-methylaminoethyl)pyrrolidin-1-yl]-1H-quinazoline-2,4-dione hydrochloride (Compound 55) (mp 153–5° C.) from {(S)-1-[(R)-1-(3-Amino-1-cyclopropyl-6-fluoro-8-methyl-2,4-dioxo-1,2,3,4-tetrahydroquinazolin-7-yl)pyrrolidin-3-yl]-ethyl}methylcarbamic acid tert-butyl ester (Example 28 ppp) using General Method E.

(ddd) 3-Amino-7-[7-(1-aminoethyl)-5-azaspiro[2,4]hept-5-yl]-1-cyclopropyl-6-fluoro-8-methyl-1H-quinazoline-2,4-dione hydrochloride (Compound 56) (mp 178–80° C., MS CI: m/z 388 (MH⁺)) from {1-[5-(3-amino-1-cyclopropyl-6-fluoro-8-methyl-2,4-dioxo-1,2,3,4-tetrahydroquinazolin-7-yl)-5-aza-spiro[2.4]hept-7-yl]-ethyl}carbamic acid tert-butyl ester (Example 28qqq) using General Method E.

(eee) 1-(3-Amino-8-chloro-1-cyclopropyl-6-fluoro-2,4-dioxo-1,2,3,4-tetrahydroquinazolin-7-yl)piperidine-3-carboxylic acid amide (Compound 58) (mp 141–144° C., MS CI: m/z 396 (MH⁺)) from [7-(3-carbamoylpiperidin-1-yl)-8-chloro-1-cyclopropyl-6-fluoro-2,4-dioxo-1,4-dihydro-2H-quinazolin-3-yl]-carbamic acid tert-butyl ester using General Method A (Example 8hh).

(fff) 3-Amino-[7-trans-3-aminomethyl-4-trifluoromethylpyrrolidin-1-yl]-8-chloro-1-cyclopropyl-6-fluoro-1H-quinazoline-2,4-dione hydrochloride (Compound 59) (mp 171–173° C., MS CI: m/z 436 (MH⁺)) from {7-[trans-3-(tert-butoxycarbonylaminomethyl)-4-trifluoromethylpyrrolidin-1-yl]-8-chloro-1-cyclopropyl-6-fluoro-2,4-dioxo-1,4-dihydro-2H-quinazolin-3-yl}carbamic acid tert-butyl ester (Example 8ii) using General Method E.

(ggg) 3-Amino-8-chloro-1-cyclopropyl-6-fluoro-7-{3-[(2,2,2-trifluoro-ethylamino)methyl]pyrrolidin-1-yl}-1H-quinazoline-2,4-dione hydrochloride (Compound 60) (mp 163–164° C., MS CI: m/z 450 (MH⁺)) from 8-chloro-1-cyclopropyl-6-fluoro-2,4-dioxo-7-{3-[(2,2,2-trifluoroethylamino)methyl]-pyrrolidin-1-yl}-1,4-dihydro-2H-quinazolin-3-yl)carbamic acid tert-butyl ester (Example 8jj) using General Method E.

(hhh) 3-Amino-8-chloro-1-cyclopropyl-6-fluoro-7-(5-methylhexahydro-pyrrolo[3,4-c]pyrrol-2-yl)-1H-quinazoline-2,4-dione hydrochloride (Compound 61) (mp 133–1355° C., MS CI: m/z 394 (MH$^+$)) from [8-chloro-1-cyclopropyl-6-fluoro-7-(5-methylhexahydropyrrolo[3,4-c]pyrrol-2-yl)-2,4-dioxo-1,4-dihydro-2H-quinazolin-3-yl]carbamic acid tert-butyl ester (Example 8kk) using General Method E.

(jjj) 3-Amino-8-chloro-1-cyclopropyl-7-(2,7-diazaspiro[4.4]non-2-yl)-6-fluoro-1H-quinazoline-2,4-dione (Compound 62) (mp 147–149° C., MS CI: m/z 394 (MH$^+$)) from [8-chloro-1-cyclopropyl-7-(2,7-diazaspiro[4.4]non-2-yl)-6-fluoro-2,4-dioxo-1,4-dihydro-2H-quinazolin-3-yl]carbamic acid tert-butyl ester (Example 8ll) using General Method E.

(jjj) 3-Amino-7-(3-aminomethyl-3-benzylpyrrolidin-1-yl)-8-chloro-1-cyclopropyl-6-fluoro-1H-quinazoline-2,4-dione hydrochloride (Compound 63) (mp 148–150° C., MS CI: m/z 458 (MH$^+$)) from (7-[3-benzyl-3-(tert-butoxycarbonylaminomethyl)pyrrolidin-1-yl]-8-chloro-1-cyclopropyl-6-fluoro-2,4-dioxo-1,4-dihydro-2H-quinazolin-3-yl} carbamic acid tert-butyl ester (Example 8 mm) using General Method E.

(kkk) 3-Amino-7-[(R)-3-((S)-1-aminoethyl)pyrrolidin-1-yl]-8-chloro-1-cyclopropyl-6-fluoro-1H-quinazoline-2,4-dione hydrochloride (Compound 64) (mp 164–166° C., MS CI: m/z 382 (MH$^+$)) from {7-[(R)-3-((S)-1-tert-butoxycarbonylaminoethyl)pyrrolidin-1-yl]-8-chloro-1-cyclopropyl-6-fluoro-2,4-dioxo-1,4-dihydro-2H-quinazolin-3-yl}carbamic acid tert-butyl ester (Example 8nn) using General Method E.

(lll) 3-Amino-8-chloro-1-cyclopropyl-6-fluoro-7-(3-hydroxyimino-pyrrolidin-1-yl)-1H-quinazoline-2,4-dione (Compound 65) (mp 147–9° C., MS CI: m/z 368 (MH$^+$) from) [8-chloro-1-cyclopropyl-6-fluoro-7-(3-hydroxyimino-pyrrolidin-yl)-2,4-dioxo-1,4-dihydro-2H-quinazolin-3-yl]carbamic acid tert-butyl ester (Example 8oo) using General Method E.

(mmm) 3-Amino-7-[trans-3-amino-4-trifluoromethylpyrrolidin-1-yl]-8-chloro-1-cyclopropyl-6-fluoro-1H-quinazoline-2,4-dione hydrochloride (Compound 66) (mp 181–183° C., MS CI: m/z 422 (MH$^+$)) from [7-(trans-3-tert-butoxycarbonylamino-4-trifluoromethylpyrrolidin-1-yl)-8-chloro-1-cyclopropyl-6-fluoro-2,4-dioxo-1,4-dihydro-2H-quinazolin-3-yl]carbamic acid tert-butyl ester (Example 8 pp) using General Method E.

(nnn) 3-Amino-8-chloro-1-cyclopropyl-6-fluoro-7-[(R)-3-(S) 1-methylaminoethyl)pyrrolidin-1-yl]-1H-quinazoline-2,4-dione hydrochloride (Compound 67) (mp 122–124° C., MS CI: m/z 396 (MH$^+$)) from (7-{(R)-3-(S)-1-(tert-butoxycarbonylmethylamino)ethyl]pyrrolidin-1-yl}-8-chloro-1-cyclopropyl-6-fluoro-2,4-dioxo-1,4-dihydro-2H-quinazolin-3-yl)carbamic acid tert-butyl ester (Example 8qq) using General Method E.

(ooo) 3-Amino-7-(trans-3-amino-4-phenylpyrrolidin-1-yl)-8-chloro-1-cyclopropyl-6-fluoro-1H-quinazoline-2,4-dione hydrochloride (Compound 68) (mp 174–175° C., MS CI: m/z 430 (MH$^+$)) from [7-(trans-3-tert-butoxycarbonylamino-4-phenylpyrrolidin-1-yl)-8-chloro-1-cyclopropyl-6-fluoro-2,4-dioxo-1,4-dihydro-2H-quinazolin-3-yl]carbamic acid tert-butyl ester (Example 8rr) using General Method E.

(ppp) 3-Amino-7-[trans-3-amino-4-(4-hydroxyphenyl)pyrrolidin-1-yl]-8-chloro-1-cyclopropyl-6-fluoro-1H-quinazoline-2,4-dione hydrochloride. (Compound 69) (mp>200° C., MS CI: m/z 446 (MH$^+$)) using 7-[trans-3-tert-butoxycarbonylamino-4-(4-hydroxyphenyl)pyrrolidin-1-yl]-8-chloro-1-cyclopropyl-6-fluoro-2,4-dioxo-1,4-dihydro-2H-quinazolin-3-yl]carbamic acid tert-butyl ester (Example 8ss) and General Method E.

(qqq) N-[1-(3-Amino-8-chloro-1-cyclopropyl-6-fluoro-2,4-dioxo-1,2,3,4-tetrahydroquinazolin-7-yl)pyrrolidin-3-ylmethyl]methanesulfonamide hydrochloride (Compound 70) (mp 109–112° C., MS CI: m/e 446 (M$^+$)) from {8-chloro-1-cyclopropyl-6-fluoro-7-[3-(methanesulfonylaminomethyl)-pyrrolidin-1-yl]-2,4-dioxo-1,4-dihydro-2H-quinazolin-3-yl}carbamic acid tert-butyl ester (Example 36) using General Method E.

(rrr) 3-Amino-7-(3-aminomethylpiperidin-1-yl)-8-chloro-1-cyclopropyl-6-fluoro-1H-quinazoline-2,4-dione hydrochloride (Compound 71) (mp 131–133° C., MS CI: m/z 382 (MH$^+$)) from {7-[3-(tert-butoxycarbonylaminomethyl)piperidin-1-yl]-8-chloro-1-cyclopropyl-6-fluoro-2,4-dioxo-1,4-dihydro-2H-quinazolin-3-yl}carbamic acid tert-butyl ester (Example 8tt) using General Method E.

(sss) 3-Amino-8-chloro-1-cyclopropyl-6-fluoro-7-[3-(isopropylamino-methyl)pyrrolidin-1-yl]-1H-quinazoline-2,4-dione hydrochloride (Compound 72) (mp 125–127° C., MS CI: m/z 410 (MH$^+$)) from (7-{3-[(tert-butoxycarbonylisopropylamino)methyl]pyrrolidin-1-yl}-8-chloro-1-cyclopropyl-6-fluoro-2,4-dioxo-1,4-dihydro-2H-quinazolin-3-yl) carbamic acid tert-butyl ester (Example 8uu) using General Method E.

(ttt) 3-Amino-7-(3-aminomethylpyrrolidin-1-yl)-6,8-dichloro-1-cyclopropyl-1H-quinazoline-2,4-dione hydrochloride (Compound 73) (mp 147–149° C., MS CI: m/z 384 (MH$^+$)) from {7-[3-(tert-butoxycarbonylaminomethyl)-pyrrolidin-1-yl]-6,8-dichloro-1-cyclopropyl-2,4-dioxo-1,4-dihydro-2H-quinazolin-3-yl}carbamic acid tert-butyl ester using General Method E.

(uuu) N-[1-(3-Amino-8-chloro-1-cyclopropyl-6-fluoro-2,4-dioxo-1,2,3,4-tetrahydroquinazolin-7-yl)pyrrolidin-3-ylmethyl]methanesulfonamide (Compound 74) (mp 109–112° C., MS CI: m/z 446 (MH$^+$)) from {8-chloro-1-cyclopropyl-6-fluoro-7-[3-(methanesulfonylaminomethyl)pyrrolidin-1-yl]-2,4-dioxo-1,4-dihydro-2H-quinazolin-3-yl}carbamic acid tert-butyl ester (Example 36) using General Method E.

(vvv) 3-Amino-7-[(R)-3-(S)-(1-aminoethyl)pyrrolidin-1-yl]-1-cyclopropyl-6-fluoro-8-methyl-1H-quinazoline-2,4-dione hydrochloride (Compound 75) (mp 194–196° C., $^1$H NMR (200 MHz, DMSO-d$_6$): δ 8.25 (bs, 3H), 7.47 (d, 1H), 4.68 (bs, 3H), 3.59–3.23 (m, 7H), 2.49 (s, 3H), 2.02–1.92 (m, 1H), 1.80–1.60 (m, 1H), 1.30 (d, 3H), 1.12–1.08 (m, 2H), 0.62–0.50 (m, 2H); MS ES: m/z 362 (MH$^+$)) from {1-[1-[(R)-3-(S)-(3-amino-1-cyclopropyl-6-fluoro-8-methyl-2,4-dioxo-1,2,3,4-tetrahydroquinazolin-7-yl)pyrrolidin-3-yl]ethyl}carbamic acid tert-butyl ester (Example 28k) using General Method A.

(www) 3-Amino-7-[(R)-3-(1-amino-1-methylethyl)pyrrolidin-1-yl]-1-cyclopropyl-6-fluoro-8-methyl-1H-quinazoline-2,4-dione hydrochloride (Compound 76) (mp 200–202° C., MS ES: m/z 376 (MH$^+$)) from {1-[(R)-1-(3-amino-1-cyclopropyl-6-fluoro-8-methyl-2,4-dioxo-1,2,3,4-tetrahydroquinazolin-7-yl)pyrrolidin-3-yl]-1-methylethyl}carbamic acid tert-butyl ester (Example 28l) using Method A.

(xxx) 3-Amino-7-[3-(1-aminoethyl)-3-methoxypyrrolidin-1-yl]-1-cyclopropyl-6-fluoro-8-methyl-1H-quinazoline-2,4-dione hydrochloride (Compound 77) (mp 190–192° C., $^1$H NMR (200 MHz, DMSO-d$_6$): δ 8.07 (bs, 3H), 7.49 (d, 1H), 3.89–3.10 (m, 121H), 2.42 (s, 3H), 2.39–2.08 (m, 2H), 1.29 (d, 3H), 1.07–1.03 (m, 2H), 0.62–0.52 (m, 2H); MS ES: m/z 392 (MH$^+$)) from {1-[1-(3-amino-1-cyclopropyl-6-fluoro-8-methyl-2,4-dioxo-1,2,3,4-tetrahydroquinazolin-7-yl)-3-methoxypyrrolidin-3-yl]ethyl}carbamic acid tert-butyl ester (Example 28m) using General Method A.

(yyy) 3-Amino-7-[3-(1-aminoethyl)-3-fluoropyrrolidin-1-yl]-1-cyclopropyl-6-fluoro-8-methoxy-1H-quinazoline-2,4-dione hydrochloride (Compound 78) (mp 190–192° C., MS ES: m/z 396 (MH$^+$)) from {1-[1-(3-amino-1-cyclopropyl-6-fluoro-8-methoxy-2,4-dioxo-1,2,3,4-tetrahydro-quinazolin-7-yl)-3-fluoropyrrolidin-3-yl]ethyl}carbamic acid tert-butyl ester (Example 28o) using General Method A.

(zzz) 3-Amino-7-(3-aminopyrrolidin-1-yl)-1-cyclopropyl-6-fluoro-5-methyl-1H-quinazoline-2,4-dione hydrochloride (Compound 79) (mp 238–240° C., MS ES: m/z 334 (MH$^+$)) from [1-(3-amino-1-cyclopropyl-6-fluoro-5-methyl-2,4-dioxo-1,2,3,4-tetrahydroquinazolin-7-yl)pyrrolidin-3-yl]carbamic acid tert-butyl ester (Example 28p) using General Method A.

(aaaa) 3-Amino-7-[(R)-3-(S)-(1-aminoethyl)pyrrolidin-1-yl]-1-cyclopropyl-6-fluoro-5-methyl-1H-quinazoline-2,4-dione hydrochloride (Compound 80) (mp 245–247° C., MS ES: m/z 362 (MH$^+$)) from {1-(S)-[1-(R)-(3-amino-1-cyclopropyl-6-fluoro-5-methyl-2,4-dioxo-1,2,3,4-tetrahydroquinazolin-7-yl)pyrrolidin-3-yl]ethyl}carbamic acid tert-butyl ester (Example 28q) using General Method A.

(bbbb) 3-Amino-7-(3-aminomethyl-3-methoxymethylpyrrolidin-1-yl)-1-cyclopropyl-6-fluoro-8-methyl-1H-quinazoline-2,4-dione hydrochloride (Compound 81) (mp 172–177° C., MS ES: m/z 392 (MH$^+$)) from [1-(3-amino-1-cyclopropyl-6-fluoro-8-methyl-2,4-dioxo-1,2,3,4-tetrahydroquinazolin-7-yl)-3-methoxymethylpyrrolidin-3-ylmethyl]carbamic acid tert-butyl ester (Example 28r) using General Method A.

(cccc) 3-Amino-7-(3-aminomethyl-3-fluoromethylpyrrolidin-1-yl)-1-cyclopropyl-6-fluoro-1H-quinazoline-2,4-dione hydrochloride (Compound 82) (mp 160–163° C., MS ES: m/z 380 (MH$^+$)) from [1-(3-amino-1-cyclopropyl-6-fluoro-8-methyl-2,4-dioxo-1,2,3,4-tetrahydroquinazolin-7-yl)-3-fluoromethylpyrrolidin-3-ylmethyl]carbamic acid tert-butyl ester (Example 28s) using General Method A.

(dddd) 3-Amino-7-(trans-3-aminomethyl-4-trifluoromethylpyrrolidin-1-yl)-1-cyclopropyl-6-fluoro-8-methoxy-1H-quinazoline-2,4-dione hydrochloride (Compound 83) (mp 205–207° C., MS ES: m/z 432 (MH$^+$)) from [trans-(3-amino-1-cyclopropyl-6-fluoro-8-methoxy-2,4-dioxo-1,2,3,4-tetrahydroquinazolin-7-yl)-4-trifluoromethyllpyrrolidin-3-ylmethyl]carbamic acid tert-butyl ester (Example 28t) using General Method A.

(eeee) 3-Amino-7-[3-(1-aminoethyl)piperidin-1-yl]-1-cyclopropyl-6-fluoro-8-methoxy-1H-quinazoline-2,4-dione hydrochloride (Compound 84) (mp 198° C., MS ES: m/z 392 (MH$^+$)) from {1-[1-(3-amino-1-cyclopropyl-6-fluoro-8-methoxy-2,4-dioxo-1,2,3,4-tetrahydroquinazolin-7-yl)piperidin-3-yl]ethyl}carbamic acid tert-butyl ester (Example 28u) using General Method A.

(ffff) 3-Amino-7-[3-(aminoethyl)piperidin-1-yl]-1-cyclopropyl-6-fluoro-8-methyl-1H-quinazoline-2,4-dione hydrochloride (Compound 85) (mp 200° C., $^1$H NMR (200 MHz, DMSO-d$_6$): δ 8.25 (bs, 3H), 7.52 (d, 1H), 6.36 (bs, 3H), 3.54–2.80 (m, 6H), 2.48 (s, 3H), 2.02–1.15 (m, 8H), 1.02–0.50 (m, 4H); MS ES: m/z 376 (MH+)) from {1-[1-(3-amino-1-cyclopropyl-6-fluoro-8-methyl-2,4-dioxo-1,2,3,4-tetrahydroquinazolin-7-yl)piperidin-3-yl]ethyl}carbamic acid tert-butyl ester Example 28v) using General Method A.

(gggg) 3-Amino-7-[4-(1-aminoethyl)-3,3-dimethylpyrrolidin-1-yl]-1-cyclopropyl-6-fluoro-8-methoxy-1H-quinazoline-2,4-dione hydrochloride (Compound 86) (mp 230° C., MS ES: m/z 406 (MH$^+$)) from {1-[1-(3-amino-1-cyclopropyl-6-fluoro-8-methoxy-2,4-dioxo-1,2,3,4-tetrahydroquinazolin-7-yl)-4,4-dimethylpyrrolidin-3-yl]ethyl}carbamic acid tert-butyl ester (Example 28w) using General Method A.

(hhhh) 3-Amino-7-[4-(1-aminoethyl)-3,3-dimethylpyrrolidin-1-yl]-1-cyclopropyl-6-fluoro-8-methyl-1H-quinazoline-2,4-dione hydrochloride. (Compound 87) (mp 246° C., MS ES: m/z 390 (MH$^+$)) from {1-[1-(3-amino-1-cyclopropyl-6-fluoro-8-methyl-2,4-dioxo-1,2,3,4-tetrahydroquinazolin-7-yl)-4,4-dimethylpyrrolidin-3-yl]ethyl}carbamic acid tert-butyl ester (Example 28x) using General Method A.

(iiii) 3-Amino-7-(3-amino-3-phenylpyrrolidin-1-yl)-1-cyclopropyl-6-fluoro-8-methyl-1H-quinazoline-2,4-dione hydrochloride (Compound 88) (mp 236° C., MS ES: m/z 410 (MH$^+$)) from [1-(3-amino-1-cyclopropyl-6-fluoro-8-methyl-2,4-dioxo-1,2,3,4-tetrahydroquinazolin-7-yl)-3-phenylpyrrolidin-3-yl]carbamic acid tert-butyl ester (Example 28z) using General Method A.

(jjjj) 3-Amino-7-[3-(1-aminoethyl)-4-methylpyrrolidin-1-yl]-1-cyclopropyl-6-fluoro-8-methyl-1H-quinazoline-2,4-dione hydrochloride (Compound 89) (mp 240° C., MS ES: m/z 376 (MH$^+$)) from {1-[1-(3-amino-1-cyclopropyl-6-fluoro-8-methyl-2,4-dioxo-1,2,3,4-tetrahydroquinazolin-7-yl)-4-methylpyrrolidin-3-yl]ethyl}carbamic acid tert-butyl ester (Example 28y) using General Method A.

(kkkk) 3-Amino-7-(3-aminomethyl-3-phenylpyrrolidin-1-yl)-1-cyclopropyl-6-fluoro-8-methyl-1H-quinazoline-2,4-dione hydrochloride (Compound 90) (mp 227–231° C., MS ES: m/z 424 (MH$^+$)) from [1-(3-amino-1-cyclopropyl-6-fluoro-8-methyl-2,4-dioxo-1,2,3,4-tetrahydroquinazolin-7-yl)3-phenylpyrrolidin-3-ylmethyl]carbamic acid tert-butyl ester (Example 28aa) using General Method A.

(llll) 3-Amino-7-(7-aminomethyl-5-azaspiro[2,4]hept-5-yl)-1-cyclopropyl-6-fluoro-8-methyl-1H-quinazoline-2,4-dione hydrochloride (Compound 91) (mp 167° C., MS ES: m/z 374 (MH$^+$)) from [5-(3-amino-1-cyclopropyl-6-fluoro-8-methyl-2,4-dioxo-1,2,3,4-tetrahydroquinazolin-7-yl)-5-azaspiro[2.4]hept-7-ylmethyl]carbamic acid tert-butyl ester (Example 28bb) using General Method A.

(mmmm) 3-Amino-7-(7-aminomethyl-5-azaspiro[2,4]hept-5-yl)-1-cyclopropyl-6-fluoro-8-methoxy-1H-quinazoline-2,4-dione hydrochloride (Compound 92) (mp 178° C., MS ES: m/z 390 (MH$^+$)) from [5-(3-amino-1-cyclopropyl-6-fluoro-8-methoxy-2,4-dioxo-1,2,3,4-tetrahydroquinazolin-7-yl)-5-azaspiro[2.4]hept-7-ylmethyl]carbamic acid tert-butyl ester (Example 28 cc) using General Method A.

(nnnn) 3-Amino-7-(3-aminomethyl-3-hydroxypyrrolidin-1-yl)-1-cyclopropyl-6-fluoro-8-methoxy-1H-quinazoline-2,4-dione hydrochloride (Compound 93) (mp 202° C., MS ES: m/z 380 (MH$^+$)) from [1-(3-amino-1-cyclopropyl-6-fluoro-8-methoxy-2,4-dioxo-1,2,3,4-tetrahydroquinazolin-7-yl)-3-hydroxypyrrolidin-3-ylmethyl]carbamic acid tert-butyl ester (Example 28dd) using General Method A.

(oooo) 3-Amino-7-(3-aminomethylpiperidin-1-yl)-1-cyclopropyl-6-fluoro-8-methyl-1H-quinazoline-2,4-dione hydrochloride (Compound 95) (mp 219–221° C., MS ES: m/z 362 (MH$^+$)) from [1-(3-amino-1-cyclopropyl-6-fluoro-8-methyl-2,4-dioxo-1,2,3,4-tetrahydroquinazolin-7-yl)piperidin-3-ylmethyl]carbamic acid tert-butyl ester (Example 28ee) using General Method A.

(pppp) 3-Amino-7-(3-amino-4-methoxypyrrolidin-1-yl)-1-cyclopropyl-6-fluoro-8-methyl-1H-quinazoline-2,4-dione hydrochloride (Compound 96) (mp>250° C., MS ES: m/z 364 (MH$^+$)) from [1-(3-amino-1-cyclopropyl-6-fluoro-8-methyl-2,4-dioxo-1,2,3,4-tetrahydroquinazolin-7-yl)-4-methoxypyrrolidin-3-yl]carbamic acid tert-butyl ester (Example 28ff) using General Method A.

(qqqq) 3-Amino-7-(3-amino-4-methoxypyrrolidin-1-yl)-1-cyclopropyl-6-fluoro-8-methoxy-1H-quinazoline-2,4-dione hydrochloride (Compound 97) (mp>250° C., MS ES: m/z 380 (MH$^+$)) from [1-(3-amino-1-cyclopropyl-6-fluoro-8-methoxy-2,4-dioxo-1,2,3,4-tetrahydroquinazolin-7-yl)-4- methoxypyrrolidin-3-yl]carbamic acid tert-butyl ester (Example 28gg) using General Method A.

(rrrr) 3-Amino-7-(3-amino-4-fluoropyrrolidin-1-yl)-1-cyclopropyl-6-fluoro-8-methoxy-1H-quinazoline-2,4-dione hydrochloride (Compound 98) (mp>250° C., MS ES: m/z 368 (MH$^+$)) from [1-(3-amino-1-cyclopropyl-6-fluoro-8-methoxy-2,4-dioxo-1,2,3,4-tetrahydroquinazolin-7-yl)-4-fluoropyrrolidin-3-yl]carbamic acid tert-butyl ester (Example 28hh) using General Method A.

(ssss) 3-Amino-7-(3-aminomethyl-3-methylpyrrolidin-1-yl)-1-cyclopropyl-6-fluoro-8-methyl-1H-quinazoline-2,4-dione hydrochloride (Compound 99) (mp 210° C., MS ES: m/z 362 (MH$^+$)) from [1-(3-amino-1-cyclopropyl-6-fluoro-8-methyl-2,4-dioxo-1,2,3,4-tetrahydroquinazolin-7-yl)-3-methylpyrrolidin-3-ylmethyl]carbamic acid tert-butyl ester (Example 28ii) using General Method A.

(tttt) 3-Amino-7-[(R)-3 (-((S)-1-aminoethyl)pyrrolidin-1-yl]-1-cyclopropyl-8-ethyl-6-fluoro-1H-quinazoline-2,4-dione hydrochloride (Compound 100) (mp 155–157° C., MS ES: m/z 376 (MH$^+$)) from {(S)-1-[(R)-1-(3-amino-1-cyclopropyl-8-ethyl-6-fluoro-2,4-dioxo-1,2,3,4-tetrahydroquinazolin-7-yl)pyrrolidin-3-yl]ethyl}carbamic acid tert-butyl ester (Example 28jj) using General Method A.

(uuuu) 1-(3-Amino-1-cyclopropyl-6-fluoro-8-methoxy-2,4-dioxo-1,2,3,4-tetrahydroquinazolin-7-yl)pyrrolidine-3-carboxylic acid trifluoroacetate (Compound 101) (mp 252° C. (decomp), MS ES: m/z 379 (MH$^+$)) from 1-(3-amino-1-cyclopropyl-6-fluoro-8-methoxy-2,4-dioxo-1,2,3,4-tetrahydroquinazolin-7-yl)pyrrolidine-3-carboxylic acid tert-butyl ester (Example 28kk) using General Method B.

(vvvv) 1-(3-Amino-1-cyclopropyl-6-fluoro-8-methyl-2,4-dioxo-1,2,3,4-tetrahydroquinazolin-7-yl)pyrrolidine-3-carboxylic acid trifluoroacetate (Compound 102) (mp 226° C. (decomp), MS ES: m/z 363 (MH+)) from 1-(3-amino-1-cyclopropyl-6-fluoro-8-methyl-2,4-dioxo-1,2,3,4-tetrahydroquinazolin-7-yl)pyrrolidine-3-carboxylic acid tert-butyl ester (Example 28ll) using General Method A.

(wwww) 3-Amino-7-(1-aminomethyl-3-azabicyclo[3.1.0]hex-3-yl)-1-cyclopropyl-6-fluoro-8-methoxy-1H-quinazoline-2,4-dione hydrochloride (Compound 103) (mp 183–185° C., MS ES: m/z 376 MH$^+$)) from [3-(3-amino-1-cyclopropyl-6-fluoro-8-methoxy-2,4-dioxo-1,2,3,4-tetrahydroquinazolin-7-yl)-3-azabicyclo[3.1.0]hex-1-ylmethyl]yl]carbamic acid tert-butyl ester (Example 28 mm) using General Method A.

(xxxx) 3-Amino-7-(1-aminomethyl-3-azabicyclo[3.1.0]hex-3-yl)-1-cyclopropyl-6-fluoro-8-methyl-1H-quinazoline-2,4-dione hydrochloride (Compound 104) (mp 189–194° C., MS ES: m/z 360 (MH$^+$)) from [3-(3-amino-1-cyclopropyl-6-fluoro-8-methyl-2,4-dioxo-1,2,3,4-tetrahydroquinazolin-7-yl)-3-azabicyclo[3.1.0]hex-1-ylmethyl]yl]carbamic acid tert-butyl ester (Example 28nn) using General Method A.

(yyyy) 3-Amino-7-[(S)-3-((R)-1-aminoethyl)pyrrolidin-1-yl]-1-cyclopropyl-6-fluoro-8-methoxy-1H-quinazoline-2,4-dione hydrochloride (Compound 105) (mp 175–179° C., MS ES: m/z 378 (MH$^+$)) from {(R)-1-[(S)-1-(3-amino-1-cyclopropyl-6-fluoro-8-methoxy-2,4-dioxo-1,2,3,4-tetrahydroquinazolin-7-yl)pyrrolidin-3-yl]ethyl}carbamic acid tert-butyl ester (Example 28oo) using General Method A.

(zzzz) 3-Amino-7-[(S)-3-((R)-1-aminoethyl)pyrrolidin-1-yl]-1-cyclopropyl-6-fluoro-8-methyl-1H-quinazoline-2,4-dione hydrochloride (Compound 106) (mp 172–176° C., MS (ES: m/z 362 (MH$^+$)) from {(R)-1-[(S)-1-(3-amino-1-cyclopropyl-6-fluoro-8-methoxy-2,4-dioxo-1,2,3,4-tetrahydroquinazolin-7-yl)pyrrolidin-3-yl]ethyl}carbamic acid tert-butyl ester (Example 28 pp) using General Method A.

(aaaaa) 3-Amino-1-cyclopropyl-6-fluoro-8-methyl-7-(octahydropyrrolo [3,4-b]pyridin-6-yl)-1H-quinazoline-2,4-dione hydrochloride (Compound 107) (mp 220° C., MS ES: m/z 374 (MH$^+$)) from 6-(3-amino-1-cyclopropyl-6-fluoro-8-methyl-2,4-dioxo-1,2,3,4-tetrahydroquinazolin-7-yl)octahydropyrrolo[3,4-b]pyridine-1-carboxylic acid tert-butyl ester (Example 28qq) using General Method A.

(bbbbb) 3-Amino-7-(trans-3-aminomethyl-4-methylpyrrolidin-1-yl)-8-chloro-1-cyclopropyl-6-fluoro-1H-quinazoline-2,4-dione hydrochloride (Compound 108) (mp 215–217° C., MS ES: m/z 382 (MH+)) from {7-[trans-3-(tert-butoxycarbonyl-aminomethyl)-4-methylpyrrolidin-1-yl]-8-chloro-1-cyclopropyl-6-fluoro-2,4-dioxo-1,4-dihydro-2H-quinazolin-3-yl}carbamic acid tert-butyl ester (Compound 109) (Example 8xx) using General Method A.

(ccccc) 3-Amino-7-(trans-3-aminomethyl-4-methylpyrrolidin-1-yl)-1-cyclopropyl-6-fluoro-8-methoxy-1H-quinazoline-2,4-dione hydrochloride (Compound 110) (mp 189° C., MS ES: m/z 378 (MH+)) from [trans-1-(3-amino-1-cyclopropyl-6-fluoro-8-methoxy-2,4-dioxo-1,2,3,4-tetrahydroquinazolin-7-yl)-4-methylpyrrolidin-3-ylmethyl]carbamic acid tert-butyl ester (Example 28rr) using General Method A.

(ddddd) 3-Amino-7-(trans-3-aminomethyl-4-methylpyrrolidin-1-yl)-1-cyclopropyl-6-fluoro-8-methyl-1H-quinazoline-2,4-dione hydrochloride (Compound 111) (mp 220° C., MS ES: m/z 362 (MH$^+$)) from [trans-1-(3-amino-1-cyclopropyl-6-fluoro-8-methyl-2,4-dioxo-1,2,3,4-tetrahydroquinazolin-7-yl)-4-methylpyrrolidin-3-ylmethyl]carbamic acid tert-butyl ester (Example 28ss) using General Method A.

(eeeee) 3-Amino-7-(trans-3-amino-4-methylpyrrolidin-1-yl)-1-cyclopropyl-6-fluoro-8-methoxy-1H-quinazoline-2,4-dione hydrochloride (Compound 112) (mp 209° C., MS ES: m/z 364 (MH$^+$)) from [trans-1-(3-amino-1-cyclopropyl-6-fluoro-8-methoxy-2,4-dioxo-1,2,3,4-tetrahydroquinazolin-7-yl)-4-methylpyrrolidin-3-yl]carbamic acid tert-butyl ester (Example 28tt) using General Method A.

(fffff) 3-Amino-7-(3-aminomethylmorpholin-1-yl)-1-cyclopropyl-6-fluoro-8-methoxy-1H-quinazoline-2,4-dione hydrochloride (Compound 113) (mp 195° C., MS ES: m/z 380 (MH$^+$)) from [4-(3-amino-1-cyclopropyl-6-fluoro-8-methoxy-2,4-dioxo-1,2,3,4-tetrahydroquinazolin-7-yl)morpholin-2-ylmethyl]carbamic acid tert-butyl ester (Example 28uu) using General Method A.

(ggggg) 3-Amino-7-(3-aminomethylpiperidin-1-yl)-1-cyclopropyl-6-fluoro-8-methoxy-1H-quinazoline-2,4-dione hydrochloride (Compound 114) (mp 201° C., MS ES: m/z 378 (MH$^+$)) from [1-(3-amino-1-cyclopropyl-6-fluoro-8-methoxy-2,4-dioxo-1,2,3,4-tetrahydroquinazolin-7-yl)piperidin-3-ylmethyl]-carbamic acid tert-butyl ester (Example 28vv) using General Method A.

(hhhhh) 3-Amino-7-[3-(1-aminoethyl)-4-methylpyrrolidin-1-yl]-1-cyclopropyl-6-fluoro-8-methoxy-1H-quinazoline-2,4-dione hydrochloride (Compound 115) (mp 204.5° C., MS ES: m/z 392 (MH$^+$)) from {1-[1-(3-amino-1-cyclopropyl-6-fluoro-8-methoxy-2,4-dioxo-1,2,3,4-tetrahydroquinazolin-7-yl)-4-methylpyrrolidin-3-yl]ethyl}carbamic acid tert-butyl ester (Example 28ww) using General Method A.

(iiiii) 3-Amino-7-(3-amino-3-phenylpyrrolidin-1-yl)-8-chloro-1-cyclopropyl-6-fluoro-1H-quinazoline-2,4-dione hydrochloride (Compound 116) (mp 198–200° C., MS ES: m/z 430 (MH$^+$)) from [7-(3-tert-butoxycarbonylamino-3-phenylpyrrolidin-1-yl)-8-chloro-1-cyclopropyl-6-fluoro-2,4-dioxo-1,4-dihydro-2H-quinazolin-3-yl]carbamic acid tert-butyl ester (Example 6ww) using General Method A.

(jjjj) 3-Amino-7-(3-amino-3-methylpyrrolidin-1-yl)-1-cyclopropyl-6-fluoro-8-methyl-1H-quinazoline-2,4-dione hydrochloride (Compound 117) (mp 237–240° C., MS ES: m/z 348 (MH$^+$)) from [1-(1-cyclopropyl-6-fluoro-8-methyl-2,4-dioxo-1,2,3,4-tetrahydroquinazolin-7-yl)-3-methylpyrrolidin-3-yl]]carbamic acid tert-butyl ester (Example 28xx) using General Method A.

(kkkkk) 3-Amino-1-cyclopropyl-6-fluoro-8-methyl-7-pyrrolidin-1yl-1H-quinazoline-2,4-dione hydrochloride (Compound 118) (mp 178–180° C., MS ES: m/z 319 (MH$^+$)) from 3-amino-1-cyclopropyl-6-fluoro-8-methyl-7-pyrrolidin-1-yl-1H-quinazoline-2,4-dione (Example 28yy) using General Method A.

(lllll) 3-Amino-1-cyclopropyl-6-fluoro-8-methoxy-7-pyrrolidin-1yl-1H-quinazoline-2,4-dione hydrochloride (Compound 119) (mp 92–94° C., MS ES: m/z 335 (MH$^+$)) from 3-amino-1-cyclopropyl-6-fluoro-8-methoxy-7-pyrrolidin-1-yl-1H-quinazoline-2,4-dione (Example 28zz) using General Method A.

(mmmmm) 3-Amino-1-cyclopropyl-6-fluoro-7-[3-(1-hydroxy-1-methylethyl)pyrrolidin-1-yl]-8-methyl-1H-quinazoline-2,4-dione hydrochloride (Compound 120) (mp 116–120° C., MS ES: m/z 377 (MH$^+$)) from 3-amino-1-cyclopropyl-6-fluoro-7-[3-(1-hydroxy-1-methylethyl) pyrrolidin-1-yl]-8-methyl-1H-quinazoline-2,4-dione (Example 28aaa) using General Method E.

(nnnnn) 3-Amino-1-cyclopropyl-6-fluoro-7-[3-(1-hydroxy-1-methylethyl) pyrrolidin-1-yl]-8-methoxy-1H-quinazoline-2,4-dione hydrochloride (Compound 121) (mp 134° C. (decomp), MS ES: m/z 393 (MH$^+$)) from 3-amino-1-cyclopropyl-6-fluoro-7-[3-(1-hydroxy-1-methylethyl) pyrrolidin-1-yl]-8-methoxy-1H-quinazoline-2,4-dione (Example 28bbb) using General Method E.

(ooooo) 3-Amino-1-cyclopropyl-6-fluoro-5-methyl-7-[(R)-3-((S)-1-methylaminoethyl)pyrrolidin-1-yl]-1H-quinazoline-2,4-dione hydrochloride (Compound 122) (mp 182–185° C., MS ES: m/z 376 (MH$^+$)) from {(S)-1-[(R)-3-amino-1-cyclopropyl-6-fluoro-5-methyl-7-[(R)-3-((S)-1-methylaminoethyl)pyrrolidin-1-yl]-1H-quinazoline-2,4-dione (Example 28 ccc) using General Method E.

(ppppp) (S)-1-[(R)-1-(3-Amino-1-cyclopropyl-7-[3-(1-ethylaminoethyl)pyrrolidin-1-yl)-6-fluoro-8-methoxy-1H-quinazoline-2,4-dione hydrochloride (Compound 123) (mp 185–190° C., MS ES: m/z 406 (MH+)) from (S)-1-[(R)-1-(3-amino-1-cyclopropyl-7-[3-(1-ethylaminoethyl)pyrrolidin-1-yl)-6-fluoro-8-methoxy-1H-quinazoline-2,4-dione (Example 28ddd) using General Method E.

(qqqqq) 3-Amino-1-cyclopropyl-7-[(R)-3-((S)-1-ethylaminoethyl)pyrrolidin-1-yl]-6-fluoro-8-methyl-1H-quinazoline-2,4-dione hydrochloride (Compound 124) (mp 210–215° C., MS ES: m/z 390 (MH$^+$)) from 3-amino-1-cyclopropyl-7-[(R)-3-((S)-1-ethylaminoethyl)pyrrolidin-1-yl]-6-fluoro-8-methyl-1H-quinazoline-2,4-dione (Example 28eee) using General Method E.

(rrrrr) 3-Amino-7-(6-amino-1-methyl-3-azabicyclo[3.2.0]hept-3-yl)-1-cyclopropyl-6-fluoro-8-methoxy-1H-quinazoline-2,4-dione hydrochloride (Compound 125) (mp>190° C., MS ES: m/z 390 (MH$^+$)) from 3-amino-7-(6-amino-1-methyl-3-azabicyclo[3.2.0]hept-3-yl)-1-cyclopropyl-6-fluoro-8-methoxy-1H-quinazoline-2,4-dione (Example 28fff) using General Method E.

(sssss) 3-Amino-7-(4-aminomethylpiperidin-1-yl)-1-cyclopropyl-6-fluoro-8-methoxy-1H-quinazoline-2,4-dione hydrochloride (Compound 126) (mp 201° C., MS ES: m/z 378 (MH+)) from 3-amino-7-(4-aminomethylpiperidin-1-yl)-1-cyclopropyl-6-fluoro-8-methoxy-1H-quinazoline-2,4-dione (Example 28hhh) using General Method E.

(ttttt) 3-Amino-7-(3-aminomethylazetidin-1-yl)-1-cyclopropyl-6-fluoro-8-methoxy-1H-quinazoline-2,4-dione hydrochloride (Compound 127) (MS ES: m/z 350 (MH$^+$)) from 3-amino-7-(3-aminomethylazetidin-1-yl)-1-cyclopropyl-6-fluoro-8-methoxy-1H-quinazoline-2,4-dione (Example 28ggg) using General Method E.

(uuuuu) cis-3-Amino-7-(3-aminomethyl-4-fluoropyrrolidin-1-yl)-1-cyclopropyl-6-fluoro-8-methoxy-1H-quinazoline-2,4-dione hydrochloride (Compound 128) (mp 169–179° C., MS ES: m/z 382 (MH+)) from cis-[1-(3-amino-1-cyclopropyl-6-fluoro-8-methoxy-2,4-dioxo-1,2,3,4-tetrahydroquinazolin-7-yl)-4-fluoropyrrolidin-3-ylmethyl]carbamic acid tert-butyl ester (Example 28iii) using General Method A.

(vvvvv) trans-3-Amino-7-(3-aminomethyl-4-fluoropyrrolidin-1-yl)-1-cyclopropyl-6-fluoro-8-methoxy-1H-quinazoline-2,4-dione hydrochloride (Compound 129) (mp 144–147° C., MS ES: m/z 382 (MH$^+$)) from trans-[1-(3-amino-1-cyclopropyl-6-fluoro-8-methoxy-2,4-dioxo-1,2,3,4-tetrahydroquinazolin-7-yl)-4-fluoropyrrolidin-3-ylmethyl]carbamic acid tert-butyl ester (Example 28jjj) using General Method A.

(wwwww) 3-Amino-7-(1-amino-5-azaspiro[2.4]hept-5-yl)-1-cyclopropyl-6-fluoro-8-methoxy-1H-quinazoline-2,4-dione hydrochloride (Compound 130) (mp>250° C., MS APCI: m/z 376 (MH+)) from [1-(3-amino-1-cyclopropyl-6-fluoro-8-methoxy-2,4-dioxo-1,2,3,4-tetrahydroquinazolin-7-yl)-(1-amino-5-azaspiro[2.4]hept-5-yl)]carbamic acid tert-butyl ester (Example 28kkk) using General Method A.

(xxxxx) 3-Amino-7-(3a-aminomethyloctahydroisoindol-2-yl)-1-cyclopropyl-6-fluoro-8-methoxy-1H-quinazoline-2,4-dione hydrochloride (Compound 131) (mp>250° C., MS APCI: m/z 418 (MH+)) from 1-(3-amino-1-cyclopropyl-6-fluoro-8-methoxy-2,4-dioxo-1,2,3,4-tetrahydroquinazolin-7-yl)-3-aminomethyloctahydroisoindol-2-yl]carbamic acid tert-butyl ester (Example 28lll) using General Method A (yyyyy) 3-Amino-7-(3a-aminomethyloctahydroisoindol-2-yl)-1-cyclopropyl-6-fluoro-8-methyl-1H-quinazoline-2,4-dione hydrochloride (Compound 132) (mp>250° C., MS APCI: m/z 402 (MH$^+$)) from 1-(3-amino-1-cyclopropyl-6-fluoro-8-methyl-2,4-dioxo-1,2,3,4-tetrahydroquinazolin-7-yl)-3-aminomethyloctahydroisoindol-2-yl]carbamic acid tert-butyl ester (Example 28 mmm) using General Method A (zzzzz) 3-Amino-7-[(R)-3-((S)-1-aminoethylpyrrolidin-1-yl]-1-cyclopropyl-6-fluoro-8-methoxy-1H-quinazoline-2,4-dione hydrochloride (Compound 133) (mp 228–230° C., MS APCI: m/z 378 (MH$^+$)) from {(S)-1-[(R)-1-(3-amino-1-cyclopropyl-6-fluoro-8-methoxy-2,4-dioxo-1,2,3,4-tetrahydroquinazolin-7-yl)pyrrolidin-3-yl]ethyl}carbamic acid tert-butyl ester (Example 28nnn) using General Method E (aaaaaa) 3-Amino-7-(6-amino-3-azabicyclo[3.1.0]hex-3-yl)-1-cyclopropyl-6-fluoro-8-methyl-1H-quinazoline-2,4-dione hydrochloride (Compound 134) (mp 180–182° C., MS ES: m/z 346 (MH$^+$)) from [3-(3-amino-1-cyclopropyl-6-fluoro-8-methyl-2,4-dioxo-1,2,3,4-tetrahydroquinazolin-7-yl)-3-azabicyclo[3.1.0]hex-6-yl]carbamic acid tert-butyl ester (Example 28n) using General Method A.

EXAMPLE 10

Synthesis of {7-[(S)-3-(tert-butoxycarbonylamino) pyrolidin-1-yl]-5-benzylamino-1-cyclopropyl-6,8-difluoro-1,4-dihydro-2,4-dioxo-2H-quinazolin-3-yl}carbamic acid tert-butyl ester

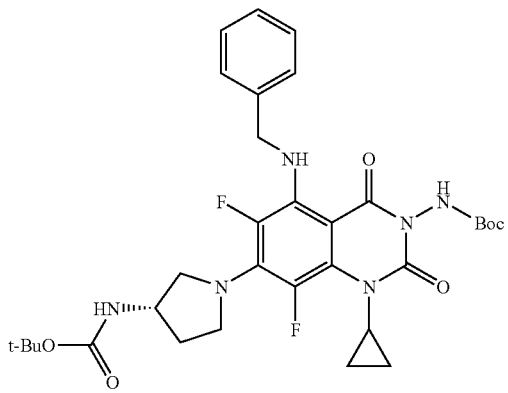

A solution of {7-[(S)-3-(tert-butoxycarbonylamino)pyrrolidin-1-yl]-1-cyclopropyl-1,4-dihydro-2,4-dioxo-5,6,8-trifluoro-2H-quinazolin-3-yl}carbamic acid tert-butyl ester from Example 8 (0.51 g, 0.914 mmol), triethylamine (1.3 mL, 9.3 mmol), and benzylamine (0.50 mL, 4.6 mmol) in dimethyl sulfoxide (7.5 mL) is heated at 100° C. for 16 hours in a sealed glass tube. The mixture is concentrated under high vacuum and the residue purified by column chromatography (1:2 ethyl acetate/hexanes) to afford {7-[(S)-3-(tert-butoxycarbonylamino)pyrrolidin-1-yl]-5-benzylamino-1-cyclopropyl-6,8-difluoro-1,4-dihydro-2,4-dioxo-2H-quinazolin-3-yl}carbamic acid tert-butyl ester as a solid (0.51 g). $^1$NMR (CDCl$_3$): δ 8.50 (bs, 1H), 7.37–7.18 (m, 5H), 6.56 (bs, 1H), 4.76–4.62 (bd, 1H), 4.59–4.48 (m, 2H), 4.34–4.18 (m, 1H), 3.93–3.49 (m, 3H), 3.48–3.20 (m, 2H), 2.24–2.04 (m, 1H), 1.96–1.74 (m, 1H), 1.49 (s, 9H), 1.46 (s, 9H), 1.13–1.00 (m, 2H), 0.75–0.61 (m, 2H).

EXAMPLE 11

Synthesis of {7-[(S)-3-(tert-Butoxycarbonyl-N-methylamino)pyrrolidin-1-yl]-8-chloro-1-cyclopropyl-6-fluoro-2,4-dioxo-1,4-dihydro-2H-quinazolin-3-yl}-methylcarbamic acid tert-butyl ester

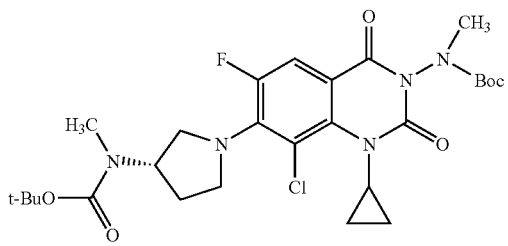

To a solution of {7-[(S)-3-(tert-butoxycarbonyl-N-methylamino)-pyrrolidin-1-yl]-8-chloro-1-cyclopropyl-6-fluoro-2,4-dioxo-1,4-dihydro-2H-quinazolin-3-yl}carbamic acid tert-butyl ester from Example 8 (0.238 g, 0.421 mmol) in N,N-dimethylformamide (5 mL) at −78° C. under nitrogen atmosphere is added sodium hydride (60% dispersion in mineral oil, 0.025 g, 0.631 mmol). After 30 minutes, iodomethane (0.052 mL, 0.842 mmol) is added, and the reaction mixture is warmed to room temperature. After 1 hour, the reaction mixture is diluted with ethyl acetate and washed with saturated ammonium chloride solution, water, and brine. The organic layer is dried over MgSO$_4$, filtered, and the filtrate concentrated. The resulting residue is purified by flash column chromatography (1:1 ethyl acetate/hexanes) to afford the title compound (0.118 g). $^1$H NMR (CDCl$_3$): δ 7.63 (dd, 1H), 4.78 (bs, 1H), 3.87–3.45 (m, 6H), 2.62–2.44 (m, 6H), 2.31–2.12 (m, 2H), 1.49–1.47 (m, 18H), 1.23–1.07 (m, 2H), 0.75–0.53 (m, 2H). MS CI: m/z 582 (MH$^+$).

EXAMPLE 12

Synthesis of {5-Amino-7-[(S)-3-(tert-butoxycarbonylamino)pyrrolidin-1-yl]-1-cyclopropyl-6,8-difluoro-1,4-dihydro-2,4-dioxo-2H-quinazolin-3-yl}carbamic acid tert-butyl ester

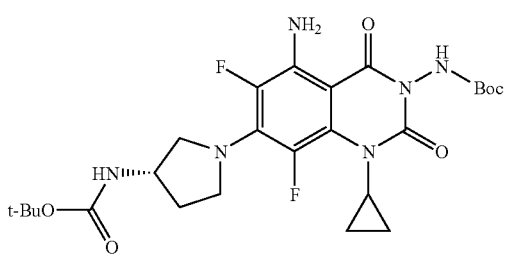

{7-[(S)-3-(tert-Butoxycarbonylamino)pyrrolidin-1-yl]-5-benzylamino-1-cyclopropyl-6,8-difluoro-1,4-dihydro-2,4-dioxo-2H-quinazolin-3-yl}carbamic acid tert-butyl ester from Example 10 (0.435 g, 0.676 mmol) in tetrahydrofuran (20 mL) is hydrogenated at room temperature and atmospheric pressure over 20% palladium hydroxide on carbon (0.114 g) for 27 hours. The mixture is filtered through Celite, the solid is washed with chloroform, and the combined filtrates concentrated under vacuum. Purification by column chromatography (2:3 ethyl acetate/hexanes) gives {5-amino-7-[(S)-3-(tert-butoxycarbonylamino)pyrrolidin-1-yl]-1-cyclopropyl-6,8-difluoro-1,4-dihydro-2,4-dioxo-2H-quinazolin-3-yl}-carbamic acid tert-butyl ester as a solid (0.284 g). $^1$H NMR (CDCl$_3$): δ 6.61 (bs, 1H), 5.94 (bs, 2H), 4.82–4.69 (bd, 1H), 4.40–4.21 (m, 1H), 4.00–3.59 (m, 3H), 3.55–3.41 (m, 1H), 3.35–3.21 (m, 1H), 2.32–2.08 (m, 1H), 2.01–1.80 (m, 1H), 1.50 (s, 9H), 1.46 (s, 9H), 1.17–1.01 (m, 2H), 0.77–0.63 (m, 2H).

EXAMPLE 13

Synthesis of 8-Chloro-1-cyclopropyl-6-fluoro-3-methylamino-7-[(S)-3-methylaminopyrrolidin-1-yl]-1H-quinazolin-2,4-dione

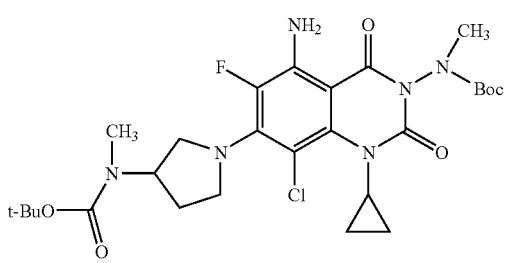

Hydrogen chloride gas is bubbled into diethyl ether (30 mL) for 15 minutes. The resulting solution is then cooled to 0° C. and added to {7-[(S)-3-(tert-butoxycarbonylmethylamino)pyrrolidin-1-yl]-8-chloro-1-cyclopropyl-6-fluoro-2,4-dioxo-1,4-dihydro-2H-quinazolin-3-yl}methyl-carbamic acid tert-butyl ester from Example 11 (0.118 g, 0.202 mmol). The reaction mixture is slowly warmed to room temperature. After 30 hours, the precipitate is filtered, washed with ether and hexanes, and dried under vacuum to afford the hydrochloride salt of the title compound as a solid (0.0632 g, mp 77–79° C.). MS CI: m/z 382 (MH+).

EXAMPLE 14

Synthesis of (8-Chloro-1-cyclopropyl-6,7-difluoro-2,4-dioxo-1,4-dihydro-2H-quinazolin-3-yl)carbamic acid tert-butyl ester

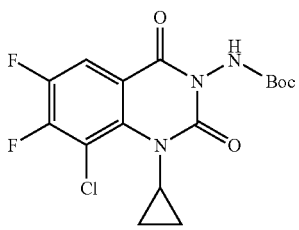

To a solution of (3-chloro-2-cyclopropylamino-4,5-difluorobenzoyl)-hydrazinecarboxylic acid tert-butyl ester (Example 6c) (1.93 g, 5.34 mmol) in tetrahydrofuran (50 mL) is added potassium carbonate (3.69 g, 26.7 mol) and triphosgene (2.06 g, 6.95 mmol). The reaction mixture is refluxed for 90 minutes, cooled to room temperature, and diluted with ethyl acetate. The organic layer is washed with water and brine, then dried over MgSO4 and filtered. The filtrate is concentrated under vacuum and purified via flash column chromatography (1:2 ethyl acetate/hexanes) to afford the title compound (1.27 g). MS EI: m/z 386 (M+).

EXAMPLE 15

Synthesis of 2-Amino-4,5-difluorobenzoic acid, 2,2-dibenzylhydrazide

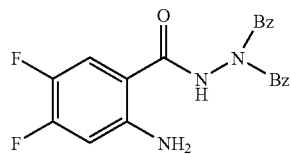

4,5-Difluoroanthranilic acid (4.73 g, 27.3 mmol) and N,N-dibenzylhydrazine (8.69 g, 42 mmol) are combined in 200 mL of methylene chloride. 1-ethyl-3-(3-dimethylaminopropyl)carbodiimide hydrochloride (EDAC) (7.85 g, 41 mmol) is then added to this solution, and the mixture is stirred for 18 hours at 25° C., The solution is washed with saturated NaHCO3, brine, and dried over magnesium sulfate. The solution is concentrated to give 15.8 g of a dark oil and purified via chromatography (SiO2, CHCl3) to give 3.4 g of the title compound as a solid. MS CI: m/z 368 (MH+).

EXAMPLE 16

Synthesis of 3-Dibenzylamino-6,7-difluoro-1H-quinazoline-2,4-dione

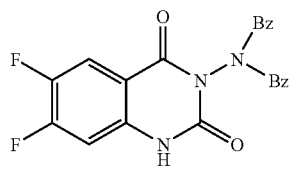

2-Amino-4,5-difluorobenzoic acid, 2,2-dibenzylhydrazide (Example 15) (0.81 g, 2.2 mmol) and triphosgene (0.33 g, 1.1 mmol) are combined in 100 mL of methylene chloride and stirred at 25° C. for 20 hours. The solution is poured into 200 mL of saturated NaHCO3, the layers are separated, and the aqueous layer is washed three times with ethyl acetate. The combined organic layers are dried over magnesium sulfate and then concentrated to give 0.86 g of the title compound as a solid. MS CI: m/z 394 (MH+).

EXAMPLE 17

Synthesis of 3-Dibenzylamino-6,7-difluoro-1-substituted-1H-quinazoline-2,4-dione (a) 3-Dibenzylamino-6,7-difluoro-1-cyclopropylmethyl-1H-quinazoline 2,4-dione

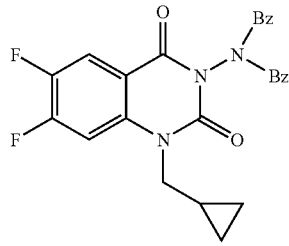

A solution of 3-dibenzylamino-6,7-difluoro-1H-quinazoline-2,4-dione (Example 16) (0.43 g, 1.1 mmol) in 10 mL of N,N-dimethylformamide is added to a suspension of sodium hydride (0.05 g, 1.3 mmol) in 10 mL of N,N-dimethylformamide and stirred for 30 minutes. Bromomethylcyclopropane (0.16 mL, 1.6 mmol) is added, and the mixture is stirred at 25° C. for 18 hours. The reaction is quenched with 1 mL of water and concentrated in vacuo. The residue is dissolved in chloroform, washed with water, brine, and dried over magnesium sulfate. The solution is concentrated and purified via chromatography (SiO2, CHCl3) to give 0.33 g of the title compound as a solid. MS CI: m/z 448 (MH+).

(b) 3-Dibenzylamino-6,7-difluoro-1-ethyl-1H-quinazoline-2,4-dione

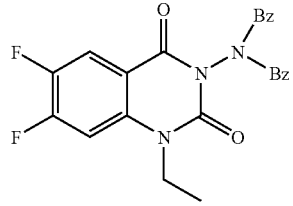

A solution of 3-dibenzylamino-6,7-difluoro-1H-quinazoline-2,4-dione (Example 16) (0.43 g, 1.1 mmol) in 10 mL of N,N-dimethylformamide is added to a suspension of sodium hydride (0.05 g, 1.3 mmol) in 10 mL of N,N-dimethylformamide and stirred for 30 minutes. Ethyl iodide (0.13 mL, 1.6 mmol) is added, and the mixture is stirred at 25° C. for 18 hours. The reaction is quenched with 1 mL of water and concentrated in vacuo. The residue is dissolved in chloroform, washed with water, brine, and dried over magnesium sulfate. The solution is concentrated and purified via chromatography (SiO$_2$, CHCl$_3$) to give 0.34 g of the title compound as a solid, mp 133–135° C., MS CI, m/z 422 (MH$^+$).

EXAMPLE 18

Chlorination

General Chlorination Method

To a solution of a benzoylhydrazinecarboxylic acid tert-butyl ester (Example 7) in acetic acid (5 mL) is added N-chlorosuccinimide (1.2 eq.). After 1 hour, the reaction mixture is diluted with ethyl acetate and washed with saturated NaHCO$_3$, water, and brine. The organic layer is dried over MgSO$_4$ and filtered. The filtrate is concentrated under vacuum and purified via flash column chromatography (ethyl acetate/hexanes) to afford the corresponding chloro-benzoylhydrazinecarboxylic acid tert-butyl ester.

The following compounds are synthesized according to the General Chlorination Method above:

(a) N'-{4-[3-(tert-Butoxycarbonylaminomethyl)pyrrolidin-1-yl]-3-chloro-2-cyclopropylamino-5-fluorobenzoyl}hydrazinecarboxylic acid tert-butyl ester (MS CI: m/z 542 (MH$^+$)) from N'-{4-[3-(tert-butoxycarbonylamino-methyl)pyrrolidin-1-yl]-2-cyclopropylamino-5-fluorobenzoyl}-hydrazinecarboxylic acid tert-butyl ester (Example 7a).

(b). N'-4-[4-(tert-Butoxycarbonylpiperazin-1-yl)-3-chloro-2-cyclopropylamino-5-fluorobenzoyl]hydrazinecarboxylic acid tert-butyl ester (MS CI: m/z 528 (MH$^+$)) from N'-4-[4-(tert-butoxycarbonylpiperazin-1-yl)-2-cyclopropylamino-5-fluorobenzoyl]hydrazinecarboxylic acid tert-butyl ester (Example 7b).

(c) N'-{4-[3-(tert-Butoxycarbonylaminomethyl)-3-methylpyrrolidin-1-yl]-3-chloro-2-cyclopropylamino-5-fluorobenzoyl}hydrazinecarboxylic acid tert-butyl ester (MS CI: m/z 556 (MH$^+$)) from N'-{4-[3-(tert-butoxycarbonylaminomethyl)-3-methylpyrrolidin-1-yl]-2-cyclopropylamino-5-fluorobenzoyl}hydrazinecarboxylic acid tert-butyl ester (Example 7c).

(d) N'-[4-(6-tert-Butoxycarbonylamino-3-azabicyclo[3.1.0]hex-3-yl)-3-chloro-2-cyclopropylamino-5-fluorobenzoyl]hydrazinecarboxylic acid tert-butyl ester (MS CI: m/z 540 (MH$^+$)) from N'-[4-(6-tert-butoxycarbonylamino-3-azabicyclo[3.1.0]hex-3-yl)-2-cyclopropylamino-5-fluorobenzoyl]-hydrazinecarboxylic acid tert-butyl ester (Example 7d).

(e) N'-{4-[(S)-3-(tert-Butoxycarbonyl-N-methylamino)pyrrolidin-1-yl]-3-chloro-2-cyclopropylamino-5-fluorobenzoyl}hydrazinecarboxylic acid tert-butyl ester (MS CI: m/z 542 (MH$^+$)) from N'-{4-[(S)-3-(tert-butoxycarbonyl-N-methylamino)pyrrolidin-1-yl]-2-cyclopropylamino-5-fluorobenzoyl}-hydrazinecarboxylic acid tert-butyl ester (Example 7e).

(f) N'-{4-[(S)-3-(tert-Butoxycarbonyl-N-amino)pyrrolidin-1-yl]-3-chloro-2-(2,4-difluoroanilino)-5-fluorobenzoyl}hydrazinecarboxylic acid tert-butyl ester (CDCl$_3$): δ 9.70 (bs, 1H), 7.76 (d, 1H), 6.93–6.82 (m, 1H), 6.70–6.62 (m, 2H), 6.48–6.34 (m, 2H), 4.91–4.87 (bs, 1H), 4.29–4.20 (m, 1H), 3.78–3.60 (m, 2H), 3.50–3.28 (m, 2H), 2.33–2.20 (m, 1H), 1.94–1.66 (m, 1H), 1.44 (s, 9H), 1.42 (s, 9H), (MS CI: m/z 601 (MH$^+$)) from N'-{4-[(S)-3-(tert-butoxycarbonylamino)pyrrolidin-1-yl]-2-(2,4-difluoroanilino)-5-fluorobenzoyl}-hydrazinecarboxylic acid tert-butyl ester (Example 7f).

(g) N'-[4-((S)-7-tert-Butoxycarbonylamino-5-azaspiro[2.4]hept-5-yl)-3-chloro-2-cyclopropylamino-5-fluorobenzoyl]hydrazinecarboxylic acid tert-butyl ester (MS CI: 554 (MH$^+$)) from N'-[(S)-4-(7-tert-butoxycarbonylamino-5-azaspiro[2.4]hept-5-yl)-2-cyclopropylamino-5-fluorobenzoyl]hydrazinecarboxylic acid tert-butyl ester (Example 7k).

(h) N'-[4-(Pyrrolidin-1-yl)-3-chloro-2-cyclopropylamino-5-fluoro-benzoyl]hydrazinecarboxylic tert-butyl ester (MS CI: m/z 413 (MH$^+$)) from N'-[4-(pyrrolidin-1-yl)-2-cyclopropylamino-5-fluorobenzoyl]hydrazinecarboxylic acid tert-butyl ester (Example 7m).

(i) N'-{4-[3-(tert-Butoxycarbonylamino)pyrrolidin-1-yl)-3-chloro-5-fluoro-2-isopropylaminobenzoyl}hydrazinecarboxylic acid tert-butyl ester (MS: m/z 530 (MH$^+$)) from N'-{4-[3-(tert-butoxycarbonylamino)pyrrolidin-1-yl]-5-fluoro-2-isopropylaminobenzoyl}hydrazine carboxylic acid tert-butyl ester (Example 7 n).

(j) N'-{4-[3-(tert-Butoxycarbonylamino)pyrrolidin-1-yl]-2-cyclobutylamino-3-chloro-5-fluorobenzoyl}hydrazinecarboxylic acid tert-butyl ester (MS EI: m/e 542 (MH$^+$)) from N'-{4-[3-(tert-butoxycarbonylamino)-pyrrolidin-1-yl]-2-cyclobutylamino-5-fluorobenzoyl}hydrazinecarboxylic acid tert-butyl ester (Example 7q).

(k) N'-(1-{4-[3-(tert-Butoxycarbonylamino-methyl)piperidin-1-yl]-3-chloro-2-cyclopropylamino-5-fluorophenyl}methanoyl)hydrazinecarboxylic acid tert-butyl ester (MS CI: m/e 556 (MH$^+$)) from N'-(1-{4-[3-(tert-butoxycarbonylaminomethyl)piperidin-1-yl]-2-cyclopropylamino-5-fluoro-phenyl}methanoyl)hydrazinecarboxylic acid tert-butyl ester (Example 7z).

(l) N'-[1-(4-{3-[(tert-Butoxycarbonylisopropylamino)methyl]-pyrrolidin-1-yl}-3-chloro-2-cyclopropylamino-5-fluorophenyl)methanoyl]-hydrazine-carboxylic acid tert-butyl ester (MS CI: m/e 584 (MH$^+$)) from N'-[1-(4-{3-[(tert-butoxycarbonylisopropylamino)methyl]pyrrolidin-1-yl}-2-cyclopropylamino-5-fluorophenyl)methanoyl]hydrazinecarboxylic acid tert-butyl ester (Example 7aa).

(m) N'-(1-{4-[3-(tert-Butoxycarbonylaminomethyl)pyrrolidin-1-yl]-3,5-dichloro-2-cyclopropylaminophenyl}methanoyl)hydrazinecarboxylic acid tert-butyl ester (MS CI: m/e 558 (MH$^+$)) from N'-(1-{4-[3-(tert-butoxycarbonylamino-methyl)pyrrolidin-1-yl]-5-chloro-2-cyclopropylaminophenyl}methanoyl)-hydrazinecarboxylic acid tert-butyl ester (Example 7bb).

EXAMPLE 19

Chlorination of Substituted Benzoic Acids (a) Synthesis of 3-Chloro-4,5-difluoroanthranilic acid

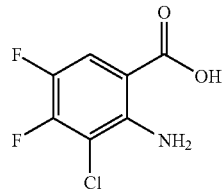

To a solution of 4,5-difluoroanthranilic acid (2.45 g, 14.2 mmol) in dichloromethane (25 mL) is added acetic acid (10 mL) and hypochlorous acid tert-butyl ester (1.75 mL, 15.6 mmol). After 2 hours, the reaction mixture is diluted with ethyl acetate and washed with water and brine. The organic layer is dried over MgSO$_4$, filtered, and concentrated. The resulting residue is purified via flash column chromatography (5% isopropyl alcohol/1% formic acid/94% dichloromethane) to afford 3-chloro-4,5-difluoroanthranilic acid as an oil (2.97 g). MS CI: m/z 206 (M$^+$).

(b) 5-Chloro-4-fluoroanthranilic acid

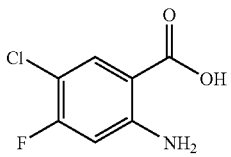

To a solution of 4-fluoroanthranilic acid (0.882 g, 5.69 mmol) in methylene chloride (50 ML) and acetic acid (10 mL) is added tert-butyl hypochlorite (0.71 mL, 6.25 mmol) solution in dichloromethane (1 mL) dropwise over 1 minute. After 90 minutes, the reaction mixture is washed with water and brine. The organic layer is dried over MgSO$_4$, filtered, and the filtrate concentrated to afford 5-chloro-4-fluoroanthranilic acid (1.20 g). MS CI: m/e 188 (M$^+$).

EXAMPLE 20

Synthesis of 2-Bromo-3-chloro-4,5-difluorobenzoic acid

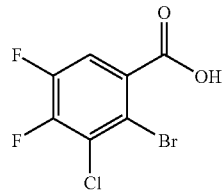

A solution of cuprous bromide (10.96 g, 49.2 mmol)) in acetonitrile (100 mL) is cooled to 0° C. and then tert-butyl nitrite (7.31 mL, 61.5 mmol) and 3-chloro-4,5-difluoroanthranilic acid (Example 19) (8.51 g, 41.0 mmol) are added. The mixture is slowly warmed to room temperature, and after 20 hours, the solvent is removed under vacuum. The resulting residue is dissolved in ethyl acetate and washed with 1.0 M hydrochloric acid, water, and brine. The organic layer is dried over MgSO$_4$ and filtered. The filtrate is concentrated under vacuum and purified via flash column chromatography (5% isopropyl alcohol/1% formic acid/94% dichloromethane) to afford 2-bromo-3-chloro-4,5-difluorobenzoic acid as a solid (7.96 g). MS CI: m/z 271 (MH$^+$).

EXAMPLE 21

Synthesis of 4-[3-(tert-butoxycarbonylamino)pyrrolidin-1-yl]-2,3-difluorobenzoic acid ethyl ester

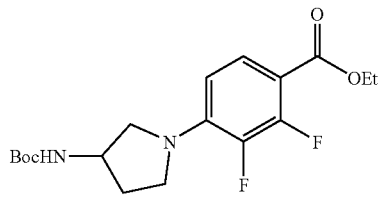

To a solution of 4-[3-(tert-butoxycarbonylamino)pyrrolidin-1-yl]-2,3-difluorobenzoic acid ethyl ester (Example 2h) (3.50 g, 9.50 mmol) in dichloromethane (80 mL) is added acetic acid (8 mL) and tert-butyl hypochlorite (1.75 mL, 15.6 mmol). After 20 minutes, the reaction mixture is diluted with ethyl acetate and washed with water and brine. The organic layer is dried over sodium sulfate, filtered, and the filtrate concentrated. The resulting residue is purified by column chromatography (1:4 ethyl acetate/hexanes) to afford the title compound (3.75 g) as an oil. $^1$H NMR (CDCl$_3$): δ 7.69 (dd, 1H), 4.85–4.76 (bd, 1H), 4.50–4.20 (m, 3H), 3.90–3.74 (m, 2H), 3.62–3.36 (m, 2H), 2.40–2.20 (m, 1H), 1.91–1.84 (m, 1H), 1.45 (s, 9H), 1.40 (s, 9H).

EXAMPLE 22

Synthesis of 2-cyclopropylamino-4,5-difluorobenzoic acid methyl ester

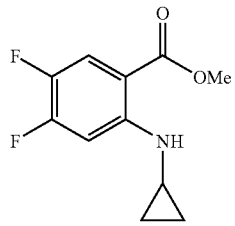

To a solution of 2-cyclopropylamino-4,5-difluorobenzoic acid (Example 5a) (6.0 g, 28.1 mmol), dichloromethane (100 mL), and methanol (20 mL) is added (trimethylsilyl)diazomethane (2.9 M solution in hexane) dropwise until the evolution of gas stops. The solution is stirred at room temperature for 0.5 hour and 88% formic acid is added dropwise until the evolution of gas again stops. Water is added, and the solution is extracted with dichloromethane, dried over MgSO$_4$, filtered, and the solvent removed under reduced pressure. The residue is purified by silica gel column chromatography using hexane/EtOAc (9:1) as the eluent to afford a 5.4 g of the title compound as a clear oil. MS CI: m/z 228 (MH+).

EXAMPLE 23

(a) Synthesis of 1-Cyclopropyl-6,7-difluoro-1H-quinazoline-2,4-dione

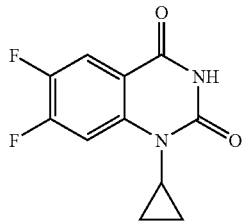

To a solution of 2-cyclopropylamino-4,5-difluorobenzoic acid ethyl ester (Example 22) (5.0 g, 22.0 mmol) in dry dichloromethane (120 mL) under a $N_2$ atmosphere is added chlorosulfanyl isocyanate (3.11 g, 22 mmol). The solution is reacted at room temperature for 4 hours, and the solvent is removed under reduced pressure. The residue is cooled to −20° C., and a cold brine solution (100 mL) buffered with $NaHCO_3$ is added. The solution is warmed to room temperature for 1 hour. The volume is reduced by half with a stream of air, and the solid is collected by filtration. The dry solid is added to a solution of triethylamine (5 mL) in THF (250 mL) and refluxed overnight. The reaction is cooled, the solvent removed under reduced pressure, dissolved in water (100 mL), and acidified to pH 1–2 with 1.0 M hydrochloric acid. The resulting precipitate is collected via filtration to afford 2.0 g of the title compound. MS CI: m/z 239 (MH+).

(b) 1-Cyclopropyl-6,7-difluoro-8-methoxy-1H-quinazoline-2,4-dione

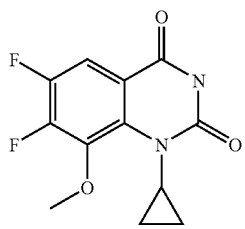

A solution of 1-cyclopropyl-3-(3-methoxy-2,4,5-trifluorobenzoyl)urea (Example 27b, 0.94 g, 3.26 mmol) in tetrahydrofuran (20 mL) and N,N-dimethylformamide (5 mL) is treated with sodium hydride (0.275 g, 6.8 mmol, 60% in mineral oil dispersion) and heated at reflux for 16 hours. The mixture is cooled, treated with saturated $NH_4Cl$ and extracted with dichloromethane. The organic layer is then washed with brine, dried over $Na_2SO_4$ and concentrated under reduced pressure. Flash column chromatography (1:3 ethyl acetate/hexanes) afforded the title compound. MS (EI, M+1) m/z 269.

(c) Synthesis of 8,9-Difluoro-3-methyl-2,3-dihydro-1-oxa-3a,5-diaza-phenalene-4,6-dione

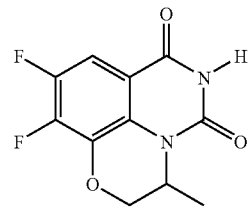

A solution of 1.5 g (6.2 mmol) of 7,8-difluoro-3-methyl-3,4-dihydro-2H-1,4-benzoxazine-5-carboxylic acid methyl ester (Example 32a) in 25 mL of dichloromethane is cooled to −20° C. and treated dropwise with 0.92 g (6.5 mmol) of chlorosulfonyl isocyanate. The reaction is stirred at room temperature for 18 hours and the solvent removed in vacuo. The residue is treated with a saturated sodium bicarbonate solution and extracted with dichloromethane. The organic layer is dried ($MgSO_4$), filtered, and concentrated in vacuo. The residue is dissolved in 50 mL of tetrahydrofuran, and the resulting solution is treated with 5.0 g (5.0 mmol) of triethylamine. After heating at reflux for 4 hours, the solvent is removed in vacuo, and the residue is triturated with 5 mL of dichloromethane/ethyl acetate (80:20). The insoluble material is removed by filtration, washed with the above solvent mixture (2 mL) to give 0.25 g of the title compound, mp 259–261° C. The filtrate is chromatographed over flash grade silica gel (230–400 mesh) eluting with dichloromethane/ethyl acetate (80:20) to give 0.38 g of starting material. Continued elution afforded an additional 0.2 g of the title compound. $^1$H NMR (400 MHz, $CDCl_3$): 11.78 (s, 1H), 7.50 (m, 1H), 4.68 (m, 1H), 4.52 (d, 1H), 4.17 (d, 1H), 1.23 (d, 3H).

(d) Synthesis of 8,9-Difluoro-5-methyl-6,7-dihydro-5H-pyrido[3,2,1-ij]quinazoline-1,3-dione

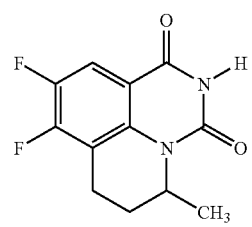

A solution of 1.07 g (4.4 mmol) of 5,6-difluoro-2-methyl-1,2,3,4-tetrahydro-quinoline-8-carboxylic acid methyl ester (Example 32) in 25 mL of dichloromethane is cooled to −20° C. and treated dropwise with 0.85 g (6.0 mmol) of chlorosulfonyl isocyanate. The reaction is stirred at −20° C. for 1 hour, treated with 1.0 g (12 mmol) of solid sodium acetate, and the solvent is removed in vacuo. The residue is cooled in an ice bath and triturated with a saturated solution of sodium acetate in brine. The precipitate is removed by filtration, washed with the sodium acetate solution and dried in vacuo. The dried precipitate is washed with ether to remove starting material and dried in vacuo. The dried solid is suspended in 40 mL of dry tetrahydrofuran, cooled to 5° C. and treated portionwise with 1.2 g (12 mmol) of sodium tert-butoxide. After the addition is complete, the reaction mixture is stirred at 5° C. for 30 minutes, the bath is removed, and the reaction is stirred to room temperature over 1 hour. The solvent is removed in vacuo; the residue is dissolved in water, cooled to 5° C. and acidified with formic acid. The resulting precipitate is removed by filtration, washed with water and dried in vacuo affording 0.8 g of the title compound, mp 212–214° C.

(e) 1-Cyclopropyl-6-fluoro-7-methylsulfanyl-1H-pyrido[2,3-d]pyrimidine-2,4-dione

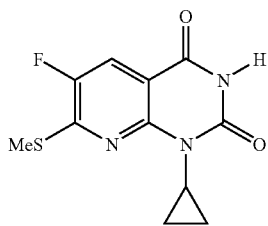

A solution of 4.1 g (15.2 mmol) of ethyl 2-cyclopropylamino-5-fluoro-6-methylsulfanylnicotinate (Example 34) in 125 mL of dichloromethane is cooled to −20° C. and treated dropwise with 5.24 g (37 mmol) of chlorosulfonyl isocyanate. The reaction is stirred at −20° C. for 3 hours and allowed to come to room temperature overnight. The mixture is recooled to −20° C. and treated with 6.8 g (80 mmol) of solid sodium acetate. After stirring for 1 hour without cooling, the solvent is removed in vacuo without heating. The residue is triturated with a saturated solution of sodium acetate in brine and extracted with ethyl acetate (3×75 mL). The combined organic layers are dried (MgSO$_4$), filtered and evaporated in vacuo. The residue is suspended in 100 mL of tetrahydrofuran and treated with 3.6 g (32 mmol) of solid sodium tert-butoxide and stirred at room temperature for 36 hours. The solvent is removed in vacuo, the residue triturated with 100 mL of 0.1 M formic acid and extracted with ethyl acetate (3×100 mL). The combined organic layers are washed with water, dried (MgSO$_4$), filtered and evaporated in vacuo to give a residue which is chromatographed over flash grade silica gel (230–400 mesh) eluting with dichloromethane to give 0.75 g of the title compound, mp 220–222° C.

General Procedure A

Sodium hydride (3 eq., 60% mineral oil dispersion) is added portionwise to a solution of 1-cyclopropyl-3-benzoylurea (Example 27) in 20:1 tetrahydrofuran/N,N-dimethylformamide at −25° C. The mixture is stirred at room temperature for 30 minutes, then refluxed overnight. It is poured into ice water, and the solution is acidified with 10% hydrochloric acid and extracted with ethyl acetate. The extract is washed with brine, dried, and concentrated. The residue is purified by silica gel column chromatography (ethyl acetate/hexanes) to afford 8-substituted 1-cyclopropyl-6,7-difluoro-1H-quinazoline-2,4-diones.

The following compounds are synthesized according to General Procedure A of Example 23:

(e) 1-Cyclopropyl-6,7-difluoro-8-methyl-1H-quinazoline-2,4-dione (¹H NMR (200 MHz, CDCl$_3$): δ 8.61 (bs, 1H), 7.83 (dd, 1H), 3.37–3.35 (m, 1H), 2.60 (dd, 3H), 1.31–1.12 (m, 2H), 0.71–0.63 (m, 2H) from 1-cyclopropyl-3-(2,4,5-trifluoro-3-methylbenzoyl)urea (Example 27c).

(f) 1-Cyclopropyl-6,7-difluoro-5-methyl-1H-quinazoline-2,4-dione (¹H NMR (200 MHz, CDCl$_3$): δ 8.37 (bs, 1H), 7.96 (dd, 1H), 2.81–2.74 (m, 1H), 2.61 (d, 3H), 1.2.6–1.14 (m, 2H), 0.81–0.73 (m, 2H)) from 1-cyclopropyl-3-(3,4,6-trifluoro-2-methylbenzoyl)urea (Example 27d).

(g) 1-cyclopropyl-6,7-difluoro-8-ethyl-1H-quinazoline-2,4-dione (¹H NMR (200 MHz, CDCl$_3$): δ 9.41 (bs, 1H), 7.86–7.77 (m, 1H), 3.40–3.20 (m, 3H), 1.30–1.10 (m, 5H), 0.75–0.67 (m, 2H)) from 1-cyclopropyl-3-(3-ethyl-2,4,5-trifluorobenzoylurea (Example 27e).

(i) 7-Chloro-1-cyclopropyl-6-fluoro-1H-pyrido[2,3-d]pyrimidine-2,4-dione (mp 214–216° C.) from 1-cyclopropyl-3-(2,6-dichloro-5-fluoro-pyridine-3-carbonyl)urea (Example 27a).

EXAMPLE 24

(a) Synthesis of 3-Amino-1-cyclopropyl-6,7-difluoro-]H-quinazoline-2,4-dione

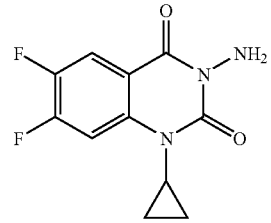

To a solution of 1-cyclopropyl-6,7-difluoro-1H-quinazoline-2,4-dione (Example 23a, 2.0 g, 8.92 mmol) in dioxane (7.5 mL) and dimethylformamide (7.5 mL) is added NaH (60% dispersion in oil, 428 mg, 10.7 mmol). The solution is heated to 60° C. for 10 minutes and cooled to room temperature. To the cooled solution is added O-(2,4-dinitrophenyl)hydroxylamine (1.77 g, 8.92 mmol), and the solution is heated to 80° C. for 30 minutes. The resulting red solution is cooled to room temperature, poured over crushed ice, and extracted with EtOAc. The combined organic layers are dried over MgSO$_4$, filtered, and the solvent removed under reduced pressure. The resulting solid is triturated with Et$_2$O and air dried to afford 1.44 g of the title compound. MS CI: m/z 254 (MH$^+$).

(b) 3-Amino-7-chloro-1-cyclopropyl-6-fluoro-1H-pyrido[2,3-d]pyrimidine-2,4-dione

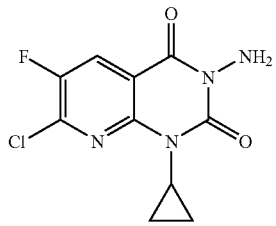

A solution of 3.83 g (15 mmol) of 7-chloro-1-cyclopropyl-6-fluoro-1H-pyrido[2,3-d]pyrimidine-2,4-dione (Example 23i) in 50 mL of dimethylformamide-dioxane (1:1) is cooled to 0° C. and treated portionwise with 0.8 g (20 mmol) of 60% sodium hydride/mineral oil. The reaction is stirred to room temperature for 30 minutes, re-cooled to 0° C. and 3.2 g (16 mmol) of 2,4-dinitrophenylhydroxylamine is added all at once. After stirring at room temperature overnight, the dioxane is removed in vacuo and the residue is diluted to 300 mL with ice and water and stirred at 5° C. for 1 hour. The precipitate is removed by filtration, washed with water, ether and dried in vacuo to give 2.65 g of the title compound, mp 192–194° C. A second crop, (0.6 g) could be isolated by evaporating the filtrate and triturating the residue with petroleum ether.

(c) 3-Amino-1-cyclopropyl-6-fluoro-2,4-dioxo-1,2,3,4-tetrahydro-pyrido[2,3-d]pyrimidine-7-thiosulfonic acid

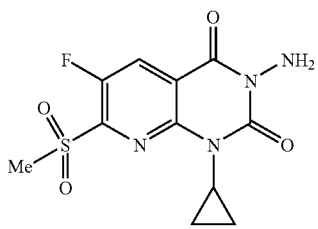

A solution of 0.47 g (1.57 mmol) of 1-cyclopropyl-6-fluoro-2,4-dioxo-1,2,3,4-tetrahydro-pyrido[2,3-d]pyrimidine-7-thiosulfonic acid (Example 35) in 20 mL of dimethylformamide/dioxane (1:1) is treated portionwise with 0.08 g (2.0 mmol) of 60% sodium hydride/mineral oil. The reaction is stirred at room temperature for 1 hour and 0.32 g (1.6 mmol) of 2,4-dinitrophenylhydroxylamine is added all at once. After stirring at room temperature overnight, the dioxane is removed in vacuo and the residue is diluted to 100 mL with ice and water and stirred at 5° C. for 1 hour. The aqueous solution is extracted with ethyl acetate (3×50 mL) with the combined organic layers being washed with water, dried (MgSO$_4$), filtered and evaporated in vacuo to give 0.4 g of the title compound, mp 167–169° C.

General Procedure A (Example 24)

To a solution of a 1-cyclopropyl-6,7-difluoro-1H-quinazoline-2,4-dione (Example 23) in 1:1 dry tetrahydrofuran or dioxane and dry N,N-dimethylformamide is added portionwise sodium hydride (1.1 eq., 60% mineral oil dispersion) at room temperature. After stirring at 50° C. for 20 to 30 minutes, the resulting solution is cooled to room temperature and 2,4-dinitrophenylhydroxylamine (4 eq.) is added. The mixture is heated at 60° C. to 80° C. for 30 minutes, cooled, and the dioxane removed reduced pressure. The residue is poured into ice water and extracted with ethyl acetate. The organic layers are combined, washed with brine, dried with Na$_2$SO$_4$, and concentrated in vacuo. The residue is purified by flash column chromatography (ethyl acetate/hexanes) to afford a 3-amino-1-cyclopropyl-6,7-difluoro-1H-quinazoline-2,4-dione.

The compounds are synthesized according to General Procedure A of Example 24:

(d) 3-Amino-1-cyclopropyl-6,7-difluoro-8-methoxy-1H-quinazoline-2,4-dione (MS EI: m/z 284 (MH$^+$)) from 1-cyclopropyl-6,7-difluoro-8-methoxy-1H-quinazoline-2,4-dione (Example 23b).

(e) 3-Amino-1-cyclopropyl-6,7-difluoro-8-methyl-1H-quinazoline-2,4-dione ($^1$H NMR (200 MHz, CDCl$_3$): δ 7.86 (dd, 1H), 5.20 (bs, 2H), 3.48–3.38 (m, 1H), 2.61 (dd, 3H), 1.29–1.17 (m, 2H), 0.73–0.62 (m, 2H)) from 1-cyclopropyl-6,7-difluoro-8-methyl-1H-quinazoline-2,4-dione (Example 23e).

(f) 3-Amino-1-cyclopropyl-6,7-difluoro-5-methyl-1H-quinazoline-2,4-dione ($^1$H NMR (200 MHz, CDCl$_3$): δ 7.45 (dd, 1H), 5.28 (bs, 2H), 2.94–2.83 (m, 1H), 2.77 (d, 3H), 1.41–1.31 (m, 2H), 0.98–0.93 (m, 2H)) from 1-cyclopropyl-6,7-difluoro-5-methyl-1H-quinazoline-2,4-dione (Example 23f).

(g) 3-Amino-1-cyclopropyl-6,7-difluoro-8-ethyl-1H-quinazoline-2,4-dione ($^1$H NMR (200 MHz, CDCl$_3$): δ 7.84–7.75 (t, 1H), 5.37 (bs, 2H), 3.50–3.40 (m, 1H), 3.37–3.21 (m, 2H), 1.29–1.15 (m, 5H), 0.75–0.66 (m, 2H)) from 1-cyclopropyl-6,7-difluoro-8-ethyl-1H-quinazoline-2,4-dione (Example 23g).

(h) 5-Amino-8,9-difluoro-3-methyl-2,3-dihydro-1-oxa-3a,5-diaza-phenalene-4,6-dione (mp 171–173° C.) from 8,9-difluoro-3-methyl-2,3-dihydro-1-oxa-3a,5-diaza-phenalene-4,6-dione (Example 23c).

(i) 2-Amino-8,9-difluoro-5-methyl-6,7-dihydro-5H-pyrido[3,2,1-ij]quinazoline-1,3-dione, mp 140–142° C., $^1$H NMR (400 MHz, CDCl$_3$): 7.90 (m, 1H), 5.30 (bs, 2H), 5.07 (m, 1H), 3.08 (m, 1H), 2.85 (m, 1H), 2.15 (m, 1H), 1.95 (m, 1H), 1.31 (d, 3H)) from 8,9-difluoro-5-methyl-6,7-dihydro-5H-pyrido[3,2,1-ij]quinazoline-1,3-dione (Example 23d).

EXAMPLE 25

Synthesis of {3-Amino-7-[(S)-3-(tert-butoxycarbonylamino)pyrrolidin-1-yl]-1-cyclopropyl-6-fluoro-1H-quinazoline-2,4-dione

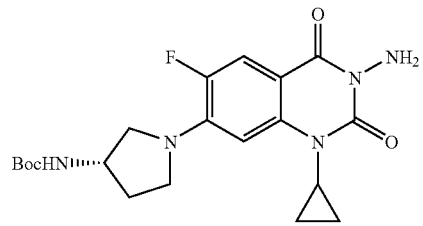

To a solution of 3-amino-1-cyclopropyl-6,7-difluoro-1H-quinazoline-2,4-dione (Example 24a) (50.0 mg, 0.20 mmol) and triethylamine (74 mg, 0.74 mmol) in acetonitrile (3 mL) is added (S)-pyrrolidin-3-yl carbamic acid tert-butyl ester (74 mg, 0.40 mmol). The solution is refluxed for 18 hours, the solvent is removed under reduced pressure, and the residue triturated with water. The solid is collected by filtration and air dried to afford 74 mg of the title compound. MS CI: m/z 420 (MH$^+$).

EXAMPLE 26

Synthesis of Benzamides

General Procedure A

A solution of an appropriately substituted benzoic acid, oxalyl chloride (1.5 eq.), and dichloromethane is treated with N,N-dimethylformamide (2 drops), the solution is stirred at room temperature for 2 hours. The mixture is concentrated under reduced pressure, and the residue is dissolved in dry THF and slowly added to a solution of ammonia in diethyl ether at −70° C. The mixture is then allowed to warm to ambient temperature and stirred for 30 minutes. The mixture is then filtered and the resulting solid dissolved in ethyl acetate, washed with water, and dried over Na$_2$SO$_4$. The solvent is then concentrated in vacuo to provide the desired amide.

The following compounds are synthesized according to the General Procedure A method above:

(a) 3,4,6-Trifluoro-2-methylbenzamide. ($^1$H NMR (200 MHz, CDCl$_3$): δ 6.89–6.77 (m, 1H), 6.41 (bs, 1H), 5.95 (bs, 1H), 2.39 (d, 3H)) from 3,4,6-trifluorobenzoic acid (Hagen S. et al., *Heterocycl. Chem.*, 1990; 27[6]:1609–1616).

(b) 3-Ethyl-2,4,5-trifluorobenzamide, ($^1$H NMR (200 MHz, CDCl$_3$): δ 7.78–7.60 (m, 1H), 6.61 (bs, 2H), 2.67 (q, 2H), 1.15 (t, 3H)) from 3-ethyl-2,4,5-trifluorobenzoic acid (Takemura, PCT Int. Appl., 1996, WO 9623782).

EXAMPLE 27

Synthesis of 1-cyclopropyl-3-benzoyl substituted ureas (a) 1-Cyclopropyl-3-(2,6-dichloro-5-fluoro-pyridine-3-carbonyl) urea

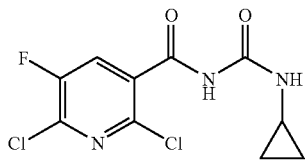

A solution of 5.8 g (27.8 mmol) of 2,6-dichloro-5-fluoronicotinamide (*Chem. Pharm. Bull.*, 1987; 35:2280) in 60 mL of dichloromethane is treated dropwise with 5.1 g (40 mmol) of oxalyl chloride, and the reaction mixture is heated at reflux for 18 hours. The solvent is removed in vacuo, and the residue is dissolved in 50 mL of dichloromethane, which is also removed in vacuo. The residue is dissolved in 50 mL of dichloromethane, cooled to −20° C. and treated dropwise with 2.28 g (40 mmol) of cyclopropylamine. The reaction mixture is stirred at −20° to −10° C. for ½ hour, then allowed to come to room temperature over 2 hours. The solvent is removed in vacuo and the residue is triturated with 25 mL of dichloromethane, which is also removed in vacuo to give 8.0 g of the title compound, mp 171–173° C.

General Procedure A

To a solution of substituted benzamide (Example 26) in 1,2-dichloroethane is added oxalyl chloride (1.5 eq.) and the mixture refluxed for 16 hours. The solvent is then removed under reduced pressure to obtain a crude isocyanate. The isocyanate is then taken up into dioxane, cooled to 0° C. and treated with cyclopropylamine (1.5 eq.) in dioxane. The mixture is then warmed to ambient temperature and stirred for 3 hours. The mixture is then concentrated under reduced pressure, dissolved in ethyl acetate, washed with water, dried over Na$_2$SO$_4$ and evaporated under reduced pressure. The resulting residue is then purified by flash column chromatography (ethyl acetate/hexanes) to afford the 1-cyclopropyl-3-benzoyl urea.

The following compounds are synthesized according to the General Procedure A method above:

(b) 1-Cyclopropyl-3-(2,4,5-trifluoro-3-methoxy-benzoyl) urea (MS ES (MH$^+$): m/z 289) from 2,4,5-trifluoro-3-methoxybenzamide (Masuzawa K., Suzue S., Hirai K., Ishizaki T., Eur. Pat. Appl., 1987, EP 230295).

(c) 1-Cyclopropyl-3-(2,4,5-trifluoro-3-methylbenzoyl) urea ($^1$H NMR (200 MHz, CDCl$_3$): δ 8.69 (d, 1H), 8.48 (bs, 1H), 7.75–7.62 (m, 1H), 2.83–2.71 (m, 1H), 2.30 (dd, 3H), 0.87–0.78 (m, 2H), 0.67–0.59 (m, 2H)) from 2,4,5-trifluoro-3-methylbenzamide (Masuzawa K., Suzue S., Hirai K., Ishizaki T., Eur. Pat. Appl., 1987, EP 237955).

(d) 1-Cyclopropyl-3-(3,4,6-trifluoro-2-methylbenzoyl) urea ($^1$H NMR (200 MHz, CDCl$_3$): δ 8.99 (bs, 1H), 8.37 (bs, 1H), 6.93–6.80 (m, 1H), 2.74–2.65 (m, 1H), 2.35 (d, 3H), 0.84–0.71 (m, 2H), 0.66–0.58 (m, 2H)) from 3,4,6-trifluoro-2-methylbenzamide (Example 26a).

(e) 1-Cyclopropyl-3-(3-ethyl-2,4,5-trifluorobenzoyl)urea ($^1$H NMR (200 MHz, CDCl$_3$): δ 8.76–8.69 (bd, 1H), 8.50 (bs, 1H), 7.76–7.63 (m, 1H), 2.84–2.72 (m, 3H), 1.27–1.20 (m, 3H), 0.91–0.81 (m, 2H), 0.71–0.61 (m, 2H)) from 3-ethyl-2,4,5-trifluorobenzamide (Example 26b).

EXAMPLE 28

(a) Synthesis of {(R)-1-[(S)-1-(3-Amino-1-cyclopropyl-6-fluoro-8-methoxy-2,4-dioxo-1,2,3,4-tetrahydroquinazolin-7-yl)pyrrolidin-3-yl]ethyl}-carbamic acid tert-butyl ester

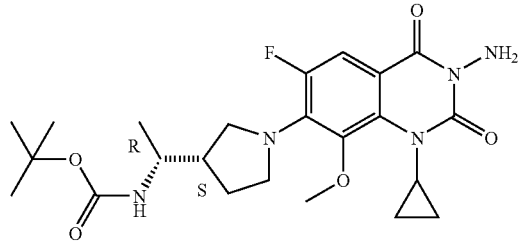

A solution of 0.57 g (2.0 mmol) of 3-amino-1-cyclopropyl-6,7-difluoro-8-methoxy-1H-quinazoline-2,4-dione (Example 24d), 0.64 g (3.0 mmol) of ((S)-(R)-1-pyrrolidin-3-ylethyl)carbamic acid tert-butyl ester (*J. Het. Chem.*, 1992; 29:1481), 0.81 g (8.0 mmol) of triethylamine and 10 mL of dimethyl sulfoxide is heated at 110° C. for 4 hours. The reaction mixture is cooled to room temperature, poured into 150 mL of ice and water, and extracted with ethyl acetate (2×125 mL). The combined organic layers are washed with water, dried (MgSO$_4$), filtered and evaporated in vacuo to give 1.1 g of crude product. Chromatography on flash grade silica gel (230–400 mesh) eluting with dichloromethane/ethanol (9:1) provided 0.92 g of the title compound, mp 96–98° C.

(b) Synthesis of {(S)-1-[(S)-1-(3-Amino-1-cyclopropyl-6-fluoro-8-methoxy-2,4-dioxo-1,2,3,4-tetrahydroquinazolin-7-yl-pyrrolidin-3-yl]ethyl}-carbamic acid tert-butyl ester

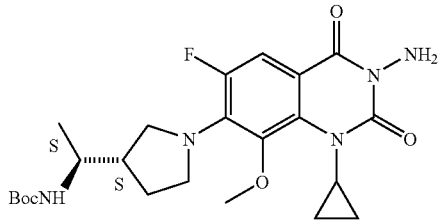

A solution of 0.57 g (2.0 mmol) of 3-amino-1-cyclopropyl-6,7-difluoro-8-methoxy-1H-quinazoline-2,4-dione (Example 24d), 0.64 g (3.0 mmol) of ((S)-(S)-1-pyrrolidin-3-ylethyl)carbamic acid tert-butyl ester (*J Het. Chem.*, 1992; 29:1481), 0.81 g (8.0 mmol) of triethylamine, and 10 mL of dimethyl sulfoxide is heated at 110° C. for 4 hours. The reaction mixture is cooled to room temperature, poured into 150 mL of ice and water and extracted with ethyl acetate (2×125 mL). The combined organic layers are washed with water, dried (MgSO$_4$), filtered and evaporated in vacuo to give 1.08 g of crude product. Chromatography on flash grade silica gel (230–400 mesh) eluting with dichloromethane/ethanol (9:1) provided 0.9 g of the title compound, mp 87–89° C.

(c) Synthesis of {(R)-1-[(S)-1-(3-Amino-1-cyclopropyl-6-fluoro-8-methyl-2,4-dioxo-1,2,3,4-tetrahydro-quinazolin-7-yl)-pyrrolidin-3-yl]-ethyl}-carbamic acid tert-butyl ester

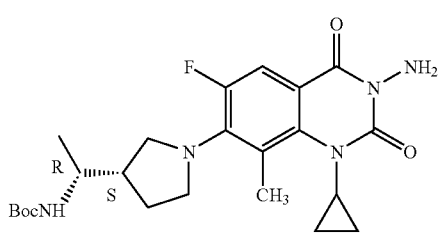

A solution of 0.5 g (1.9 mmol) of 3-amino-1-cyclopropyl-6,7-difluoro-8-methyl-1H-quinazoline-2,4-dione (Example 24e), 0.64 g (3.0 mmol) of ((S)-(R)-1-pyrrolidin-3-ylethyl) carbamic acid tert-butyl ester, 0.81 g (8.0 mmol) of triethylamine and 10 mL of dimethyl sulfoxide is heated at 110° C. for 24 hours. After thin layer chromatography showed incomplete reaction, an additional 0.43 g (2.0 mmol) of pyrrolidine derivative and 0.81 g (8.0 mmol) of triethylamine are added and the reaction is heated at 120° C. for 18 hours. The reaction mixture is cooled to room temperature, poured into 200 mL of ice and water and extracted with ethyl acetate (2×125 mL). The combined organic layers are washed with water, dried (MgSO$_4$), filtered and evaporated in vacuo to give 1.1 g of crude product. Chromatography on flash grade silica gel (230–400 mesh) eluting with ethyl acetate provided 0.4 g of the title compound, mp 86–88° C.

(d) Synthesis of {(S)-1-[(S)-1-(3-Amino-1-cyclopropyl-6-fluoro-8-methyl-2,4 dioxo-1,2,3,4-tetrahydroquinazolin-7-yl)pyrrolidin-3-yl]ethyl}-carbamic acid tert-butyl ester

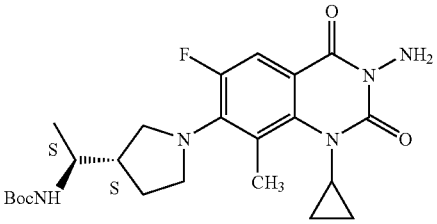

A solution of 0.5 g (1.9 mmol) of 3-amino-1-cyclopropyl-6,7-difluoro-8-methyl-1H-quinazoline-2,4-dione (Example 24e), 0.64 g (3.0 mmol) of ((S)-(S)-1-pyrrolidin-3-ylethyl) carbamic acid tert-butyl ester, 0.81 g (8.0 mmol) of triethylamine and 10 mL of dimethyl sulfoxide is heated at 110° C. for 24 hours. After thin layer chromatography showed incomplete reaction, an additional 0.43 g (2.0 mmol) of pyrrolidine derivative and 0.81 g (8.0 mmol) of triethylamine are added and the reaction is heated at 120° C. for 18 hours. The reaction mixture is cooled to room temperature, poured into 200 mL of ice and water and extracted with ethyl acetate (2×125 mL). The combined organic layers are washed with water, dried (MgSO$_4$), filtered and evaporated in vacuo to give 1.3 g of crude product. Chromatography on flash grade silica gel (230–400 mesh) eluting with 400 mL of dichloromethane/ethyl acetate (8:2), 600 mL of (6:4) and 1 L of (4:6) provided 0.46 g of the title compound, mp 84–86° C.

(e) Synthesis of [(S)-1-(5-Amino-8-fluoro-3-methyl-4,6-dioxo-2,3,5,6-tetrahydro-4H-1-oxa-3a, 5-diazaphenalen-9-yl)pyrrolidin-3-yl]carbamic acid tert-butyl ester

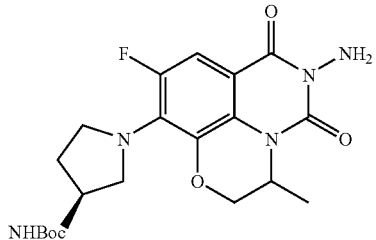

A solution of 0.2 g (0.75 mmol) of 5-amino-8,9-difluoro-3-methyl-2,3-dihydro-1-oxa-3a,5-diazaphenalene-4,6-dione (Example 24h), 0.58 g (2.0 mmol) of (S)-3-pyrrolidinylcarbamic acid tert-butyl ester (*J. Med. Chem.*, 1992; 35:1764), 0.5 g (0.5 mmol) of triethylamine and 20 mL of acetonitrile is heated at reflux for 18 hours. The solvent is removed in vacuo and the residue is partitioned between dichloromethane-water. The organic layer is washed with water, dried (MgSO$_4$) and concentrated in vacuo. The residue is chromatographed over flash grade silica gel (230–400 mesh) eluting with dichloromethane/ethanol (95:5) to give 0.34 g of the title compound, mp 114–116° C.

(f) {(S)-1-[(R)-1-(5-Amino-8-fluoro-3-methyl-4,6-dioxo-2,3,5,6-tetrahydro-4H-1-oxa-3a,5-diazaphenalen-9-yl)pyrrolidin-3-yl]ethyl}carbamic acid tert-butyl ester

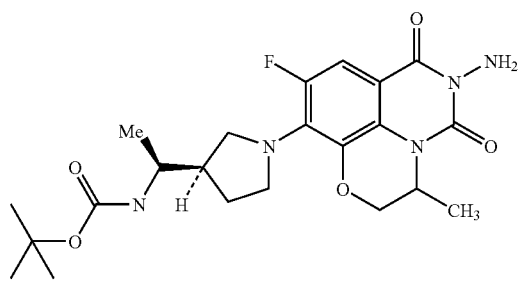

A solution of 0.11 g (0.41 mmol) of 5-amino-8,9-difluoro-3-methyl-2,3-dihydro-1-oxa-3a,5-diazaphenalene-4,6-dione (Example 24h), 0.26 g (1.3 mmol) of ((R)-(S)-1-pyrrolidin-3-ylethyl)carbamic acid tert-butyl ester (*J. Het. Chem.*, 1992; 29:1481), 0.25 g (2.5 mmol) of triethylamine and 10 mL of acetonitrile is heated at reflux for 18 hours. The solvent is removed in vacuo and the residue is partitioned between ethyl acetate/water. The organic layer is washed with water, dried (MgSO$_4$) and concentrated in vacuo. The residue is chromatographed over flash grade silica gel (230–400 mesh) eluting with dichloromethane/ethanol (95:5) to give 0.14 g of the title compound. $^1$H NMR (400 MHz, CDCl$_3$): 7.43 (d, 1H), 5.24 (bs, 2H), 4.82 (m, 1H), 4.56 (m, 1H), 4.33 (d, 1H), 3.99 (m, 1H), 3.86 (m, 1H), 3.73 (m, 1H), 3.59 (m, 2H), 2.18 (m, 1H), 3.01 (m, 1H), 1.67 (m, 1H), 1.44 (s, 9H), 1.40 (m, 3H), 1.25 (m, 1H), 1.20 (d, 3H).

(g) [(S)-1-(2-Amino-9-fluoro-5-methyl-1,3-dioxo-2,3,6,7-tetrahydro-1H,5H-pyrido[3,2,1-ij]quinazolin-8-yl)pyrrolidin-3-yl]carbamic acid tert-butyl ester

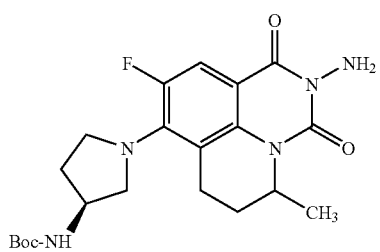

A solution of 0.12 g (0.45 mmol) of 5-amino-8,9-difluoro-5-methyl-6,7-dihydro-5H-pyrido[3,2,1-ij]quinazoline-1,3-dione (Example 24i), 0.34 g (1.8 mmol) of (S)-3-pyrrolidinylcarbamic acid tert-butyl ester (*J. Med. Chem.*, 1992; 35:1764), 0.2 g (2.0 mmol) of triethylamine and 7 mL of dimethyl sulfoxide is heated at 110° C. for 18 hours. The reaction is cooled to room temperature, diluted with 80 mL of ice and water and stirred at 5° C. for 1 hour. The resulting precipitate is removed by filtration, washed with water and dried in vacuo. The solid is chromatographed over flash grade silica gel (230–400 mesh) eluting with dichloromethane/ethanol (9:1) to give 0.14 g of the title compound, mp 98–100° C.

(h) {(R)-3-[(S)-1-(2-Amino-9-fluoro-5-methyl-1,3-dioxo-2,3,6,7-tetrahydro-1H,5H-pyrido[3,2,1-ij]quinazolin-8-yl)pyrrolidin-3-y}ethylcarbamic acid tert-butyl ester

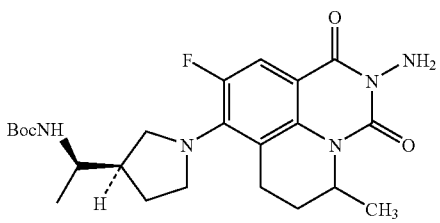

A solution of 0.12 g (0.45 mmol) of 5-amino-8,9-difluoro-5-methyl-6,7-dihydro-5H-pyrido[3,2,1-ij]quinazoline-1,3-dione (Example 24i), 0.39 g (1.8 mmol) of ((R)-(S)-1-pyrrolidin-3-ylethyl)carbamic acid tert-butyl ester (*J. Het. Chem.*, 1992; 29:1481), in 5 mL of dimethyl sulfoxide is heated at 110° C. for 18 hours. The reaction is cooled to room temperature, diluted with 80 mL of ice and water and stirred at 5° C. for 1 hour. The resulting precipitate is removed by filtration, washed with water and dried in vacuo. The solid is chromatographed over flash grade silica gel (230–400 mesh) eluting with dichloromethane/ethanol (9:1) to give 0.13 g of the title compound, mp 93–95° C.

(i) [1-(3-Amino-1-cyclopropyl-6-fluoro-2,4-dioxo-1,2,3,4-tetrahydro-pyrido[2,3-d]pyrimidin-7-yl)pyrrolidin-3-yl]carbamic acid tert-butyl ester

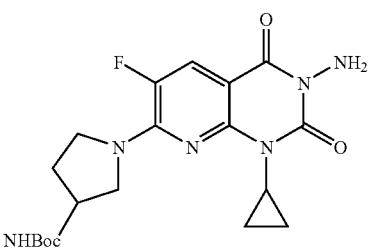

A solution of 0.11 g (0.4 mmol) of 3-amino-7-chloro-1-cyclopropyl-6-fluoro-1H-pyrido[2,3-d]pyrimidine-2,4-dione (Example 24b), 0.105 g (0.56 mmol) of (S)-3-pyrrolidinylcarbamic acid tert-butyl ester (*J. Med. Chem.*, 1992; 35:1764), 1.2 mL of N,N-diisopropylethylamine and 3 mL of acetonitrile is heated at 50° C. for 18 hours. The reaction mixture is diluted with 9 mL of water, cooled to 0° C. and the solid is removed by filtration, washed with 50% aqueous acetonitrile and dried in vacuo to give 0.14 g of the title compound, mp 108–110° C.

(j) {(S)-1-[(R)-1-(3-Amino-1-cyclopropyl-6-fluoro-2,4-dioxo-1,2,3,4-tetrahydropyrido[2,3-d]pyrimidin-7-yl)pyrrolidin-3-yl]ethyl}-carbamic acid tert-butyl ester

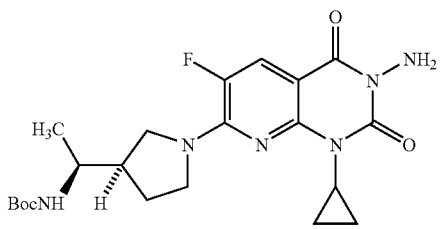

A solution of 0.12 g (0.38 mmol) of 3-amino-1-cyclopropyl-6-fluoro-2,4-dioxo-1,2,3,4-tetrahydro-pyrido[2,3-d]pyrimidine-7-thiosulfonic acid (Compound 24c) in 10 mL of acetonitrile is treated with 0.24 g (1.14 mmol) of ((R)-(S)-1-pyrrolidin-3-ylethyl)carbamic acid tert-butyl ester (*J. Het. Chem.*, 1992; 29:1481), 0.25 g (2.5 mmol) of triethylamine and stirred at room temperature for 18 hours then 50° C. for 1 hour. The solvent is removed in vacuo and the residue is partitioned between ethyl acetate (50 mL) and water (25 mL). The organic layer is washed with water, dried (MgSO₄), filtered and evaporated in vacuo to give 0.28 g. Chromatography on flash grade silica gel (230–400 mesh) column (2×12 cm) eluting with dichloromethane/ethanol (95:5) provided 0.1 g of the title compound, mp 175–177° C.

General Procedure A

A solution of Example 24, 1–2.5 eq of heterocyclic amine side chain, and 3–3.5 eq. 1,8-diazabicyclo-5,4,0-undecen-7-ene (DBU) or triethylamine are stirred in dimethyl sulfoxide (1 mL) at 130° C. for 3 to 48 hours. After cooling to room temperature, the reaction mixture is diluted with ethyl acetate and washed with saturated NaHCO₃, water, and brine. The organic layer is dried over MgSO₄, filtered, and the filtrate concentrated. The resulting residue is purified via flash column chromatography (isopropanol/dichloromethane) to afford the product.

General Procedure B

A solution of Example 24 and heterocyclic diamine side chain (1.5–3.0 eq.) is stirred in dimethyl sulfoxide at 130° C. for 3 hours. After cooling to room temperature the reaction mixture is diluted with ethyl acetate and washed with saturated NaHCO₃, water, and brine. The organic layer is; dried over MgSO₄, filtered, and the filtrate concentrated. The resulting residue is redissolved in dichloromethane and while stirring, di-tert-butyl dicarbonate (0.41 g, 1.87 mmol) is added. After 1 hour, the reaction mixture is concentrated and the product is purified via flash column chromatography (1:1 EtOAc/hexanes) to afford the product.

General procedure C

A solution of Example 24, heterocyclic diamine side chain (1.5–3.0 eq.) and tetramethyl guanidine (1–5.0 eq.) is stirred in dimethyl sulfoxide at (80° C.–130° C.) for 36 to 24 hours. After cooling to room temperature the reaction mixture is diluted with water and saturated NH₄Cl. The solid is washed with water and dried to give the crude solid. The product is purified via flash column chromatography (SiO₂) using (CHCl₃/MeOH or ethyl acetate/hexanes) to afford the product.

The following compounds are synthesized according to the General Procedures A, B, and C of Example 28:

(k) {1-[(R)-1-((S)-3-Amino-1-cyclopropyl-6-fluoro-8-methyl-2,4-dioxo-1,2,3,4-tetrahydroquinazolin-7-yl)pyrrolidin-3-yl]ethyl}carbamic acid tert-butyl ester (MS ES: m/z 462 (MH+)) from 3-amino-1-cyclopropyl-6,7-difluoro-8-methyl-1H-quinazoline-2,4-dione (Example 24e) and (R)-((S)-1-pyrrolidin-3-yl)ethylcarbamic acid tert-butyl ester (Kimura Y., Atarashi S., Takahashi M., Hayakkawa I., *Chem. Pharm. Bull.*, 1994; 42:1442) using General Method A.

(l) {1-[(S)-1-(3-Amino-1-cyclopropyl-6-fluoro-8-methyl-2,4-dioxo-1,2,3,4-tetrahydroquinazolin-7-yl)pyrrolidin-3-yl]-1-methylethyl}carbamic acid tert-butyl ester (MS ES: m/z 476 (MH⁺)) from 3-amino-1-cyclopropyl-6,7-difluoro-8-methyl-1H-quinazoline-2,4-dione (Example 24e) and [(S)-(pyrrolidin-3-yl)-1-methylethyl]carbamic acid tert-butyl ester using General Method A.

(m) {1-[1-(3-Amino-1-cyclopropyl-6-fluoro-8-methyl-2,4-dioxo-1,2,3,4-tetrahydroquinazolin-7-yl)-3-methoxypyrrolidin-3-yl]ethyl}carbamic acid tert-butyl ester (MS ES: m/z 492 (MH⁺)) from 3-amino-1-cyclopropyl-6,7-difluoro-8-methyl-1H-quinazoline-2,4-dione (Example 24e) and [1-(3-methoxypyrrolidin-3-yl)ethyl]carbamic acid tert-butyl ester (Example A5b) using General Method A.

(n) [3-(3-(Amino-1-cyclopropyl-6-fluoro-8-methyl-2,4-dioxo-1,2,3,4-tetrahydroquinazolin-7-yl)-3-azabicyclo[3.1.0]hex-6-yl]carbamic acid tert-butyl ester (MS ES: m/z 446 (MH⁺)) from 3-amino-1-cyclopropyl-6,7-difluoro-8-methyl-1H-quinazoline-2,4-dione (Example 24e) and 3-azabicyclo[3.1.0]hex-6-ylcarbamic acid tert-butyl ester (Brighty K. E., 1991, EP 413455) using General Method A.

(o) {1-[1-(3-Amino-1-cyclopropyl-6-fluoro-8-methoxy-2,4-dioxo-1,2,3,4-tetrahydroquinazolin-7-yl)-3-fluoropyrrolidin-3-yl]ethyl}carbamic acid tert-butyl ester (MS ES: m/z 496 (MH⁺)) from 3-amino-1-cyclopropyl-6,7-difluoro-8-methoxy-1H-quinazoline-2,4-dione (Example 24d) and (4-fluoro-pyrrolidin-3-yl)ethylcarbamic acid tert-butyl ester (Example A5c) using General Method A.

(p) [1-(3-Amino-1-cyclopropyl-6-fluoro-5-methyl-2,4-dioxo-1,2,3,4-tetrahydroquinazolin-7-yl)pyrrolidin-3-yl]carbamic acid tert-butyl ester (MS ES: m/z 434 (MH⁺)) from 3-amino-1-cyclopropyl-6,7-difluoro-5-methyl-1H-quinazoline-2,4-dione (Example 24f) and (pyrrolidin-3-yl)carbamic acid tert-butyl ester using General Method A.

(q) {1-(R)-[1-(S)-(3-Amino-1-cyclopropyl-6-fluoro-5-methyl-2,4-dioxo-1,2,3,4-tetrahydroquinazolin-7-yl)pyrrolidin-3-yl]ethyl}carbamic acid tert-butyl ester (MS ES:m/z 462 (MH+)) from 3-amino-1-cyclopropyl-6,7-difluoro-5-methyl-1H-quinazoline-2,4-dione (Example 24f) and ((R)-((S)-1-pyrrolidin-3-yl-ethyl)amine using General Method A.

(r) [1-(3-Amino-1-cyclopropyl-6-fluoro-8-methyl-2,4-dioxo-1,2,3,4-tetrahydroquinazolin-7-yl)-3-methoxymethylpyrrolidin-3-ylmethyl]carbamic acid tert-butyl ester (MS ES: m/z 493 (MH⁺)) from 3-amino-1-cyclopropyl-6,7-difluoro-8-methyl-1H-quinazoline-2,4-dione (Example 24e) and (3-methoxymethylpyrrolidin-3-ylmethyl)carbamic acid tert-butyl ester (Example A5d) using General Method A.

(s) [1-(3-Amino-1-cyclopropyl-6-fluoro-8-methyl-2,4-dioxo-1,2,3,4-tetrahydroquinazolin-7-yl)-3-fluoromethylpyrrolidin-3-ylmethyl]carbamic acid tert-butyl ester (¹H NMR (200 MHz, CDCl₃): δ 7.60 (d, 1H), 5.18 (bs, 1H), 4.97 (bs, 2H), 4.61–4.10 (m, 4H), 3.72–3.19 (m, 5H), 2.46 (s, 3H), 2.00–1.71 (m, 2H), 1.45 (s, 9H), 1.21–1.10 (m, 2H), 0.68–0.56 (m, 2H)) from 3-amino-1-cyclopropyl-6,7-difluoro-8-methyl-1H-quinazoline-2,4-dione (Example 24e) and 1-(3-fluoromethylpyrrolidin-3-ylmethyl)carbamic acid tert-butyl ester (Li Q., Wang W., Berst K. B., Claiborne A., Hasvold L., Raye K., Tufano M., et al., *Bioorg. Med. Chem. Lett.,* 1998; 8:1953–1958) using General Method A.

(t) [trans-(3-Amino-1-cyclopropyl-6-fluoro-8-methoxy-2,4-dioxo-1,2,3,4-tetrahydroquinazolin-7-yl)-4-trifluoromethylpyrrolidin-3ylmethyl]carbamic acid tert-butyl ester ($^1$H NMR (200 MHz, CDCl$_3$): δ 7.56 (d, 1H), 5.17 (s, 2H), 4.75 (bs, 1H), 3.97–3.68 (m, 3H), 3.57 (s, 3H), 3.51–3.13 (m, 4H), 2.98–2.60 (m, 2H), 1.45 (s, 9H), 1.20–1.08 (m, 2H), 0.71–0.55 (m, 2H)) from 3-amino-1-cyclopropyl-6,7-difluoro-8-methoxy-1H-quinazoline-2,4-dione (Example 24d) and [trans-(4-trifluoromethylpyrrolidin-3-ylmethyl]carbamic acid tert-butyl ester (Li Q., Wang W., Berst K. B., Claiborne A., Hasvold L., Raye K., Tufano M., et al., *Bioorg. Med. Chem. Lett.,* 1998; 8:1953–1958) using General Method A.

(u) {1-[1-(3-Amino-1-cyclopropyl-6-fluoro-8-methoxy-2,4-dioxo-1,2,3,4-tetrahydroquinazolin-7-yl)piperidin-3-yl]ethyl}carbamic acid tert-butyl ester (MS (ES, M+1) m/z 492 (M$^+$)) from 3-amino-1-cyclopropyl-6,7-difluoro-8-methoxy-1H-quinazoline-2,4-dione (Example 24d) and (1-piperidin-3-ylethyl)carbamic acid tert-butyl ester (Example A5e) using General Method A.

(v) {1-[1-(3-Amino-1-cyclopropyl-6-fluoro-8-methyl-2,4-dioxo-1,2,3,4-tetrahydroquinazolin-7-yl)piperidin-3-yl]ethyl}carbamic acid tert-butyl ester (MS ES: m/z 476 (MH$^+$)) from 3-amino-1-cyclopropyl-6,7-difluoro-8-methyl-1H-quinazoline-2,4-dione (Example 24e) and 1-(piperidin-3-yl)ethylcarbamic acid tert-butyl ester (Example A5e) using General Method A.

(w) {1-[1-(3-Amino-1-cyclopropyl-6-fluoro-8-methoxy-2,4-dioxo-1,2,3,4-tetrahydroquinazolin-7-yl)-4,4-dimethylpyrrolidin-3-yl]ethyl}carbamic acid tert-butyl ester (MS ES: m/z 506 (MH$^+$)) from 3-amino-1-cyclopropyl-6,7-difluoro-8-methoxy-1H-quinazoline-2,4-dione (Example 24d) and [1-(4,4-dimethylpyrrolidin-3-yl)ethyl]carbamic acid tert-butyl ester (Example A5f) using General Method A.

(x) {1-[1-(3-Amino-1-cyclopropyl-6-fluoro-8-methyl-2,4-dioxo-1,2,3,4-tetrahydroquinazolin-7-yl)-4,4-dimethylpyrrolidin-3-yl]ethyl}carbamic acid tert-butyl ester (MS ES: m/z 490 (MH$^+$)) from 3-amino-1-cyclopropyl-6,7-difluoro-8-methyl-1H-quinazoline-2,4-dione (Example 24e) and [1-(4,4-dimethylpyrrolidin-3-yl)ethyl]carbamic acid tert-butyl ester (Example A5f) using General Method A.

(y) {1-[1-(3-Amino-1-cyclopropyl-6-fluoro-8-methyl-2,4-dioxo-1,2,3,4-tetrahydroquinazolin-7-yl)-4-methylpyrrolidin-3-yl]ethyl}carbamic acid tert-butyl ester (MS ES: m/z 476 (MH$^+$)) from 3-amino-1-cyclopropyl-6,7-difluoro-8-methyl-1H-quinazoline-2,4-dione (Example 24e) and [1-(4-methylpyrrolidin-3-yl)ethyl]carbamic acid tert-butyl ester (Example A5g) using General Method A.

(z) [1-(3-Amino-1-cyclopropyl-6-fluoro-8-methyl-2,4-dioxo-1,2,3,4-tetrahydroquinazolin-7-yl)-3-phenylpyrrolidin-3-yl]carbamic acid tert-butyl ester ($^1$H NMR (200 MHz, CDCl$_3$): δ 7.61 (d, 1H), 7.50–7.12 (m, 5H), 5.19 (bs, 2H), 4.07–3.70 (m, 3H), 3.62–3.34 (m, 2H), 2.68–2.52 (m, 1H), 2.45 (s, 3H), 1.68 (m, 2H), 1.50–0.95 (m, 11H), 0.62 (m, 2H)) from 3-amino-1-cyclopropyl-6,7-difluoro-8-methyl-1H-quinazoline-2,4-dione (Example 24e) and (3-phenylpyrrolidin-3-yl)carbamic acid tert-butyl ester (Example A30) (using General Method A).

(aa) [1-(3-Amino-1-cyclopropyl-6-fluoro-8-methyl-2,4-dioxo-1,2,3,4-tetrahydroquinazolin-7-yl)-3-phenylpyrrolidin-3-ylmethyl]carbamic acid tert-butyl ester ($^1$H NMR (200 MHz, CDCl$_3$): δ 7.68 (d, 1H), 7.50–7.29 (m, 5H), 6.72 (s, 1H), 5.24 (s, 2H), 4.18–3.85 (m, 3H), 3.78–3.52 (m, 2H), 2.70 (m, 1H), 2.58–2.39 (m, 4H), 1.62–0.62 (m, 15H) from 3-amino-1-cyclopropyl-6,7-difluoro-8-methyl-1H-quinazoline-2,4-dione (Example 24e) and (3-phenylpyrrolidin-3-ylmethyl)carbamic acid tert-butyl ester (Example A5p) using General Method A.

(bb) [5-(3-Amino-1-cyclopropyl-6-fluoro-8-methyl-2,4-dioxo-1,2,3,4-tetrahydroquinazolin-7-yl)-5-azaspiro[2.4]hept-7-ylmethyl]carbamic acid tert-butyl ester (MS ES: m/z 474 (MH$^+$)) from 3-amino-1-cyclopropyl-6,7-difluoro-8-methyl-1H-quinazoline-2,4-dione (Example 24e) and (5-azaspiro[2,4]hept-7-ylmethyl)carbamic acid tert-butyl ester (Example A5h) using General Method A.

(cc) [5-(3-Amino-1-cyclopropyl-6-fluoro-8-methoxy-2,4-dioxo-1,2,3,4-tetrahydroquinazolin-7-yl)-5-azaspiro[2.4]hept-7-ylmethyl]carbamic acid tert-butyl ester (MS ES: m/z 490 (MH$^+$)) from 3-amino-1-cyclopropyl-6,7-difluoro-8-methoxy-1H-quinazoline-2,4-dione (Example 24d) and 5-azaspiro[2,4]hept-7-ylmethyl)carbamic acid tert-butyl ester (Example A5h) using General Method A.

(dd) [1-(3-Amino-1-cyclopropyl-6-fluoro-8-methoxy-2,4-dioxo-1,2,3,4-tetrahydroquinazolin-7-yl)-3-hydroxypyrrolidin-3-ylmethyl]carbamic acid tert-butyl ester (MS ES: m/z 480 (MH$^+$)) from 3-amino-1-cyclopropyl-6,7-difluoro-8-methoxy-1H-quinazoline-2,4-dione (Example 24d) and (3-hydroxypyrrolidin-3-ylmethyl)carbamic acid tert-butyl ester (Example A5i) using General Method A.

(ee) [1-(3-Amino-1-cyclopropyl-6-fluoro-8-methyl-2,4-dioxo-1,2,3,4-tetrahydroquinazolin-7-yl)piperidin-3-ylmethyl]carbamic acid tert-butyl ester (REF) (MS ES: m/z 462 (MH+)) from 3-amino-1-cyclopropyl-6,7-difluoro-8-methyl-1H-quinazoline-2,4-dione (Example 24e) and (piperidin-3-ylmethyl)carbamic acid tert-butyl ester (Hilpert K., Ackermann J., Banner D. W., Gast A., Gubernator K., Hadvary P., Labler L., et al., *J. Med. Chem.,* 1994; 37[23]: 3889–3901) using General Method A.

(ff) [1-(3-Amino-1-cyclopropyl-6-fluoro-8-methyl-2,4-dioxo-1,2,3,4-tetrahydroquinazolin-7-yl)-4-methoxypyrrolidin-3-yl]carbamic acid tert-butyl ester ($^1$H NMR (200 MHz, CDCl$_3$): δ 7.60–7.54 (d, 1H), 5.16 (s, 2H), 4.82 (s, 1H), 4.20–3.85 (m, 5H), 3.42 (s, 3H), 3.23 (t, 2H), 2.41 (s, 3H), 1.47 (s, 9H), 1.18–1.10 (m, 2H), 0.61 (s, 2H)) from 3-amino-1-cyclopropyl-6,7-difluoro-8-methyl-1H-quinazoline-2,4-dione (Example 24e) and 4-(methoxypyrrolidin-3-yl)carbamic acid tert-butyl ester (Li Q., Cooper C. S., Anthony K. L., Lee C. M., Plattner J. J., Ma Z., Wang W., 1996, WO 9639407) using Method A.

(gg) [1-(3-Amino-1-cyclopropyl-6-fluoro-8-methoxy-2,4-dioxo-1,2,3,4-tetrahydroquinazolin-7-yl)-4-methoxypyrrolidin-3-yl]carbamic acid tert-butyl ester ($^1$H NMR (200 MHz, CDCl$_3$): δ 7.21 (d, 1H), 5.23–5.14 (m, 3H), 4.33–3.22 (m, 13H), 1.40 (s, 9H), 1.18 (m, 2H), 0.60 (s, 2H)) from 3-amino-1-cyclopropyl-6,7-difluoro-8-methoxy-1H-quinazoline-2,4-dione (Example 24d) and 4-(methoxypyrrolidin-3-yl)carbamic acid tert-butyl ester (Li Q., Cooper C. S., Anthony K. L., Lee C. M., Plattner J. J., Ma Z., Wang W., 1996, WO 9639407) using Method A.

(hh) [1-(3-Amino-1-cyclopropyl-6-fluoro-8-methoxy-2,4-dioxo-1,2,3,4-tetrahydroquinazolin-7-yl)-4-fluoropyrrolidin-3-yl]carbamic acid tert-butyl ester ($^1$H NMR (200 MHz, DMSO-d$_6$): δ 7.40–7.34 (d, 1H), 5.30–4.80 (m, 3H) 4.50–3.10 (m, 10H), 1.47 (s, 9H), 1.30–0.50 (m, 4H)) from 3-amino-1-cyclopropyl-6,7-difluoro-8-methoxy-1H-quinazoline-2,4-dione (Example 24d) and 4-(fluoropyrrolidin-3-yl)carbamic acid tert-butyl ester (Li Q., Wang W., Berst K. B., Claiborne A., Hasvold L., Raye K., Tufano M., et al., *Bioorg. & Med. Chem. Lett.,* 1998; 8:1953–1958) using General Method A.

(ii) [1-(3-Amino-1-cyclopropyl-6-fluoro-8-methyl-2,4-dioxo-1,2,3,4-tetrahydroquinazolin-7-yl)-3-methylpyrrolidin-3-ylmethyl]carbamic acid tert-butyl ester (MS ES: m/z 462 (MH+)) from 3-amino-1-cyclopropyl-6,7-difluoro-8-methyl-1H-quinazoline-2,4-dione (Example 24e) and (3-methylpyrrolidin-3-ylmethyl)carbamic acid tert-butyl ester (*J. Med. Chem*, 1992:361–367) using General Method A.

(jj) {(S)-1-[(R)-1-(3-Amino-1-cyclopropyl-8-ethyl-6-fluoro-2,4-dioxo-1,2,3,4-tetrahydroquinazolin-7-yl)pyrrolidin-3-yl]ethyl}carbamic acid tert-butyl ester (MS ES: m/z 476 (MH+)) from 3-amino-1-cyclopropyl-8-ethyl-6,7-difluoro-1H-quinazoline-2,4-dione (Example 24g) and ((R)-[(S)-1-pyrrolidin-3-yl-ethyl)ethyl]carbamic acid tert-butyl ester using General Method A.

(kk) 1-(3-Amino-1-cyclopropyl-6-fluoro-8-methoxy-2,4-dioxo-1,2,3,4-tetrahydroquinazolin-7-yl)pyrrolidine-3-carboxylic acid tert-butyl ester ($^1$H NMR (200 MHz, CDCl$_3$): δ 7.51 (d, 1H), 5.15 (s, 2H), 3.88–3.58 (m, 4H), 3.50 (s, 3H), 3.42–3.30 (m, 1H), 3.14–3.02 (m, 1H), 2.25–2.17 (m, 2H), 1.48 (s, 9H), 1.14–1.05 (m, 2H), 0.68–0.61 (m, 2H)) from 3-amino-1-cyclopropyl-6,7-difluoro-8-methoxy-1H-quinazoline-2,4-dione (Example 24d) and pyrrolidine-3-carboxylic acid tert-butyl ester (Hayakawa I., Tanaka Y., EP 101829) using General Method A.

(ll) 1-(3-Amino-1-cyclopropyl-6-fluoro-8-methyl-2,4-dioxo-1,2,3,4-tetrahydroquinazolin-7-yl)pyrrolidine-3-carboxylic acid tert-butyl ester ($^1$H NMR (200 MHz, CDCl$_3$): δ 7.61 (d, 1H), 5.16 (s, 2H), 3.70–3.40 (m, 5H), 3.17–3.03 (m, 1H), 2.43 (s, 3H), 2.29–2.19 (m, 2H), 1.47 (s, 9H), 1.22–1.12 (m, 2H), 0.67–0.57 (m, 2H)) from 3-amino-1-cyclopropyl-6,7-difluoro-8-methyl-1H-quinazoline-2,4-dione (Example 24e) and pyrrolidine-3-carboxylic acid tert-butyl ester (Hayakawa I., Tanaka Y., EP 101829) using General Method A.

(mm) [3-(3-Amino-1-cyclopropyl-6-fluoro-8-methoxy-2,4-dioxo-1,2,3,4-tetrahydroquinazolin-7-yl)-3-azabicyclo[3.1.0]hex-1-ylmethyl]yl]carbamic acid tert-butyl ester ($^1$H NMR (200 MHz, CDCl$_3$): δ 7.53 (d, 1H), 5.31 (bs, 2H), 4.73 (bs, 1H), 3.82–3.01 (m, 11H), 1.45 (s, 9H), 1.42–1.34 (m, 1H), 1.14–1.10 (m, 3H), 0.71–0.63 (m, 2H)), from 3-amino-1-cyclopropyl-6,7-difluoro-8-methoxy-1H-quinazoline-2,4-dione (Example 24d) and (3-azabicyclo[3.1.0]hex-1-ylmethyl)carbamic acid tert-butyl ester (Example A5j) using General Method A.

(nn) [3-(3-Amino-1-cyclopropyl-6-fluoro-8-methyl-2,4-dioxo-1,2,3,4-tetrahydroquinazolin-7-yl)-3-azabicyclo[3.1.0]hex-1-ylmethyl]yl]carbamic acid tert-butyl ester (MS ES: m/z 460) from 3-amino-1-cyclopropyl-6,7-difluoro-8-methyl-1H-quinazoline-2,4-dione (Example 24e) and (3-azabicyclo[3.1.0]hex-1-ylmethyl)carbamic acid tert-butyl ester (Example A5j) using General Method A.

(oo) {(R)-1-[(S)-1-(3-Amino-1-cyclopropyl-6-fluoro-8-methoxy-2,4-dioxo-1,2,3,4-tetrahydroquinazolin-7-yl)pyrrolidin-3-yl]ethyl}carbamic acid tert-butyl ester (MS ES: m/z 478 (MH+)) from 3-amino-1-cyclopropyl-6,7-difluoro-8-methoxy-1H-quinazoline-2,4-dione (Example 24d) and (R)-1-((S)-pyrrolidine-3-yl)ethyl)carbamic acid tert-butyl ester (Schroeder M. C., Kiely J. S., Johnson D. R., Szotek D. L., Domagala J. M., Stickney T. M., Kampf J. W., *J. Heterocyclic Chem.*, 1992; 29:1481) using General Method A.

(pp) {(R)-1-[(S)-1-(3-Amino-1-cyclopropyl-6-fluoro-8-methoxy-2,4-dioxo-1,2,3,4-tetrahydroquinazolin-7-yl)pyrrolidin-3-yl]ethyl}carbamic acid tert-butyl ester $^1$H NMR (200 MHz, CDCl$_3$): δ 7.51–7.44 (d, 1H), 5.17 (bs, 2H), 4.62 (bs, 0.5H), 4.58 (bs, 0.5H), 3.79–3.74 (m, 3H), 3.61–3.53 (m, 2H), 3.49 (s, 3H), 3.41–3.32 (m, 1H), 2.22–2.06 (m, 2H), 1.87–1.67 (m, 1H), 1.46 (s, 9H), 1.23–1.19 (d, 3H), 1.08–1.02 (m, 2H) 0.76–0.62 (m, 2H).(MS ES: m/z 462) from 3-amino-1-cyclopropyl-6,7-difluoro-8-methoxy-1H-quinazoline-2,4-dione (Example 24d) and (R)-1-((S)-pyrrolidine-3-yl)ethyl)carbamic acid tert-butyl ester using General Method A.

(qq) 6-(3-Amino-1-cyclopropyl-6-fluoro-8-methyl-2,4-dioxo-1,2,3,4-tetrahydroquinazolin-7-yl)octahydropyrrolo[3,4-b]pyridine-1-carboxylic acid tert-butyl ester ($^1$H NMR (200 MHz, CDCl$_3$): δ 7.61–7.55 (d, 1H), 5.16 (bs, 2H), 4.52 (bs, 0.5H), 4.48 (bs, 0.5H), 4.95–3.38 (m, 6H), 2.40 (s, 3H), 2.36–1.83 (m, 3H), 1.46 (s, 9H), 1.21–1.17 (m, 5H), 0.65–0.57 (m, 2H), from 3-amino-1-cyclopropyl-6,7-difluoro-8-methyl-1H-quinazoline-2,4-dione (Example 24e) and octahydropyrrolo[3,4-b]pyridine-5-carboxylic acid tert-butyl ester using General Method A.

(rr) [(trans)-1-(3-Amino-1-cyclopropyl-6-fluoro-8-methoxy-2,4-dioxo-1,2,3,4-tetrahydroquinazolin-7-yl)-4-methylpyrrolidin-3-ylmethyl]carbamic acid tert-butyl ester (MS ES: m/z 478 (MH+)) from 3-amino-1-cyclopropyl-6,7-difluoro-8-methoxy-1H-quinazoline-2,4-dione (Example 24d) and (trans-4-methylpyrrolidin-3-ylmethyl)carbamic acid tert-butyl ester (Kuniyoshi M., Seigo S., Keiji H., Takayoshi I., Eur. Pat. Appl. EP 208210, 1987) using General Method A.

(ss) [1-(3-Amino-1-cyclopropyl-6-fluoro-8-methyl-2,4-dioxo-1,2,3,4-tetrahydroquinazolin-7-yl)-4-methylpyrrolidin-3-ylmethyl]carbamic acid tert-butyl ester (MS ES: m/z 462 (MH+)) from 3-amino-1-cyclopropyl-6,7-difluoro-8-methyl-1H-quinazoline-2,4-dione (Example 24e) and (4-methylpyrrolidin-3-ylmethyl)carbamic acid tert-butyl ester (Kuniyoshi M., Seigo S., Keiji H., Takayoshi I., Eur. Pat. Appl. EP 208210, 1987) using General Method A.

(tt) [1-(3-Amino-1-cyclopropyl-6-fluoro-8-methoxy-2,4-dioxo-1,2,3,4-tetrahydroquinazolin-7-yl)-4-methylpyrrolidin-3-yl]carbamic acid tert-butyl ester (MS ES: m/z 464 (MH+)) from 3-amino-1-cyclopropyl-6,7-difluoro-8-methoxy-1H-quinazoline-2,4-dione (Example 24d) and (4-methylpyrrolidin-3-yl)carbamic acid tert-butyl ester (Di Cesare P., Bouzard D., Essiz M., Jacquet J. P., Ledoussai B., Kiechet J. R., Remuzon P. et al., *J. Med. Chem.*, 1992,35:4205) using General Method A.

(uu) [1-(3-Amino-1-cyclopropyl-6-fluoro-8-methoxy-2,4-dioxo-1,2,3,4-tetrahydroquinazolin-7-yl)morpholin-3-ylmethyl]carbamic acid tert-butyl ester (MS ES: m/z 480 (MH+)) from 3-amino-1-cyclopropyl-6,7-difluoro-8-methoxy-1H-quinazoline-2,4-dione (Example 24d) and I-(morpholin-3-ylmethyl)carbamic acid tert-butyl ester (Araki K., Kuroda T., Uemori S., Moriguchi A., Ikeda Y., Hirayama F., Yokoyama Y. et al., *J. Med. Chem.*, 1993,36:1356) using General Method A.

(vv) [1-(3-Amino-1-cyclopropyl-6-fluoro-8-methoxy-2,4-dioxo-1,2,3,4-tetrahydroquinazolin-7-yl)piperidin-3-ylmethyl]carbamic acid tert-butyl ester (MS ES: m/z 478 (MH+)) from 3-amino-1-cyclopropyl-6,7-difluoro-8-methoxy-1H-quinazoline-2,4-dione (Example 24d) and 1-piperidin-3-ylmethylcarbamic acid tert-butyl ester (Hilpert K., et al., *J. Med. Chem.*, 1994; 37(23):3889–3901) using General Method A.

(ww) {1-[1-(3-Amino-1-cyclopropyl-6-fluoro-8-methoxy-2,4-dioxo-1,2,3,4-tetrahydroquinazolin-7-yl)-4-methylpyrrolidin-3-yl]ethyl}carbamic acid tert-butyl ester (MS ES: m/z 492 (MH+)) from 3-amino-1-cyclopropyl-6,7-difluoro-8-methoxy-1H-quinazoline-2,4-dione (Example 24d) and [1-(4-methylpyrrolidin-3-yl)ethyl]carbamic acid tert-butyl ester (A5g) using General Method A.

(xx) [1-(1-Cyclopropyl-6-fluoro-8-methyl-2,4-dioxo-1,2,3,4-tetrahydroquinazolin-7-yl)-3-methylpyrrolidin-3-yl]]

carbamic acid tert-butyl ester (¹H NMR (200 MHz, CDCl₃): δ 7.61 (d, 1H), 5.15 (s, 2H), 4.74 (s, 1H), 3.71–3.37 (m, 6H), 2.45–2.20 (m, 4H), 1.45 (s, 12H), 1.21–1.08 (m, 2H), 0.61 (d, 2H)) from 3-amino-1-cyclopropyl-6,7-difluoro-8-methyl-1H-quinazoline-2,4-dione (Example 24e) and 3-methylpyrrolidin-3-ylcarbamic acid tert-butyl ester (Yoshida T., Yamamoto Y., Orita H., Kakiuchi M., Takahashi Y., Itakura M., Kado N. et al., *Chem. Pharm. Bull.,* 1996; 44[7]: 1376–1386) using General Method A (yy) 3-Amino-1-cyclopropyl-6-fluoro-8-methyl-7-pyrrolidin-1-yl-1H-quinazoline-2,4-dione (¹H NMR (200 MHz, CDCl₃): δ7.61–7.54 (d, 1H), 5.15 (bs, 2H), 3.51–3.40 (m, 5H), 2.39 (s, 3H), 2.01–1.95 (m, 4H), 1.21–1.11 (m, 2H), 0.67–0.62 (m, 2H)) from 3-amino-1-cyclopropyl-6,7-difluoro-8-methyl-1H-quinazoline-2,4-dione (Example 24e) and pyrrolidine using General Method A.

(zz) 3-Amino-1-cyclopropyl-6-fluoro-8-methoxy-7-pyrrolidin-1-yl-1H-quinazoline-2,4-dione (¹H NMR (200 MHz, CDCl₃): δ 7.49–7.42 (d, 1H), 5.13 (bs, 2H), 3.66–3.54 (m, 4H), 3.50 (s, 3H), 3.42–3.31 (m, 1H), 2.02–1.92 (m, 4H), 1.17–1.07 (m, 2H), 0.69–0.61 (m, 2H)) from 3-amino-1-cyclopropyl-6,7-difluoro-8-methoxy-1H-quinazoline-2,4-dione (Example 24d) and pyrrolidine using General Method A.

(aaa) 3-Amino-1-cyclopropyl-6-fluoro-7-[3-(1-hydroxyethyl-1-methyl)-pyrrolidin-1-yl]-8-methyl-1H-quinazoline-2,4-dione (¹H NMR (200 MHz, CDCl₃): δ 7.59 (d, 1H), 5.15 (s, 2H), 3.68–3.53 (m, 2H), 3.44–3.31 (m, 3H), 2.42 (s, 3H), 2.00–1.82 (m, 2H), 1.58 (s, 1H), 1.28 (s, 6H), 1.20–1.10 (m, 2H), 1.00–0.80 (m, 1H), 0.66–0.60 (m, 2H)) from 3-amino-1-cyclopropyl-6,7-difluoro-8-methyl-1H-quinazoline-2,4-dione (Example 24e) and 1-methyl-1-pyrrolidin-3-yl-ethanol (Example A5n) using General Method A.

(bbb) 3-Amino-1-cyclopropyl-6-fluoro-7-[3-(1-hydroxy-1-methylethyl)-pyrrolidin-1-yl]-8-methoxy-1H-quinazoline-2,4-dione (¹H NMR (200 MHz, CDCl₃): δ 7.50 (d, 1H), 5.14 (s, 2H), 3.86–3.70 (m, 2H), 3.49 (s, 3H), 3.60–3.30 (m, 3H), 2.40–2.22 (m, 1H), 2.00–1.80 (m, 2H), 1.30 (s, 6H), 1.09–0.85 (m, 2H), 0.75–0.57 (m, 2H)) from 3-amino-1-cyclopropyl-6,7-difluoro-8-methoxy-1H-quinazoline-2,4-dione (Example 24d) and 1-methyl-1-pyrrolidin-3-yl-ethanol (Example A5n) using General Method A.

(ccc) 1-[(R)-1-(3-(S)-Amino-1-cyclopropyl-6-fluoro-5-methyl-7-[3-(1-methylaminoethyl)pyrrolidin-1-yl]-1H-quinazoline-2,4-dione (MS ES: m/z 376 (MH⁺)) from 3-amino-1-cyclopropyl-6,7-difluoro-5-methyl-1H-quinazoline-2,4-dione (Example 24e) and methyl-((R)-((S)-1-pyrrolidin-3-yl)ethyl)amine using General Method A.

(ddd) 1-[(R)-1-(3-(S)-Amino-1-cyclopropyl-7-[3-(1-ethylaminoethyl)-pyrrolidin-1-yl]-6-fluoro-8-methoxy-1H-quinazoline-2,4-dione (MS ES: m/z 406 (MH⁺)) from 3-amino-1-cyclopropyl-6,7-difluoro-8-methoxy-1H-quinazoline-2,4-dione (Example 24d) and ethyl-((R)-((S)-1-pyrrolidin-3-yl)ethyl)amine (Domagala J. M., Hagen S. E., Joannides T., Kiely J. S., Laborde E., Schroeder M. C., Sesnie J. A., et al., *J. Med. Chem.,* 1993; 36[7]:871–882) using General Method A.

(eee) 3-Amino-1-cyclopropyl-7-[(R)-3-((S)-1-ethylaminoethyl)-pyrrolidin-1-yl]-6-fluoro-8-methyl-1H-quinazoline-2,4-dione (MS ES: m/z 390 (MH⁺)) from 3-amino-1-cyclopropyl-6,7-difluoro-8-methyl-1H-quinazoline-2,4-dione (Example 24e) and ethyl-((R)-((S)-1-pyrrolidin-3-yl)ethyl)amine using General Method A.

(fff) 3-Amino-7-(6-amino-1-methyl-3-azabicyclo[3.2.0]hept-3-yl)-1-cyclopropyl-6-fluoro-8-methoxy-1H-quinazoline-2,4-dione (MS ES: m/z 390 (MH⁺)) from 3-amino-1-cyclopropyl-6,7-difluoro-8-methoxy-1H-quinazoline-2,4-dione (Example 24d) and 1-methyl-3-azabicyclo[3.2.0]hept-6-ylamine (Kim C. S., Kim J. W., Lee J. M., Youn Y. S., Shin Y. J., Lee K. H., Kim J. H. WO 94/15933) using General Method A.

(ggg) 3-Amino-7-(3-aminomethylazetidin-1-yl)-1-cyclopropyl-6-fluoro-8-methoxy-1H-quinazoline-2,4-dione (MS ES: m/z 350 (MH⁺)) from 3-amino-1-cyclopropyl-6,7-difluoro-8-methoxy-1H-quinazoline-2,4-dione (Example 24d) and azetidin-3-ylmethylamine (Okada T., Ezumi K., Yamakawa M., Sato H., Tsuji T., Tsushima T., Motokawa K., Komatsu Y., *Chem. Pharm. Bull.,* 1993; 41:126–131) using General Method A.

(hhh) 3-Amino-7-(4-aminomethylpiperidin-1-yl)-1-cyclopropyl-6-fluoro-8-methoxy-1H-quinazoline-2,4-dione (MS ES: m/z 378 (MH⁺)) from 3-amino-1-cyclopropyl-6,7-difluoro-8-methoxy-1H-quinazoline-2,4-dione (Example 24d) and piperidin-4-ylmethylamine using General Method A.

(iii) [(cis)-1-(3-Amino-1-cyclopropyl-6-fluoro-8-methoxy-2,4-dioxo-1,2,3,4-tetrahydroquinazolin-7-yl)-4-fluoropyrrolidin-3-ylmethyl]carbamic acid tert-butyl ester (MS ES: m/z 482 (MH⁺)) from 3-amino-1-cyclopropyl-6,7-difluoro-8-methoxy-1H-quinazoline-2,4-dione (Example 24d) and (cis-4-fluoropyrrolidin-3-ylmethyl)carbamic acid tert-butyl ester [A5k]) using General Method A.

(jjj) [(trans)-1-(3-Amino-1-cyclopropyl-6-fluoro-8-methoxy-2,4-dioxo-1,2,3,4-tetrahydroquinazolin-7-yl)-4-fluoropyrrolidin-3-ylmethyl]carbamic acid tert-butyl ester (MS ES: m/z 482 (MH⁺)) from 3-amino-1-cyclopropyl-6,7-difluoro-8-methoxy-1H-quinazoline-2,4-dione (Example 24d) and (trans-4-methylpyrrolidin-3-ylmethyl)carbamic acid tert-butyl ester [A5l] using General Method A.

(kkk) [1-(3-amino-1-cyclopropyl-6-fluoro-8-methoxy-2,4-dioxo-1,2,3,4-tetrahydroquinazolin-7-yl)-(1-amino-5-azaspiro[2.4]hept-5-yl)]carbamic acid tert-butyl ester (MS APCI: m/z 476 (MH⁺)) from 3-amino-1-cyclopropyl-6,7-difluoro-8-methoxy-1H-quinazoline-2,4-dione (Example 14d) and 1-amino-5-aza-spiro[2.4]hept-5-yl)]carbamic acid tert-butyl ester (Li Q., Chu D. T. W., Claiborne A., Cooper C. S., Lee C. M., Raye K., Berst K. B., et al., *J. Med. Chem.,* 1996; 39[16]:3070–3088) using General Method C.

(lll) [1-(3-Amino-7-(3a-aminomethyloctahydroisoindol-2-yl)-1-cyclopropyl-6-fluoro-8-methoxy-2,4-dioxo-1,2,3,4-tetrahydroquinazolin-7-yl]carbamic acid tert-butyl ester (MS APCI: m/z 518 (MH⁺)) from 3-amino-1-cyclopropyl-6,7-difluoro-8-methoxy-1H-quinazoline-2,4-dione (Example 24d) and (3a-aminomethyloctahydro-isoindol-2-yl)carbamic acid tert-butyl ester (Ma Z., Chu D. T. W., Cooper C. S., Li Q., Fung A. K. L., Wang S., Shen L. L., et al., *J. Med. Chem.,* 1999; 42(20):4202–4213) using General Method C.

(mmm) 3-Amino-7-(3a-aminomethyloctahydroisoindol-2-yl)-1-cyclopropyl-6-fluoro-8-methyl-1H-quinazoline-2,4-dione (MS APCI: m/z 502 (MH⁺)) from 3-amino-1-cyclopropyl-6,7-difluoro-8-methyl-1H-quinazoline-2,4-dione (Example 24e) and 3a-aminomethyloctahydroisoindol-2-yl-carbamic acid-tert-butyl ester (Ma Z., Chu D. T. W., Cooper C. S., Li Q., Fung A. K. L., Wang S., Shen L. L., et al., *J. Med. Chem.,* 1999; 42(20); 4202–4213) using General Method C.

(nnn) {(S)-1-[(R)-1-(3-amino-1-cyclopropyl-6-fluoro-8-methoxy-2,4-dioxo-1,2,3,4-tetrahydroquinazolin-7-yl)pyrrolidin-3-yl]ethyl}carbamic acid tert-butyl ester (MS APCI: m/z 476 (MH⁺)) from 3-amino-1-cyclopropyl-6,7-difluoro-8-methoxy-1H-quinazoline-2,4-dione (Example 14d) and ((R)-(S)-1-pyrrolidin-3-yl)ethylcarbamic acid tert-butyl ester (*J. Het. Chem.*, 1992; 29:1481) using General Method C.

(ooo) {1-[1-(3-Amino-1-cyclopropyl-6-fluoro-8-methyl-2,4-dioxo-1,2,3,4-tetrahydro-quinazolin-7-yl)-pyrrolidin-3-yl]-propyl}-carbamic acid tert-butyl ester (MS: m/e 476 (MH$^+$)) from 3-amino-1-cyclopropyl-6,7-difluoro-8-methyl-1H-quinazoline-2,4-dione (Example 24e) and (1-pyrrolidin-3-yl-propyl)-carbamic acid tert-butyl ester (Kimura Y., Atarashi S., Takahashi M., Hayakkawa I., *Chem. Pharm. Bull.*, 1994; 42:1442) using General Method A.

(ppp) {(S)-1-[(R)-1-(3-Amino-1-cyclopropyl-6-fluoro-8-methyl-2,4-dioxo-1,2,3,4-tetrahydro-quinazolin-7-yl)pyrrolidin-3-yl]-ethyl}-methyl-carbamic acid dimethylethyl ester (MS: m/e 476 (MH$^+$)) from 3-amino-1-cyclopropyl-6,7-difluoro-8-methyl-1H-quinazoline-2,4-dione (Example 24e) and methyl-(R)-((S)-1-pyrrolidin-3-yl)ethylamine (Plummer J. S., Emery L. A., Stier M. A., Suto M. J., *Tetrahedron Lett.*, 1993; 34(47):7529–7532) using General Method A.

(qqq) {1-[5-(3-Amino-1-cyclopropyl-6-fluoro-8-methyl-2,4-dioxo-1,2,3,4-tetrahydroquinazolin-7-yl)-5-aza-spiro[2.4]hept-7-yl]ethyl}carbamic acid tert-butyl ester (MS CI: m/e 488 (MH$^+$)) from 3-amino-1-cyclopropyl-6,7-difluoro-8-methyl-1H-quinazoline-2,4-dione (Example 24e) and [1-(5-aza-spiro[2.4]hept-7-yl)ethyl]carbamic acid tert-butyl ester (Example A5a) using General Method A.

EXAMPLE 29

(7,8-Difluoro-3-methyl-2,3-dihydro-1,4-benzoxazin-4yl)-oxoacetaldehyde oxime

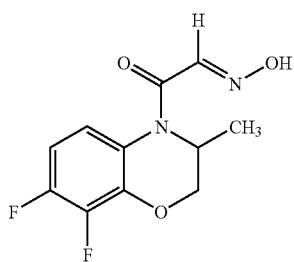

A solution of 8.27 g (50 mmol) of chloral hydrate in 125 mL of water is treated with 112.8 g (0.35 mmol) of sodium sulfate decahydrate. The mixture is stirred and treated with a solution of 7,8-difluoro-3-methyl-3,4-dihydro-2H-benz[1,4]oxazine (*Chem. Pharm. Bull.*, 1984; 32:4907) hydrochloride (prepared by dissolving 8.26 g (44.6 mmol) of the free base in 50 mmol of concentrated hydrochloric acid in 70 mL of 50% aqueous ethanol). The reaction is stirred and a solution of 9.8 g (140 mmol) of hydroxylamine hydrochloride in 50 mL of water is added. After heating at 75 to 80° C. for 3 hours, the reaction is stirred at room temperature overnight. The resulting precipitate is removed by filtration, washed with water, and the wet filter cake is dissolved in dichloromethane. The organic solution is washed with water, dried (MgSO$_4$), decolorized with charcoal, filtered and concentrated in vacuo to give 10.5 g of the title compound, mp 188–190° C.

EXAMPLE 30

Synthesis of 6,7-Difluoro-3-methyl-3,4-dihydro-5-oxa-2a-aza-acenaphthylene-1,2-dione

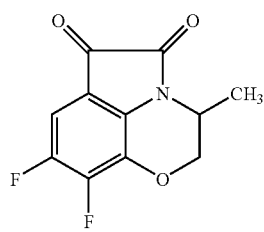

A solution of 45 mL of 98% sulfuric acid in 18 mL of water is heated to 50° C. to 60° C. and treated portionwise over 30 minutes with 10.5 g (41 mmol) of (7,8-difluoro-3-methyl-2,3-dihydro-1,4-benzoxazin-4-yl)oxoacetaldehyde oxime (Example 29). After the addition is complete, the reaction is heated to 80° C. for 15 minutes and poured onto 200 mL of ice and water. The mixture is stirred until the ice melts and the solid is removed by filtration, washed with water and the wet filter cake is dissolved in dichloromethane. The organic solution is washed with water (2×200 mL), dried (MgSO$_4$), filtered and concentrated in vacuo affording 7.1 g of the title compound, mp 169–171° C.

EXAMPLE 31

Synthesis of 7,8-Difluoro-3-methyl-3,4-dihydro-2H-1,4-benzoxazine-5-carboxylic acid

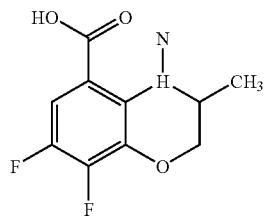

A suspension of 6.9 g (28.8 mmol) of 6,7-difluoro-3-methyl-3,4-dihydro-5-oxa-2a-aza-acenaphthylene-1,2-dione (Example 30) in 250 mL of 4.5% aqueous sodium hydroxide is treated dropwise with 16.4 mL of 30% hydrogen peroxide over 1 hour. The reaction is filtered to remove a trace of insoluble material and the filtrate is acidified to pH 4.5 with acetic acid. After cooling to 5° C., the precipitate is removed by filtration, washed with water and dried in vacuo to give 5.5 g of the title compound, mp 200–202° C.

EXAMPLE 32

Synthesis of Anthranilic Esters (a) 7,8-Difluoro-3-methyl-3,4-dihydro-2H-1,4-benzoxazine-5-carboxylic

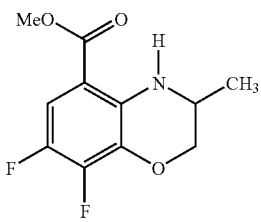

A solution of 2.1 g (9.1 mmol) of 7,8-difluoro-3-methyl-3,4-dihydro-2H-1,4-benzoxazine-5-carboxylic acid (Example 31) in 50 mL of methanol is cooled to 0° C. and saturated with hydrogen chloride gas. The reaction is stirred at room temperature for 18 hours, recooled to 0° C. and resaturated with hydrogen chloride gas. After stirring an additional 24 hours at room temperature, the solvent is removed in vacuo and the residue is partitioned between dichloromethane/5% aqueous sodium bicarbonate (200:100 mL). The organic layer is separated, washed with 5% aqueous sodium bicarbonate, water, dried (MgSO4), filtered, and concentrated in vacuo affording 1.9 g of the title compound. $^1$H NMR (400 MHz, CDCl$_3$): 7.27 (bs, 1H), 7.24 (m, 1H), 4.26 (m, 1H), 3.82 (s, 3H), 3.75 (m, 1H), 3.62 (m, 1H), 1.22 (d, 3H).

(b) Synthesis of 5,6-Difluoro-2-methyl-1,2,3,4-tetrahydro-quinoline-8-carboxylic acid methyl ester

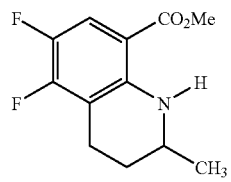

A solution of 8.0 g (33.7 mmol) of 5,6-difluoro-2-methylquinoline-8-carboxylic acid methyl ester (Example 33) in 100 mL of glacial acetic acid is treated with 2.15 g of platinum on carbon (0.8 g of active catalyst+62.8% water) and then shaken in a hydrogen atmosphere at temperatures of 24° C. to 29° C. and pressures of 23.9 to 46.6 psi for 3 hours. The catalyst is removed by filtration and the solvent is removed in vacuo at 50° C. The residue is triturated with water (50 mL) and extracted with dichloromethane (2×200 mL). The combined organic layers are stirred with 5% sodium bicarbonate solution, washed with water, dried (MgSO$_4$), filtered and evaporated in vacuo. The residue is chromatographed over flash grade silica gel (230–400 mesh) eluting with dichloromethane to give 5.6 g of the title compound as a light yellow oil. $^1$H NMR (400 MHz, CDCl$_3$): 7.66 (bs, 1H), 7.49 (m, 1H), 3.82 (s, 3H), 3.46 (m, 1H), 2.88 (m, 1H), 2.67 (m, 1H), 1.97 (m, 1H), 1.27 (d, 3H).

EXAMPLE 33

Synthesis of 5,6-Difluoro-2-methylquinoline-8-carboxylic acid methyl ester

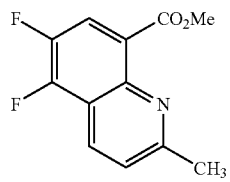

In a stainless steel reactor, a solution of 9.53 g (36.9 mmol) of 8-bromo-5,6-difluoro-2-methylquinoline (Chem. Pharm. Bull., 1996; 44:642), 6.8 g (67.6 mmol) of triethylamine, 0.67 g (3.0 mmol) of palladium (II) acetate, 1.28 g (3.1 mmol) of 1,3-bis(diphenyl-phosphino)propane in 90 mL of dimethylformamide and 65 mL of methanol is flushed with nitrogen gas and pressurized to 550 psi with carbon monoxide. The reaction is rocked and heated to 75° C. for 24 hours, cooled to room temperature and evaporated in vacuo. The residue is triturated with water (50 mL) and extracted with dichloromethane (2×200 mL). The combined organic layers are washed with water (2×50 mL), dried (MgSO$_4$), filtered and evaporated in vacuo. The residue is chromatographed over flash grade silica gel (230–400 mesh) eluting with dichloromethane (200 mL), then dichloromethane/ethyl acetate (90:10) to give 8.0 g of the title compound, mp 99–101° C.

EXAMPLE 34

Synthesis of 2-cyclopropylamino-5-fluoro-6-methylsulfanylnicotinic acid ethyl ester

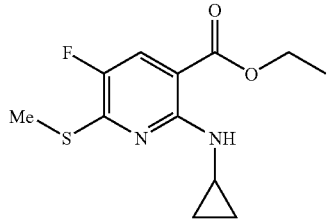

A solution of 8.7 g (34.8 mmol) of 2-chloro-5-fluoro-6-methylsulfanylnicotinic acid ethyl ester (J. Med. Chem., 1993; 36:2676) and 5.7 g (100 mmol) of cyclopropylamine in 100 mL of acetonitrile is heated at reflux for 18 hours. After TLC showed the presence of unreacted starting material, 4.12 g (72 mmol) of cyclopropylamine is added and the reaction mixture is refluxed for 48 hours. The solvent is removed in vacuo and the residue is partitioned between dichloromethane (250 mL) and water (100 mL). The organic layer is washed with water, dried (MgSO$_4$), filtered, and concentrated in vacuo. The residue is chromatographed over flash grade silica gel (230–400 mesh) eluting with dichloromethane to give 6.5 g of the title compound, mp 67–69° C.

EXAMPLE 35

Synthesis of 1-Cyclopropyl-6-fluoro-2,4-dioxo-1,2,3,4-tetrahydropyrido[2,3-d]pyrimidine-7-thiosulfonic acid)

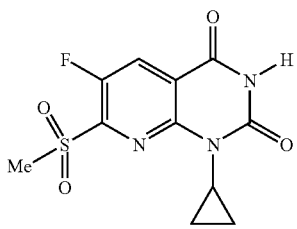

A solution of 0.65 g (2.4 mmol) of 1-cyclopropyl-6-fluoro-7-methylsulfanyl-1H-pyrido[2,3-d]pyrimidine-2,4-dione (Example 23e) in 20 mL of formic acid is treated with 1.83 g (19.5 mmol) of urea-hydrogen peroxide and the reaction mixture is stirred at room temperature overnight. The resulting precipitate is removed by filtration, washed with water, ethyl acetate and dried in vacuo to give 0.63 g of the title compound, mp 300–302° C.

EXAMPLE 36

Synthesis of {8-Chloro-1-cyclopropyl-6-fluoro-7-[3-(methanesulfonylamino-methyl)pyrrolidin-1-yl]-2,4-dioxo-1,4-dihydro-2H-quinazolin-3-yl}carbamic acid tert-butyl ester

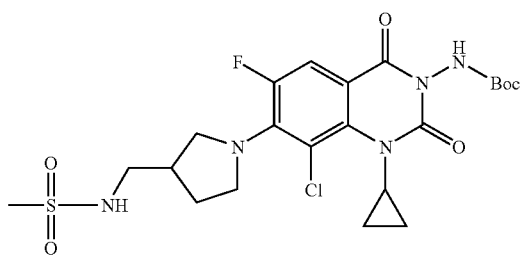

A solution of (8-chloro-1-cyclopropyl-6,7-difluoro-2,4-dioxo-1,4-dihydro-2H-quinazolin-3-yl)carbamic acid tert-butyl ester (Example 14, 0.37 g, 0.97 mmol) in acetonitrile (20 mL) is added pyrrolidin-3-yl-methylamine (0.115 g, 1.16 mmol) and triethylamine (2.7 mL, 19.3 mmol). After refluxing for 20 hours, the reaction mixture is cooled to room temperature and diluted with ethyl acetate. The organic layer is washed with saturated sodium bicarbonate, water, and brine. The organic layer is dried over MgSO$_4$, filtered, and the filtrate concentrated. The resulting residue is redissolved in methylene chloride (10 mL) at 0° C. and while stirring, triethylamine (0.33 mL, 2.34 mmol) and methanesulfonyl chloride (0.072 mL, 0.94 mmol) is added. After 2 hours, the reaction mixture is diluted with ethyl acetate and washed with saturated sodium bicarbonate, water, and brine. The organic layer is dried over MgSO$_4$, filtered, and the filtrate concentrated and the product is purified via flash column chromatography (1:1 EtOAc/hexanes) to afford {8-chloro-1-cyclopropyl-6-fluoro-7-[3-(methanesulfonylaminomethyl)pyrrolidin-1-yl]-2,4-dioxo-1,4-dihydro-2H-quinazolin-3-yl}carbamic acid tert-butyl ester (0.043 g). MS CI: m/e 446 ((MH$^+$)-Boc).

Amine Side Chain Synthesis

EXAMPLE A1

(a) 5-Benzyl-5-azaspiro[2,4]heptan-1-carboxylic acid ethyl ester

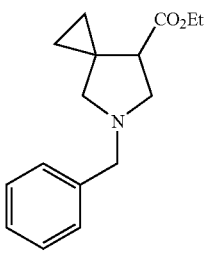

A solution of cyclopropylidene acetic acid ethyl ester (192 g, 1520 mmol [Salaun J., Bennani F., Compain J. C., Fadel A., Ollivier J. J,. *Org Chem.*, 1980; 45(21):4129–3415]) and N-(methoxymethyl)-N-(trimethylsilylmethyl)-benzylamine (572 g, 2410 mmol [Gerlach K., Hoffmann H. M. R., Wartchow R. J., *Chem. Soc.*, Perkin Trans. 11, 1998(22): 3867–3872]) in dichloromethane (5.5 L) was treated with a solution of 1.0N trifluoroacetic acid in dichloromethane (80 mL) and the reaction is stirred at ambient temperature for 30 minutes. The solvent is then evaporated at reduced pressure and the product purified by Kugelrohr distillation (277 g). MS CI: m/z 260 (MH$^+$).

EXAMPLE A2

(a) Synthesis of 1-(5-Benzyl-5-azaspiro[2.4]hept-7-yl)ethanone

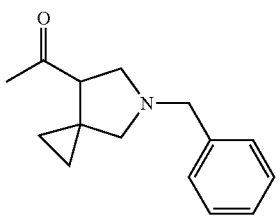

A solution (−78° C.) of 5-benzyl-5-azaspiro[2.4]heptane-7-carboxylic acid ethyl ester (Example A1a, 8.15 g, 31.4 mmol) in diethyl ether (200 mL) under a nitrogen atmosphere is treated with methyllithium (1.4 M in diethyl ether, 22.4 mL, 31.4 mmol) over a period of 10 minutes. After 1 hour, reaction mixture is warmed to −10° C. and quenched with saturated aqueous ammonium chloride. The mixture is poured into a separatory funnel and the organic layer is washed with saturated aqueous ammonium chloride, water, and brine. The organic layer is then dried with MgSO$_4$, filtered, and the filtrate concentrated. The resulting residue is purified via flash column chromatography (1% triethylamine/7% isopropanol/92% CH$_2$Cl$_2$) to afford the title compound (3.93 g). MS CI: m/z 230 (MH$^+$).

EXAMPLE A3

(a) Synthesis of 1-(5-Benzyl-5-azaspiro[2.4]hept-7-yl)ethanone oxime

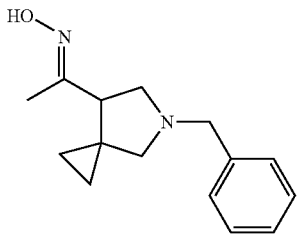

1-(5-benzyl-5-azaspiro[2.4]hept-7-yl)ethanone (Example A2a, 3.93 g, 17.1 mmol) and hydroxylamine hydrochloride (1.78 g, 25.7 mmol) are stirred in pyridine (10 mL) at 90° C. After 20 hours, the reaction mixture is diluted with ethyl acetate and the organic layer is washed with saturated NaHCO$_3$, water, and brine. The organic layer is dried with MgSO$_4$, filtered, and the filtrate concentrated to afford 1-(5-benzyl-5-azaspiro[2.4]hept-7-yl)ethanone oxime as an oil (3.07 g). MSCI: m/z 245 (MH$^+$).

General Method A

A solution of substrate, hydroxylamine hydrochloride (1.2 eq.), sodium acetate (0.9 eq.) in ethanol is stirred at room temperature for 2 hours. The solvent is removed in vacuo and the residue is partitioned between ethyl acetate and saturated sodium chloride solution. The aqueous is re-extracted with ethyl acetate and the combined extracts are dried over Na$_2$SO$_4$, filtered and concentrated under vacuum to afford the title compound.

The compounds below were prepared according to General Method A.

(b) 1-(1-Benzylpiperidin-3-yl)ethanone oxime ($^1$H NMR (200 MHz, CDCl$_3$): δ 7.48–7.28 (m, 5H), 3.92–3.68 (m, 2H), 3.28–3.0 (m, 4H), 2.88–2.62 (m, 2H), 2.38–1.72 (m, 3H), 1.3–1.18 (m, 3H)) from 1-(1-benzylpiperidin-3-yl)ethanone (Example A23).

(c) 1-(1-Benzyl-4,4-dimethylpyrrolidin-3-yl)ethanone oxime ($^1$H NMR (200 MHz, CDCl$_3$): δ 7.68–7.30 (m, 5H), 6.60–5.80 (bs, 1H), 3.80–2.38 (m, 6H), 1.90 (s, 3H), 1.38–0.96 (m, 7H)) from 1-(1-benzyl-4,4-dimethylpyrrolidin-3-yl)ethanone (Example A18b).

(d) 1-(1-Benzyl-4-methylpyrrolidin-3-yl)ethanone oxime ($^1$H NMR (200 MHz, CDCl$_3$): δ 7.41–7.15 (m, 51H), 3.78–3.44 (m, 3H), 2.98–2.80 (m, 1H), 2.75–2.39 (m, 3H), 2.35–2.08 (m, 2H), 1.90 (m, 3H), 1.18–0.95 (m, 3H)) from 1-(1-benzyl-4-methylpyrrolidin-3-yl)ethanone (Example A23b).

EXAMPLE A4

(a) Synthesis of 1-(5-Benzyl-5-azaspiro[2.4]hept-7-yl)-ethyl]carbamic acid tert-butyl ester

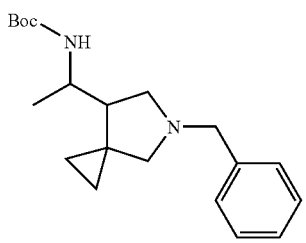

To a solution of 1-(5-benzyl-5-azaspiro[2.4]hept-7-yl) ethanone oxime (Example A3,a, 2.90 g, 11.9 mmol) in methanol (100 mL) is added Raney-Nickel (2 g). Hydrogen is introduced to the reaction mixture at high pressure (48 psi) for 20 hours and the reaction mixture is filtered through celite, washed with methanol, and the combined filtrates concentrated in vacuo. The resulting residue is redissolved in dichloromethane (25 mL) and treated with di-tert-butyl dicarbonate (3.24 g, 14.9 mmol). After 1 hour, the mixture is concentrated and the product purified via flash column chromatography (1% triethylamine/7% isopropanol/92% dichloromethane) to afford [1-(5-benzyl-5-azaspiro[2.4] hept-7-yl)-ethyl]carbamic acid tert-butyl ester (1.47 g). MS CI: m/z 331 (MH$^+$).

General Method A

Di-tert-butyl dicarbonate (0.69 g, 0.3 mmol) is added to a solution of amine in methanol (4 mL) at 0° C. After stirring at room temperature for 2 hours, the mixture is concentrated and the residue is purified by chromatography (SiO$_2$, ethyl acetate/hexanes) to afford the title carbamic esters.

General Method B

An ice-cold solution of substrate in 2:1 methanol and water is treated with di-tert-butyl dicarbonate (1.25 eq.). The resulting solution is stirred at room temperature for 18 hours and extracted with dichloromethane. The organic extracts are washed with brine, dried over Na$_2$SO$_4$, filtered and concentrated under vacuum. The residue is purified by flash column chromatography (ethyl acetate/hexanes) to afford the title compounds.

General Method C

To a solution of substrate in dichloromethane is added di-tert-butyl dicarbonate (2 eq.) and triethylamine (2 eq.). The resulting mixture is stirred at room temperature for 18 hours and diluted with water. The organic extract is washed with water, brine, dried over Na$_2$SO$_4$, filtered and concentrated in vacuo. The residue is then purified by column chromatography to afford the title compound.

Examples A4b–A4m are prepared according to General Methods A, B, and C.

(b) 3-(1-tert-Butoxycarbonylaminoethyl)-3-methoxypyrrolidine-1-carboxylic acid benzyl ester ($^1$H NMR (200 MHz, CDCl$_3$): δ 7.37–7.29 (m, 5H), 5.13 (s, 2H), 4.70 (bs, 1H), 3.91–3.22 (m, 8H), 2.03–1.75 (m, 2H), 1.43 (s, 9H), 1.16–1.11 (m, 3H)) from 3-(1-aminoethyl)-3-methoxypyrrolidine-1-carboxylic acid benzyl ester (Example A13a) using General Method A.

(c) 3-(1-tert-Butoxycarbonylaminoethyl)-3-fluoropyrrolidine-1-carboxylic acid benzyl ester ($^1$H NMR (200 MHz, CDCl$_3$): δ 7.35 (s, 5H), 5.13 (s, 2H), 4.79 (d, 1H), 3.97–3.26 (m, 5H), 2.17–1.75 (m, 2H), 1.44 (s, 9H), 1.24 (d, 3H)) from 3-(1-aminoethyl)-3-fluoropyrrolidine-1-carboxylic acid benzyl ester (Example A13b) using General Method A.

(d) (1-Benzyl-3-methoxymethylpyrrolidin-3-ylmethyl) carbamic acid tert-butyl ester ($^1$H NMR (200 MHz, CDCl$_3$): δ 7.35–7.17 (m, 5H), 5.78 (bs, 1H), 3.56 (s, 2H), 3.32 (s, 3H), 3.27 (s, 2H), 3.21–3.12 (m, 2H), 2.71–2.62 (m, 1H), 2.54–2.30 (m, 3H), 1.78–1.54 (m, 2H), 1.46 (s, 9H)) from (1-benzyl-3-methoxymethylpyrrolidin-3-yl)methylamine (Example A13c) using General Method B.

(e) [1-(1-Benzylpiperidin-3-yl)ethyl]carbamic acid tert-butyl ester ($^1$H NMR (200 MHz, CDCl$_3$): δ 7.3 (s, 5H), 4.46–4.30 (m, 1H), 3.62–3.42 (m, 4H), 2.94–2.62 (m, 3H), 2.0–1.0 (m, 8H), 1.44 (s, 9H)) from 1-(1-benzylpiperidin-3-yl)ethylamine (Example A13d) using General Method C.

(f) [1-(1-Benzyl-4,4-dimethylpyrrolidin-3-yl)ethyl]carbamic acid tert-butyl ester ($^1$H NMR (200 MHz, CDCl$_3$): Isomer-1: δ 7.36–7.22 (m, 5H), 3.82–3.38 (m, 2H), 2.98–1.78 (m, 5H), 1.52–1.0 (m, 19H); Isomer-2: δ 7.35–7.25 (m, 5H), 4.35–4.18 (m, 1H), 3.70–3.45 (m, 2H), 2.90–1.54 (m, 6H), 1.43 (s, 9H), 1.18–0.92 (m, 9H)) from 1-(1-Benzyl-4,4-dimethylpyrrolidin-3-yl)ethylamine (Example A13e) using General Method C.

(g) [1-(1-Benzyl-4-methylpyrrolidin-3-yl)ethyl]carbamic acid tert-butyl ester ($^1$H NMR (200 MHz, CDCl$_3$): δ 7.38–7.13 (m, 5H), 3.71–3.32 (m, 4H), 3.08–1.53 (m, 6H), 1.52–1.31 (m, 9H), 1.14–0.94 (m, 6H). MS ES: m/z 319 (MH$^+$)) from 1-(1-benzyl-4-methylpyrrolidin-3-yl)ethylamine (Example A13f) using General Method C.

(h) (5-Benzyl-5-azaspiro[2,4]hept-7-ylmethyl)carbamic acid tert-butyl ester (MS ES: m/z 317 (MH$^+$)) from 1-(5-benzyl-5-azaspiro[2,4]hept-7-yl)methylamine (Example A13g) using General Method C.

(i) (1-Benzyl-3-hydroxypyrrolidin-3-ylmethyl)carbamic acid tert-butyl ester (MS ES: m/z 307 (MH$^+$)) from 3-aminomethyl-1-benzylpyrrolidin-3-ol (Grohe K., Schriewer M., Haller I., Metzger K., Endermann R., Zeiler H., EP 0326916) using General, Method C.

(j) [3-(1 Phenylethyl)-3-azabicyclo[3.1.0]hex-1-ylmethylcarbamic acid tert-butyl ester (MS ES: m/z 317 (MH$^+$)) from 1-[3-(1-phenylethyl)-3-azabicyclo[3.1.0]hex-1-yl]methylamine (Example A13h) using General Method C.

(k) (1,3-Dibenzylpyrrolidin-3-ylmethyl)carbamic acid tert-butyl ester (MS EI+: m/z 381 (MH$^+$)) using 1-(1,3-dibenzylpyrrolidin-3-yl)methylamine (Example A13i) using General Method C.

(l) (1-Benzyl-4-fluoropyrrolidin-3-ylmethyl)carbamic acid tert-butyl ester ($^1$H NMR (200 MHz, CDCl$_3$): δ 7.30 (s, 5H), 5.04 (m, 1H), 5.04 (m, 1H), 4.77 (m, 1H), 3.63 (s, 2H), 3.20 (t, 2H), 2.86–3.00 (m, 2H), 2.76 (d, 1H), 2.20–2.60 (m, 2H), 1.45 (s, 9H)) from (1-benzyl-4-fluoropyrrolidin-3yl) methylamine (Bouzard D., Di Cesare P., Essiz M., Jacquet J. P., Kiechel J. R., Remuzon P., Weber A., et al., *J. Med. Chem.*, 1990; 33:1344–1352) using General Method C.

(m) cis-(1-Benzyl-4-fluoropyrrolidin-3-ylmethyl)carbamic acid tert-butyl ester ($^1$H NMR (200 MHz, CDCl$_3$): δ 7.30 (s, 5H), 5.04 (m, 1H), 4.77 (m, 1H), 3.63 (s, 2H), 3.20 (t, 2H), 3.00–2.86 (m, 2H), 2.76 (d, 1H), 2.60–2.20 (m, 2H), 1.45 (s, 9H)) from cis-(1-benzyl-4-fluoro-pyrrolidin-3-yl) methylamine (Matsumoto J., Nakano J., Chiba K., Minamida A., Nishimura Y., Jpn. Kokai Tokkyo Koho, 1987; 11 pp., JP 62072660, A2 19870403) using General Method C.

(n) trans-(1-Benzyl-4-fluoropyrrolidin-3-ylmethyl)carbamic acid tert-butyl ester ($^1$H NMR (200 MHz, CDCl$_3$): δ 7.30 (s, 5H), 5.25 (m, 1H), 4.77 (m, 1H), 3.85 (m, 2H), 3.55 (t, 2H), 3.40–2.40 (m, 5H), 1.47 (s, 9H) from trans-(1-benzyl-4-fluoropyrrolidin-3-yl)methylamine (Matsumoto J., Nakano J., Chiba K., Minamida A., Nishimura Y., Jpn. Kokai Tokkyo Koho, 1987; 11 pp., JP 62072660, A2 19870403) using General Method C.

(o) (1-Benzyl-3-phenylpyrrolidine-3-ylmethyl)carbamic acid tert-butyl ester (MS ES: m/z 367 (MH$^+$)) from (1-benzyl-3-phenylpyrrolidine-3-yl)methylamine ester (Hagen S., Domagala J. M., Heifetz C. L., Sanchez J. P., Solomon M., *J. Med. Chem.*, 1990; 33:849–854) using General Method C.

EXAMPLE A5

(a) Synthesis of [1-(5-Azaspiro[2.4]hept-7-yl)ethyl]carbamic acid tert-butyl ester

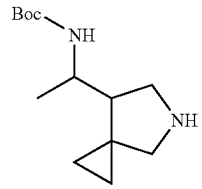

A solution of [1-(5-benzyl-5-azaspiro[2.4]hept-7-yl) ethyl]carbamic acid tert-butyl ester (Example A4a, 1.47 g) in methanol (30 mL) in a Parr shaker is treated with 10% palladium on carbon (0.5 g) and hydrogen introduced (50 psi) for 24 hours. The reaction mixture is filtered through celite, washed with methanol, and the combined filtrate concentrated in vacuo to afford the title compound. MS CI: m/z 241 (MH$^+$).

General Method A

To a solution of substrate in methanol is added ammonium formate (5 eq.) and 10% palladium on charcoal (0.75 wt. vol. eq.). After 2 hours at reflux, the reaction mixture is cooled, diluted with dichloromethane and filtered. The filtrate is concentrated to afford the title compound.

Examples A5b–A5o are prepared using General Method A.

(b) [1-(3-Methoxypyrrolidin-3-yl)ethyl]carbamic acid tert-butyl ester ($^1$H NMR (200 MHz, CDCl$_3$): δ 5.30 (bs, 1H), 5.03 (dd, 1H), 3.92 (bs, 1H), 3.28–2.82 (m, 7H), 1.97–1.72 (m, 2H), 1.44 (s, 9H), 1.19–1.14 (m, 3H)) from 3-(1-tert-butoxycarbonylaminoethyl)-3-methoxypyrrolidine-1-carboxylic acid benzyl ester (Example A4b) using General Method A.

(c) [1-(3-Fluoropyrrolidin-3-yl)ethyl]carbamic acid tert-butyl ester ($^1$H NMR (200 MHz, CDCl$_3$): δ 4.89 (d, 1H), 3.95–3.61 (m, 1H), 3.21–2.70 (m, 4H), 2.11–1.53 (m, 1H), 1.44 (s, 9H), 1.26 (d, 3H)) from 3-(1-tert-butoxycarbonylaminoethyl)-3-fluoropyrrolidine-1-carboxylic acid benzyl ester (Example A4c) using General Method A.

(d) (3-Methoxymethylpyrrolidin-3-ylmethyl)carbamic acid tert-butyl ester ($^1$H NMR (200 MHz, CDCl$_3$): δ 5.25 (bs, 1H), 3.35 (s, 3H), 3.30 (s, 2H), 3.27–3.15 (m, 2H), 3.09–2.94 (m, 2H), 2.78 (s, 2H), 1.68–1.56 (m, 2H), 1.45 (s, 9H). (MS ES: m/z 245 (MH$^+$)) from (1-benzyl-3-methoxymethylpyrrolidin-3-ylmethyl)carbamic acid tert-butyl ester (Example A4d) using General Method A.

(e) (1-Piperidin-3-ylethyl)carbamic acid tert-butyl ester (¹H NMR (200 MHz, CDCl₃): δ 4.52–4.32 (m, 1H), 3.68–3.18 (m, 4H), 2.74–2.42 (m, 1H), 2.02–1.2 (m, 5H), 1.44 (s, 9H), 1.30–1.04 (m, 3H)) from [1-(1-benzylpiperidin-3-yl)ethyl]carbamic acid tert-butyl ester (Example A4e) using General Method A.

(f) [1-(4,4-Dimethylpyrrolidin-3-yl)ethyl]carbamic acid tert-butyl ester (¹H NMR (200 MHz, CDCl₃): 6.28–5.85 (bs, 1H), 4.75 (d, 1H), 3.92–1.80 (m, 6H), 1.43 (s, 9H), 1.30–1.0 (9H)) from [1-(1-benzyl-4,4-dimethylpyrrolidin-3-yl)ethyl] carbamic acid tert-butyl ester (Example A4f).

(g) [1-(4-Methylpyrrolidin-3-yl)ethyl]carbamic acid tert-butyl ester (¹H NMR (200 MHz, CDCl₃): δ 4.88–4.40 (m, 1H), 4.02–3.38 (m, 4H), 3.25–2.75 (m, 2H), 2.46–1.88 (m, 2H), 1.44 (s, 9H), 1.31–1.04 (m, 6H)) from [1-(1-benzyl-4-methylpyrrolidin-3-yl)ethyl]carbamic acid tert-butyl ester (Example A4g).

(h) (5-Azaspiro[2,4]hept-7-ylmethyl)carbamic acid tert-butyl ester (MS ES: m/z 227 (MH⁺)) from (5-benzyl-5-azaspiro[2,4]hept-7-ylmethyl)carbamic acid tert-butyl ester (Example A4h).

(i) (3-Hydroxypyrrolidin-3-ylmethyl)carbamic acid tert-butyl ester (MS ES: m/z 217 (MH⁺)) using (1-benzyl-3-hydroxypyrrolidin-3-ylmethyl)carbamic acid tert-butyl ester (Example A4i).

(j) (3-Azabicyclo[3.1.0]hex-1-ylmethyl)carbamic acid tert-butyl ester (MS ES: m/z 213 (MH⁺)) using [3-(1-phenylethyl)-3-azabicyclo[3.1.0]hex-1-ylmethylcarbamic acid tert-butyl ester (Example A4j).

(k) cis-(4-Fluoropyrrolidin-3-ylmethyl)carbamic acid tert-butyl ester (¹H NMR (200 MHz, CDCl₃): δ 5.60–5.00 (m, 4H), 3.60–3.10 (m, 4H), 3.00 (t, 1H), 2.75–2.30 (m, 1H), 1.44 (s, 9H)) using cis-(1-benzyl-4-fluoropyrrolidin-3-ylmethyl)carbamic acid tert-butyl ester (Example A4l).

(l) trans-(4-Fluoropyrrolidin-3-ylmethyl)carbamic acid tert-butyl ester (¹H NMR (200 MHz, CDCl₃): δ 6.60–5.70 (m, 2H), 5.25 (bs, 0.5H), 4.98 (bs, 0.5H), 3.70–2.90 (m, 5H) 2.90–2.50 (m, 1H), 1.44 (s, 9H)) using trans-(1-benzyl-4-fluoropyrrolidin-3-ylmethyl)carbamic acid tert-butyl ester (Example A4m).

(m) 3-Hydroxy-4-hydroxymethylpyrrolidine (¹H NMR (200 MHz, DMSO-d₆): δ 5.50–4.30 (bs, 3H), 4.30–1.50 (m, 8H)) using 1-benzyl-3-hydroxy-4-hydroxymethylpyrrolidine (Jaeger E., Biel J. H., *J. Org. Chem.*, 1965; 30:740–744).

(n) 1-Methyl-1-pyrrolidin-3-yl-ethanol (MS ES: m/z 130 (MH⁺)) from 2-(1-benzylpyrrolidin-3-yl)propan-2-ol (Example A25).

(o) (3-benzylpyrrolidin-3-ylmethyl)carbamic acid tert-butyl ester (mp 183–185° C.) from (1,3-dibenzylpyrrolidin-3-ylmethyl)carbamic acid tert-butyl ester (Example A4K).

(p) A5p (3-Phenylpyrrolidine-3-ylmethyl)carbamic acid tert-butyl ester (MS APCI: m/z 277 (MH⁺)) from (1-benzyl-3-phenylpyrrolidine-3-ylmethyl)carbamic acid tert-butyl ester (Example A4o).

EXAMPLE A6

Synthesis of 1-Benzylpyrrolidin-3-one oxime

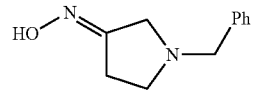

To a solution of 1-benzylpyrrolidin-3-one (1.0 g, 5.71 mmol) in pyridine (5 mL) is added hydroxylamine hydrochloride (0.59 g, 8.57 mmol). After stirring at 90° C. for 5 hours, the reaction mixture is diluted with ethyl acetate and washed with saturated sodium bicarbonate, water, and brine. The organic layer is dried over MgSO₄, filtered, and filtrate concentrated to afford 1-benzylpyrrolidin-3-one oxime (1.11 g) as an oil. MS CI: m/z 191 (MH⁺).

EXAMPLE A7

Synthesis of Pyrrolidin-3-one oxine

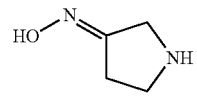

In a Parr shaker, 1-benzylpyrrolidin-3-one oxime (1.5 g) in methanol (20 mL) is treated with 20% palladium on carbon (0.5 g) under Hydrogen pressure (50 psi) for 24 hours. The mixture is then filtered through Celite, washed with methanol, and the combined filtrate concentrated in vacuo to afford the title compound as an oil (1.2 g). MS CI: m/e 101 (M⁺+1).

EXAMPLE A8

Synthesis of 3-Ethylidenepyrrolidine-1-carboxylic acid benzyl ester

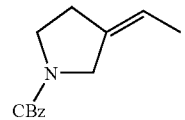

Under an inert atmosphere, sodium-hydride (0.160 g, 7 mmol) and ethyltriphenylphosphonium bromide (2 g, 5.4 mmol) are mixed in dry dimethyl sulfoxide (10 mL) and stirred for 40 minutes. 3-Oxopyrrolidine-1-carboxylic acid benzyl ester (1.18 g, 5.4 mmol (*J. Med. Chem.*, 1992; 35:1392)) in dry dimethyl sulfoxide (5 mL) is added to the reaction and the mixture is stirred at 70° C. for 3 hours. The reaction is cooled, diluted with cold water and extracted with ethyl acetate. The organic phase is washed with brine, dried over Na₂SO₄ and evaporated. The residue is purified by column chromatography (65:35 hexanes/ethyl acetate) to afford the title compound (0.650 g) as a viscous oil. ¹H NMR (200 MHz, CDCl₃): δ 7.37–7.28 (m, 5H), 5.40–5.32 (m, 1H), 5.15 (s, 2H), 3.97 (bs, 2H), 3.60–3.44 (m, 2H), 2.49 (bs, 2H), 1.65–1.60 (m, 3H).

EXAMPLE A9

Synthesis of 2-Methyl-1-oxa-5-azaspiro[2,4]heptane-5-carboxylic acid benzyl ester

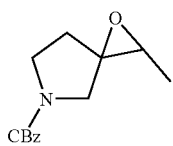

A solution of 3-ethylidenepyrrolidine-1-carboxylic acid benzyl ester (Example A8, 0.65 g, 2.8 mmol) and 3-chloroperoxybenzoic acid (0.86 g, 5 mmol) in dichloromethane (15 mL) is stirred at room temperature for 3 hours. The excess peracid is decomposed by the addition of 10% sodium sulfite. The organic layer is washed with 5% sodium bicarbonate solution, dried over $Na_2SO_4$ and evaporated. The residue is purified by column chromatography (1:1 hexanes/ethyl acetate) to afford the title compound (0.310 g). $^1$H NMR (200 MHz, $CDCl_3$): δ 7.36–7.26 (m, 5H), 5.14 (s, 2H), 3.73–3.55 (m, 3H), 3.34 (d. 1H), 3.20–3.13 (m, 1H), 2.26–2.11 (m, 1H), 1.90–1.62 (m, 1H), 1.33 (d, 3H).

EXAMPLE A10

Synthesis of 3-(1-Aminoethyl)-3-hydroxypyrrolidine-1-carboxylic acid benzyl ester

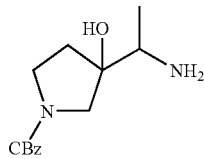

A solution of 2-methyl-1-oxa-5-azaspiro[2,4]heptane-5-carboxylic acid benzyl ester (Example A9, 0.31 g, 1.25 mmol) in methanol (10 mL) and ammonium hydroxide (7 mL) is heated in a sealed tube at 100° C. for 16 hours. After cooling, the reaction mixture is dissolved ethyl acetate, washed with water, dried over $Na_2SO_4$ and evaporated to afford the title compound (0.340 g). $^1$H NMR (200 MHz, $CDCl_3$): δ 7.33–7.26 (m, 5H), 5.28 (bs, 2H), 5.07 (s, 2H), 3.56–3.16 (m, 5H), 2.03–1.76 (m, 2H), 1.15 (d, 3H).

EXAMPLE A11

Synthesis of 3-Hydroxy-3-{1-[(2-hydroxybenzylidene)amino]ethyl}pyrrolidine-1-carboxylic acid benzyl ester A solution of 3-(1-aminoethyl)-3-hydroxypyrrolidine-1-carboxylic acid benzyl ester (Example A10, 0.34 g, 0.93 mmol) and salicylaldehyde (0.147 g, 1.2 mmol) in dry ethanol (5 mL) is refluxed for 3 hours. After evaporation of the solvent, the residue is purified by column chromatography (30:70:0.01 ethyl acetate/hexanes/ammonium hydroxide) to afford the title compound (0.12 g). $^1$H NMR (200 MHz, $CDCl_3$): δ 8.39 (s, 1H), 7.41–7.25 (m, 7H), 6.97–6.85 (m, 2H), 5.09 (s, 2H), 3.65–3.34 (m, 5H), 2.01–1.87 (m, 2H), 1.37–1.32 (m, 3H).

EXAMPLE A12

Synthesis of 3-Methoxy-3-{1-[(2-methoxybenzylidene)amino]ethyl}pyrrolidine-1-carboxylic acid benzyl ester To a stirred solution of 3-hydroxy-3-{1-[(2-hydroxybenzylidene)amino]-ethyl}pyrrolidine-1-carboxylic acid benzyl ester (Example A11, 0.120 g, 0.33 mmol) in tetrahydrofuran (5 mL) at 0° C. is added 0.024 g (1 mmol) of sodium hydride. The mixture is stirred at room temperature for 2 hours and methyl iodide (3 mL) is added and stirring was continued overnight. After evaporation, ethyl acetate and water are added to the residue. The organic layer is separated, dried over $Na_2SO_4$ and concentrated to afford the title compound (0.125 g). $^1$H NMR (200 MHz, $CDCl_3$): δ 8.70 (s, 1H), 7.95 (d, 1H), 7.41–7.32 (m, 6H), 7.01–6.88 (m, 2H), 5.09 (s, 2H), 3.86 (s, 3H), 3.72–3.22 (m, 8H), 2.33–1.73 (m, 2H), 1.27–1.24 (m, 3H).

EXAMPLE A13

(a) Synthesis of 3-(1-Aminoethyl)-3-methoxypyrrolidine-1-carboxylic acid benzyl ester

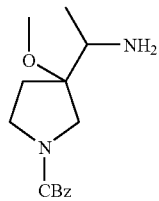

A solution of 3-methoxy-3-{1-[(2-methoxybenzylidene)amino]ethyl-pyrrolidine-1-carboxylic acid benzyl ester (Example A12, 0.120 g, 0.3 mmol) in 3 M hydrogen chloride in methanol (1 mL) is heated at 40° C. overnight. The reaction is basified, extracted with ethyl acetate and the organic layer is dried over $Na_2SO_4$. After concentration, the residue is purified by column chromatography (20:80 methanol/dichloromethane) to afford the title compound (0.060 g). $^1$H NMR (200 MHz, $CDCl_3$): δ 7.38–7.29 (m, 5H), 5.12 (s, 2H), 3.64–3.19 (m, 8H), 2.47 (bs, 2H), 2.07–1.80 (m, 2M), 1.16–1.10 (m, 3H).

(b) 3-(1-Aminoethyl)-3-fluoropyrrolidine-1-carboxylic acid benzyl ester

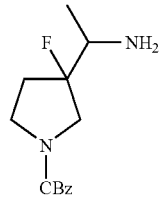

A solution of 3-(1-azidoethyl)-3-fluoropyrrolidine-1-carboxylic acid benzyl ester (Example A16, 0.16 g, 0.5 mmol) in methanol (10 mL) is treated with Raney nickel (100 mg, wet weight) and shaken in a hydrogen atmosphere at room temperature and at 55 psi for 17 hours. The catalyst is removed by filtration through Celite, and the solvent is removed in vacuo to afford the title compound (0.12 g). $^1$H NMR (200 MHz, CDCl$_3$): δ 7.30 (s, 5H), 5.12 (s, 2H), 3.84–3.22 (m, 5H), 2.23–1.79 (m, 4H), 1.20 (d, 3H).

(c) 1-(1-Benzyl-3-methoxymethylpyrrolidin-3-yl)methylamine

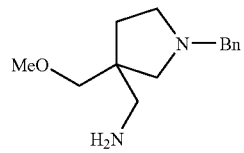

Hydrazine hydrate (85% solution in water, 0.372 g, 6.32 mmol) is added to a solution of 2-(1-benzyl-3-methoxymethylpyrrolidin-3-ylmethyl)isoindole-1,3-dione (Example A20, 1.581 g, 4.34 mmol) in ethanol (50 mL). The resulting mixture is refluxed for 4.5 hours, cooled and acidified with concentrated hydrochloric acid. The precipitate is removed by filtration and the filtrate is concentrated in vacuo. The residue is dissolved in ethanol/water (2:1) and the insoluble material is removed by filtration. The filtrate is basified to pH 10 with 1N sodium hydroxide solution and extracted with dichloromethane. The combined organic extracts are dried over Na$_2$SO$_4$, filtered and concentrated under vacuum to afford the title compound (0.910 g). $^1$H NMR (200 MHz, CDCl$_3$): δ 7.41–7.15 (m, 5H), 3.57 (s, 2H), 3.33 (s, 3H), 3.30 (s, 2H), 2.71 (s, 2H), 2.64–2.51 (m, 2H), 2.42–2.24 (m, 2H), 1.68–1.52 (m, 2H), 1.38–1.10 (m, 2H).

General Method A

Lithium aluminium hydride (2 eq.) is slowly added to a solution of oxime, nitrile, or amide derivative in dry tetrahydrofuran. After the addition is complete, the mixture is refluxed for 2 to 6 hours, cooled in an ice bath and quenched with saturated sodium sulfate solution. The solid is removed by filtration and the filtrate is concentrated in vacuo to afford the title compound.

Examples A13d–i are prepared according to General Method A.

(d) 1-(1-Benzylpiperidin-3-yl)ethylamine ($^1$H NMR (200 MHz, DMSO-d$_6$): δ 7.38–7.18 (m, 5H), 3.52–3.22 (m, 2H), 2.82–2.58 (m, 3H), 1.92–0.75 (m, 10H)) from 1-(1-benzylpiperidin-3-yl)ethanone oxime (Example A3b).

(e) 1-(1-Benzyl-4,4-dimethylpyrrolidin-3-yl)ethylamine ($^1$H NMR (200 MHz, CDCl$_3$): δ 7.36–7.22 (m, 5H), 3.66–3.42 (m, 2H), 2.94–2.10 (m, 5H), 1.32–0.88 (m, 10H)) from 1-(1-benzyl-4,4-dimethylpyrrolidin-3-yl)ethanone oxime (Example A3c).

(f) 1-(1-Benzyl-4-methylpyrrolidin-3-yl)ethylamine ($^1$H NMR (200 MHz, CDCl$_3$): δ 7.38–7.11 (m, 5H), 3.63–3.12 (m, 2H), 2.78–2.27 (m, 5H), 2.23–1.18 (m, 4H), 1.10–0.78 (m, 6H)) from 1-(1-benzyl-4-methylpyrrolidin-3-yl)ethanone oxime (Example A3d).

(g) 1-(5-Benzyl-5-azaspiro[2,4]hept-7-yl)methylamine ($^1$H NMR (CDCl$_3$): δ 7.36–7.21 (m, 5H), 3.68–3.53 (m, 2H), 3.1 (dd, 1H), 2.61–2.38 (m, 5H), 2.1–1.92 (m, 1H), 1.29 (bs, 2H), 0.72–0.32 (m, 4H)) from 5-benzyl-5-azaspiro[2,4]heptane-7-carboxylic acid amide (Example A24).

(h) 1-[3-(1-Phenylethyl)-3-azabicyclo[3.1.0]hex-1-yl]methylamine (MS ES: m/z 217 (MH$^+$)) from 3-(1-phenyl-ethyl)-3-azabicyclo[3.1.0]hexane-1-carbonitrile (Takemura M., Kimura Y., Kawakami K., EP 0807630).

(i) 1,3-Dibenzyl-3-pyrrolidinemethanamine (MS El: m/z 281 (MH$^+$)) from 1,3-dibenzyl-3-pyrrolidine carboxamide (Example A29).

EXAMPLE A14

Synthesis of 3-Fluoro-3-(1-hydroxyethyl)pyrrolidine-1-carboxylic acid benzyl ester

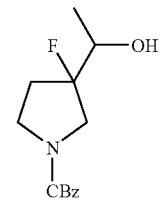

A solution of 0.247 g, (1 mmol) of 2-methyl-1-oxa-5-azaspiro[2,4]-heptane-5-carboxylic acid benzyl ester (Example A9) in dichloromethane (3 mL) is added to a polypropylene flask containing 0.5 mL of hydrogen fluoride-pyridine at –40° C. The reaction is allowed to come to room temperature and stirring is continued for 3 hours. The reaction mixture is poured into an aqueous ice-cold ammonium hydroxide solution (30 mL) and extracted with dichloromethane. The organic layer is dried, filtered and concentrated to afford the title compound (0.267 g). $^1$H NMR (200 MHz, CDCl$_3$): δ 7.35 (s, 5H), 5.13 (s, 2H), 3.96–3.34 (m, 5H), 2.20–1.98 (m, 3H), 1.33–1.26 (m, 3H).

EXAMPLE A15

Synthesis of 3-Fluoro-3-(1-methanesulfonyloxyethyl)pyrrolidine-1-carboxylic acid benzyl ester To a –10° C. solution of 3-fluoro-3-(1-hydroxyethyl)pyrrolidine-1-carboxylic acid benzyl ester (Example A14, 0.267 g, 1.00 mmol), triethylamine (0.4 g, 4 mmol) and dichloromethane (10 mL) is added methanesulfonyl chloride (0.229 g, 2.00 mmol). The mixture is stirred at room temperature for 2 hours and concentrated in vacuo. The residue is partitioned between ethyl acetate and water. The organic layer is dried over Na$_2$SO$_4$ and concentrated to afford the title compound (0.330 g). $^1$H NMR (200 MHz, CDCl$_3$): δ 7.36 (s, 5H), 5.14 (s, 2H), 4.99–4.81 (m, 1H), 3.76–3.37 (m, 4H), 3.06 (s, 3H), 2.25–1.96 (m, 2H), 1.52–1.47 (m, 3H).

EXAMPLE A16

Synthesis of 3-(1-Azidoethyl)-3-fluoropyrrolidine-1-carboxylic acid benzyl ester To a solution of 3-fluoro-3-(1-methanesulfonyloxyethyl)pyrrolidine-1-carboxylic acid benzyl ester (Example A15, 0.25 g, 0.72 mmol) in N,N-dimethylformamide (5 mL) is added sodium azide (0.13 g, 2 mmol). The reaction mixture is heated at 120° C. overnight. The mixture is diluted with water and extracted with ethyl acetate. The extracts are washed with brine, dried over Na$_2$SO$_4$ and concentrated to afford the title compound (0.160 g). $^1$H NMR (200 MHz, CDCl$_3$): δ 7.28 (s, 5H), 5.08 (s, 2H), 3.80–3.25 (m, 5H), 2.13–1.75 (m, 2H), 1.40 (d, 3H).

Example A17

Synthesis of 2-Methoxymethylacrylic acid ethyl ester

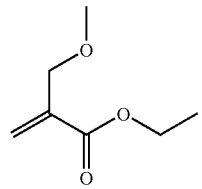

A solution of ethyl α-(bromomethyl)acrylate (0.99 g, 5.1 mmol [Villieras J., Rambaud M., *Synthesis*, 1982:924–926]) in methanol (10 mL) is added to an ice-cold solution of sodium methoxide (0.33 g, 6.1 mmol) in methanol (50 mL). The suspension is refluxed for 21 hours, cooled, diluted with water and extracted with dichloromethane. The organic extracts are dried over Na$_2$SO$_4$, filtered and concentrated under vacuum. The resulting residue is purified by flash column chromatography (1:5 ethyl acetate/hexanes) to afford the title compound (0.211 g). $^1$H NMR (200 MHz, CDCl$_3$): δ 6.33–6.26 (m, 1H), 5.88–5.80 (m, 1H), 4.23 (q, 2H), 4.19–4.10 (m, 2H), 3.41 (s, 3H), 1.31 (t, 3H).

EXAMPLE A18

General Method A

A solution of substrate and N-(methoxymethyl)-N-(trimethyl-silylmethyl)benzylamine (1.3 eq.) in dichloromethane at 0° C. is treated with trifluoroacetic acid (0.07 eq). The mixture is stirred at room temperature for 3 hours, diluted with dichloromethane and washed successively with a saturated NaHCO$_3$ solution and brine. The organic extracts are dried over Na$_2$SO$_4$, filtered, and concentrated under vacuum to afford the title compounds.

The examples below (Example A18a–e) were prepared according to General Method A.

(a) 1-Benzyl-3-methoxymethylpyrrolidine-3-carboxylic acid ethyl ester ($^1$H NMR (200 MHz, CDCl$_3$): δ 7.45–7.16 (m, 5H), 4.19 (q, 2H), 3.78–3.67 (m, 2H), 3.55 (s, 2H), 3.31 (s, 3H), 3.11–2.92 (m, 1H), 2.89–2.49 (m, 2H), 2.42–2.21 (m, 2H), 1.99–1.78 (m, 1H), 1.26 (t, 3H)) from 2-methoxymethylacrylic acid ethyl ester (Example A17).

(b) 1-(1-Benzyl-4,4-dimethylpyrrolidin-3-yl)ethanone ($^1$H NMR (200 MHz, CDCl$_3$): δ 7.36–7.22 (m, 5H), 3.60 (d, 2H), 3.05–2.20 (m, 5H), 2.15 (s, 3H), 1.30 (s, 3H), 0.96 (s, 3H)) from mesityl oxide.

(c) 1-Benzyl-4-methylpyrrolidine-3-carboxylic acid ethyl ester ($^1$H NMR (200 MHz, CDCl$_3$): δ 7.44–7.13 (m, 5H), 4.21–4.04 (q, 1H), 3.71–3.49 (m, 3H), 2.94–2.71 (m, 3H), 2.61–2.41 (m, 2H), 2.28–2.04 (m, 1H), 1.32–1.18 (t, 3H), 1.16–1.04 (d, 3H). MS ES: m/z 248 (MH$^+$)) from ethyl crotonate.

(d) Pyrrolidine-3-carboxylic acid tert-butyl ester (MS ES: m/z 172 (MH$^+$)) from tert-butylacrylate.

(e) Ethyl 1,3-dibenzyl-3-pyrrolidinecarboxylic acid (MS EI+: m/z 324 (MH$^+$)) from ethyl-2-phenylmethylacrylic acid (Vassailiou S., Mucha A., Cuniasse P., Georgiadis D., Lucet-Levannier K., Beau F., Kannan R, et al., *J. Med. Chem.*, 1999; 42(14):2610–2620).

EXAMPLE A19

Synthesis of (1-Benzyl-3-methoxymethylpyrrolidin-3-yl)methanol

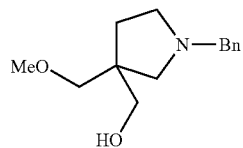

A solution of 1-benzyl-3-methoxymethylpyrrolidine-3-carboxylic acid ethyl ester (Example A18a, 2.30 g, 8.3 mmol) in anhydrous tetrahydrofuran (10 mL) is added dropwise to an ice-cold suspension of lithium aluminum hydride (0.821 g, 22 mmol) in tetrahydrofuran (50 mL). The resulting mixture is stirred at room temperature for 18 hours, cooled and quenched by the sequential dropwise addition of 1N sodium hydroxide and water. The solids are removed by filtration, re-suspended in hot tetrahydrofuran and filtered. The combined filtrates are concentrated in vacuo and the residue is partitioned between dichloromethane and water. The organic extracts are dried over Na$_2$SO$_4$, filtered and concentrated under vacuum to afford the title compound (1.71 g). 1N NMR (200 MHz, CDCl$_3$): δ 7.41–7.17 (m, 5H), 3.84–3.43 (m, 4H), 3.34 (s, 2H), 3.32 (s, 3H), 2.85–2.60 (m, 2H), 2.54–2.14 (m, 3H), 1.98–1.50 (m, 2H).

EXAMPLE A20

2-(1-Benzyl-3-methoxymethylpyrrolidin-3-ylmethyl)isoindole-1,3-dione

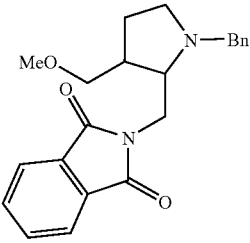

A solution of (1-benzyl-3-methoxymethylpyrrolidin-3-yl)methanol (Example A19, 1.71 g, 7.27 mmol), triphenylphosphine (2.16 g, 8.22 mmol), phthalimide (1.14 g, 7.73 mmol), and anhydrous tetrahydrofuran is cooled to 0° C. and treated with diethyl azodicarboxylate (1.62 g, 9.31 mmol). The resulting mixture is stirred at room temperature for 18 hours and concentrated under vacuum. The residue is purified by flash column chromatography (1:5 ethyl acetate/hexanes) to afford the title compound, (0.58 g) as a solid. $^1$H NMR (200 MHz, CDCl$_3$): δ 7.91–7.80 (m, 2H), 7.78–7.66 (m, 2H), 7.39–7.11 (m, 5H), 3.95–3.72 (m, 2H), 3.65–3.40 (m, 2H), 3.31 (s, 2H), 3.27 (s, 3H), 2.72–2.34 (m, 4H), 2.02–1.82 (m, 1H), 1.76–1.56 (m, 1H). MS ES: m/z 365 (MH$^+$).

EXAMPLE A21

Synthesis of 1-Benzylpiperidine-3-carboxylic acid benzyl ester

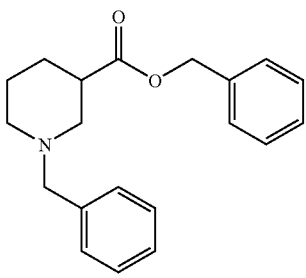

To a solution added of nipecotic acid (8.0 g, 61.9 mmol) in N,N-dimethylformamide (80 mL) is benzyl bromide (31.8 g, 186 mmol) and potassium carbonate (42.8 g, 310 mmol). The mixture is heated at 70° C. for 18 hours and diluted with ethyl acetate and water. The organic extract is washed with 1.0 M hydrochloric acid, water and brine, dried over $Na_2SO_4$, filtered and concentrated in vacuo. The residue is purified by column chromatography (1:7 ethyl acetate/hexanes) to afford the title compound (8.6 g). $^1$H NMR (200 MHz, DMSO-$d_6$): δ 7.27–7.42 (m, 10H), 5.07 (s, 2H), 3.45 (s, 2H), 2.88–2.49 (m, 3H), 2.32–1.32 (m, 6H).

EXAMPLE A22

Synthesis of 1-Benzylpiperidine-3-carboxylic acid

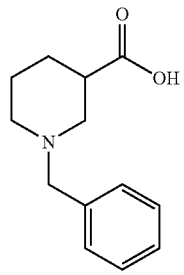

To a solution 3.0 g (9.7 mmol) of 1-benzylpiperidine-3-carboxylic acid benzyl ester (Example A21) in methanol (20 mL) was added 1N sodium hydroxide (20 mL), and the reaction is stirred at room temperature for 18 hours. The methanol is removed in vacuo and the basic aqueous solution is acidified to pH 4 with 1.0 M hydrochloric acid. After washing with ethyl acetate, the aqueous acid layer is lyophilized. The solid is suspended in methanol (10 mL), stirred for 10 minutes and filtered. The filtrate is evaporated in vacuo to afford the title compound (2.0 g). $^1$H NMR (200 MHz, DMSO-$d_6$): δ 7.38–7.23 (m, 5H), 3.58 (s, 2H), 2.98–2.40 (m, 3H), 2.30–1.25 (m, 6H).

EXAMPLE A23

General procedure A

Methyl lithium (1.1 eq.) is added dropwise to a −70° C. solution of substrate in tetrahydrofuran (15 mL). The resulting mixture is stirred at −70° C. for 1 hour, and then warmed to room temperature for 18 hours. The reaction is diluted with ice water and ether and the organic layer is separated. The aqueous layer is extracted with ether and the combined extracts are dried with $Na_2SO_4$ and concentrated in vacuo to afford the title compound.

The following compounds are prepared according to general procedure A.

(a) 1-(1-Benzylpiperidin-3-yl)ethanone ($^1$H NMR (200 MHz, DMSO-$d_6$): δ 7.38–7.22 (m, 5H), 3.45 (s, 2H), 2.85–2.48 (m, 3H), 2.05 (s, 3H), 2.16–1.06 (m, 6H)) from 1-benzylpiperidine-3-carboxylic acid (Example A22).

(b)-(1-Benzyl-4-methylpyrrolidin-3-yl)ethanone ($^1$H NMR (200 MHz, CDCl$_3$): δ 7.42–7.18 (m, 5H), 3.71–3.45 (m, 3H), 2.89–2.33 (m, 5H), 2.16 (s, 3H), 1.12 (d, 3H)) from 1-benzyl-4-methylpyrrolidine-3-carboxylic acid ethyl ester (Example A18c).

EXAMPLE A24

Synthesis of 5-Benzyl-5-azaspiro[2,4]heptane-7-carboxylic acid amide

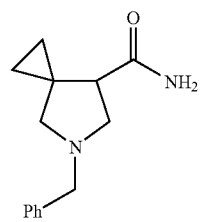

5-Benzyl-5-azaspiro[2,4]heptane-7-carboxylic acid amide (3.32 g) is prepared from 5-benzyl-5-azaspiro[2,4]heptane-7-carboxylic acid (Example A28b, 5.0 g, 21.64 mmol) in dichloromethane by conversion to the acid chloride using oxalyl chloride (5.0 mL, 65 mmol) and N,N-dimethylformamide (3 drops). The mixture is allowed to stir for 2 hours then concentrate in vacuo. The residue is redissolved in dichloromethane and the mixture is again concentrated in vacuo. The residue is dissolved in ether and treated with a solution of ammonia in ether. After 1 hour, the mixture is concentrated in vacuo to provide the title compound. $^1$H NMR (CDCl$_3$): δ 7.6 (bs, 1H), 7.38–7.23 (m, 5H), 5.42 (bs, 1H), 3.75–3.57 (m, 2H), 3.19 (d, 1H), 2.83–2.64 (m, 2H), 2.4 (d, 2H), 0.96–0.58 (m, 4H).

EXAMPLE A25

Synthesis of 2(1-Benzylpyrrolidin-3-yl)propan-2-ol

To a 5° C. solution of 1-benzylpyrrolidine-3-carboxylic acid ethyl ester (0.467 g, 2.0 mmol) in tetrahydrofuran (25 mL) is added an etherial solution of methylmagnesium bromide (3.3 mL, 10 mmol). The reaction mixture is stirred at room temperature for 2 hours, cooled to 0° C. and saturated aqueous ammonium chloride (10 mL) is added followed by water (10 mL). The mixture is extracted with ethyl acetate (2×100 mL) and the combined organic extracts are washed with brine, dried over Na$_2$SO$_4$, filtered and concentrated under vacuum to afford the title compound (0.43 g). $^1$H NMR (200 MHz, CDCl$_3$): δ 7.30–7.22 (m, 5H), 3.59 (s, 2H), 3.0 (bs, 1H), 2.80–2.66 (m, 2H), 2.48–2.30 (m, 2H), 2.20–2.05 (m, 1H), 1.94–1.80 (m, 2H), 1.19 (s, 3H), 1.16 (s, 3H).

EXAMPLE A26

Synthesis of 2-Benzyloctahydropyrrolo[3,4-c]pyridine-5-carboxylic acid tert-butyl ester

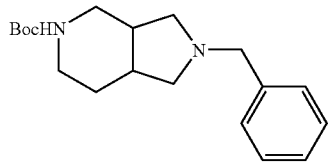

2-Benzyloctahydropyrrolo[3,4-c]pyridine (21.6 g, 100 mmol [Himmler T., Petersen U., Bremm K-D., Endermann R., Stegemann M., Wetzstein H-G., 1995, U.S. Pat. No. 5,578,604] is dissolved in 1000 mL of dichloromethane containing triethylamine (16.7 mL, 120 mmol). Then di-t-butyldicarbonate (22.6 g, 120 mmol) is added and the mixture is stirred at room temperature for 18 hours. The organic layer is washed with saturated NaHCO$_3$, brine, dried, and concentrated to provide 30 g of the title compound as an oil; MS EI+: 318 (MH$^+$).

EXAMPLE A27

Synthesis of octahydropyrrolo[3,4-c]pyridine-5-carboxylic acid tert-butyl ester

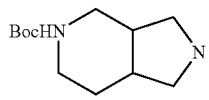

2-Benzyloctahydropyrrolo[3,4-c]pyridine-5-carboxylic acid tert-butyl ester (Example A26, 24.98 g, 78.8 mmol) in 400 mL of methanol is treated with 2.5 g of 20% Pd/C and shaken for 20.5 hours under 50 PSI of hydrogen. The solution is filtered and concentrated to afford 17.8 g of the title compound as a solid. MS APCI: m/z 228 (MH$^+$).

EXAMPLE A28

(a) Synthesis of 1,3-Dibenzylpyrrolidine-3-carboxylic acid

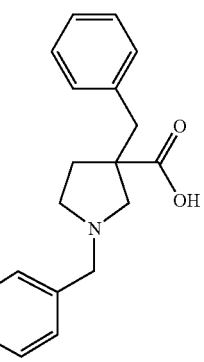

To a solution of 1,3-dibenzylpyrrolidine-3-carboxylic acid ethyl ester (Example A18e, 13.1 g, 41 mmol) in 250 mL of methanol is added 2N NaOH (46 mL, 92 mmol) and the reaction is heated to reflux for 24 hours. The solution is cooled, concentrated, redissolved in water and extracted with ether. The pH of the aqueous layer is adjusted to 7 and the precipitated solid is collected, to give 9.3 g of the title compound, MS EI+: m/z 296 (MH$^+$), mp 209–210° C.

(b) 5-Benzyl-5-azaspiro[2,4]heptane-7-carboxylic acid (MS ES: m/z 232) from 5-benzyl-7-ethoxycarbonyl-5-azaspiro[2,4]heptane (A1) using the method of Example A28a

EXAMPLE A29

Synthesis of 1,3-Dibenzylpyrrolidine-3-carboxylic acid amide

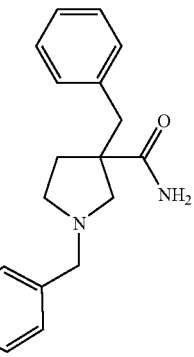

A mixture of 1,3-dibenzylpyrrolidine-3-carboxylic acid (Example A28, 4.0 g, 13.5 mmol), 1,1'-carbonyldiimidazole (2.42 g, 14.9 mmol), and triethylamine (2.08 mL, 14.9 mmol) in tetrahydrofuran (100 mL) is heated at reflux for 1.5 hours. The solution is cooled, poured into NH$_4$OH (300 mL), and stirred for 18 hours. The mixture is extracted with chloroform, the organic layer is washed with water, dried, and concentrated to afford 4.13 g of the title compound as an oil; MS EI+: m/z 295 (MH$^+$).

EXAMPLE A30

Synthesis of (3-Phenylpyrrolin-3-yl)carbamic acid tert-butyl ester

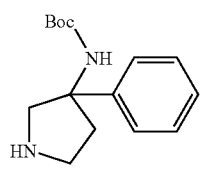

(1-Benzyl-3-phenylpyrrolidin-3-yl)carbamic acid tert-butyl ester (Hagen S. E., Domagala J. M., Heifetz C. L., Sanchez J. P., Solomon M., *J. Med. Chem.*, 1990; 33(2): 849–854) (2.79 g, 7.9 mmol) in 100 mL of methanol is treated with 1.0 g of 20% Pd/C and shaken for 17 hours under 50 psi of hydrogen. The solution is filtered and concentrated to afford 2.07 g of the title compound as a foam; MS EI+: m/z 263 (MH$^+$).

The compounds of the present invention are potent inhibitors of bacterial growth both in animals and on surfaces, and also are inhibitors of bacterial enzymes. The invention compounds have been evaluated in a number of standard in vitro and in vivo assays routinely used by those in the antibacterial art to measure antibacterial activity of test compounds.

Antibacterial Assay

The compounds of the present invention are tested against an assortment of Gram negative and Gram positive organisms using standard microtitration techniques (Cohen et al., *Antimicrob. Agents Chemother.*, 1985; 28:766; Heifetz et al., *Antimicrob. Agents Chemother*, 1974; 6:124). The results of the evaluation of representative 3-aminoquinazolin-2,4-diones of Formula I are shown in Table 2 and compared to two 3-hydroxyquinazolin-2,4-diones.

DNA Gyrase Assay

The effects of invention compounds on the activity of DNA gyrase is determined in the supercoiling inhibition assay, following reaction conditions recommended by the enzyme supplier (Lucent, Ltd., Leicester, UK). Reactions are performed in buffer G (35 mM Tris-HCl (pH 7.5), 24 mM KCl, 4 mM MgCl$_2$, 2 mM DTT, 1.8 mM spermidine, 1 mM ATP, 0.1 mg/mL bovine serum albumin). Relaxed plasmid pBR322 (0.25 µg, Lucent, Ltd., Leicester, UK) is reacted with 1 U *E. coli* gyrase (Lucent, Ltd., Leicester, UK), in the absence or presence of test compounds, for 30 minutes at 37° C. Reactions are stopped by the addition of SDS and proteinase K to respective final concentrations of 1% and 0.5 mg/mL. After an additional 30 minutes at 37° C., one-tenth volume of 10X loading buffer (0.3% bromophenol blue, 16% Ficoll, 10 mM Na$_2$HPO$_4$) is added, and reactions are loaded onto agarose gels and electrophoresed. The concentration of representative invention compounds of Formula I inhibiting 50% of the supercoiling activity of DNA gyrase is given as an IC$_{50}$ and recorded in Table 2.

TABLE 2

Antibacterial and *E. coli* gyrase Activities

| Compound Number or Structure | Minimum Inhibitory Concentrations µg/mL | | | | | | *E. coli* gyrase IC$_{50}$ (µM) |
|---|---|---|---|---|---|---|---|
| | Gram Negatives | | | Gram Positives | | | |
| | *E. coli* MC4100 | *E. coli* B90 | *E. coli* Tol C | *E. faecalis* RB1 | *S. aureus* 29213 | *S. pyogenes* C203 | |
| 1 | 2.0 | 1.0 | 0.25 | 1.0 | 0.5 | 0.13 | 1.0 |
| 2 | 16.0 | 4.0 | 2.0 | >64 | >64 | >64 | 26.0 |
| 7 | 2.0 | 0.5 | 0.25 | 8.0 | 8.0 | 4.0 | 1.3 |
| 9 | 2.0 | 1.0 | 0.5 | 32.0 | 16.0 | 16.0 | 3.0 |
| 11 | 2.0 | 0.5 | 0.25 | 8.0 | 8.0 | 4.0 | 11.0 |
| 12 | 16.0 | 0.25 | 0.13 | 4.0 | 2.0 | 8.0 | 2.1 |
| 14 | 4.0 | 0.25 | 0.5 | 8.0 | 8.0 | 4.0 | 2.4 |
| 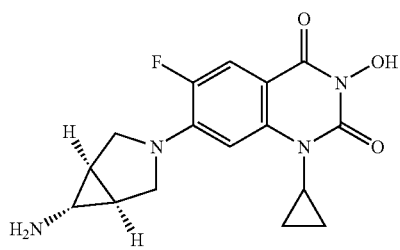 | 1.0 | 0.25 | 0.25 | 4.0 | 4.0 | 2.0 | 0.9 |

TABLE 2-continued

Antibacterial and *E. coli* gyrase Activities

| | Minimum Inhibitory Concentrations µg/mL | | | | | | *E. coli* gyrase |
| | Gram Negatives | | | Gram Positives | | | |
| Compound Number or Structure | *E. coli* MC4100 | *E. coli* B90 | *E. coli* Tol C | *E. faecalis* RB1 | *S. aureus* 29213 | *S. pyogenes* C203 | $IC_{50}$ (µM) |
|---|---|---|---|---|---|---|---|
| [structure: 6-fluoro-7-(octahydropyrrolo-pyridinyl)-3-hydroxy-1-cyclopropyl-quinazoline-2,4-dione] | 8.0 | 2.0 | 1.0 | 64.0 | 32.0 | 32.0 | 5.0 |

The in vivo activity of invention compounds is evaluated according to the procedure of Miller et al., *Proc. Soc. Exp. Biol. Med.*, 1944; 57:261. The median protective dose ($PD_{50}$) is determined in mice given lethal systemic infections. Two 3-aminoquinazolin-2,4-diones of the invention are compared to a 3-hydroxyquinazolin-2,3-dione, and the results are presented in Table 3. The results establish the unexpected superiority of the 3-amino invention compounds compared to similar 3-hydroxy analogs.

TABLE 3

In Vivo Median Protective Dose ($PD_{50}$) in Mice

| Compound Number or Structure | Organism | PD50 (mg/kg) |
|---|---|---|
| 1 | *S. pyogenes* | 12 |
| 10 | *E. coli* | 72 |
| [structure: 6-fluoro-3-hydroxy-7-(aminocyclopropyl-pyrrolidinyl)-1-cyclopropyl-quinazoline-2,4-dione] | *S. pyogenes* | >100 |

Cross Resistance Antibacterial Assay

The compounds of the present invention are tested against an assortment of ciprofloxacin resistant *E. coli* and *S. aureus* organisms described below using standard microtitration techniques (Cohen, et al., *Antimicrob. Agents Chemother*, 1985; 28:766; Heifetz, et al., *Antimicrob. Agents Chemother*, 1974; 6:124). The results of the evaluation are shown in Table 4 and compared to two 3-hydroxyquinazolin-2,4-diones.

*E. coli* and *S. aureus* organisms:

*E. coli* JL4: *E. coli* W3110+Tol C⁻(Tol C pump deficient strain with *E. coli* W3110 background)

*E. coli* LLM-1: Isogenic to *E. coli* JL4 with a D87G mutation (aspartic acid to glycine at position 87) in the QRDR (quinolone resistance determining region)

*S. aureus* UC-76: Typical sensitive laboratory strain (Wild type)

*S. aureus* 2552: Isogenic to *S. aureus* UC-76, with upregulated norA pump

*S. aureus* 2554: Isogenic to *S. aureus* 2552, with point mutation at position 80 of grlA.subunit

*S. aureus* 2558: Isogenic to *S. aureus* 2554, with point mutation at position 84 of gyrA subunit

TABLE 4

Antibacterial Activities Against Ciprofloxacin Resistant Strains

| | Minimum Inhibitory Concentrations µg/mL | | | | | |
| Compound Number or Structure | *E. coli* JL4 | *E. coli* LLM1 | *S. aureus* UC-76 | *S. aureus* 2552 | *S. aureus* 2554 | *S. aureus* 2558 |
|---|---|---|---|---|---|---|
| 1 | 0.13 | 0.5 | 0.13 | 1 | 1 | 1 |
| 3 | 0.5 | 1 | 1 | 2 | 2 | 4 |
| 12 | 0.06 | 0.25 | 1 | 1 | 1 | 2 |

TABLE 4-continued

Antibacterial Activities Against Ciprofloxacin Resistant Strains

| Compound Number or Structure | Minimum Inhibitory Concentrations µg/mL ||||||
| --- | --- | --- | --- | --- | --- | --- |
| | E. coli JL4 | E. coli LLM1 | S. aureus UC-76 | S. aureus 2552 | S. aureus 2554 | S. aureus 2558 |
| [Structure: 6-fluoro-1-cyclopropyl-3-hydroxy-7-(3-amino-6-azabicyclo[3.1.0]hex-6-yl)quinazoline-2,4-dione] | 0.25 | 4 | 4 | 32 | 32 | >64 |
| [Structure: 6-fluoro-1-cyclopropyl-3-hydroxy-7-(3-aminopyrrolidin-1-yl)quinazoline-2,4-dione] | 0.5 | 2 | 4 | >64 | >64 | >64 |

The quinolone mimics provided by this invention display Gram-negative and Gram-positive activity. The compounds also show inhibition of bacterial DNA gyrase/activity. The compounds demonstrate in vivo protective activity in mice and are not highly cytotoxic to mammalian cells, thus indicating selectivity for bacteria. The compounds of Formula I are thus useful for treating and preventing bacterial disease and growth in both animals and on surfaces. The compounds can be applied to wood and metal surfaces, for instance, to eliminate bacterial growth. The compounds can be administered to animals such as humans, horses, dogs, sheep, and cattle to prevent and treat bacterial infections.

The compounds of the present invention can be prepared and administered in a wide variety of oral and parenteral dosage forms for convenient administration to animals. Thus, the compounds of the present invention can be administered by injection, that is, intravenously, intramuscularly, intracutaneously, subcutaneously, intraduodenally, or intraperitoneally. Also, the compounds of the present invention can be administered by inhalation, for example, intranasally. Additionally, the compounds of the present invention can be administered transdermally. It will be obvious to those skilled in the art that the following dosage forms may comprise as the active component, either a compound of Formula I or a corresponding pharmaceutically acceptable salt of a compound of Formula I. The formulations typically will comprise from about 1 to about 95 percent by weight of the active invention compound. The compounds can be dissolved or suspended in liquids, such as ethanol, and applied to wood or metal surfaces to prevent and/or kill bacterial growth.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For parenteral injection liquid preparations can be formulated in solution in aqueous polyethylene glycol solution.

Aqueous solutions suitable for oral use can be prepared by dissolving the active component in water and adding suitable colorants, flavors, stabilizing, and thickening agents as desired.

Aqueous suspensions suitable for oral use can be made by dispersing the finely divided active component in water with viscous material, such as natural or, synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is divided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of invention compound in a unit dose preparation may be varied or adjusted from 0.1 mg to 100 mg, preferably from 0.5 mg to 100 mg, according to the particular application and the potency of the active component as determined by a skilled physician. The composition can, if desired, also contain other compatible therapeutic agents.

In therapeutic use as agents for the treatment of infections caused by a bacteria, the compounds utilized in the pharmaceutical method of this invention are administered at the initial dosage of about 0.01 mg to about 500 mg/kg daily. A daily dose range of about 0.01 mg to about 100 mg/kg is preferred. The dosages, however, may be varied depending upon the requirements of the patient, the severity of the condition being treated, and the particular compound being employed. Determination of the proper dosage for a particular situation is within the skill of the medical art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day, if desired.

The following additional examples illustrate typical formulations for use according to the invention.

EXAMPLE 37

| 1. Tablet Formulation | |
|---|---|
| Ingredient | Amount (mg) |
| Compound No. 10 | 50 |
| Cornstarch (mix) | 15 |
| Cornstarch (paste) | 5 |
| Lactose | 50 |
| Calcium stearate | 2 |
| Dicalcium phosphate | 28 |
| | 150 |

Compound 10 is blended to uniformity with the cornstarch mix, lactose, and dicalcium phosphate. The cornstarch paste is prepared as a 10% aqueous paste, and it is blended to uniformity with the other mixture. The wet granulation is passed through a standard 8-mesh screen. The wet granules are dried and then blended to uniformity with the calcium stearate and pressed into a tablet. Such tablets are administered orally to patients suffering from bacterial infections at the rate of from one to about four times a day.

What is claimed is:
1. A compound of Formula I

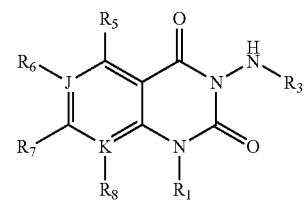

or a pharmaceutically acceptable salt thereof wherein:
  $R_1$ and $R_3$ independently are H,
    $C_1$–$C_{12}$ alkyl and substituted alkyl,
    $C_2$–$C_{12}$ alkenyl and substituted alkenyl,
    $C_2$–$C_{12}$ alkynyl and substituted alkynyl,
    $C_3$–$C_{12}$ cycloalkyl and substituted cycloalkyl,
    aryl and substituted aryl,
    heterocyclic and substituted heterocyclic,
    or heteroaryl and substituted heteroaryl;
  $R_5$, $R_6$, and $R_8$ independently are H,
    $(O)_n C_1$–$C_{12}$ alkyl and substituted alkyl,
    $(O)_n C_2$–$C_{12}$ alkenyl and substituted alkenyl,
    $(O)_n C_2$–$C_{12}$ alkynyl and substituted alkynyl,
  wherein n is 0 or 1,
    halo,
    $NO_2$,
    CN,
    NR'R";
  R' and R" independently are H,
    $C_1$–$C_{12}$ alkyl and substituted alkyl,
    $C_2$–$C_{12}$ alkenyl and substituted alkenyl,
    $C_2$–$C_{12}$ alkynyl and substituted alkynyl,
    CO—$C_1$–$C_{12}$ alkyl and substituted alkyl,
    or R' and R" taken together with the nitrogen to which they are attached form a 3- to 7-membered ring containing from 1 to 3 heteroatoms selected from N, O, and S, said ring being unsubstituted or substituted with up to 4 substituent groups;
  $R_1$ and $R_8$ can be taken together with the atoms to which they are attached to form a cyclic ring having from 1 to 3 heteroatoms selected from N, O, and S, and optionally substituted by R' and R";
  $R_7$ is
    $C_2$–$C_{12}$ alkenyl and substituted alkenyl,
    $C_2$–$C_{12}$ alkynyl and substituted alkynyl,
    $NO_2$,
    CN,
    NR'R",
    COOR',
    aryl,
    fused aryl,
    heterocyclic,
    fused heterocyclic,
    bicyclic heterocyclic, or
    spiro heterocyclic,
  wherein all ring groups can be substituted; and
  J and K are C.

2. A compound of Formula II

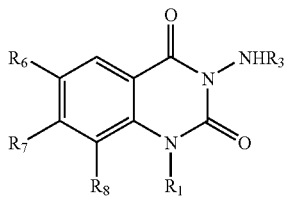

or a pharmaceutically acceptable salt thereof,
wherein:
$R_1$ and $R_3$ independently are H,
  $C_1$–$C_{12}$ alkyl and substituted alkyl,
  $C_2$–$C_{12}$ alkenyl and substituted alkenyl,
  $C_2$–$C_{12}$ alkynyl and substituted alkynyl,
  $C_3$–$C_{12}$ cycloalkyl and substituted cycloalkyl,
  aryl and substituted aryl,
  heterocyclic and substituted heterocyclic,
  or heteroaryl and substituted heteroaryl;
$R_6$ and $R_8$ independently are H,
  $(O)_n C_1$–$C_{12}$ alkyl and substituted alkyl,
  $(O)_n C_2$–$C_{12}$ alkenyl and substituted alkenyl
  $(O)_n C_2$–$C_{12}$ alkynyl and substituted alkynyl,
wherein n is 0 or 1,
  halo,
  $NO_2$,
  CN,
  NR'R";
$R_7$ is
  $C_2$–$C_{12}$ alkenyl and substituted alkenyl,
  $C_2$–$C_{12}$ alkynyl and substituted alkynyl,
  $NO_2$,
  CN,
  NR'R",
  COOR',
  aryl,
  fused aryl,
  heterocyclic,
  fused heterocyclic,
  bicyclic heterocyclic, or
  spiro heterocyclic,
wherein all ring groups can be substituted.

3. A compound of Formula V

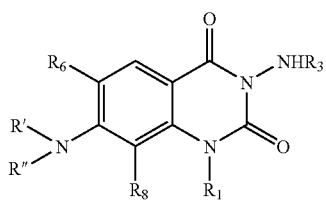

or a pharmaceutically acceptable salt thereof,
wherein:
$R_1$ and $R_3$ independently are H,
  $C_1$–$C_{12}$ alkyl and substituted allyl,
  $C_2$–$C_{12}$ alkenyl and substituted alkenyl,
  $C_2$–$C_{12}$ alkynyl and substituted alkynyl,
  $C_3$–$C_{12}$ cycloalkyl and substituted cycloalkyl,
  aryl and substituted aryl,
  heterocyclic and substituted heterocyclic,
  or heteroaryl and substituted heteroaryl;
$R_6$ and $R_8$ independently are H,
  $(O)_n C_1$–$C_{12}$ alkyl and substituted alkyl,
  $(O)_n C_2$–$C_{12}$ alkenyl and substituted alkenyl,
  $(O)_n C_2$–$C_{12}$ alkynyl and substituted alkynyl,
wherein n is 0 or 1,
  halo,
  $NO_2$,
  CN,
  NR'R";
R' and R" independently are H,
  $C_1$–$C_{12}$ alkyl and substituted alkyl,
  $C_2$–$C_{12}$ alkenyl and substituted alkenyl,
  $C_2$–$C_{12}$ alkynyl and substituted alkynyl,
  CO—$C_1$–$C_{12}$ alkyl and substituted alkyl,
  or R' and R" taken together with the nitrogen to which they are attached form a 3- to 7-membered ring containing from 1 to 3 heteroatoms selected from N, O, and S; said ring being unsubstituted or substituted with up to 4 substituent groups.

4. A compound of claim 1 wherein $R_7$ is selected from:

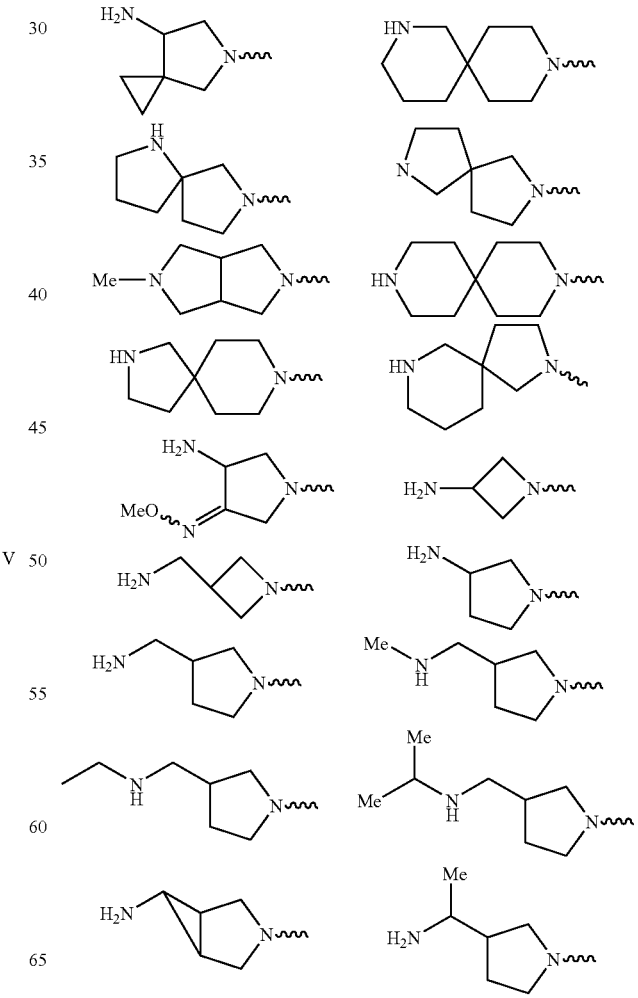

-continued
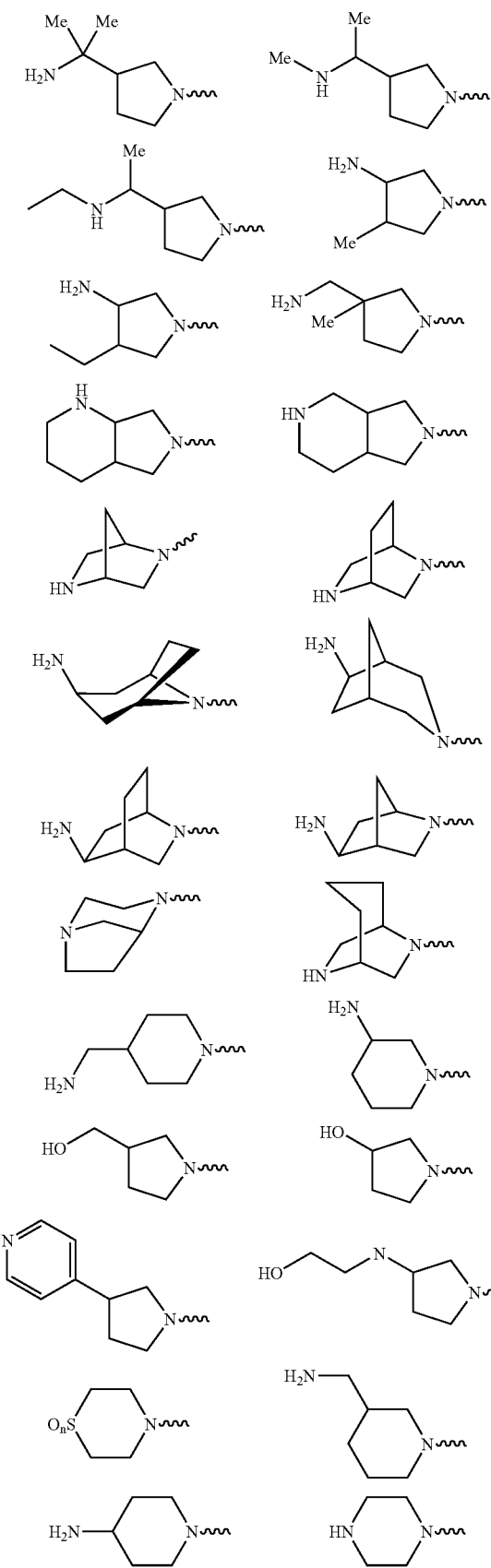
-continued
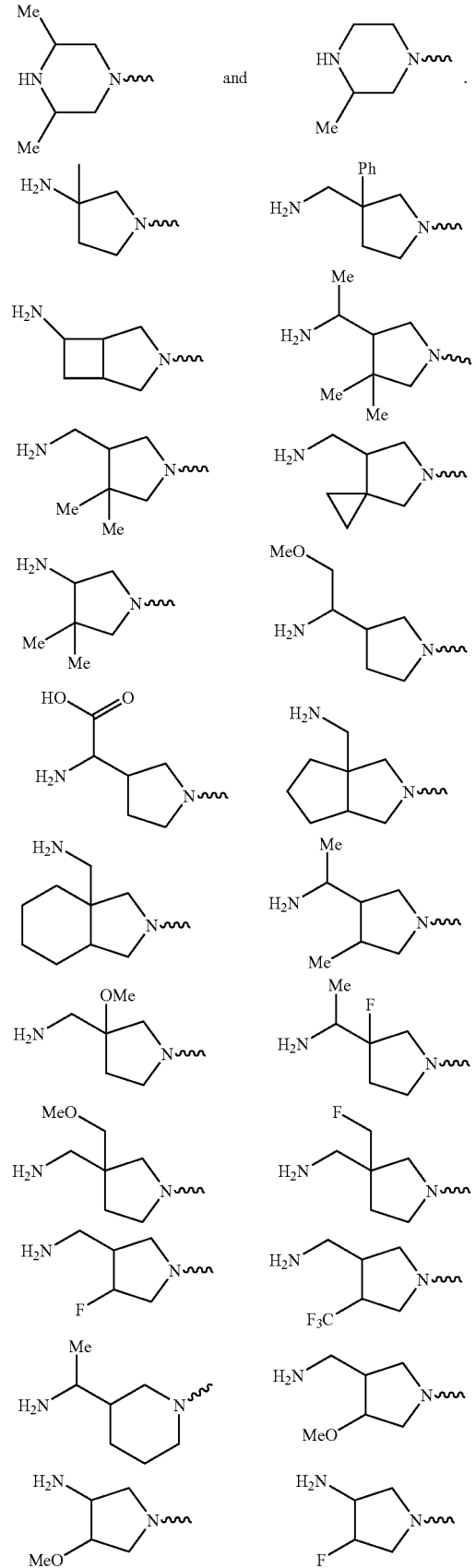

-continued

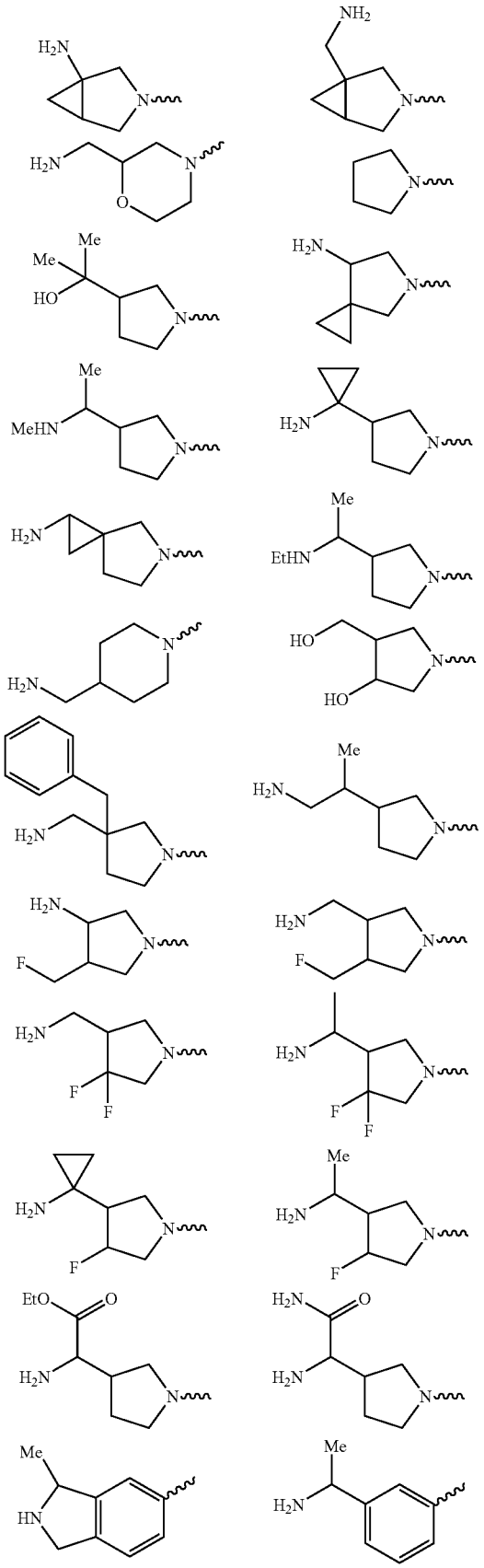
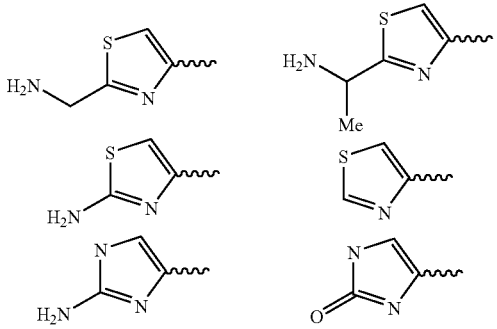

5. A compound of claim 4 wherein $R_7$ is pyrrolidinyl, substituted pyrrolidinyl, piperazinyl, substituted piperazinyl, piperidinyl or substituted piperidinyl.

6. A compound selected from:
3-Amino-7-(3-aminomethylpyrrolidin-1-yl)-8-chloro-1-cyclopropyl-6-fluoro-1H-quinazoline-2,4-dione;
3-Amino-8-chloro-1-cyclopropyl-6-fluoro-7-piperazin-1-yl-1H-quinazoline-2,4-dione;
3-Amino-7-[3-(aminomethyl)-3-methylpyrrolidin-1-yl]-8-chloro-1-cyclopropyl-6-fluoro-1H-quinazoline-2,4-dione;
3-Amino-7-(6-amino-3-aza-bicyclo[3.1.0]hex-3-yl)-8-chloro-1-cyclopropyl-6-fluoro-1H-quinazolin-2,4-dione;
3-Amino-7-((S)-3-N-methylaminopyrrolidin-1-yl)-8-chloro-1-cyclopropyl-6-fluoro-1H-quinazoline-2,4-dione;
3-Amino-7-((S)-3-aminopyrrolidin-1-yl)-8-chloro-1-(2,4-difluoroanilino)-6-fluoro-1H-quinazoline-2,4-dione;
3-Amino-7-[(S)-3-aminopyrrolidin-1-yl]-1-cyclopropylamino-6,8-difluoro-1H-quinazoline-2,4-dione;
3-Amino-7-[(S)-3-aminopyrrolidin-1-yl]-1-cyclopropylamino-5,8-difluoro-1H-quinazoline-2,4-dione;
3-Amino-7-((S)-3-aminopyrrolidin-1-yl)-1-cyclopropyl-5,6,8-trifluoro-1H-quinazoline-2,4-dione;
3-Amino-7-(3-aminopyrrolidin-1-yl)-8-chloro-1-cyclopropyl-6-fluoro-1H-quinazoline-2,4-dione;
7-((S)-3-Aminopyrrolidin-1-yl)-1-cyclopropyl-3,5-diamino-6,8-difluoro-1H-quinazoline-2,4-dione;
3-Amino-7-(3-hydroxymethylpyrrolidin-1-yl)-8-chloro-1-cyclopropyl-6-fluoro-1H-quinazoline-2,4-dione;
3-Amino-7-(3-aminoethylpyrrolidin-1-yl)-8-chloro-1-cyclopropyl-6-fluoro-1H-quinazoline-2,4-dione;
3-Amino-7-((S)-7-amino-5-azaspiro[2.4]hept-5-yl)-8-chloro-1-cyclopropyl-6-fluoro-1H-quinazoline-2,4-dione;
3-Amino-7-[(R)-3-(1-amino-1-methylethyl)pyrrolidin-1-yl]-8-chloro-1-cyclopropyl-6-fluoro-1H-quinazoline-2,4-dione;
3-Amino-7-(3-aminomethylpyrrolidin-1-yl)-1-cyclopropyl-6-fluoro-1H-quinazoline-2,4-dione;
3-Amino-7-(pyrrolidin-1-yl)-8-chloro-1-cyclopropyl-6-fluoro-1H-quinazoline-2,4-dione;
3-Amino-7-(3-aminopyrrolidin-1-yl)-8-chloro-6-fluoro-1-isopropyl-1H-quinazoline-2,4-dione;
3-Amino-7-(3-aminopyrrolin-1-yl)-1-sec-butyl-8-chloro-6-fluoro-1H-quinazoline-2,4-dione;
3-Amino-7-[3-aminopyrrolidin-1-yl]-1-cyclopropyl-6-fluoro-8-methoxy-1H-quinazoline-2,4-dione;
3-Amino-7-[3-aminopyrrolidin-1-yl]-8-chloro-1-cyclobutylamino-6-fluoro-1H-quinazoline-2,4-dione;

3-Amino-7-(3-aminopyrrolidin-1-yl)-1-cyclopropyl-8-fluoro-1H-quinazoline-2,4-dione;

3-Amino-7-(3-aminopyrrolidin-1-yl)-6-chloro-1-cyclopropyl-8-fluoro-1H-quinazoline-2,4-dione;

3-Amino-7-((S)-3-aminopyrrolidin-1-yl)-1-cyclopropylmethyl-8-fluoro-1H-quinazoline-2,4-dione;

3-Amino-7-[(R)-3-(1-amino-1-methylethyl)pyrrolidin-1-yl]-1-cyclopropylmethyl-8-fluoro-1H-quinazoline-2,4-dione;

3-Amino-7-((S)-3-aminopyrrolidin-1-yl)-1-ethyl-8-fluoro-1H-quinazoline-2,4-dione;

3-Amino-1-ethyl-6-fluoro-7-[(R)-3-(1-amino-1-methylethyl)-pyrrolidin-1-yl]-1H-quinazoline-2,4-dione;

3-Amino-7-((S)-3-aminopyrrolidin-1-yl)-1-cyclopropyl-6-fluoro-1H-quinazoline-2,4-dione;

3-Amino-7-(3-aminopyrrolidin-1-yl)-1-cyclopropyl-6-fluoro-8-methyl-1H-quinazoline-2,4-dione;

3-Amino-7-(3-aminomethylpyrrolidin-1-yl)-1-cyclopropyl-6-fluoro-8-methyl-1H-quinazoline-2,4-dione;

3-Amino-7-(3-aminopyrrolidin-1-yl)-1-cyclopropyl-8-fluoro-6-methoxy-1H-quinazoline-2,4-dione;

3-Amino-7-(3-aminomethylpyrrolidin-1-yl)-1-cyclopropyl-6-fluoro-8-methoxy-1H-quinazoline-2,4-dione;

3-Amino-7-(3-aminopyrrolidin-1-yl)-1-cyclopropyl-8-ethoxy-6-fluoro-1H-quinazoline-2,4-dione;

3-Amino-7-(3-aminopyrrolidin-1-yl)-1-cyclopropyl-6-fluoro-2,4-dioxo-1,2,3,4-tetrahydroquinazoline-8-carbonitrile;

3-Amino-8-chloro-1-cyclopropyl-6-fluoro-7-(3-[1,2,3-triazol]-1-yl-pyrrolidin-1-yl)-1H-quinazoline-2,4-dione;

3-Amino-7-[(S)-3-((R)-1-aminoethyl)pyrrolidin-1-yl]-1-cyclopropyl-6-fluoro-8-methoxy-1H-quinazoline-2,4-dione;

3-Amino-7-[(S)-3-((S)-1-aminoethyl)pyrrolidin-1-yl]-1-cyclopropyl-6-fluoro-8-methoxy-1H-quinazoline-2,4-dione;

3-Amino-7-[(S)-3-((R)-1-aminoethyl)pyrrolidin-1-yl]-1-cyclopropyl-6-fluoro-8-methyl-1H-quinazoline-2,4-dione;

3-Amino-7-[(S)-3-((S)-1-aminoethyl)pyrrolidin-1-yl]-1-cyclopropyl-6-fluoro-8-methyl-1H-quinazoline-2,4-dione;

5-Amino-9-((S)-3-aminopyrrolidin-1-yl)-8-fluoro-3-methyl-2,3-dihydro-1-oxa-3a,5-diazaphenalene-4,6-dione;

5-Amino-9-[(R)-3-((S)-1-aminoethyl)pyrrolidin-1-yl]-8-fluoro-3-methyl-2,3-dihydro-1-oxa-3a,5-diazaphenalene-4,6-dione;

2-Amino-8-((S)-3-aminopyrrolidin-1-yl)-9-fluoro-5-methyl-6,7-dihydro-5H-pyrido[3,2,1-ij]quinazoline-1,3-dione;

2-Amino-8-[(R)-3-((S)-1-aminoethyl)pyrrolidin-1-yl]-9-fluoro-5-methyl-6,7-dihydro-5H-pyrido[3,2,1-ij]quinazoline-1,3-dione;

3-Amino-7-((S)-3-aminopyrrolidin-1-yl)-1-cyclopropyl-6-fluoro-1H-pyrido [2,3-d]pyrimidine-2,4-dione;

3-Amino-7-(6-amino-3-azabicyclo [3.1.0]hex-3-yl)-1-cyclopropyl-6-fluoro-1H-pyrido[2,3-d]pyrimidine-2,4-dione;

3-Amino-7-(3-aminomethyl-3-methylpyrrolidin-1-yl)-1-cyclopropyl-6-fluoro-1H-pyrido[2,3-d]pyrimidine-2,4-dione;

3-Amino-1-cyclopropyl-6-fluoro-7-(octahydropyrrolo[3,4-c]pyridin-2-yl)-1H-pyrido[2,3-d]pyrimidine-2,4-dione;

3-Amino-1-cyclopropyl-6-fluoro-7-(octahydropyrrolo[3,4-b]pyridin-2-yl)-1H-pyrido[2,3-d]pyrimidine-2,4-dione;

3-Amino-7-[(R)-3-(1-amino-1-methylethyl)pyrrolidin-1-yl]-1-cyclopropyl-6-fluoro-1H-pyrido[2,3-d]pyrimidine-2,4-dione;

3-Amino-7-(3-aminomethylpiperidin-1-yl)-1-cyclopropyl-6-fluoro-1H-pyrido[2,3-d]pyrimidine-2,4-dione;

trans-3-Amino-7-(3-aminomethyl-4-trifluoromethylpyrrolidin-1-yl)-1-cyclopropyl-6-fluoro-1H-pyrido[2,3-d]pyrimidine-2,4-dione;

3-Amino-1-cyclopropyl-6-fluoro-7-[(R)-3-((R)-1-methylamino-ethyl)pyrrolidin-1-yl]-1H-pyrido [2,3-d]pyrimidine-2,4-dione;

3-Amino-7-[(R)-3-((S)-1-aminoethyl)pyrrolidin-1-yl]-1-cyclopropyl-6-fluoro-1H-pyrido[2,3-d]pyrimidine-2,4-dione;

3-Amino-7-[3-(1-aminopropyl)pyrrolidin-1-yl]-1-cyclopropyl-6-fluoro-8-methyl-1H-quinazoline-2,4-dione;

3-Amino-1-cyclopropyl-6-fluoro-8-methyl-7-[(R)-3-((S)-1-methylaminoethyl)pyrrolidin-1-yl]-1H-quinazoline-2,4-dione;

3-Amino-7-[7-(1-aminoethyl)-5-azaspiro[2.4]hept-5-yl]-1-cyclopropyl-6-fluoro-8-methyl-1H-quinazoline-2,4-dione;

1-(3-Amino-8-chloro-1-cyclopropyl-6-fluoro-2,4-dioxo-1,2,3,4-tetrahydroquinazolin-7-yl)piperidine-3-carboxylic acid amide;

3-Amino-[7-trans-3-aminomethyl-4-trifluoromethylpyrrolidin-1-yl]-8-chloro-1-cyclopropyl-6-fluoro-1H-quinazoline-2,4-dione;

3-Amino-8-chloro-1-cyclopropyl-6-fluoro-7-{3-[(2,2,2-trifluoro-ethylamino)methyl]pyrrolidin-1-yl}-1H-quinazoline-2,4-dione;

3-Amino-8-chloro-1-cyclopropyl-6-fluoro-7-(5-methyl-hexahydro-pyrrolo[3,4-c]pyrrolo-2-yl)-1H-quinazoline-2,4-dione;

3-Amino-8-chloro-1-cyclopropyl-7-(2,7-diazaspiro[4.4]non-2-yl)-6-fluoro-1H-quinazoline-2,4-dione;

3-Amino-7-(3-aminomethyl-3-benzylpyrrolidin-1-yl)-8-chloro-1-cyclopropyl-6-fluoro-1H-quinazoline-2,4-dione;

3-Amino-7-[(R)-3-((S)-1-aminoethyl)pyrrolidin-1-yl]-8-chloro-1-cyclopropyl-6-fluoro-1H-quinazoline-2,4-dione;

3-Amino-8-chloro-1-cyclopropyl-6-fluoro-7-(3-hydroxyimino-pyrrolidin-1-yl)-1H-quinazoline-2,4-dione;

3-Amino-7-[trans-3-amino-4-trifluoromethylpyrrolidin-1-yl]-8-chloro-1-cyclopropyl-6-fluoro-1H-quinazoline-2,4-dione;

3-Amino-8-chloro-1-cyclopropyl-6-fluoro-7-[(R)-3-(S)-1-methylaminoethyl)pyrrolidin-1-yl]-1H-quinazoline-2,4-dione;

3-Amino-7-(trans-3-amino-4-phenylpyrrolidin-1-yl)-8-chloro-1-cyclopropyl-6-fluoro-1H-quinazoline-2,4-dione;

3-Amino-7-[trans-3-amino-4-(4-hydroxyphenyl)pyrrolidin-1-yl]-8-chloro-1-cyclopropyl-6-fluoro-1H-quinazoline-2,4-dione;

N-[1-(3-Amino-8Chloro-1-cyclopropyl-6-fluoro-2,4-dioxo-1,2,3,4-tetrahydroquinazolin-7-yl)pyrrolidin-3-ylmethyl]methanesulfonamide;

3-Amino-7-(3-aminomethylpiperidin-1-yl)-8-chloro-1-cyclopropyl-6-fluoro-1H-quinazoline-2,4-dione;

3-Amino-8-chloro-1-cyclopropyl-6-fluoro-7-[3-(isopropylamino-methyl)pyrrolidin-1-yl]-1H-quinazoline-2,4-dione;

3-Amino-7-(3-aminomethylpyrrolidin-1-yl)-6,8-dichloro-1-cyclopropyl-1H-quinazoline-2,4-dione;

N-[1-(3-Amino-8-chloro-1-cyclopropyl-6-fluoro-2,4-dioxo-1,2,3,4-tetrahydroquinazolin-7-yl)pyrrolidin-3-yl-methyl]methanesulfonamide;

3-Amino-7-[(R)-3-(S)-(1-aminoethyl)pyrrolidin-1-yl]-1-cyclopropyl-6-fluoro-8-methyl-1H-quinazoline-2,4-dione;

3-Amino-7-[(R)-3-(1-amino-1-methylethyl)pyrrolidin-1-yl]-1-cyclopropyl-6-fluoro-8-methyl-1H-quinazoline-2,4-dione;

3-Amino-7-[3-(1-aminoethyl)-3-methoxypyrrolidin-1-yl]-1-cyclopropyl-6-fluoro-8-methyl-1H-quinazoline-2,4-dione;

3-Amino-7-[3-(1-aminoethyl)-3-fluoropyrrolidin-1-yl]-1-cyclopropyl-6-fluoro-8-methoxy-1H-quinazoline-2,4-dione;

3-Amino-7-(3-aminopyrrolidin-1-yl)-1-cyclopropyl-6-fluoro-5-methyl-1H-quinazoline-2,4-dione;

3-Amino-7-[(R)-3-(S)-(1-aminoethyl)pyrrolidin-1-yl]-1-cyclopropyl-6-fluoro-5-methyl-1H-quinazoline-2,4-dione;

3-Amino-7-(3-aminomethyl-3-methoxymethylpyrrolidin-1-yl)-1-cyclopropyl-6-fluoro-8-methyl-1H-quinazoline-2,4-dione;

3-Amino-7-(3-aminomethyl-3-fluoromethylpyrrolidin-1-yl)-1-cyclopropyl-6-fluoro-1H-quinazoline-2,4-dione;

3-Amino-7-(trans-3-aminomethyl-4-trifluoromethylpyrrolidin-1-yl)-1-cyclopropyl-6-fluoro-8-methoxy-1H-quinazoline-2,4-dione;

3-Amino-7-[3-(1-aminoethyl)piperidin-1-yl]-1-cyclopropyl-6-fluoro-8-methoxy-1H-quinazoline-2,4-dione;

3-Amino-7-[3-(aminoethyl)piperidin-1-yl]-1-cyclopropyl-6-fluoro-8-methyl-1H-quinazoline-2,4-dione;

3-Amino-7-[4-(1-aminoethyl)-3,3-dimethylpyrrolidin-1-yl]-1-cyclopropyl-6-fluoro-8-methoxy-1H-quinazoline-2,4-dione;

3-Amino-7-[4-(1-aminoethyl)-3,3-dimethylpyrrolidin-1-yl]-1-cyclopropyl-6-fluoro-8-methyl-1H-quinazoline-2,4-dione;

3-Amino-7-(3-amino-3-phenylpyrrolidin-1-yl)-1-cyclopropyl-6-fluoro-8-methyl-1H-quinazoline-2,4-dione;

3-Amino-7-[3-(1-aminoethyl)-4-methylpyrrolidin-1-yl]-1-cyclopropyl-6-fluoro-8-methyl-1H-quinazoline-2,4-dione;

3-Amino-7-(3-aminomethyl-3-phenylpyrrolidin-1-yl)-1-cyclopropyl-6-fluoro-8-methyl-1H-quinazoline-2,4-dione;

3-Amino-7-(7-aminomethyl-5-azaspiro[2,4]hept-5-yl)-1-cyclopropyl-6-fluoro-8-methyl-1H-quinazoline-2,4-dione;

3-Amino-7-(7-aminomethyl-5-azaspiro[2,4]hept-5-yl)-1-cyclopropyl-6-fluoro-8-methoxy-1H-quinazoline-2,4-dione;

3-Amino-7-(3-aminomethyl-3-hydroxypyrrolidin-1-yl)-1-cyclopropyl-6-fluoro-8-methoxy-1H-quinazoline-2,4-dione;

3-Amino-7-(3-aminomethylpiperidin-1-yl)-1-cyclopropyl-6-fluoro-8-methyl-1H-quinazoline-2,4-dione;

3-Amino-7-(3-amino 1-methoxypyrrolidin-1-yl)-1-cyclopropyl-6-fluoro-8-methyl-1H-quinazolin-2,4-dione;

3-Amino-7-(3-amino-4-methoxypyrrolidin-1-yl)-1-cyclopropyl-6-fluoro-8-methoxy-1H-quinazoline-2,4-dione;

3-Amino-7-(3-amino-4-fluoropyrrolidin-1-yl)-1-cyclopropyl-6-fluoro-8-methoxy-1H-quinazoline-2,4-dione;

3-Amino-7-(3-aminomethyl-3-methylpyrrolidin-1-yl)-1-cyclopropyl-6-fluoro-8-methyl-1H-quinazoline-2,4-dione;

3-Amino-7-[(R)-3 (-((S)-1-aminoethyl)pyrrolidin-1-yl]-1-cyclopropyl-8-ethyl-6-fluoro-1H-quinazoline-2,4-dione;

1-(3-Amino-1-cyclopropyl-6-fluoro-8-methoxy-2,4-dioxo-1,2,3,4-tetrahydroquinazolin-7-yl)pyrrolidine-3-carboxylic acid trifluoroacetate;

1-(3-Amino-1-cyclopropyl-6-fluoro-8-methyl-2,4-dioxo-1,2,3,4 tetrahydroquinazolin-7-yl)pyrrolidine-3-carboxylic acid trifluoroacetate;

3-Amino-7-(1-aminomethyl-3-azabicyclo[3.1.0]hex-3-yl)-1-cyclopropyl-6-fluoro-8-methoxy-1H-quinazoline-2,4 dione;

3-Amino-7-(1-aminomethyl-3-azabicyclo[3.1.0]hex-3-yl)-1-cyclopropyl-6-fluoro-8-methyl-1H-quinazoline-2,4-dione;

3-Amino-7-[(S)-3-((R)-1-aminoethyl)pyrrolidin-1-yl]-1-cyclopropyl-6-fluoro-8-methoxy-1H-quinazoline-2,4-dione;

3-Amino-7-[(S)-3-((R)-1-aminoethyl)pyrrolidin-1-yl]-1-cyclopropyl-6-fluoro-8-methyl-1H-quinazoline-2,4-dione;

3-Amino-1-cyclopropyl-6-fluoro-8-methyl-7-(octahydropyrrolo[3,4-b]pyridin-6-yl)-1H-quinazoline-2,4-dione;

3-Amino-7-(trans-3-aminomethyl-4-methylpyrrolidin-1-yl)-8-chloro-1-cyclopropyl-6-fluoro-1H-quinazoline-2,4-dione;

3-Amino-7-(trans-3-aminomethyl-4-methylpyrrolidin-1-yl)-1-cyclopropyl-6-fluoro-8-methoxy-1H-quinazoline-2,4-dione;

3-Amino-7-(trans-3-aminomethyl-4-methylpyrrolidin-1-yl)-1-cyclopropyl-6-fluoro-8-methyl-1H-quinazoline-2,4-diode;

3-Amino-7-(trans-3-amino-4-methylpyrrolidin-1-yl)-1-cyclopropyl-6-fluoro-8-methoxy-1H-quinazoline-2,4-dione;

3-Amino-7-(3-aminomethylmorpholin-1-yl)-1-cyclopropyl-6-fluoro-8-methoxy-1H-quinazoline-2,4-dione;

3-Amino-7-(3-aminomethylpiperidin-1-yl)-1-cyclopropyl-6-fluoro-8-methoxy-1H-quinazoline-2,4-dione;

3-Amino-7-[3-(1-aminoethyl)-1-methylpyrrolidin-1-yl]-1-cyclopropyl-6-fluoro-8-methoxy-1H-quinazoline-2,4-dione;

3-Amino-7-(3-amino-3-phenylpyrrolidin-1-yl)-8-chloro-1-cyclopropyl-6-fluoro-1H-quinazoline-2,4-dione, 3-Amino-7-(3-amino-3-methylpyrrolidin-1-yl)-1-cyclopropyl-6-fluoro-8-methyl-1H-quinazoline-2,4-dione;

3-Amino-1-cyclopropyl-6-fluoro-8-methyl-7-pyrrolidin-1yl-1H-quinazoline-2,4-dione;

3-Amino-1-cyclopropyl-6-fluoro-8-methoxy-7-pyrrolidin-1yl-1H-quinazoline-2,4-dione;

3-Amino-1-cyclopropyl-6-fluoro-7-[3-(1-hydroxy-1-methylethyl)-pyrrolidin-1-yl]-8-methyl-1H-quinazoline-2,4-dione;

3-Amino-1-cyclopropyl-6-fluoro-7-[3-(1-hydroxy-1-methylethyl)-pyrrolidin-1-yl]-8-methoxy-1H-quinazoline-2,4-dione;

3-Amino-1-cyclopropyl-6-fluoro-5-methyl-7-[(R)-3-((S)-1-methylaminoethyl)pyrrolidin-1-yl]-1H-quinazoline-2,4-dione;

(S)-1-[(R)-1-(3-Amino-1-cyclopropyl-7-[3-(1-ethylaminoethyl)pyrrolidin-1-yl)-6-fluoro-8-methoxy-1H-quinazoline-2,4-dione;

3-Amino-1-cyclopropyl-7-[(R)-3-((S)-1-ethylaminoethyl)pyrrolidin-1-yl]-6-fluoro-8-methyl-1H-quinazoline-2,4-dione;

3-Amino-7-(6-amino-1-methyl-3-azabicyclo[3.2.0]hept-3-yl)-1-cyclopropyl-6-fluoro-8-methoxy-1H-quinazoline-2,4-dione;

3-Amino-7-(4-aminomethylpiperidin-1-yl)-1-cyclopropyl-6-fluoro-8-methoxy-1H-quinazoline-2,4-dione;

3-Amino-7-(3-aminomethylazetidin-1-yl)-1-cyclopropyl-6-fluoro-8-methoxy-1H-quinazoline-2,4-dione;

cis-3-Amino-7-(3-aminomethyl-4-fluoropyrrolidin-1-yl)-1-cyclopropyl-6-fluoro-8-methoxy-1H-quinazoline-2,4-dione;

trans-3-Amino-7-(3-aminomethyl-4-fluoropyrrolidin-1-yl)-1-cyclopropyl-6-fluoro-8-methoxy-1H-quinazoline-2,4-dione;

3-Amino-7-(1-amino-5-azaspiro[2.4]hept-5-yl)-1-cyclopropyl-6-fluoro-8-methoxy-1H-quinazoline-2,4-dione;

3-Amino-7-(3-aminomethyloctahydroisoindol-2-yl)-1-cyclopropyl-6-fluoro-8-methoxy-1H-quinazoline-2,4-dione;

3-Amino-7-(3-aminomethyloctahydroisoindol-2-yl)-1-cyclopropyl-6-fluoro-8-methyl-1H-quinazoline-2,4-dione;

3-Amino-7-[(R)-3-((S)-1-aminoethylpyrrolidin-1-yl]-1-cyclopropyl-6-fluoro-8-methoxy-1H-quinazoline-2,4-dione;

3-Amino-7-(6-amino-3-azabicyclo[3.1.0]hex-3-yl)-1-cyclopropyl-6-fluoro-8-methyl-1H-quinazoline-2,4-dione;

3-Amino-7-(3-(1-amino-1-methylethyl)pyrrolidin-1-yl]-1-cyclopropyl-6-fluoro-8-methoxy-1H-quinazoline-2,4-dione;

3-Amino-1-cyclopropyl-6-fluoro-7-[3-(isopropylaminomethyl) pyrrolidin-1-yl]-8-methoxy-1H-quinazoline-2,4-dione;

3-Amino-1-cyclopropyl-6-fluoro-8-methoxy-7-[(4aS,7aS)-octahydropyrrolo[3,4-b]pyridin-6-yl-1H-quinazoline-2,4-dione;

3-Amino-7-(3-amino-4-fluoromethylpyrrolidin-1-yl)-1-cyclopropyl-6-fluoro-8-methoxy-1H-quinazoline-2,4-dione;

3-Amino-7-(3-aminomethyl-3-methylpyrrolidin-1-yl)-1-cyclopropyl-6-fluoro-8-methoxy-1H-quinazoline-2,4-dione;

3-Amino-7-(4-aminopiperidin-1-yl)-1-cyclopropyl-6-fluoro-8-methoxy-1H-quinazoline-2,4-dione;

3-Amino-7-(3-aminopiperidin-1-yl)-1-cyclopropyl-6-fluoro-8-methoxy-1H-quinazoline-2,4-dione;

3-Amino-1-cyclopropyl-6-fluoro-8-methoxy-7-[(R)-3-((S)-1-methylaminoethyl)pyrrolidin-1-yl]-1H-quinazoline-2,4-dione;

3-Amino-7-(3-aminoazetidin-1-yl)-1-cyclopropyl-6-fluoro-8-methoxy-1H-quinazoline-2,4-dione;

3-Amino-7-[(3R,4S)-3-((S)-1-aminoethyl)-4-fluoropyrrolidin-1-yl]-1-cyclopropyl-6-fluoro-8-methyl-1H-quinazoline-2,4-dione;

3-Amino-7-[(3R,4S)-3-((S)-1-aminoethyl)-4-fluoropyrrolidin-1-yl]-1-cyclopropyl-8-methyl-1H-quinazoline-2,4-dione;

3-Amino-7-[(3R,4R)-3-(R)-1-aminoethyl)-4-fluoropyrrolidin-1-yl]-1-cyclopropyl-6-fluoro-8-methyl-1H-quinazoline-2,4-dione;

3-Amino-7-[(3R,4R)-3-((R)-1-aminoethyl)-4-fluoropyrrolidin-1-yl]-1-cyclopropyl-8-methyl-1H-quinazoline-2,4-dione;

3-Amino-7-[(3R,4S)-3-(-1-amino-1-methylethyl)-4-fluoropyrrolidin-1-yl]-1-cyclopropyl-6-fluoro-8-methyl-1H-quinazoline-2,4-dione;

3-Amino-7-[(3R,4S)-3-(-1-amino-1-methylethyl)-4-fluoropyrrolidin-1-yl]-1-cyclopropyl-8-methyl-1H-quinazoline-2,4-dione;

3-Amino-7-[(3R,4R)-3-(-1-amino-1-methylethyl)-4-fluoropyrrolidin-1-yl]-1-cyclopropyl-6-fluoro-8-methyl-1H-quinazoline-2,4-dione;

3-Amino-7-[(3R,4R)-3-(-1-amino-1-methylethyl)-4-fluoropyrrolidin-1-yl]-1-cyclopropyl-8-methyl-1H-quinazoline-2,4-dione;

3-Amino-7-[(3R,4S)-3-((R)-1-amino-2-methoxyethyl)-4-fluoropyrrolidin-1-yl]-1-cyclopropyl-6-fluoro-8-methyl-1H-quinazoline-2,4-dione;

3-Amino-7-[(3R,4S)-3-((R)-1-amino-methoxyethyl)-4-fluoropyrrolidin-1-yl]-1-cyclopropyl-8-methyl-1H-quinazoline-2,4-dione;

3-Amino-7-[(3R,4R)-3-((S)-1-amino-2-methoxyethyl)-4-fluoropyrrolidin-1-yl]-1-cyclopropyl-6-fluoro-8-methyl-1H-quinazoline-2,4-diode;

3-Amino-7-[(3R,4R)-3-((S)-1-amino-2-methoxyethyl)-4-fluoropyrrolidin-1-yl]-1 cyclopropyl-8-methyl-1H-quinazoline-2,4-dione;

3-Amino-7-[(3R,4S)-3-((R)-1-amino-2-methoxyethyl)-4-methylpyrrolidin-1-yl]-1-cyclopropyl-6-fluoro-8-methyl-1H-quinazoline-2,4-dione;

3-Amino-7-[(3R,4S)-3-((R)-1-amino-2-methoxyethyl)-4-methylpyrrolidin-1-yl]-1-cyclopropyl-8-methyl-1H-quinazoline-2,4-dione;

3-Amino-7-[(3R,4R)-3-((S)-1-amino-2-methoxyethyl)-4-methylpyrrolidin-1-yl]-1-cyclopropyl-6-fluoro-8-methyl-1H-quinazoline-2,4-dione;

3-Amino-7-[(3R,4R)-3-((S)-1-amino-2-methoxyethyl)-4-methylpyrrolidin-1-yl]-1-cyclopropyl-8-methyl-1H-quinazoline-2,4-dione;

3-Amino-7-[(R)-4-((R)-1-amino-2-methoxyethyl)-3,3-dimethylpyrrolidin-1-yl]-1-cyclopropyl-6-fluoro-8-methyl-1H-quinazoline-2,4-dione;

3-Amino-7-[(R)-4-(R)-1-amino-2-methoxyethyl)-3,3-dimethylpyrrolidin-1-yl]-1-cyclopropyl-8-methyl-1H-quinazoline-2,4-dione;

3-Amino-7-[(R)-4-((S)-1-amino-2-methoxyethyl)-3,3-dimethylpyrrolidin-1-yl]-1-cyclopropyl-6-fluoro-8-methyl-1H-quinazoline-2,4-dione;

3-Amino-7-[(R)-4-(S)-1-amino-2-methoxyethyl)-3,3-dimethylpyrrolidin-1-yl]-1-cyclopropyl-8-methyl-1H-quinazoline-2,4-dione;

3-Amino-7-[(R)-3-((R)-1-amino-2-phenoxyethyl)pyrrolidin-1-yl]-1-cyclopropyl-6-fluoro-8-methyl-1H-quinazoline-2,4-dione;

3-Amino-7-[(R)-3-(R)-1-amino-2-phenoxyethyl)pyrrolidin-1-yl]-1-cyclopropyl-8-methyl-1H-quinazoline-2,4-dione;

3-Amino-7-[(3R,4S)-3-((R)-1-amino-2-phenoxyethyl)-4-methylpyrrolidin-1-yl]-1-cyclopropyl-6-fluoro-8-methyl-1H-quinazoline-2,4-dione;

3-Amino-7-[(3R,4S)-3-((R)-1-amino-2-phenoxyethyl)-4-methylpyrrolidin-1-yl]-1-cyclopropyl-8-methyl-1H-quinazoline-2,4-dione;

3-Amino-7-[(3R,4S)-3-((R)-1-amino-2-phenoxyethyl)-4-fluoropyrrolidin-1-yl]-1-cyclopropyl-6-fluoro-8-methyl-1H-quinazoline-2,4-dione;

3-Amino-7-[(3R,4S)-3-((R)-1-amino-2-phenoxyethyl)-4-fluoropyrrolidin-1-yl]-1-cyclopropyl-8-methyl-1H-quinazoline-2,4-dione;

3-Amino-7-[(R)-3-((S)-1-amino-2-phenoxyethyl)pyrrolidin-1-yl]-1-cyclopropyl-6-fluoro-8-methyl-1H-quinazoline-2,4-dione;
3-Amino-7-[(R)-3-((S)-1-amino-2-phenoxyethyl)pyrrolidin-1-yl]-1-cyclopropyl-8-methyl-1H-quinazoline-2,4-dione;
3-Amino-7-[(3R,4S)-3-((S)-1-amino-2-phenoxyethyl)-4-methylpyrrolidin-1-yl]-1-cyclopropyl-6-fluoro-8-methyl-1H-quinazoline-2,4-dione;
3-Amino-7-[(3R,4S)-3-((S)-1-amino-2-phenoxyethyl)-4-methylpyrrolidin-1-yl]-1-cyclopropyl-8-methyl-1H-quinazoline-2,4-dione;
3-Amino-7-[(3R,4S)-3-((S)-1-amino-2-phenoxyethyl)-4-fluoropyrrolidin-1-yl]-1-cyclopropyl-6-fluoro-8-methyl-1H-quinazoline-2,4-dione;
3-Amino-7-[(3R,4S)-3-((S)-1-amino-2-phenoxyethyl)-4-fluoropyrrolidin-1-yl]-1-cyclopropyl-8-methyl-1H-quinazoline-2,4-dione;
3-Amino-7-[(R)-4-((R)-1-amino-2-phenoxyethyl)-3,3-dimethylpyrrolidin-1-yl]-1-cyclopropyl-6-fluoro-8-methyl-1H-quinazoline-2,4-dione;
3-Amino-7-[(R)-4-((R)-1-amino-2-phenoxyethyl)-3,3-dimethylpyrrolidin-1-yl]-1-cyclopropyl-8-methyl-1H-quinazoline-2,4-dione;
3-Amino-7-[(R)-4-((S)-1-amino-2-phenoxyethyl)-3,3-dimethylpyrrolidin-1-yl]-1-cyclopropyl-6-fluoro-8-methyl-1H-quinazoline-2,4-dione;
3-Amino-7-[(R)-4-((S)-1-amino-2-phenoxyethyl)-3,3-dimethylpyrrolidin-1-yl]-1-cyclopropyl-8-methyl-1H-quinazoline-2,4-dione;
3-Amino-7-[(R)-3-((S)-1-amino-2-ethoxyethyl)pyrrolidin-1-yl]-1-cyclopropyl-6-fluoro-8-methyl-1H-quinazoline-2,4-dione;
3-Amino-7-[(R)-3-((S)-1-amino-2-ethoxyethyl)pyrrolidin-1-yl]-1-cyclopropyl-8-methyl-1H-quinazoline-2,4-dione;
3-Amino-7-[(R)-3-((R)-1-amino-2-ethoxyethyl)pyrrolidin-1-yl]-1-cyclopropyl-6-fluoro-8-methyl-1-quinazoline-2,4-dione;
3-Amino-7-[(R)-3-((R)-1-amino-2-ethoxyethyl)pyrrolidin-1-yl]-1-cyclopropyl-8-methyl-1H-quinazoline-2,4-dione;
3-Amino-7-[(3R,4S)-3-((R)-1-amino-2-ethoxyethyl)-4-methylpyrrolidin-1-yl]-1-cyclopropyl-6-fluoro-8-methyl-1H-quinazoline-2,4-dione;
3-Amino-7-[(3R,4S)-3-((R)-1-amino-2-ethoxyethyl)-4-methylpyrrolidin-1-yl]-1-cyclopropyl-8-methyl-1H-quinazoline-2,4-dione;
3-Amino-7-[(3R,4S)-3-((R)-1-amino-2-ethoxyethyl)-4-fluoropyrrolidin-1-yl]-1-cyclopropyl-6-fluoro-8-methyl-1H-quinazoline-2,4-dione;
3-Amino-7-[(3R,4S)-3-((R)-1-amino-2-ethoxyethyl)-4-fluoropyrrolidin-1-yl]-1-cyclopropyl-8-methyl-1H-quinazoline-2,4-dione;
3-Amino-7-[(R)-4-((R)-1-amino-2-ethoxyethyl)-3,3-dimethylpyrrolidin-1-yl]-1-cyclopropyl-6-fluoro-8-methyl-1H-quinazoline-2,4-dione;
3-Amino-7-[(R)-4-((R)-1-amino-2-ethoxyethyl)-3,3-dimethylpyrrolidin-1-yl]-1-cyclopropyl-8-methyl-1H-quinazoline-2,4-dione;
3-Amino-7-[(3R,4R)-3-((S)-1-amino-2-ethoxyethyl)-4-methylpyrrolidin-1-yl]-1-cyclopropyl-6-fluoro-8-methyl-1H-quinazoline-2,4-dione;
3-Amino-7-[(3R,4R)-3-((S)-1-amino-2-ethoxyethyl)-4-methylpyrrolidin-1-yl]-1-cyclopropyl-8-methyl-1H-quinazoline-2,4-dione;
3-Amino-7-[(3R,4R)-3-((S)-1-amino-2-ethoxyethyl)-4-fluoropyrrolidin-1-yl]-1 cyclopropyl-6-fluoro-8-methyl-1H-quinazoline-2,4-dione;
3-Amino-7-[(3R,4R)-3-((S)-1-amino-2-ethoxyethyl)-4-fluoropyrrolidin-1-yl]-1-cyclopropyl-8-methyl-1H-quinazoline-2,4-dione;
3-Amino-7-[(R)-3-((S)-1-amino-3-methoxypropyl)pyrrolidin-1-yl]-1-cyclopropyl-6-fluoro-8-methyl-1H-quinazoline-2,4-dione;
3-Amino-7-[(R)-3-((S)-1-amino-3-methoxypropyl)pyrrolidin-1-yl]-1-cyclopropyl-8-methyl-1H-quinazoline-2,4-dione;
3-Amino-7-[(3R,4S)-3-((S)-1-amino-3-methoxypropyl)-4-methylpyrrolidin-1-yl]-1-cyclopropyl-6-fluoro-8-methyl-1H-quinazoline-2,4 dione;
3-Amino-7-[(3R,4S)-3-((S)-1-amino-3-methoxypropyl)-4-methylpyrrolidin-1-yl]-1-cyclopropyl-8-methyl-1H-quinazoline-2,4-dione;
3-Amino-7-[(3R,4S)-3-((S)-1-amino-3-methoxypropyl)-4-fluoropyrrolidin-1-yl]-1-cyclopropyl-fluoro-8-methyl-1H-quinazoline-2,4-dione;
3-Amino-7-[(3R,4S)-3-((S)-1-amino-3-methoxypropyl)-4-fluoropyrrolidin-1-yl]-1-cyclopropyl-8-methyl-1H-quinazoline-2,4-dione;
3-Amino-7-[(R)-3-((R)-1-amino-3-methoxypropyl)pyrrolidin-1-yl]-1-cyclopropyl-6-fluoro-8-methyl-1H-quinazoline-2,4-dione;
3-Amino-7-[(R)-3-((R) 1-amino-3-methoxypropyl)pyrrolidin-1-yl]-1-cyclopropyl-8-methyl-1H-quinazoline-2,4-dione;
3-Amino-7-[(3R,4R)-3-((R)-1-amino-3-methoxypropyl)-4-methylpyrrolidin-1-yl]-1-cyclopropyl-6-fluoro-8-methyl-1H-quinazoline-2,4-dione;
3-Amino-7-[(3R,4R)-3-((R)-1-amino-3-methoxypropyl)-4-methylpyrrolidin-1-yl]-1-cyclopropyl-8-methyl-1H-quinazoline-2,4-dione;
3-Amino-7-[(3R,4R)-3-((R)-1-amino-3-methoxypropyl)-4-fluoropyrrolidin 1-yl]-1-cyclopropyl-6-fluoro-8-methyl-1H-quinazoline-2,4-dione;
3-Amino-7-[(3R,4R)-3-((R)-1-amino-3-methoxypropyl)-4-fluoropyrrolidin-1-yl]-1-cyclopropyl-8-methyl-1H-quinazoline-2,4-dione;
{(R)-2-Amino-2-[(R)-1-(3-amino-1-cyclopropyl-6-fluoro-8-methyl-2,4-dioxo-1,2,3,4-tetrahydroquinazolin-7-yl)pyrrolidin-3-yl]ethyl}urea;
{(R)-2-Amino-2-[(R)-1-(3-amino-1 cyclopropyl-8-methyl-2,4-dioxo-1,2,3,4-tetrahydroquinazolin-7-yl)pyrrolidin-3-yl]ethyl}urea;
{(S)-2-Amino-2-[(R)-1-(3-amino-1-cyclopropyl-6-fluoro-8-methyl-2,4-dioxo-1,2,3,4-tetrahydroquinazolin-7-yl)pyrrolidin-3-yl]ethyl}urea;
{(S)-2-Amino-2-[(R)-1-(3-amino-1-cyclopropyl-8-methyl-2,4-dioxo-1,2,3,4-tetrahydroquinazolin-7-yl)pyrrolidin-3-yl]ethyl}urea;
{(R)-2-Amino-2-[(3R,4S)-1-(3-amino 1-cyclopropyl-6-fluoro-8-methyl-2,4-dioxo-1,2,3,4-tetrahydroquinazolin-7-yl)-4-methylpyrrolidin-3-yl]ethyl}urea;
{(R)-2-Amino-2-[(3R,4S)-1-(3-amino-1-cyclopropyl-8-methyl-2,4-dioxo-1,2,3,4-tetrahydroquinazolin-7-yl)-4-methylpyrrolidin-3-yl]ethyl}urea;
{(S)-2-Amino-2-[(3R,4R)-1-(3-amino-1-cyclopropyl-6-fluoro-8-methyl-2,4-dioxo-1,2,3,4-tetrahydroquinazolin-7-yl)-4-methylpyrrolidin-3-yl]ethyl}urea;
{(S)-2-Amino-2-[(3R,4R)-1-(3-amino-1-cyclopropyl-8-methyl-2,4-dioxo-1,2,3,4-tetrahydroquinazolin-7-yl)-4-methylpyrrolidin-3-yl]ethyl}urea;

{2-Amino-2-[(1-(3-amino-1-cyclopropyl-6-fluoro-8-methyl-2,4-dioxo-1,2,3,4-tetrahydroquinazolin-7-yl)-4-fluoropyrrolidin-3-yl]ethyl}urea;
{2-Amino-2-[(1-(3-amino-1-cyclopropyl-8-methyl-2,4-dioxo-1,2,3,4-tetrahydroquinazolin-7-yl)-4-fluoropyrrolidin-3-yl]ethyl}urea;
{2-Amino-2-[(1-(3-amino-1-cyclopropyl-6-fluoro-8-methyl-2,4-dioxo-1,2,3,4-tetrahydroquinolin-7-yl)-4,4-dimethylpyrrolidin-3-yl]ethyl}urea;
{2-Amino-2-[(1-(3-amino-1-cyclopropyl-8-methyl-2,4-dioxo-1,2,3,4-tetrahydroquinazolin-7-yl)-4,4-dimethylpyrrolidin-3-yl]ethyl}urea;
3-Amino-7-[(3R,4S)-3-((S)-1-aminoethyl)-4-fluoropyrrolidin-1-yl]-1-cyclopropyl-6-fluoro-8-methoxy-1H-quinazoline-2,4-dione;
3-Amino-7-[(3R,4S)-3-((S)-1-aminoethyl)-4-fluoropyrrolidin-1-yl]-1-cyclopropyl-8-methoxy-1H-quinazoline-2,4-dione;
3-Amino-7-[(3R,4R)-3-(R)-1-aminoethyl)-4-fluoropyrrolidin-1-yl]-1-cyclopropyl-6-fluoro-8-methoxy-1H-quinazoline-2,4-dione;
3-Amino-7-[(3R,4R)-3-((R)-1-aminoethyl)-4-fluoropyrrolidin-1-yl]-1-cyclopropyl-8-methoxy-1H-quinazoline-2,4-dione;
3-Amino-7-[(3R,4S)-3-(-1-amino-1-methylethyl)-4-fluoropyrrolidin-1-yl]-1-cyclopropyl-6-fluoro-8-methoxy-1H-quinazoline-2,4-dione;
3-Amino-7-[(3R,4S)-3-(-1-amino-1-methylethyl)-4-fluoropyrrolidin-1-yl]-1-cyclopropyl-8-methoxy-1H-quinazoline-2,4-dione;
3-Amino-7-[(3R,4R)-3-(-1-amino-1-methylethyl)-4-fluoropyrrolidin-1-yl]-1-cyclopropyl-6-fluoro-8-methoxy-1H-quinazoline-2,4-dione;
3-Amino-7-[(3R,4R)-3-(-1-amino-1-methylethyl)-4-fluoropyrrolidin-1-yl]-1-cyclopropyl-8-methoxy-1H-quinazoline-2,4-dione;
3-Amino-7-[(3R,4S)-3-((R)-1-amino-2-methoxyethyl)-4-fluoropyrrolidin-1-yl]-1-cyclopropyl-6-fluoro-8-methoxy-1H-quinazoline-2,4-dione;
3-Amino-7-[(3R,4S)-3-((R)-1-amino-2-methoxyethyl)-4-fluoropyrrolidin-1-yl]-1-cyclopropyl-8-methoxy-1H-quinazoline-2,4-dione;
3-Amino-7-[(3R,4R)-3-((S)-1-amino-2-methoxyethyl)-4-fluoropyrrolidin-1-yl]-1-cyclopropyl-6-fluoro-8-methoxy-1H-quinazoline-2,4-dione;
3-Amino-7-[(3R,4R)-3-((S)-1-amino-2-methoxyethyl)-4-fluoropyrrolidin-1-yl]-1-cyclopropyl-8-methoxy-1-quinazoline-2,4-dione;
3-Amino-7-[(3R,4S)-3-((R)-1-amino-2-methoxyethyl)-4-methylpyrrolidin-1-yl]-1-cyclopropyl-6-fluoro-8-methoxy-1H-quinazoline-2,4-dione;
3-Amino-7-[(3R,4S)-3-((R)-1-amino-2-methoxyethyl)-4-methylpyrrolidin-1-yl]-1-cyclopropyl-8-methoxy-1H-quinazoline-2,4-dione;
3-Amino-7-[(3R,4R)-3-((S)-1-amino-2-methoxyethyl)-4-methylpyrrolidin-1-yl]-1-cyclopropyl-6-fluoro-8-methoxy-1H-quinazoline-2,4 dione;
3-Amino-7-[(3R,4R)-3-((S)-1-amino-2-methoxyethyl)-4-methylpyrrolidin-1-yl]-1-cyclopropyl-8-methoxy-1H-quinazoline-2,4-dione;
3-Amino-7-[(R)-4-((R)-1-amino-2-methoxyethyl)-3,3-dimethylpyrrolidin-1-yl]-1-cyclopropyl-6-fluoro-8-methoxy-1H-quinazoline-2,4-dione;
3-Amino-7-[(R)-4-(R)-1-amino-2-methoxyethyl)-3,3-dimethylpyrrolidin-1-yl]-1-cyclopropyl-8-methoxy-1H-quinazoline-2,4-dione;
3-Amino-7-[(R)-4-((S)-1-amino-2-methoxyethyl)-3,3-dimethylpyrrolidin-1-yl]-1-cyclopropyl-6-fluoro-8-methoxy-1H-quinazoline-2,4-dione;
3-Amino-7-[(R)-4-(S)-1-amino-2-methoxyethyl)-3,3-dimethylpyrrolidin-1-yl]-1-cyclopropyl-8-methoxy-1H-quinazoline-2,4-dione;
3-Amino-7-[(R)-3-((R)-1-amino-2-phenoxyethyl)pyrrolidin-1-yl]-1-cyclopropyl-6-fluoro-8-methoxy-1H-quinazoline-2,4-dione;
3-Amino-7-[(R)-3-(R)-1-amino-2-phenoxyethyl)pyrrolidin-1-yl]-1-cyclopropyl-8-methoxy-1H-quinazoline-2,4-dione;
3-Amino-7-[(3R,4S)-3-((R)-1-amino-2-phenoxyethyl)-4-methylpyrrolidin-1-yl]-1-cyclopropyl-6-fluoro-8-methoxy-1H-quinazoline-2,4-dione;
3-Amino-7-[(3R,4S)-3-((R)-1-amino-2-phenoxyethyl)-4-methylpyrrolidin-1-yl]-1-cyclopropyl-8-methoxy-1H-quinazoline-2,4-dione;
3-Amino-7-[(3R,4S)-3-((R)-1-amino-2-phenoxyethyl)-4-fluoropyrrolidin-1-yl]-1-cyclopropyl-6-fluoro-8-methoxy-1H-quinazoline-2,4-dione;
3-Amino-7-[(3R,4S)-3-((R)-1-amino-2-phenoxyethyl)-4-fluoropyrrolidin-1-yl]-1 cyclopropyl-8-methoxy-1H-quinazoline-2,4-dione;
3-Amino-7-[(R)-3-((S)-1-amino-2-phenoxyethyl)pyrrolidin-1-yl]-1-cyclopropyl-6-fluoro-8-methoxy-1H-quinazoline-2,4-dione;
3-Amino-7-[(R)-3-((S)-1-amino-2-phenoxyethyl)pyrrolidin-1-yl]-1-cyclopropyl-8-methoxy-1H-quinazoline-2,4-dione;
3-Amino-7-[(3R,4S)-3-((S)-1-amino-2-phenoxyethyl)-4-methylpyrrolidin-1-yl]-1-cyclopropyl-6-fluoro-8-methoxy-1H-quinazoline-2,4-dione;
3-Amino-7-[(3R,4S)-3-((S)-1-amino-2-phenoxyethyl)-4-methylpyrrolidin-1-yl]-1-cyclopropyl-8-methoxy-1H-quinazoline-2,4-dione;
3-Amino-7-[(3R,4S)-3-((S)-1-amino-2-phenoxyethyl)-4-fluoropyrrolidin-1-yl]-1-cyclopropyl-6-fluoro-8-methoxy-1H-quinazoline-2,4-dione;
3-Amino-7-[(3R,4S)-3-((S)-1-amino-2-phenoxyethyl)-4-fluoropyrrolidin-1-yl]-1-cyclopropyl-8-methoxy-1H-quinazoline-2,4-dione;
3-Amino-7-[(R)-4-((R)-1-amino-2-phenoxyethyl)-3,3-dimethylpyrrolidin-1-yl]-1-cyclopropyl-6-fluoro-8-methooxy-1H-quinazoline-2,4-dione;
3-Amino-7-[(R)-4-((R)-1-amino-2-phenoxyethyl)-3,3-dimethylpyrrolidin-1-yl]-1-cyclopropyl-8-methoxy-1H-quinazoline-2,4-dione;
3-Amino-7-[(R)-4-((S)-1-amino-2-phenoxyethyl)-3,3-dimethylpyrrolidin-1-yl]-1-cyclopropyl-6-fluoro-8-methoxy-1H-quinazoline-2,4-dione;
3-Amino-7-[(R)-4-((S)-1-amino-2-phenoxyethyl)-3,3-dimethylpyrrolidin-1-yl]-1-cyclopropyl-8-methoxy-1H-quinazoline-2,4-dione;
3-Amino-7-[(R)-3-((S)-1-amino-2-ethoxyethyl)pyrrolidin-1-yl]-1-cyclopropyl-6-fluoro-8-methoxy-1H-quinazoline-2,4-dione;
3-Amino-7-[(R)-3-((S)-1-amino-2-ethoxyethyl)pyrrolidin-1-yl]-1-cyclopropyl-8-methoxy-1-quinazoline-2,4-dione;
3-Amino-7-[(R)-3-((R)-1-amino-2-ethoxyethyl)pyrrolidin-1-yl]-1-cyclopropyl-6-fluoro-8-methoxy-1H-quinazoline-2,4-dione;
3-Amino-7-[(R)-3-((R)-1-amino-2-ethoxyethyl)pyrrolidin-1-yl]-1-cyclopropyl-8-methoxy-1H-quinazoline-2,4-dione;

3-Amino-7-[(3R,4S)-3-((R)-1-amino-2-ethoxyethyl)-4-methylpyrrolidin-1-yl]-1-cyclopropyl-6-fluoro-8-methoxy-1H-quinazoline-2,4-dione;

3-Amino-7-[(3R,4S)-3-((R)-1-amino-2-ethoxyethyl)-4-methylpyrrolidin-1-yl]-1-cyclopropyl-8-methoxy-1H-quinazoline-2,4-dione;

3-Amino-7-[(3R,4S)-3-((R)-1-amino-2-ethoxyethyl)-4-fluoropyrrolidin-1-yl]-1-cyclopropyl-6-fluoro-8-methoxy-1H-quinazoline-2,4-dione;

3-Amino-7-[(3R,4S)-3-((R)-1-amino-2-ethoxyethyl-4-fluoropyrrolidin-1-yl]-1-cyclopropyl-8-methoxy-1H-quinazoline-2,4-dione;

3-Amino-7-[(R)-4-((R)-1-amino-2-ethoxyethyl)-3,3-dimethylpyrrolidin-1-yl]-1-cyclopropyl-6-fluoro-8-methoxy-1H-quinazoline-2,4-dione;

3-Amino-7-[(R)-4-((R)-1-amino-2-ethoxyethyl)-3,3-dimethylpyrrolidin-1-yl]-1-cyclopropyl-8-methoxy-1H-quinazoline-2,4-dione;

3-Amino-7-[(3R,4R)-3-((S)-1-amino-2-ethoxyethyl)-4-methylpyrrolidin-1-yl]-1-cyclopropyl-6-fluoro-8-methoxy-1H-quinazoline-2,4-dione;

3-Amino-7-[(3R,4R)-3-((S)-1-amino-2-ethoxyethyl)-4-methylpyrrolidin-1-yl]-1-cyclopropyl-8-methoxy-1H-quinazoline-2,4-dione;

3-Amino-7-[(3R,4R)-3-((S)-1-amino-2-ethoxyethyl)-4-fluoropyrrolidin 1-yl]-1-cyclopropyl-6-fluoro-8-methoxy-1H-quinazoline-2,4-dione;

3-Amino-7-[(3R,4R)-3-((S)-1-amino-2-ethoxyethyl)-4-fluoropyrrolidin-1-yl]-1-cyclopropyl-6-methoxy-1H-quinazoline-2,4-dione;

3-Amino-7-[(R)-3-((S)-1-amino-3-methoxypropyl)pyrrolidin-1-yl]-1-cyclopropyl-6-fluoro-8-methoxy-1H-quinazoline-2,4-dione;

3-Amino-7-[(R)-3-((S)-1-amino-3-methoxypropyl)pyrrolidin-1-yl]-1-cyclopropyl-8-methoxy-1H-quinazoline-2,4-dione;

3-Amino-7-[(3R,4S)-3-((S)-1-amino-3-methoxypropyl)-4-methylpyrrolidin-1-yl]-1-cyclopropyl-6-fluoro-8-methoxy-1H-quinazoline-2,4-dione;

3-Amino-7-[(3R,4S)-3-((S)-1-amino-3-methoxypropyl)-4-methylpyrrolidin-1-yl]-1-cyclopropyl-8-methoxy-1H-quinazoline-2,4-dione;

3-Amino-7-[(3R,4S)-3-((S)-1-amino-3-methoxypropyl)-4-fluoropyrrolidin-1-yl]-1-cyclopropyl-6-fluoro-8-methoxy-1H-quinazoline-2,4-dione;

3-Amino-7-[(3R,4S)-3-((S)-1-amino-3-methoxypropyl)-4-fluoropyrrolidin-1-yl]-1-cyclopropyl-8-methoxy-1H-quinazoline-2,4-dione;

3-Amino-7-[(R)-3-((R)-1-amino-3-methoxypropyl)pyrrolidin-1-yl]-1-cyclopropyl-6-fluoro-8-methoxy-1 quinazoline-2,4-dione;

3-Amino-7-[(R)-3-((R)-1-amino-3-methoxypropyl)pyrrolidin-1-yl]-1-cyclopropyl-8-methoxy-1H-quinazoline-2,4-dione;

3-Amino-7-[(3R,4R)-3-((R)-1-amino-3-methoxypropyl)-4-methylpyrrolidin-1-yl]-1-cyclopropyl-6-fluoro-8-methoxy-1H-quinazoline-2,4-dione;

3-Amino-7-[(3R,4R)-3-((R)-1-amino-3-methoxypropyl)-4-methylpyrrolidin-1-yl]-1-cyclopropyl-8-methoxy-1H-quinazoline-2,4-dione;

3-Amino-7-[(3R,4R)-3-((R)-1-amino-3-methoxypropyl)-4-fluoropyrrolidin-1-yl]-1-cyclopropyl-6-fluoro-8-methoxy-1H-quinazoline-2,4-dione;

-Amino-7-[(3R,4R)-3-((R)-1-amino-3-methoxypropyl)-4-fluoropyrrolidin-1-yl]-1-cyclopropyl-8-methoxy-1H-quinazoline-2,4-dione;

{(R)-2-Amino-2-[(R)-1-(3-amino-1-cyclopropyl-6-fluoro-8-methoxy-2,4-dioxo-1,2,3,4-tetrahydroquinazolin-7-yl)pyrrolidin-3-yl]ethyl}urea;

{(R)-2-Amino-2-[(R)-1-(3-amino-1-cyclopropyl-8-methoxy-2,4-dioxo-1,2,3,4-tetrahydroquinazolin-7-yl)pyrrolidin-3-yl]ethyl}urea;

{(S)-2-Amino-2-[(R)-1-(3-amino-1-cyclopropyl-6-fluoro-8-methoxy-2,4-dioxo-1,2,3,4-tetrahydroquinazolin-7-yl)pyrrolidin-3-yl]ethyl}urea;

{(S)-2-Amino-2-[(R)-1-(3-amino-1-cyclopropyl-8-methoxy-2,4-dioxo-1,2,3,4-tetrahydroquinazolin-7-yl)pyrrolidin-3-yl]ethyl}urea;

{(R)-2-Amino-2-[(3R,4S)-1-(3-amino-1-cyclopropyl-6-fluoro-8-methoxy-2,4-dioxo-1,2,3,4-tetrahydroquinazolin-7-yl)-4-methylpyrrolidin-3-yl]ethyl}urea;

{(R)-2-Amino-2-[(3R,4S)-1-(3-amino-1-cyclopropyl-8-methoxy-2,4-dioxo-1,2,3,4-tetrahydroquinazolin-7-yl)-4-methylpyrrolidin-3-yl]ethyl}urea;

{(S)-2-Amino-2-[(3R,4R)-1-(3-amino-1-cyclopropyl-6-fluoro-8-methoxy-2,4-dioxo-1,2,3,4-tetrahydroquinazolin-7-yl)-4-methylpyrrolidin-3-yl]ethyl}urea;

{(S)-2-Amino-2-[(3R,4R)-1-(3-amino-1-cyclopropyl-8-methoxy-2,4-dioxo-1,2,3,4-tetrahydroquinazolin-7-yl)-4-methylpyrrolidin-3-yl]ethyl}urea;

{2-Amino-2-[(1-(3-amino-1-cyclopropyl-6-fluoro-8-methoxy-2,4-dioxo-1,2,3,4-tetrahydroquinazolin-7-yl)-4-fluoropyrrolidin-3-yl]ethyl}urea;

{2-Amino-2-[(1-(3-amino-1-cyclopropyl-8-methoxy-2,4-dioxo-1,2,3,4-tetrahydroquinazolin-7-yl)-4-fluoropyrrolidin-3-yl]ethyl}urea;

{2-Amino-2-[(1-(3-amino-1-cyclopropyl-6-fluoro-8-methoxy-2,4-dioxo-1,2,3,4-tetrahydroquinazolin-7-yl)-4,4-dimethylpyrrolidin-3-yl]ethyl}urea;

{2-Amino-2-[(1-(3-amino-1-cyclopropyl-8-methoxy-2,4-dioxo 1,2,3,4-tetrahydroquinazolin-7-yl)-4,4-dimethylpyrrolidin-3-yl]ethyl}urea;

3-Amino-7-[3-(1-aminoethyl)-4-fluoropyrrolidin-1-yl]-1-cyclopropyl-8-methyl-1H-pyrido[4,3-d]pyrimidine-2,4-dione;

3-Amino-7-[3-(1-amino-1-methylethyl)-4-fluoropyrrolidin-1-yl]-1-cyclopropyl-8-methyl-1H-pyrido [4,3-d]pyrimidine-2,4-dione;

3-Amino-7-[3-(1-amino-2-methoxyethyl)-4-fluoropyrrolidin-1-yl]-1-cyclopropyl-8-methyl-1H-pyrido [4,3-d]pyrimidine-2,4-dione;

3-Amino-7-[3-(1-amino-2-methoxyethyl)-4-methylpyrrolidin-1-yl]-1-cyclopropyl-8-methyl-1H-pyrido [4,3-d]pyrimidine-2,4-dione;

3-Amino-7-[4-(1-amino-2-methoxyethyl)-3,3-dimethylpyrrolidin-1-yl]-1-cyclopropyl-8-methyl-1H-pyrido [4,3-d]pyrimidine-2,4-dione;

3-Amino-7-[3-(1-amino-2-phenoxyethyl)-pyrrolidin-1-yl]-1-cyclopropyl-8-methyl-1H-pyrido[4,3-d]pyrimidine-2,4-dione;

3-Amino-7-[3-(1-amino-2-phenoxyethyl)-4-methylpyrrolidin-1-yl]-1-cyclopropyl-8-methyl-1H-pyrido[4,3-d] pyrimidine-2,4-dione;

3-Amino-7-[3-(1-amino-2-phenoxyethyl)-4-fluoropyrrolidin-1-yl]-1-cyclopropyl-8-methyl-1H-pyrido[4,3-d] pyrimidine-2,4-dione;

3-Amino-7-[4-(1-amino-2-phenoxyethyl)-3,3-dimethylpyrrolidin-1-yl]-1-cyclopropyl-8-methyl-1H-pyrido [4,3-d]pyrimidine-2,4-dione;

3-Amino-7-[3-(1-amino-2-ethoxyethyl)pyrrolidin-1-yl]-1-cyclopropyl-8-methyl-1H-pyrido[4,3-d]pyrimidine-2,4-dione;

3-Amino-7-[3-(1-amino-2-ethoxyethyl)-4-methylpyrrolidin-1-yl]-1-cyclopropyl-8-methyl-1H-pyrido[4,3d]pyrimidine-2,4-dione;
3-Amino-7-[3-(1-amino-2-ethoxyethyl)-4-fluoropyrrolidin-1-yl]-1-cyclopropyl-8-methyl-1H-pyrido[4,3-d]pyrimidine-2,4-dione;
3-Amino-7-[3-(1-amino-2-ethoxyethyl)-4,4-dimethylpyrrolidin-1-yl]-1-cyclopropyl-8-methyl-1H-pyrido [4,3-d]pyrimidine-2,4-dione;
3-Amino-7-[3-(1-amino-2-methoxypropyl)pyrrolidin-1-yl]-1-cyclopropyl-8-methyl-1H-pyrido[4,3-d]pyrimidine-2,4-dione;
3-Amino-7-[3-(1-amino-2-methoxypropyl)-4-methylpyrrolidin-1-yl]-1-cyclopropyl-8-methyl-1H-pyrido[4,3-d]pyrimidine-2,4-dione;
3-Amino-7-[3-(1-amino-2-methoxypropyl)-4-fluoropyrrolidin-1-yl]-1-cyclopropyl-8-methyl-1H-pyrido[4,3-d]pyrimidine-2,4-dione;
{2-Amino-2-[1-(3-amino-1-cyclopropyl-8-methyl-2,4-dioxo-1,2,3,4-tetrahydropyrido[4,3d]pyrimidin-7-yl)pyrrolidin-3-yl]ethylurea;
{2-Amino-2-[1-(3-amino-1-cyclopropyl-8-methyl-2,4-dioxo-1,2,3,4-tetrahydropyrido[4,3-d]pyrimidin-7-yl)-4-methylpyrrolidin-3-yl]ethylurea;
{2-Amino-2-[1-(3-amino-1-cyclopropyl-8-methyl-2,4-dioxo-1,2,3,4-tetrahydropyrido[4,3-d]pyrimidin-7-yl)-4-fluoropyrrolidin-3-yl]ethylurea;
{2-Amino-2-[1-(3-amino-1-cyclopropyl-8-methyl-2,4-dioxo-1,2,3,4-tetrahydropyrido[4,3-d]pyrimidin-7-yl)-4,4-dimethylpyrrolidin-3-yl]ethylurea;
3-Amino-7-[3-(1-aminoethyl)-4-fluoropyrrolidin-1-yl]-1-cyclopropyl-6-fluoro-8-methyl-1H-pyrido[3,2-d]pyrimidine-2,4-dione;
3-Amino-7-(3-(1-aminoethyl)-4-fluoropyrrolidin-1-yl]-1-cyclopropyl-8-methyl-1H-pyrido [3,2-d]pyrimidine-2,4-dione;
3-Amino-7-[3-(1-amino-1-methylethyl)-4-fluoropyrrolidin-1-yl]-1-cyclopropyl-6-fluoro-8-methyl-1H-pyrido[3,2-d]pyrimidine-2,4-dione;
3-Amino-7-[3-(1-amino-1-methylethyl)-4-fluoropyrrolidin-1-yl]-1-cyclopropyl-8-methyl-1H-pyrido[3,2-d]pyrimidine-2,4-dione;
3-Amino-7-[3-(1-amino-2-methoxyethyl)-4-fluoropyrrolidin-1-yl]-1-cyclopropyl-6-fluoro-8-methyl-1H-pyrido[3,2-d]pyrimidine-2,4-dione;
3-Amino-7-[3-(1-amino-2-methoxyethyl)-4-fluoropyrrolidin-1-yl-1-cyclopropyl-8-methyl-1H-pyrido[3,2-d]pyrimidine-2,4-dione;
3-Amino-7-[3-(1-amino-2-methoxyethyl)-4-methylpyrrolidin-1-yl]-1-cyclopropyl-6-fluoro-8-methyl-1H-pyrido[3,2-d]pyrimidine-2,4-dione;
3-Amino-7-[3-(1-amino-2-methoxyethyl)-4-methylpyrrolidin-1-yl]-1-cyclopropyl-8-methyl-1H-pyrido[3,2-d]pyrimidine-2,4-dione;
3-Amino-7-[4-(1-amino-2-methoxyethyl)-3,3-dimethylpyrrolidin-1-yl]-1-cyclopropyl-6-fluoro-8-methyl-1H-pyrido[3,2-d]pyrimidine-2,4-dione;
3-Amino-7-[4-(1-amino-2-methoxyethyl)-3,3 dimethylpyrrolidin-1-yl]-1-cyclopropyl-8-methyl-1H-pyrido[3,2-d]pyrimidine-2,4-dione;
3-Amino-7-[3-(1-amino-2-phenoxyethyl)pyrrolidin-1-yl]-1-cyclopropyl-6-fluoro-8-methyl-1H-pyrido[3,2-d]pyrimidine-2,4-dione;
3-Amino-7-[3-(1-amino-2-phenoxyethyl)pyrrolidin-1-yl]-1-cyclopropyl-8-methyl-1H-pyrido[3,2-d]pyrimidine-2,4-dione;
3-Amino-7-[3-(1-amino-2-phenoxyethyl)-4-methylpyrrolidin-1-yl]-1-cyclopropyl-6-fluoro-8-methyl-1-pyrido[3,2-d]pyrimidine-2,4-dione;
3-Amino-7-[3-(1-amino-2-phenoxyethyl)-4-methylpyrrolidin-1-yl]-1-cyclopropyl-8-methyl-1H-pyrido [3,2-d]pyrimidine-2,4-dione;
3-Amino-7-[3-(1-amino-2-phenoxyethyl)-4-fluoropyrrolidin-1-yl]-1-cyclopropyl-6-fluoro-8-methyl-1H-pyrido[3,2-d]pyrimidine-2,4-dione;
3-Amino-7-[3-(1-amino-2-phenoxyethyl)-4-fluoropyrrolidin-1-yl]-1-cyclopropyl-8-methyl-1H-pyrido [3,2-d]pyrimidine-2,4-dione;
3-Amino-7-[4-(1-amino-2-phenoxyethyl)-3,3-dimethylpyrrolidin-1-yl]-1-cyclopropyl-6-fluoro-8-methyl-1H-pyrido[3,2-d]pyrimidine-2,4-dione;
3-Amino-7-[4-(1-amino-2-phenoxyethyl)-3,3-dimethylpyrrolidin-1-yl]-1-cyclopropyl-8-methyl-1H-pyrido [3,2-d]pyrimidine-2,4-dione;
3-Amino-7-[3-(1-amino-2-ethoxyethyl)pyrrolidin-1-yl]-1-cyclopropyl-6-fluoro-8-methyl-1H-pyrido[3,2-d]pyrimidine-2,4-dione;
3-Amino-7-[3-(1-amino-2-ethoxyethyl)pyrrolidin-1-yl]-1-cyclopropyl-8-methyl-1H-pyrido [3,2-d]pyrimidine-2,4-dione;
3-Amino-7-[3-(1-amino-2-ethoxyethyl)-4-methylpyrrolidin-1-yl]-1-cyclopropyl-6-fluoro-8-methyl-1H-pyrido [3,2-d]pyrimidine-2,4-dione;
3-Amino-7-[3-(1-amino-2-ethoxyethyl)-4-methylpyrrolidin-1-yl]-1-cyclopropyl-8-methyl-1H-pyrido[3,2-d]pyrimidine-2,4-dione;
3-Amino-7-[3-(1-amino-2-ethoxyethyl)-4-fluoropyrrolidin-1-yl]-1-cyclopropyl-6-fluoro-8-methyl-1H-pyrido [3,2-d]pyrimidine-2,4-dione;
3-Amino-7-[3-(1-amino-2-ethoxyethyl)-4-fluoropyrrolidin-1-yl]-1-cyclopropyl-8-methyl-1H-pyrido[3,2-d]pyrimidine-2,4-dione;
3-Amino-7-[3-(1-amino-2-ethoxyethyl)-4,4-dimethylpyrrolidin-1-yl]-1-cyclopropyl-6-fluoro-8-methyl-1H-pyrido[3,2-d]pyrimidine-2,4-dione;
3-Amino-7-[3-(1-amino-2-ethoxyethyl)-4,4-dimethylpyrrolidin-1-yl]-1-cyclopropyl-8-methyl-1H-pyrido[3,2-d]pyrimidine-2,4-dione;
3-Amino-7-[3-(1-amino-2-methoxypropyl)pyrrolidin-1-yl]-1-cyclopropyl-6-fluoro-8-methyl-1H-pyrido[3,2-d]pyrimidine-2,4-dione;
3-Amino-7-[3-(1-amino-2-methoxypropyl)pyrrolidin-1-yl]-1-cyclopropyl-8-methyl-1H-pyrido[3,2-d]pyrimidine-2,4-dione;
3-Amino-7-[3-(1-amino-2-methoxypropyl)-4-methylpyrrolidin-1-yl]-1-cyclopropyl-6-fluoro-8-methyl-1H-pyrido[3,2-d]pyrimidine-2,4-dione;
3-Amino-7-[3-(1-amino-2-methoxypropyl)-4-methylpyrrolidin-1-yl]-1-cyclopropyl-8-methyl-1H-pyrido[3,2-d]pyrimidine-2,4-dione;
3-Amino-7-[3-(1-amino-2-methoxypropyl)-4-fluoropyrrolidin-1-yl]-1-cyclopropyl-6-fluoro-8-methyl-1H-pyrido[3,2-d]pyrimidine-2,4-dione;
3-Amino-7-[3-(1-amino-2-methoxypropyl)-4-fluoropyrrolidin-1-yl]-1-cyclopropyl-8-methyl-1H-pyrido[3,2-d]pyrimidine-2,4-dione;
{2-Amino-2-[1-(3-amino-1-cyclopropyl-6-fluoro-8-methyl-2,4-dioxo-1,2,3,4-tetrahydropyrido[3,2d]pyrimidin-7-yl)pyrrolidin-3-yl]ethylurea;
{2-Amino-2-[1-(3-amino-1-cyclopropyl-8-methyl-2,4-dioxo-1,2,3,4-tetrahydropyrido[3,2-d]pyrimidin-7-yl)pyrrolidin-3-yl]ethylurea;

{2-Amino-2-[1-(3-amino-1-cyclopropyl-6-fluoro-8-methyl-2,4-dioxo-1,2,3,4-tetrahydropyrido[3,2-d]pyrimidin-7-yl)-4-methylpyrrolidin-3-yl]ethylurea;

{2-Amino-2-[1-(3-amino-1-cyclopropyl-8-methyl-2,4-dioxo-1,2,3,4-tetrahydropyrido[3,2-d]pyrimidin-7-yl)-4-methylpyrrolidin-3-yl]ethylurea;

(2-Amino-2-[1-(3-amino-1-cyclopropyl-6-fluoro-8-methyl-2,4-dioxo-1,2,3,4-tetrahydropyrido[3,2-d]pyrimidin-7-yl)-1-fluoropyrrolidin-3-yl]ethylurea;

{2-Amino-2-[1-(3-amino-1-cyclopropyl-8-methyl-2,4-dioxo-1,2,3,4-tetrahydropyrido[3,2-d]pyrimidin-7-yl)-4-fluoropyrrolidin-3-yl]ethylurea;

{2-Amino-2-[1-(3-amino-1-cyclopropyl-6-fluoro-8-methyl-2,4-dioxo-1,2,3,tetrahydropyrido[3,2-d]pyrimidin-7-yl)-4,4-dimethylpyrrolidin-3-yl]ethylurea;

{2-Amino-2-[1-(3-amino-1-cyclopropyl-8-methyl-2,4-dioxo-1,2,3,4 tetrahydropyrido[3,2-d]pyrimidin-7-yl)-4,4-dimethylpyrrolidin-3-yl]ethylurea;

3-Amino-7-(3-aminomethylphenyl)-8-chloro-1-cyclopropyl-6-fluoro-1H-quinazoline-2,4-dione;

3-Amino-7-(3-aminomethylphenyl)-8-methyl-1-cyclopropyl-6-fluoro-1H-quinazoline-2,4-dione;

3-Amino-7-(3-aminomethylphenyl)-8-methoxy-1-cyclopropyl-6-fluoro-1H-quinazoline-2,4-dione;

3-Amino-7-(3-aminomethylphenyl)-8-chloro-1-cyclopropyl-1H-quinazoline-2,4-dione;

3-Amino-7-(3-aminomethylphenyl)-8-methyl-1-cyclopropyl-1H-quinazoline-2,4-dione;

3-Amino-7-(3-aminomethylphenyl)-8-methoxy-1-cyclopropyl-1H-quinazoline-2,4-dione;

3-Amino-7-(2-aminomethylthiazol-4-yl)-8-chloro-1-cyclopropyl-6-fluoro-1H-quinazoline-2,4-dione;

3-Amino-7-(2-aminomethylthiazol-4-yl)-8-methyl-1-cyclopropyl-6-fluoro-1H-quinazoline-2,4-dione;

3-Amino-7-(2-aminomethylthiazol-4-yl)-8-methoxy-1-cyclopropyl-6 fluoro-1H-quinazoline-2,4-dione;

3-Amino-7-(2-aminomethylthiazol-4-yl)-8-chloro-1-cyclopropyl-1H-quinazoline-2,4-dione;

3-Amino-7-(2-aminomethylthiazol-4-yl)-8-methyl-1-cyclopropyl-1H-quinazoline-2,4-dione;

3-Amino-7-(2-aminomethylthiazol-4-yl)-8-methoxy-1-cyclopropyl-1H-quinazoline-2,4-dione;

3-Amino-7-[2-(1-aminoethyl)thiazol-4-yl)-8-chloro-1-cyclopropyl-6-fluoro-1H-quinazoline-2,4-dione;

3-Amino-7-[2-(1-aminoethyl)thiazol-4-yl)-8-methyl-1-cyclopropyl-6-fluoro-1H-quinazoline-2,4-dione;

3-Amino-7-[2-(1-aminoethyl)thiazol-4-yl)-8-methoxy-1-cyclopropyl-6-fluoro-1H-quinazoline-2,4-dione;

3-Amino-7-[2-(1-aminoethyl)thiazol-4-yl)-8-chloro-1-cyclopropyl-1H-quinazoline-2,4-dione;

3-Amino-7-[2-(1-aminoethyl)thiazol-4-yl)-8-methyl-1-cyclopropyl-1H-quinazoline-2,4-dione;

3-Amino-7-[2-(1-aminoethyl)thiazol-4-yl)-8-methoxy-1-cyclopropyl-1H-quinazoline-2,4-dione;

3-Amino-7-(5-aminomethylthiophen-3-yl)-8-chloro-1-cyclopropyl-6-fluoro-1H-quinazoline-2,4-dione;

3-Amino-7-(5-aminomethylthiophen-3-yl)-8-methyl-1-cyclopropyl-6-fluoro-1H-quinazoline-2,4-dione;

3-Amino-7-(5-aminomethylthiophen-3-yl)-8-methoxy-1-cyclopropyl-6-fluoro-1H-quinazoline-2,4-dione;

3-Amino-7-(5-aminomethylthiophen-3-yl)-8-chloro-1-cyclopropyl-1H-quinazoline-2,4-dione;

3-Amino-7-(5-aminomethylthiophen-3-yl)-8-methyl-1-cyclopropyl-1H-quinazoline-2,4-dione;

3-Amino-7-(5-aminomethylthiophen-3-yl)-8-methoxy-1-cyclopropyl-1H-quinazoline-2,4-dione;

3-Amino-7-(4-aminomethyl-3,3-difluoropyrrolidin-1-yl)-8-chloro-1-cyclopropyl-6-fluoro-1H-quinazoline-2,4-dione;

3-Amino-7-(4-aminomethyl-3,3 difluoropyrrolidin-1-yl)-8-methyl-1-cyclopropyl-6-fluoro-1H-quinazoline-2,4-dione;

3-Amino-7-(4-aminomethyl-3,3 difluoropyrrolidin-1-yl)-8-methoxy-1-cyclopropyl-6-fluoro-1H-quinazoline-2,4-dione;

3-Amino-7-(4-aminomethyl-3,3-difluoropyrrolidin-1-yl)-8-chloro-1-cyclopropyl-1H-quinazoline-2,4-dione;

3-Amino-7-(4-aminomethyl-3,3-difluoropyrrolidin-1-yl)-8-methyl-1-cyclopropyl-1H-quinazoline-2,4-dione 3-Amino-7-(4-aminomethyl-3,3-difluoropyrrolidin-1-yl)-8-methoxy-1-cyclopropyl-1H-quinazoline-2,4-dione;

3-Amino-7-(4-(1-aminoethyl)-3,3-difluoropyrrolidin-1-yl)-8-chloro-1-cyclopropyl-6-fluoro-1H-quinazoline-2,4-dione;

3-Amino-7-(4-(1-aminoethyl)-3,3-difluoropyrrolidin-1-yl)-8-methyl-1-cyclopropyl-6-fluoro-1H-quinazoline-2,4-dione;

3-Amino-7-(4-(1-aminoethyl)-3,3-difluoropyrrolidin-1-yl)-8-methoxy-1-cyclopropyl-6-fluoro-1H-quinazoline-2,4-dione;

3-Amino-7-(4-(1-aminoethyl)-3,3-difluoropyrrolidin-1-yl)-8-chloro-1-cyclopropyl-1H-quinazoline-2,4—4-dione;

3-Amino-7-(4-(1-aminoethyl)-3,3-difluoropyrrolidin-1-yl)-8-methyl-1-cyclopropyl-1H-quinazoline-2,4-dione;

3-Amino-7-(4-(1-aminoethyl)-3,3-difluoropyrrolidin-1-yl)-8-methoxy-1-cyclopropyl-1H-quinazoline-2,4-dione;

3-Amino-7-(4-(1-amino-1-methylethyl)-3,3-difluoropyrrolidin-1-yl)-8-chloro-1-cyclopropyl-6-fluoro-1H-quinazoline-2,4-dione;

3-Amino-7-(4-(1-amino-1-methylethyl)-3,3-difluoropyrrolidin-1-yl)-8-methyl-1-cyclopropyl-6-fluoro-1H-quinazoline-2,4-dione;

3-Amino-7-(4-(1-amino-1-methylethyl)-3,3-difluoropyrrolidin-1-yl)-8-methoxy-1-cyclopropyl-6-fluoro-1H-quinazoline-2,4-dione;

3-Amino-7-(4-(1-amino-1-methylethyl)-3,3-difluoropyrrolidin-1-yl)-8-chloro-1-cyclopropyl-1H-quinazoline-2,4-dione;

3-Amino-7-(4-(1-amino-1-methylethyl)-3,3-difluoropyrrolidin-1-yl)-8-methyl-1-cyclopropyl-1H-quinazoline-2,4-dione;

3-Amino-7-(4-(1-amino-1-methylethyl)-3,3-difluoropyrrolidin-1-yl)-8-methoxy-1-cyclopropyl-1-H-quinazoline-2,4-dione;

3-Amino-7-(3-(1-aminoethyl)pyrrolidin-1-yl)-1-cyclopropyl-6-fluoro-5,8-dimethyl-1H-quinazoline-2,4-dione;

3-Amino-7-(3-(1-aminoethyl)pyrrolidin-1-yl)-1-cyclopropyl-5,8-dimethyl-1H-quinazoline-2,4-dione;

3-Amino-7-(3-(1-aminoethyl)pyrrolidin-1-yl)-1-cyclopropyl-6-fluoro-8-methoxy-5-methyl-1H-quinazoline-2,4-dione;

3-Amino-7-(3-(1-aminoethyl)pyrrolidin-1-yl)-1-cyclopropyl-8-methoxy-5-methyl-1H-quinazoline-2,4-dione;

3,8-Diamino-7-[3-(1-aminoethyl)pyrrolidin-1-yl]-1-cyclopropyl-6-fluoro-5-methyl-1H-quinazoline-2,4-dione; and 3,8-Diamino-7-[3-(1-aminoethyl)pyrrolidin-1-yl]-1-cyclopropyl-5-methyl-1H-quinazoline-2,4-dione.

7. A pharmaceutical composition comprising a compound of claim 1 admixed with a carrier, diluent, or excipient.

8. A pharmaceutical composition comprising a compound of claim 2 admixed with a carrier, diluent, or excipient.

9. A pharmaceutical composition comprising a compound of claim 3 admixed with a carrier, diluent, or excipient.

10. A pharmaceutical composition comprising a compound of claim 6 admixed with a carrier, diluent, or excipient.

11. A method of treating a bacterial infection in a mammal comprising administering to the mammal an antibacterial effective amount of a compound of claim 1, wherein the bacterial infection is caused by *E. faecalis, S. aureus, S. pyogenes* or *E. coli*.

12. A method of treating a bacterial infection in a mammal comprising administering to the mammal an antibacterial effective amount of a compound of claim 2, wherein the bacterial infection is caused by *E. faecalis, S. aureus, S. pyogenes* or *E. coli*.

13. A method of treating a bacterial infection in a mammal comprising administering to the mammal an antibacterial effective amount of a compound of claim 3, wherein the bacterial infection is caused by *E. faecalis, S. aureus, S. pyogenes* or *E. coli*.

14. A method of treating a bacterial infection in a mammal comprising administering to the mammal an antibacterial effective amount of a compound of claim 6, wherein the bacterial infection is caused by *E. faecalis, S. aureus, S. pyogenes* or *E. coli*.

* * * * *